(12) United States Patent
Hinuma et al.

(10) Patent No.: US 7,268,212 B2
(45) Date of Patent: Sep. 11, 2007

(54) LIGAND OF G PROTEIN-COUPLED RECEPTOR PROTEIN AND DNA THEREOF

(75) Inventors: Shuji Hinuma, Ibaraki (JP); Ryo Fujii, Ibaraki (JP); Shoji Fukusumi, Ibaraki (JP); Masaaki Mori, Ibaraki (JP); Hiromi Yoshida, Ibaraki (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 407 days.

(21) Appl. No.: 10/480,739

(22) PCT Filed: Jun. 13, 2002

(86) PCT No.: PCT/JP02/05915

§ 371 (c)(1),
(2), (4) Date: Dec. 12, 2003

(87) PCT Pub. No.: WO02/102847

PCT Pub. Date: Dec. 27, 2002

(65) Prior Publication Data

US 2004/0220384 A1    Nov. 4, 2004

(30) Foreign Application Priority Data

| Jun. 14, 2001 | (JP) | ............................. 2001-180562 |
| Jul. 17, 2001 | (JP) | ............................. 2001-216773 |
| Nov. 26, 2001 | (JP) | ............................. 2001-359826 |
| Dec. 28, 2001 | (JP) | ............................. 2001-401019 |
| May 28, 2002 | (JP) | ............................. 2002-154533 |

(51) Int. Cl.
*C07K 14/47* (2006.01)

(52) U.S. Cl. ..................................... 530/324; 530/345

(58) Field of Classification Search ..................... None
See application file for complete search history.

(56) References Cited

FOREIGN PATENT DOCUMENTS

| WO | WO95/12670 | 5/1995 |
| WO | WO 01/98494 | 12/2001 |
| WO | WO 02/44368 | 6/2002 |
| WO | WO 02/084286 | 10/2002 |
| WO | WO 02/093161 | 11/2002 |
| WO | WO 03/057236 | 7/2003 |

OTHER PUBLICATIONS

B. O'Dowd et al., "Genomics", vol. 28, No. 1, pp. 84-91 (1995).
S. Wilson et al., "British Journ. of Pharm.", vol. 125, No. 7, pp. 1387-1392 (1998).
J. Stadel et al., "Elsevier Trends Journal", vol. 18, No. 11, pp. 430-437 (1997).
E. Jacoby, "Quantitive Structure-Activity Relationships", vol. 20, No. 2, pp. 115-123 (2001).
R. Fujii et al, "The Journ. of Biol. Chem.", vol. 277, No. 37, pp. 34010-34016 (2002).
Y. Shimomura et al., "Journ. of Biol. Chem", vol. 277, No. 39, pp. 35826-35832 (2002).
B. F. O'Dowd et al.,*Genomics*, vol. 28, pp. 84-91 (1995).
D. K. Lee et al., *Molecular Brain Research*, vol. 71, pp. 96-103 (1999).
H. Tanaka et al., *PNAS*, vol. 100, pp. 6251-6256 (2003).

*Primary Examiner*—Christine J. Saoud
(74) *Attorney, Agent, or Firm*—David G. Conlin; Christine C. O'Day; Edwards Angell Palmer & Dodge LLP

(57) ABSTRACT

A GPR7 ligand containing the same or substantially the same amino acid sequence as the amino acid sequence represented by SEQ ID NO:1 wherein the N-terminal amino acid residue may optionally be brominated, is useful in developing a receptor-binding assay system with the use of the GPR7 expression system, in screening a candidate compound for a drug such as an antiobestic, etc.

6 Claims, 33 Drawing Sheets

Fig. 1

DNA sequence atgccccggt ccgcgacact ggcggccgcc gccctggccg tgtgcctgct gctggcgccg    60
cctggcctcg cgtggtacaa gccagcgggcg gggcacagct cctactcggt gggccgcgcc   120
gcggggctgc tgtccggcct ccgcaggtcc ccgtacgcgc ggcgctccca gccctacaga   180
gggggcggaac ccccggggcgg ggccggcgcc tccccggagc tgcaactgca ccccaggctg   240
cggagcctcg ctgtgtgcgt ccaggacgtc gccccaaacc tgcagaggtg cgagcgggctc   300
cccgacgcc gcgggaccta ccagtgcacc gcgaacgtct tcctgtccct gcggcgcagcc   360
gactgcctcg ccgcctga                                                  378

Fig. 2

Amino acid sequence

Met Ala Arg Ser Ala Thr Leu Ala Ala Ala Ala Leu Ala Leu Cys Leu
                    5                  10                  15
Leu Leu Ala Pro Pro Gly Leu Ala Trp Tyr Lys Pro Ala Ala Gly His
              20                  25                  30
Ser Ser Tyr Ser Val Gly Arg Ala Ala Ala Gly Leu Leu Ser Gly Leu Arg
          35                  40                  45
Arg Ser Pro Tyr Ala Arg Arg Ser Gln Pro Tyr Arg Gly Ala Glu Pro
      50                  55                  60
Pro Gly Gly Ala Gly Ala Ser Pro Glu Leu Gln Leu His Pro Arg Leu
  65                  70                  75                  80
Arg Ser Leu Ala Val Cys Val Gln Asp Val Ala Pro Asn Leu Gln Arg
                  85                  90                  95
Cys Glu Arg Leu Pro Asp Gly Arg Gly Thr Tyr Gln Cys Lys Ala Asn
              100                 105                 110
Val Phe Leu Ser Leu Arg Ala Ala Asp Cys Leu Ala Ala End
          115                 120                 125

Fig. 3

DNA sequence atggcccggt gtaggacgct ggtggccgct gccctgggc tgctcctgcc gccagccctc 60
gcgtggtaca agcccgcggc gggacccac cactactcgg tgggccgcgc ctcggggcta 120
ctgtcgagtt tccacaggtt cccgtccacg cgacgctccg agtctccagc actccgggtg 180
ggaaccggac ctctgcgcaa tttagagatg cgcccagcg taaggagcct tgccctgtgt 240
gtcaaagatg tgacccgaa cctgcagagc tgccagcggc aactcaacag ccgagggact 300
ttccagtgta agcggacgt cttcttgtcg ctgcacgaga ctgattgcca gagcacctga 360

Fig. 4

Amino acid sequence

Met Ala Arg Cys Arg Thr Leu Val Ala Ala Ala Leu Ala Leu Leu Leu
                    5                  10                  15
Pro Pro Ala Leu Ala Trp Tyr Lys Pro Ala Ala Gly Pro His His Tyr
                    20                  25                  30
Ser Val Gly Arg Ala Ser Gly Leu Leu Ser Ser Phe His Arg Phe Pro
                    35                  40                  45
Ser Thr Arg Arg Ser Glu Ser Pro Ala Leu Arg Val Gly Thr Gly Pro
          50                  55                  60
Leu Arg Asn Leu Glu Met Arg Pro Ser Val Arg Ser Leu Ala Leu Cys
65                  70                  75                  80
Val Lys Asp Val Thr Pro Asn Leu Gln Ser Cys Gln Arg Gln Leu Asn
                    85                  90                  95
Ser Arg Gly Thr Phe Gln Cys Lys Ala Asp Val Phe Leu Ser Leu His
                    100                 105                 110
Glu Thr Asp Cys Gln Ser Thr End
          115                 120

Fig. 5

DNA sequence atggtccggt gtaggacgct ggtggccggc gccctgggcgc tgctcctgac gccagccctc 60
gcgtggtaca agcccgcggc gggatcccac cactactcgg tgggccgcgc tgcggggcta 120
ctgtcgagtt tccacaggtt cccatccacg cgacgttccg agtctccagc actccgggtg 180
ggaaccgtac ctctgcgcaa cttggagatg cgcccaagcg taagaagcct tgccctgtgt 240
gtcaaagatg tgaccccgaa cctgcagagc tgccagcggc aactcaacag ccgagggact 300
ttccagtgta aggcggacgt cttcttgtcg ctgcacaagg ctgaatgcca aagcgcctga 360

Fig. 6

Amino acid sequence

Met Val Arg Cys Arg Thr Leu Val Ala Ala Ala Leu Ala Leu Leu Leu
                  5                  10                  15
Thr Pro Ala Leu Ala Trp Tyr Lys Pro Ala Ala Gly Ser His His Tyr
         20                  25                  30
Ser Val Gly Arg Ala Ala Gly Leu Leu Ser Ser Phe His Arg Phe Pro
         35                  40                  45
Ser Thr Arg Arg Ser Glu Ser Pro Ala Leu Arg Val Gly Thr Val Pro
         50                  55                  60
Leu Arg Asn Leu Glu Met Arg Pro Ser Val Arg Ser Leu Ala Leu Cys
65                  70                  75                  80
Val Lys Asp Val Thr Pro Asn Leu Gln Ser Cys Gln Arg Gln Leu Asn
         85                  90                  95
Ser Arg Gly Thr Phe Gln Cys Lys Ala Asp Val Phe Leu Ser Leu His
         100                 105                 110
Lys Ala Glu Cys Gln Ser Ala End
         115                 120

Fig. 7

```
Human  MARSATLAAAAALCLL--LAPPGLAWYKPAA                              30
Mouse  MARCRTLVAAAALAL---LPPALAWYKPAA                               27
Rat    MVRCRTLVAAAALAL--LTPALAWYKPAA                                27

Human  GHSSYSVGRAAGLLSGLRRSPYARRSQPYR                               60
Mouse  GPHHYSVGRASGLLSSFHRFPSTRRSES-                                55
Rat    GSHHYSVGRAAGLLSSFHRFPSTRRSES-                                55

Human  GAEPPGGAGASPELQLHPRLRSLAVCVQDV                               90
Mouse  -PALRVGTGPLRNLEMRPSVRSLALCVKDV                               84
Rat    -PALRVGTVPLRNLEMRPSVRSLALCVKDV                               84

Human  APNLQRCERLPDGRGTYQCKANVFLSLRAA                               120
Mouse  TPNLQSCQRQLNSRGTFQCKADVFLSLHET                               114
Rat    TPNLQSCQRQLNSRGTFQCKADVFLSLHKA                               114

Human  DCLAA                                                        125
Mouse  DCQST                                                        119
Rat    ECQSA                                                        119
```

Fig. 20

DNA sequence

```
atggccgggc ccgcgatgct ggtggccgcc gctctgcggc tgtgcttact gctggcgtcc   60
cctggcctcg cgtggtacaa gccgacggcg gggcaggggt actactccgt gggccgcgcc  120
gcggggctgc tgtccggctt ccacaggtcg ccgtacgcac ggcgctccga gccccgcggg  180
ggcacgcgat ccctggggagg ggtcggcact ttccgggaga tgcccccaa cctgcggagt  240
cttgccgtgt gcgtcgagga ggtcaccccg aacctgcaga gctgcgagcc actccccgac  300
ggccgcgcca ctttccagtg caaggccgac gtcttcctgt cgctcagcgc ctcggactgt  360
cgcaagtga                                                           369
```

Fig. 21

Amino acid sequence

Met Ala Gly Pro Ala Met Leu Val Ala Ala Ala Leu Ala Leu Cys Leu
             5                10              15

Leu Leu Ala Ser Pro Gly Leu Ala Trp Tyr Lys Pro Thr Ala Gly Gln
         20               25              30

Gly Tyr Tyr Ser Val Gly Arg Ala Ala Gly Leu Leu Ser Gly Phe His
       35               40              45

Arg Ser Pro Tyr Ala Arg Arg Ser Glu Pro Arg Gly Gly Thr Arg Ser
      50                 55              60

Leu Gly Gly Val Gly Thr Phe Arg Glu Met Arg Pro Asn Leu Arg Ser
65               70              75             80

Leu Ala Val Cys Val Glu Glu Val Thr Pro Asn Leu Gln Ser Cys Glu
             85              90              95

Pro Leu Pro Asp Gly Arg Ala Thr Phe Gln Cys Lys Ala Asp Val Phe
          100             105            110

Leu Ser Leu Ser Ala Ser Asp Cys Arg Lys End
       115               120

Fig. 26

DNA sequence

```
atgcacaacg cgtcgtactg ggggccggag cgcgccaaca cgtcgtgccc cgcgcccgca    60
cccacgctcg gctgtcccaa cgcgtccggg cgggcgccgc ccggcgccgc gccgctggcc   120
gtagccgtgc ccgttgtgta cgcggtgatc tgcgcagtgg gactggcggg caactcggcg   180
gtactgttcg tgctgctgcg ggcgccgcgc aggaagaccg tcaccaacct gttcatcctc   240
aacctggccg tggccgacga gcttttcacg ctcgtgccgc ctgtcaacat cgccgacttt   300
ctgctgaggc gctggccctt cggggagctc ctatgcaagc tcgtcgtggc cgtcgatcag   360
tacaacacct tctccagcct ctatttcctc acggtcatga gcgccgaccg ctacctggtg   420
gtgctggcca ccgccgagtc gcgccgggtg gccggccgca cgtacggcgc cgcgcgcgcg   480
gtgagcctgg ccgtctgggg ggtcgcgacc ctggtggtgc tgcccttcgc ggtgttcgcg   540
cggctcgacg aggagcaggg ccggcgccag tgcgtactgc tcttcccgca gcccgaggcc   600
ttgtggtggc gcgcgagccg cctgtacacg ctggtgctcg gcttcgccat cccagtgtcc   660
accatctgcg tcctctacac ctcgctgctg tgccgctgc gcgccatacg cctcgacagc   720
cacgccaagg ccctggaccg cgccaagaag cgggtgaccg tcctggtggt ggccatcctg   780
gccgtgtgcc tcctcgtctg gacgccctac cacctgagca cgtggtggc gctcaccacc   840
gacctcccgc agacgccgct ggtcatcgcc gtgtcctact tcatcaccag cctgagctac   900
gccaacagct gcctcaaccc tttcctctac gccttcctgg acgacagctt ccgccggagc   960
ctccgccagc tgctggcgtg ccgcaccacc tcctga                            996
```

Fig. 27

Amino acid sequence

```
Met His Asn Ala Ser Tyr Trp Gly Pro Glu Arg Ala Asn Thr Ser Cys
              5                   10                  15
Pro Ala Pro Ala Pro Thr Leu Gly Cys Pro Asn Ala Ser Gly Pro Ala
            20                  25              30
Pro Pro Leu Pro Pro Pro Leu Ala Val Ala Val Pro Val Val Tyr Ala
            35              40              45
Val Ile Cys Ala Val Gly Leu Ala Gly Asn Ser Ala Val Leu Phe Val
        50              55              60
Leu Leu Arg Ala Pro Arg Arg Lys Thr Val Thr Asn Leu Phe Ile Leu
65              70              75                      80
Asn Leu Ala Val Ala Asp Glu Leu Phe Thr Leu Val Pro Pro Val Asn
                85                  90                  95
Ile Ala Asp Phe Leu Leu Arg Arg Trp Pro Phe Gly Glu Leu Leu Cys
            100             105             110
Lys Leu Val Val Ala Val Asp Gln Tyr Asn Thr Phe Ser Ser Leu Tyr
        115             120             125
Phe Leu Thr Val Met Ser Ala Asp Arg Tyr Leu Val Val Leu Ala Thr
        130             135             140
Ala Glu Ser Arg Arg Val Ala Gly Arg Thr Tyr Gly Ala Ala Arg Ala
145             150             155                 160
Val Ser Leu Ala Val Trp Gly Val Ala Thr Leu Val Val Leu Pro Phe
                165             170             175
Ala Val Phe Ala Arg Leu Asp Glu Glu Gln Gly Arg Arg Gln Cys Val
            180             185             190
Leu Val Phe Pro Gln Pro Glu Ala Leu Trp Trp Arg Ala Ser Arg Leu
        195             200             205
Tyr Thr Leu Val Leu Gly Phe Ala Ile Pro Val Ser Thr Ile Cys Val
    210             215             220
Leu Tyr Thr Ser Leu Leu Cys Arg Leu Arg Ala Ile Arg Leu Asp Ser
225             230             235                 240
His Ala Lys Ala Leu Asp Arg Ala Lys Lys Arg Val Thr Val Leu Val
            245             250             255
Val Ala Ile Leu Ala Val Cys Leu Leu Val Trp Thr Pro Tyr His Leu
            260             265             270
Ser Thr Val Val Ala Leu Thr Thr Asp Leu Pro Gln Thr Pro Leu Val
        275             280             285
Ile Ala Val Ser Tyr Phe Ile Thr Ser Leu Ser Tyr Ala Asn Ser Cys
        290             295             300
Leu Asn Pro Phe Leu Tyr Ala Phe Leu Asp Asp Ser Phe Arg Arg Ser
305             310             315                 320
Leu Arg Gln Leu Leu Ala Cys Arg Thr Thr Ser End
        325             330
```

Fig. 28

DNA sequence

```
atgatggagg ccactgggct ggaaggcctg gaaagcacaa gctcccctg cccaggtagc    60
acaggcaccg gcctctcatg ggacaatggc accagacaca atgccacctt ccccgagccg   120
ctgcctgccc tctacgtgct gctgccggtg gtatactctg tcatctgtgc cgtggggctg   180
gtgggcaacg cagccgtcat ctgtgtgatc ctgagggctc ccaagatgaa gacagtgacc   240
cacgtgttca tcctgaacct ggccatcgcc gacgggctct tcacgctggt gctgcccacc   300
aatattgctg agcacctgct gcagcgctgg cccttggggg aggtgctctg caagctggtg   360
ctggccattg accactgcaa catctctcc agtgtctact tcctggccgc catgagtata   420
gaccgctacc tggtggttct ggccacggca cgctcccgcc gcatgcccg gcgcaccgtc   480
cacaggggcga aggtcgccag cctgtgcgtc tggctgggtg tcacagtcgc agtgctgccc   540
ttccttacct tcgcaggcgt gtacaacaat gagctgcagg tcacaagttg tgggctgagt   600
ttcccgcggc ccgagagggc ctggttccag gcaagccgca tctacacgct ggtgctgggc   660
ttcgtggtgc ccatgtgcac cctctgcgtg ctctacgcag acctgctgcg gaggctaagg   720
gccctgcggc tccactccgg agccaaggct ctgggcaagg ccaagcggaa ggttagcctc   780
ctggtcctgg ccgtgctggc cgtgggcctg cgtctgctgga cgccttcca cctggcctca   840
attgtgccc tgaccacaga cctgcccag acaccgctgg tcatcatcgt ctcctatgtg   900
gtcaccagcc tcagctacac cagctcctgc ctcaaccct tcctctatgc cttcctggat   960
cacagcttcc ggaagagcct ccgcaccgca tgtcggtgcc aggggggcata a          1011
```

Fig. 29

Amino acid sequence

Met Met Glu Ala Thr Gly Leu Glu Gly Leu Glu Ser Thr Ser Ser Pro
                    5                  10                 15
Cys Pro Gly Ser Thr Gly Thr Gly Leu Ser Trp Asp Asn Gly Thr Arg
                20              25                 30
His Asn Ala Thr Phe Pro Glu Pro Leu Pro Ala Leu Tyr Val Leu Leu
            35              40              45
Pro Val Val Tyr Ser Val Ile Cys Ala Val Gly Leu Val Gly Asn Ala
    50              55              60
Ala Val Ile Cys Val Ile Leu Arg Ala Pro Lys Met Lys Thr Val Thr
65              70              75                      80
His Val Phe Ile Leu Asn Leu Ala Ile Ala Asp Gly Leu Phe Thr Leu
                85              90                 95
Val Leu Pro Thr Asn Ile Ala Glu His Leu Leu Gln Arg Trp Pro Phe
            100             105             110
Gly Glu Val Leu Cys Lys Leu Val Leu Ala Ile Asp His Cys Asn Ile
        115             120             125
Phe Ser Ser Val Tyr Phe Leu Ala Ala Met Ser Ile Asp Arg Tyr Leu
    130             135             140
Val Val Leu Ala Thr Ala Arg Ser Arg Arg Met Pro Arg Arg Thr Val
145             150             155                     160
His Arg Ala Lys Val Ala Ser Leu Cys Val Trp Leu Gly Val Thr Val
            165             170             175
Ala Val Leu Pro Phe Leu Thr Phe Ala Gly Val Tyr Asn Asn Glu Leu
            180             185             190
Gln Val Thr Ser Cys Gly Leu Ser Phe Pro Arg Pro Glu Arg Ala Trp
        195             200             205
Phe Gln Ala Ser Arg Ile Tyr Thr Leu Val Leu Gly Phe Val Val Pro
    210             215             220
Met Cys Thr Leu Cys Val Leu Tyr Ala Asp Leu Leu Arg Arg Leu Arg
225             230             235                     240
Ala Leu Arg Leu His Ser Gly Ala Lys Ala Leu Gly Lys Ala Lys Arg
                245             250             255
Lys Val Ser Leu Leu Val Leu Ala Val Leu Ala Val Gly Leu Leu Cys
            260             265             270
Trp Thr Pro Phe His Leu Ala Ser Ile Val Ala Leu Thr Thr Asp Leu
            275             280             285
Pro Gln Thr Pro Leu Val Ile Ile Val Ser Tyr Val Val Thr Ser Leu
    290             295             300
Ser Tyr Thr Ser Ser Cys Leu Asn Pro Phe Leu Tyr Ala Phe Leu Asp
305             310             315                     320
His Ser Phe Arg Lys Ser Leu Arg Thr Ala Cys Arg Cys Gln Gly Ala
                325             330             335

LIGAND OF G PROTEIN-COUPLED RECEPTOR PROTEIN AND DNA THEREOF

CROSS-REFERENCE TO RELATED APPLICATIONS

This application is the 35 U.S.C. §371 national stage of PCT application No. PCT/JP02/05915, filed Jun. 13, 2002, which in turn claimed priority to Japanese patent application no. JP 2001-180562, filed Jun. 14, 2001, JP 2001-216773, filed Jul. 17, 2001, JP 2001-359826, filed Nov. 26, 2001, JP 2001-401019, filed Dec. 28, 2001, and JP 2002-154533, filed May 28, 2002.

FIELD OF THE INVENTION

The present invention relates to a peptide capable of binding to GPR7, etc., its DNA and use thereof, bovine-derived GPR7 and GPR8, DNAs thereof as well as use thereof.

BACKGROUND ART

Important biological functions including maintenance of homeostasis in the living body, reproduction, development of individuals, metabolism, growth, control of the nervous, circulatory, immune, digestive or metabolic system, sensory adaptation, etc. are regulated by cells that receive endogenous factors such as various hormones and neurotransmitters or sensory stimulation like light or odor, via specific receptors present on cell membranes reserved for these endogenous factors or stimulation and interact with them. Many of these receptors for hormones or neurotransmitters, which take part in such functional regulation, are coupled to guanine nucleotide-binding proteins (hereinafter, sometimes merely referred to as G proteins), and are characterized by developing a variety of functions through mediation of intracellular signal transduction via activation of the G proteins. In addition, these receptor proteins possess common seven transmembrane regions. Based on the foregoing, these receptors are thus collectively referred to as G protein-coupled receptors or seven transmembrane receptors. As such, it is known that various hormones or neurotransmitters and their receptor proteins are present and interact with each other to play important roles for regulating the biological functions. However, it often remains unclear if there are any other unknown substances (hormones, neurotransmitters, etc.) and receptors to these substances.

In recent years, accumulated sequence information of human genome DNA or various human tissue-derived cDNAs by random sequencing and rapid progress in gene analysis technology have been accelerating the investigation of human genome. With such advance, it has been clarified that there are many genes supposed to encode proteins with unknown functions. G protein-coupled receptors not only have seven transmembrane domains but many common sequences are present in their nucleic acids or amino acids. Thus, these receptors can be precisely identified to be G protein-coupled receptors in such proteins. On the other hand, these G protein-coupled receptor genes are obtained also by polymerase chain reaction (hereinafter abbreviated as PCR) utilizing such a structural similarity. In these G protein-coupled receptors thus obtained so far, ligands to some receptors that are subtypes having high homology in structure to known receptors may be readily predictable but in most cases, their endogenous ligands are unpredictable so that ligands corresponding to these receptors are not found.

For this reason, these receptors are termed orphan receptors. It is likely that unidentified endogenous ligands to such orphan receptors would participate in biological phenomena poorly analyzed because the ligands were unknown. When such ligands are associated with important physiological effects or pathologic conditions, it is expected that development of these receptor agonists or antagonists will result in breakthrough new drugs (Stadel, J. et al., TiPS, 18, 430-437, 1997; Marchese, A. et al., TiPS, 20, 370-375, 1999; Civelli, O. et al., Brain Res., 848, 63-65, 1999, Howard, A. D. et al, TiPS, 22, 132-140, 2001).

Recently, some groups attempted to investigate ligands to these orphan receptors and reported isolation/structural determination of ligands, which are novel physiologically active peptides. Independently, Reinsheid et al. and Meunier et al. introduced a cDNA coding for orphan G protein-coupled receptor LC132 or ORL1 into animal cells to express a receptor, isolated a novel peptide from porcine brain or rat brain extract, which was named orphanin FQ or nociceptin, with reference to its response and determined its sequence (Reinsheid, R. K. et al., Science, 270, 792-794, 1995; Meunier, J.-C. et al., Nature, 377, 532-535, 1995). This peptide was reported to be associated with pain. Further research on the receptor in knockout mice reveals that the peptide takes part in memory (Manabe, T. et al., Nature, 394, 577-581, 1998).

Subsequently, novel peptides such as PrRP (prolactin releasing peptide), orexin, apelin, ghrelin and GALP (galanin-like peptide), etc. were isolated as ligands to orphan G protein-coupled receptors (Hinuma, S. et al., Nature, 393, 272-276, 1998; Sakurai, T. et al., Cell, 92, 573-585, 1998; Tatemoto, K. et al., Biohem. Biophys. Res. Commun., 251, 471476, 1998; Kojima, M. et al., Nature, 402, 656-660, 1999; Ohtaki, T. et al., J. Biol. Chem., 274, 37041-37045, 1999). On the other hand, some receptors to physiologically active peptides, which were hitherto unknown, were clarified. It was revealed that a receptor to motilin associated with contraction of intestinal tracts was GPR38 (Feighner, S. D. et al., Science, 284, 2184-2188, 1999). Furthermore, SLC-1 was identified to be a receptor to MCH (Chambers, J. et al., Nature, 400, 261-265, 1999; Saito, Y. et al., Nature, 400, 265-269, 1999; Shimomura, Y. et al., Biochem. Biophys. Res. Commun. 261, 622-626, 1999; Lembo, P. M. C. et al., Nature Cell Biol., 1, 267-271, 1999; Bachner, D. et al., FEBS Lett., 457, 522-524, 1999). Also, GPR14 (SENR) was reported to be a receptor to urotensin II (Ames, R. S. et al., Nature, 401, 282-286, 1999; Mori, M. et al., Biochem. Biophys. Res. Commun., 265, 123-129, 1999; Nothacker, H.-P. et al., Nature Cell Biol., 1, 383-385, 1999, Liu, Q. et al., Biochem. Biophys. Res. Commun., 266, 174-178, 1999). Besides, receptors to neuromedin U and neuropetide FF, which are neuropeptides, have recently been clarified and furthermore, low molecular physiologically active lipids or nucleic acid derivatives such as cysteinyl leukotrienes, sphingosine-1-phosphate, lysophosphatidic acid, sphingosylphosphorylcholine, UDP-glucose, etc., have been identified to be ligands to orphan receptors (Howard, A. D. et al., TiPS, 22, 132-140, 2001). It was shown that MCH took part in obesity since its knockout mice showed the reduced body weight and lean phenotype (Shimada, M. et al., Nature, 396, 670-674, 1998), and because its receptor was revealed, it became possible to explore a receptor antagonist likely to be an antiobesity agent. It is also reported that urotensin II shows a potent action on the cardiocirculatory system, since it induces heart ischemia by intravenous injection to monkey (Ames, R. S. et al., Nature, 401, 282-286, 1999).

As described above, orphan receptors and ligands thereto often take part in a new physiological activity, and it is expected that their clarification will lead to development of new drugs. However, it is known that research on ligands to orphan receptors is accompanied by many difficulties. For example, it is generally unknown what secondary signal transduction system will take place after orphan receptors expressed on cells responded to ligands, and various response system should be examined. Moreover, tissues where ligands are present are not readily predictable so that various tissue extracts should be prepared. Furthermore, since an amount of ligand required to stimulate its receptor is sufficient even in an extremely low concentration when the ligand is a peptide, the amount of such a ligand present in vivo is a trace amount in many cases. In addition, a peptide is digested by peptidase to lose its activity, or undergoes non-specific adsorption so that its recovery becomes poor during purification. Normally, it is thus extremely difficult to extract such a ligand from the living body and isolate an amount of the ligand necessary for determination of its structure. The presence of many orphan receptors was unraveled, but only a very small part of ligands to these receptors were discovered so far due to the foregoing problems.

GPR7 is one of the reported orphan G protein-coupled receptors (SEQ ID NO:49, O'Dowd, B. F. et al., Genomics, 28, 84-91, 1995). GPR7 has a low homology to somatostatin receptor (SSTR3) and opioid receptors (δ, κ and μ). Also, GPR7 is found to have a homology of about 64% to GPR8 (SEQ ID NO:66, O'Dowd, B. F. et al., Genomics, 28, 84-91, 1995) on an amino acid level. It is reported by O'Dowd, B. F. et al. that [$^3$H] bremazocine binds to the membrane fraction of GPR7 and this binding is inhibited by β-funaltrexamine, [D-Pro4]morphiceptin or β-endorphin, which is a μ-opioid receptor selective ligand, U50 or 488, which is a κ-opioid receptor selective ligand, or naltrindole, which is a δ-opioid receptor selective ligand.

The present invention provides a novel peptide capable of binding to GPR7, etc., its DNA, a method of screening a drug using the peptide and GPR7, etc.

DISCLOSURE OF THE INVENTION

The present inventors made extensive studies to solve the foregoing problems. As a result, the inventors succeeded in acquiring DNAs encoding novel peptides (GPR7 ligands) capable of binding to GPR7, from human whole brain, mouse whole brain and rat whole brain, and found that the GPR7 ligands exhibit an appetite (eating) stimulating activity. In addition, the inventors succeeded in acquiring DNAs encoding GPR7 and GPR8, respectively, from bovine hypothalamus. As a result of further studies based on these findings, the inventors have come to accomplish the present invention.

That is, the present invention provides the following features:

(1) A peptide containing the same or substantially the same amino acid sequence as the amino acid sequence represented by SEQ ID NO:1 wherein the N-terminal amino acid residue may optionally be brominated, or its amide or ester, or a salt thereof;

(2) The peptide or its amide or ester, or a salt thereof, according to (1), which contains the same or substantially the same amino acid sequence as the amino acid sequence represented by SEQ ID NO:1;

(3) The peptide or its amide or ester, or a salt thereof, according to (1), which has the amino acid sequence represented by SEQ ID NO:1, SEQ ID NO:2, SEQ ID NO:3 or SEQ ID NO:66;

(4) The peptide or its amide or ester, or a salt thereof, according to (1), wherein the N-terminal tryptophan residue is 6-brominated and which has the amino acid sequence represented by SEQ ID NO:1, SEQ ID NO:2, SEQ ID NO:3 or SEQ ID NO:66;

(5) A peptide containing the same or substantially the same amino acid sequence as the amino acid sequence represented by SEQ ID NO:4 wherein the N-terminal amino acid residue may optionally be brominated, or its amide or ester, or a salt thereof;

(6) The peptide or its amide or ester, or a salt thereof, according to (5), which contains the same or substantially the same amino acid sequence as the amino acid sequence represented by SEQ ID NO:4;

(7) The peptide or its amide or ester, or a salt thereof, according to (5), which has the amino acid sequence represented by SEQ ID NO:4, SEQ ID NO:5, SEQ ID NO:6 or SEQ ID NO:67;

(8) The peptide or its amide or ester, or a salt thereof, according to (5), wherein the N-terminal tryptophan residue is 6-brominated and which has the amino acid sequence represented by SEQ ID NO:67;

(9) The peptide or its amide or ester, or a salt thereof, according to (5), wherein the N-terminal tryptophan residue is 6-brominated and which has the amino acid sequence represented by SEQ ID NO:4, SEQ ID NO:5, SEQ ID NO:6 or SEQ ID NO:67;

(10) A peptide containing the same or substantially the same amino acid sequence as the amino acid sequence represented by SEQ ID NO:7 wherein the N-terminal amino acid residue may optionally be brominated, or its amide or ester, or a salt thereof;

(11) The peptide or its amide or ester, or a salt thereof, according to (10), which contains the same or substantially the same amino acid sequence as the amino acid sequence represented by SEQ ID NO:7;

(12) The peptide or its amide or ester, or a salt thereof, according to (10), which has the amino acid sequence represented by SEQ ID NO:7, SEQ ID NO:8, SEQ ID NO:9, SEQ ID NO:10, SEQ ID NO:11, SEQ ID NO:12, SEQ ID NO:68 or SEQ ID NO:69;

(13) A peptide containing the same or substantially the same amino acid sequence as the amino acid sequence represented by SEQ ID NO:13 wherein the N-terminal amino acid residue may optionally be brominated, or its amide or ester, or a salt thereof;

(14) The peptide or its amide or ester, or a salt thereof, according to (13), which contains the same or substantially the same amino acid sequence as the amino acid sequence represented by SEQ ID NO:13;

(15) The peptide or its amide or ester, or a salt thereof, according to (13), which has the amino acid sequence represented by SEQ ID NO:13, SEQ ID NO:14, SEQ ID NO:15 or SEQ ID NO:70;

(16) A peptide containing the same or substantially the same amino acid sequence as the amino acid sequence represented by SEQ ID NO:16 wherein the N-terminal amino acid residue may optionally be brominated, or its amide or ester, or a salt thereof;

(17) The peptide or its amide or ester, or a salt thereof, according to (16), which contains the same or substantially the same amino acid sequence as the amino acid sequence represented by SEQ ID NO:16;

(18) The peptide or its amide or ester, or a salt thereof, according to (17), which has the amino acid sequence represented by SEQ ID NO:16, SEQ ID NO:17, SEQ ID NO:18 or SEQ ID NO:71;

(19) The peptide or its amide or ester, or a salt thereof, according to (1) through (18), which is capable of binding to a protein or its salt containing the same or substantially the same amino acid sequence as the amino acid sequence represented by SEQ ID NO:49 or SEQ ID NO:86;

(20) The peptide or its amide or ester, or a salt thereof, according to (1) through (18), which is capable of binding to a protein or its salt containing the same or substantially the same amino acid sequence as the amino acid sequence represented by SEQ ID NO:59;

(21) The peptide or its amide or ester, or a salt thereof, according to (1) through (18), which is capable of binding to a protein or its salt containing the same or substantially the same amino acid sequence as the amino acid sequence represented by SEQ ID NO:84 or SEQ ID NO:88;

(22) A partial peptide of the peptide according to any one of (1) through (21), or its amide or ester, or a salt thereof;

(23) A precursor peptide of the peptide according to any one of (1) through (21), or its amide or ester, or a salt thereof;

(24) The precursor peptide or its amide or ester, or a salt thereof, according to (23), which contains the same or substantially the same amino acid sequence as the amino acid sequence represented by SEQ ID NO:19;

(25) The peptide or its amide or ester, or a salt thereof, according to (24), which has the amino acid sequence represented by SEQ ID NO:19, SEQ ID NO:20, SEQ ID NO:21 or SEQ ID NO:72;

(26) The peptide or its amide or ester, or a salt thereof, according to (23), which contains the same or substantially the same amino acid sequence as the amino acid sequence represented by SEQ ID NO:22;

(27) The peptide or its amide or ester, or a salt thereof, according to (26), which has the amino acid sequence represented by SEQ ID NO:22, SEQ ID NO:23, SEQ ID NO:24 or SEQ ID NO:73;

(28) A polynucleotide containing a polynucleotide encoding the peptide according to any one of (1) through (21);

(29) The polynucleotide according to (28), which has the base sequence represented by SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:74, SEQ ID NO:75, SEQ ID NO:76, SEQ ID NO:77, SEQ ID NO:78 or SEQ ID NO:79;

(30) A polynucleotide containing a polynucleotide encoding the partial peptide according to (22);

(31) A polynucleotide containing a polynucleotide encoding the precursor peptide according to (23);

(32) The polynucleotide according to (31), which has the base sequence represented by SEQ ID NO:43, SEQ ID NO:44, SEQ ID NO:45, SEQ ID NO:46, SEQ ID NO:47, SEQ ID NO:48, SEQ ID NO:80 or SEQ ID NO:81;

(33) The polynucleotide according to (28) to (32), which is a DNA;

(34) A recombinant vector containing the polynucleotide according to any one of (28) to (33);

(35) A transformant transformed with the recombinant vector according to (34);

(36) A method of manufacturing the peptide, its partial peptide or its precursor peptide, or a salt thereof, according to any one of (1) to (21), which comprises culturing the transformant according to (35) and producing the peptide, partial peptide or precursor peptide according to any one of (1) to (21);

(37) An antibody to the peptide, its partial peptide or its precursor peptide, or its amide or ester, or a salt thereof, according to any one of (1) to (21);

(38) The antibody according to (37), which is a neutralizing antibody to inactivate the activity of the peptide, its partial peptide, or its amide or ester, or a salt thereof, according to any one of (1) to (21);

(39) A pharmaceutical comprising the antibody according to (37);

(40) The pharmaceutical according to (39), which is a preventive/therapeutic agent for obesity or hyperphagia;

(41) A diagnostic product comprising the antibody according to (37);

(42) The diagnostic product according to (41), which is a diagnostic product for anorexia, obesity or hyperphagia;

(43) A pharmaceutical comprising the peptide, its partial peptide, or its amide or ester, or a salt thereof, according to any one of (1) to (21);

(44) The pharmaceutical according to (43), which is a preventive/therapeutic agent for anorexia or eating stimulant;

(45) A pharmaceutical comprising the polynucleotide according to (28);

(46) The pharmaceutical according to (45), which is a preventive/therapeutic agent for anorexia or eating stimulant;

(47) A diagnostic product comprising the polynucleotide according to (28);

(48) The diagnostic product according to (47), which is a diagnostic product for anorexia, obesity or hyperphagia;

(49) A polynucleotide containing a complementary base sequence to the polynucleotide according to (28), or a part thereof;

(50) A pharmaceutical comprising the polynucleotide according to (49);

(51) The pharmaceutical according to (50), which is a preventive/therapeutic agent for obesity or hyperphagia;

(52) A method of screening a compound or its salt that alters the binding property between the peptide, its partial peptide, or its amide or ester, or a salt thereof, according to any one of (1) to (21) and a protein or its salt containing the same or substantially the same amino acid sequence as the amino acid sequence represented by SEQ ID NO:49, which comprises using the peptide, its partial peptide, or its amide or ester, or a salt thereof, according to any one of (1) to (21) and a protein or its salt containing the same or substantially the same amino acid sequence as the amino acid sequence represented by SEQ ID NO:49;

(53) A method of screening a compound or its salt that alters the binding property between the peptide, its partial peptide, or its amide or ester, or a salt thereof, according to any one of (1) to (21) and a protein or its salt containing the same or substantially the same amino acid sequence as the amino acid sequence represented by SEQ ID NO:59, which comprises using the peptide, its partial peptide, or its amide or ester, or a salt thereof, according to any one of (1) to (21) and a protein or its salt containing the same or substantially the same amino acid sequence as the amino acid sequence represented by SEQ ID NO:59;

(54) A method of screening a compound or its salt that alters the binding property between the peptide, its partial peptide, or its amide or ester, or a salt thereof, according to any one of (1) to (21) and a protein or its salt containing the same or substantially the same amino acid sequence as the amino acid sequence represented by SEQ ID NO:84, which comprises using the peptide, its partial peptide, or its amide or ester, or a salt thereof, according to any one of (1) to (21) and a protein or its salt containing the same or substantially the same amino acid sequence as the amino acid sequence represented by SEQ ID NO:84;

(55) A kit for screening a compound or its salt that alters the binding property between the peptide, its partial peptide, or its amide or ester, or a salt thereof, according to any one of (1) to (21) and a protein or its salt containing the same or substantially the same amino acid sequence as the amino acid sequence represented by SEQ ID NO:49, comprising the peptide, its partial peptide, or its amide or ester, or a salt thereof, according to any one of (1) to (21) and a protein or its salt containing the same or substantially the same amino acid sequence as the amino acid sequence represented by SEQ ID NO:49;

(56) A kit for screening a compound or its salt that alters the binding property between the peptide, its partial peptide, or its amide or ester, or a salt thereof, according to any one of (1) to (21) and a protein or its salt containing the same or substantially the same amino acid sequence as the amino acid sequence represented by SEQ ID NO:59, comprising the peptide, its partial peptide, or its amide or ester, or a salt thereof, according to any one of (1) to (21) and a protein or its salt containing the same or substantially the same amino acid sequence as the amino acid sequence represented by SEQ ID NO:59;

(57) A kit for screening a compound or its salt that alters the binding property between the peptide, its partial peptide, or its amide or ester, or a salt thereof, according to any one of (1) to (21) and a protein or its salt containing the same or substantially the same amino acid sequence as the amino acid sequence represented by SEQ ID NO:84, comprising the peptide, its partial peptide, or its amide or ester, or a salt thereof, according to any one of (1) to (21) and a protein or its salt containing the same or substantially the same amino acid sequence as the amino acid sequence represented by SEQ ID NO:84;

(58) A compound or its salt that alters the binding property between the peptide, its partial peptide, or its amide or ester, or a salt thereof, according to any one of (1) to (21) and a protein or its salt containing the same or substantially the same amino acid sequence as the amino acid sequence represented by SEQ ID NO:49, which is obtainable by using the screening method according to (52) or the screening kit according to (55);

(59) A compound or its salt that alters the binding property between the peptide, its partial peptide, or its amide or ester, or a salt thereof, according to any one of (1) to (21) and a protein or its salt containing the same or substantially the same amino acid sequence as the amino acid sequence represented by SEQ ID NO:59, which is obtainable by using the screening method according to (53) or the screening kit according to (56);

(60) A compound or its salt that alters the binding property between the peptide, its partial peptide, or its amide or ester, or a salt thereof, according to any one of (1) to (21) and a protein or its salt containing the same or substantially the same amino acid sequence as the amino acid sequence represented by SEQ ID NO:84, which is obtainable by using the screening method according to (54) or the screening kit according to (57);

(61) The compound or its salt according to (58) to (60), which is an agonist;

(62) The compound or its salt according to (58) to (60), which is an antagonist;

(63) A pharmaceutical comprising the compound or its salt according to any one of (58) to (60);

(64) A preventive/therapeutic agent for anorexia or eating stimulant comprising the agonist according to (61);

(65) A preventive/therapeutic agent for obesity or hyperphagia comprising; the antagonist according to (62);

(66) An antiobesity agent obtainable by using the screening method according to (52) or the screening kit according to (55);

(67) An antiobesity agent obtainable by using the screening method according to (53) or the screening kit according to (56);

(68) An antiobesity agent obtainable by using the screening method according to (54) or the screening kit according to (57);

(69) A method of screening a compound or its salt that alters the expression level of the peptide, its partial peptide or its precursor peptide according to any one of (1) to (21), which comprises using a DNA encoding the peptide, its partial peptide or its precursor peptide according to any one of (1) to (21);

(70) A kit for screening a compound or its salt that alters the expression level of the peptide, its partial peptide or its precursor peptide according to any one of (1) to (21), comprising a DNA encoding the peptide, its partial peptide or its precursor peptide according to any one of (1) to (21);

(71) A compound or its salt that alters the expression level of the peptide, its partial peptide or its precursor peptide according to any one of (1) to (21), which is obtainable by using the screening method according to (69) or the screening kit according to (70);

(72) The compound or its salt according to (71), which is a compound or its salt that increases the expression level;

(73) The compound or its salt according to (71), which is a compound or its salt that decreases the expression level;

(74) A pharmaceutical comprising the compound or its salt according to (71);

(75) A preventive/therapeutic agent for anorexia or eating stimulant comprising the compound or its salt according to (72);

(76) A preventive/therapeutic agent for obesity or hyperphagia comprising the compound or its salt according to (73);

(77) A method for preventing/treating anorexia, which comprises administering to a mammal an effective amount of the peptide, its partial peptide, or its amide or ester, or a salt thereof, according to any one of (1) to (21), the polynucleotide according to (28), the agonist according to (61), or the compound or its salt according to (72);

(78) A method for stimulating appetite, which comprises administering to a mammal an effective amount of the peptide, its partial peptide, or its amide or ester, or a salt thereof, according to any one of (1) to (21), the polynucleotide according to (28), the agonist according to (61), or the compound or its salt according to (72);

(79) A method for preventing/treating obesity or hyperphagia, which comprises administering to a mammal an effective amount of the antibody according to (37), the polynucleotide according to (49), the antagonist according to (62), or the compound or its salt according to (73);

(80) A protein or its salt containing the same or substantially the same amino acid sequence as the amino acid sequence represented by SEQ ID NO:86;

(81) The protein or its salt according to (80), containing the amino acid sequence represented by SEQ ID NO:86;

(82) A partial peptide or its salt of the protein according to (80);

(83) A polynucleotide containing a polynucleotide encoding the protein according to (80), or a partial peptide thereof;

(84) The polynucleotide according to (83), which is a DNA;

(85) The polynucleotide according to (84), which contains the base sequence represented by SEQ ID NO:87;

(86) A recombinant vector containing the polynucleotide according to (83);

(87) A transformant transformed by the recombinant vector according to (86);

(88) A method of manufacturing the protein according to (80), its partial peptide or a salt thereof, which comprises culturing the transformant according to (87) and producing the protein according to (80), its partial peptide or a salt thereof;

(89) A pharmaceutical comprising the protein according to (80) or the partial peptide according to (82), or a salt thereof;

(90) A pharmaceutical comprising the polynucleotide according to (83);

(91) The pharmaceutical according to (90), which is a preventive/therapeutic agent for anorexia or eating stimulant;

(92) A diagnostic product comprising the polynucleotide according to (83);

(93) The diagnostic product according to (92), which is a diagnostic product for anorexia, obesity or hyperphagia;

(94) An antibody to the protein according to (80) or the partial peptide according to (82), or a salt thereof;

(95) The antibody according to (94), which is a neutralizing antibody to inactivate signal transduction of the protein according to (80);

(96) A pharmaceutical comprising the antibody according to (94);

(97) The pharmaceutical according to (96), which is a preventive/therapeutic agent for obesity or hyperphagia;

(98) A diagnostic product comprising the antibody according to (94);

(99) The diagnostic product according to (99), which is a diagnostic product for anorexia, obesity or hyperphagia;

(100) A polynucleotide containing a complementary base sequence to the polynucleotide according to (83), or a part thereof;

(101) A pharmaceutical comprising the polynucleotide according to (100);

(102) The pharmaceutical according to (101), which is a preventive/therapeutic agent for obesity or hyperphagia;

(103) A protein or its salt containing the same or substantially the same amino acid sequence as the amino acid sequence represented by SEQ ID NO:88;

(104) The protein or its salt according to (103), which contains the amino acid sequence represented by SEQ ID NO:88;

(105) A partial peptide of the protein according to (103), or a salt thereof;

(106) A polynucleotide containing a polynucleotide encoding the protein according to (103) or a partial peptide thereof;

(107) The polynucleotide according to (106), which is a DNA;

(108) The polynucleotide according to (107), which contains the base sequence represented by SEQ ID NO:89;

(109) A recombinant vector containing the polynucleotide according to (108);

(110) A transformant transformed with the recombinant vector according to (109);

(111) A method of manufacturing the protein according to (103), its partial peptide, or a salt thereof, which comprises culturing the transformant of (110) and producing the protein according to (103) or its partial peptide;

(112) A pharmaceutical comprising the protein according to (103) or the partial peptide according to (105), or a salt thereof;

(113) A pharmaceutical comprising the polynucleotide according to (106);

(114) The pharmaceutical according to (113), which is a preventive/therapeutic agent for anorexia or eating stimulant;

(115) A diagnostic product comprising the polynucleotide according to (106);

(116) The diagnostic product according to (115), which is a diagnostic product for anorexia, obesity or hyperphagia;

(117) An antibody to the protein according to (103) or the partial peptide according to (105), or a salt thereof;

(118) The antibody according to (117), which is a neutralizing antibody to inactivate signal transduction of the protein according to (103);

(119) A pharmaceutical comprising the antibody according to (117);

(120) The pharmaceutical according to (119), which is a preventive/therapeutic agent for obesity or hyperphagia;

(121) A diagnostic product comprising the antibody according to (117);

(122) The diagnostic product according to (121), which is a diagnostic product for anorexia, obesity or hyperphagia;

(123) A polynucleotide containing a complementary base sequence to the polynucleotide according to (106), or a part thereof;

(124) A pharmaceutical comprising the polynucleotide according to (123);

(125) The pharmaceutical according to (124), which is a preventive/therapeutic agent for obesity or hyperphagia;

(126) A method of screening a compound or its salt that alters the binding property between the peptide, its partial peptide, or its amide or ester, or a salt thereof, according to any one of (1) to (21) and a protein or its salt containing the same or substantially the same amino acid sequence as the amino acid sequence represented by SEQ ID NO:86, which comprises using the peptide, its partial peptide, or its amide or ester, or a salt thereof, according to any one of (1) to (21) and a protein or its salt containing the same or substantially the same amino acid sequence as the amino acid sequence represented by SEQ ID NO:86;

(127) A method of screening a compound or its salt that alters the binding property between the peptide, its partial peptide, or its amide or ester, or a salt thereof, according to any one of (1) to (21) and a protein or its salt containing the same or substantially the same amino acid sequence as the amino acid sequence represented by SEQ ID NO:88, which comprises using the peptide, its partial peptide, or its amide or ester, or a salt thereof, according to any one of (1) to (21) and a protein or its salt containing the same or substantially the same amino acid sequence as the amino acid sequence represented by SEQ ID NO:88;

(128) A kit for screening a compound or its salt that alters the binding property between the peptide, its partial peptide, or its amide or ester, or a salt thereof, according to any one of (1) to (21) and a protein or its salt containing the same or substantially the same amino acid sequence as the amino acid sequence represented by SEQ ID NO:86, comprising the peptide, its partial peptide, or its amide or ester, or a salt thereof, according to any one of (1) to (21) and a protein or its salt containing the same or substantially the same amino acid sequence as the amino acid sequence represented by SEQ ID NO:86;

(129) A kit for screening a compound or its salt that alters the binding property between the peptide, its partial peptide, or its amide or ester, or a salt thereof, according to any one of (1) to (21) and a protein or its salt containing the same or substantially the same amino acid sequence as the amino acid sequence represented by SEQ ID NO:88, comprising the peptide, its partial peptide, or its amide or ester, or a salt thereof, according to any one of (1) to (21) and a protein or its salt containing the same or substantially the same amino acid sequence as the amino acid sequence represented by SEQ ID NO:88;

(130) A compound or its salt that alters the binding property between the peptide, its partial peptide, or its amide or ester, or a salt thereof, according to any one of (1) to (21) and a protein or its salt containing the same or substantially the same amino acid sequence as the amino acid sequence represented by SEQ ID NO:86, which is obtainable by using the screening method according to (126) or the screening kit according to (128);

(131) A compound or its salt that alters the binding property between the peptide, its partial peptide, or its amide or ester, or a salt thereof, according to any one of (1) to (21) and a protein or its salt containing the same or substantially the same amino acid sequence as the amino acid sequence represented by SEQ ID NO:88, which is obtainable by using the screening method according to (127) or the screening kit according to (129);

(132) The compound or its salt according to (130) or (131), which is an agonist;

(133) The compound or its salt according to (130) or (131), which is an antagonist;

(134) A pharmaceutical comprising the compound or its salt according to (130) or (131);

(135) A preventive/therapeutic agent for anorexia or eating stimulant, comprising the agonist according to (132);

(136) A preventive/therapeutic agent for obesity or hyperphagia, comprising the antagonist according to (133);

(137) A method of screening a compound or its salt that alters the expression level of a protein containing the same or substantially the same amino acid sequence as the amino acid sequence represented by SEQ ID NO:86, which comprises using a DNA encoding a protein containing the same or substantially the same amino acid sequence as the amino acid sequence represented by SEQ ID NO:86;

(138) A kit for screening a compound or its salt that alters the expression level of a protein containing the same or substantially the same amino acid sequence as the amino acid sequence represented by SEQ ID NO:86, comprising a DNA encoding a protein containing the same or substantially the same amino acid sequence as the amino acid sequence represented by SEQ ID NO:86;

(139) A compound or its salt that alters the expression level of a protein containing the same or substantially the same amino acid sequence as the amino acid sequence represented by SEQ ID NO:86, which is obtainable by using the screening method according to (137) or the screening kit according to (138);

(140) The compound or its salt according to (139), which is a compound or its salt that increases the expression level;

(141) The compound or its salt according to (139), which is a compound or its salt that decreases the expression level;

(142) A pharmaceutical comprising the compound or its salt according to (139);

(143) A preventive/therapeutic agent for anorexia or eating stimulant comprising the compound or its salt according to (140);

(144) A preventive/therapeutic agent for obesity or hyperphagia comprising the compound or its salt according to (141);

(145) A method of screening a compound or its salt that alters the expression level of a protein containing the same or substantially the same amino acid sequence as the amino acid sequence represented by SEQ ID NO:88, which comprises using a DNA encoding a protein containing the same or substantially the same amino acid sequence as the amino acid sequence represented by SEQ ID NO:88;

(146) A kit for screening a compound or its salt that alters the expression level of a protein containing the same or substantially the same amino acid sequence as the amino acid sequence represented by SEQ ID NO:88, comprising a DNA encoding a protein containing the same or substantially the same amino acid sequence as the amino acid sequence represented by SEQ ID NO:88;

(147) A compound or its salt that alters the expression level of a protein containing the same or substantially the same amino acid sequence as the amino acid sequence represented by SEQ ID NO:88, which is obtainable by using the screening method according to (145) or the screening kit according to (146);

(148) The compound or its salt according to (147), which is a compound or its salt that increases the expression level;

(149) The compound or its salt according to (147), which is a compound or its salt that decreases the expression level;

(150) A pharmaceutical comprising the compound or its salt according to (147);

(151) A preventive/therapeutic agent for anorexia or eating stimulant comprising the compound or its salt according to (148);

(152) A preventive/therapeutic agent for obesity or hyperphagia comprising the compound or its salt according to (149);

(153) A method for preventing/treating anorexia, which comprises administering to a mammal an effective amount of the protein according to (80), its partial peptide or a salt thereof, the polynucleotide according to (83), the protein according to (103), its partial peptide or a salt thereof, the polynucleotide according to (106), the agonist according to (132), the compound or its salt according to (140), or the compound or its salt according to (148);

(154) A method for stimulating appetite, which comprises administering to a mammal an effective amount of the protein according to (80), its partial peptide or a salt thereof, the polynucleotide according to (83), the protein according to (103), its partial peptide or a salt thereof, the polynucleotide according to (106), the agonist according to (132), the compound or its salt according to (140), or the compound or its salt according to (148);

(155) A method for preventing/treating obesity or hyperphagia, which comprises administering to a mammal an effective amount of the antibody according to (94), polynucleotide according to (100), the antibody according to (117), the polynucleotide according to (123), the antagonist according to (133), the compound or its salt according to (141), or the compound or its salt according to (149);

(156) A non-human mammal bearing the DNA according to (28), which is exogenous, or its variant DNA;

(157) The mammal according to (156), wherein the non-human mammal is a rodent;

(158) A recombinant vector bearing the exogenous DNA or its variant DNA according to (28) and capable of expressing in a mammal;

(159) A non-human embryonic stem cell, wherein the DNA according to (28) is inactivated;

(160) The embryonic stem cell according to (159), wherein the DNA is inactivated by introducing a reporter gene;

(161) The embryonic stem cell according to (159), wherein the non-human mammal is a rodent;

(162) A non-human mammal deficient in expressing the DNA according to (28), wherein the DNA is inactivated;

(163) A non-human mammal according to (162), wherein the DNA is inactivated by inserting a reporter gene therein and the reporter gene is capable of expressing under control of a promoter for the DNA according to (28);

(164) The non-human mammal according to (162), which is a rodent;

(165) A method of screening a compound or its salt that promotes or inhibits the activity of a promoter for the DNA according to (28), which comprises administering a test compound to the mammal according to (163) and detecting expression of the reporter gene;

(166) A non-human mammal bearing the DNA according to (83), which is exogenous, or its variant DNA;

(167) The mammal according to (166), wherein the non-human mammal is a rodent;

(168) A recombinant vector bearing the exogenous DNA or its variant DNA according to (83) and capable of expressing in a mammal;

(169) A non-human embryonic stem cell, wherein the DNA according to (83) is inactivated;

(170) The embryonic stem cell according to (169), wherein the DNA is inactivated by introducing a reporter gene;

(171) The embryonic stem cell according to (169), wherein the non-human mammal is a rodent;

(172) A non-human mammal deficient in expressing the DNA according to (83), wherein the DNA is inactivated;

(173) A non-human mammal according to (172), wherein the DNA is inactivated by inserting a reporter gene therein and the reporter gene is capable of expressing under control of a promoter for the DNA according to (83);

(174) The non-human mammal according to (172), which is a rodent;

(175) A method of screening a compound or its salt that promotes or inhibits the activity of a promoter for the DNA according to (83), which comprises administering a test compound to the mammal according to (173) and detecting expression of the reporter gene;

(176) A non-human mammal bearing the DNA according to (106), which is exogenous, or its variant DNA;

(177) The mammal according to (176), wherein the non-human mammal is a rodent;

(178) A recombinant vector bearing the exogenous DNA according to (106) or its variant DNA and capable of expressing in a mammal;

(179) A non-human embryonic stem cell, wherein the DNA according to (106) is inactivated;

(180) The embryonic stem cell according to (179), wherein the DNA is inactivated by introducing a reporter gene;

(181) The embryonic stem cell according to (179), wherein the non-human mammal is a rodent;

(182) A non-human mammal deficient in expressing the DNA according to (106), wherein the DNA is inactivated;

(183) The non-human mammal according to (182), wherein the DNA is inactivated by inserting a reporter gene therein and the reporter gene is capable of expressing under control of a promoter for the DNA according to (106);

(184) The non-human mammal according to (182), which is a rodent;

(185) A method of screening a compound or its salt that promotes or inhibits the activity of a promoter for the DNA according to (106), which comprises administering a test compound to the mammal according to (183) and detecting expression of the reporter gene;

(186) Use of the peptide, its partial peptide, its amide or ester, or a salt thereof, according to any one of (1) through (21), the polynucleotide according to (28), the agonist according to (61), or the compound or its salt according to (72), for manufacturing a preventive/therapeutic agent for anorexia;

(187) Use of the peptide, its partial peptide, its amide or ester, or a salt thereof, according to any one of (1) through (21), the polynucleotide according to (28), the agonist according to (61), or the compound or its salt according to (72), for manufacturing an eating stimulant;

(188) Use of the antibody according to (37), the polynucleotide according to (49), the antagonist according to (62), or the compound or its salt according to (73), for manufacturing a preventive/therapeutic agent for obesity or hyperphagia;

(189) Use of the protein according to (80) or its partial peptide or a salt thereof, the polynucleotide according to (83), the protein according to (103) or its partial peptide or a salt thereof, the polynucleotide according to (106), the agonist according to (132), the compound or its salt according to (140) or the compound or its salt according to (148), for manufacturing a preventive/therapeutic agent for anorexia;

(190) Use of the protein according to (80) or its partial peptide or a salt thereof, the polynucleotide according to (83), the protein according to (103) or its partial peptide or a salt thereof, the polynucleotide according to (106), the agonist according to (132), the compound or its salt according to (140) or the compound or its salt according to (148), for manufacturing an eating stimulant; and, (191) Use of the antibody according to (94), the polynucleotide according to (100), the antibody according to (117), the polynucleotide according to (123), the antagonist according to (133), the compound or its salt according to (141), or the compound or its salt according to (149), for manufacturing a preventive/therapeutic agent for obesity or hyperphagia.

BRIEF DESCRIPTION OF THE DRAWINGS

FIG. 1 shows the DNA sequence (SEQ ID NO: 101) of human GPR7 ligand precursor H.

FIG. 2 shows the amino acid sequence (SEQ ID NO: 22) of human GPR7 ligand precursor H.

FIG. 3 shows the DNA sequence (SEQ ID NO: 102) of mouse GPR7 ligand precursor H.

FIG. 4 shows the amino acid sequence (SEQ ID NO: 23) of mouse GPR7 ligand precursor H.

FIG. 5 shows the DNA sequence (SEQ ID NO: 103) of rat GPR7 ligand precursor H.

FIG. 6 shows the amino acid sequence (SEQ ID NO: 24) of rat GPR7 ligand precursor H.

FIG. 7 shows a comparison between human (SEQ ID NO: 22), rat (SEQ ID NO: 24) and mouse (SEQ ID NO: 23) ligand precursors H, wherein the matched amino acids are indicated in a box, and the arrow indicates the predicted cleavage site of a secretion signal.

FIG. 20 shows a DNA sequence (SEQ ID NO: 104) of bovine GPR7 ligand precursor H.

FIG. 21 shows an amino acid sequence (SEQ ID NO: 73) of bovine GPR7 ligand precursor H.

FIG. 26 shows a cDNA sequence (SEQ ID NO: 105) of bovine GPR7.

FIG. 27 shows an amino acid sequence (SEQ ID NO: 86) of bovine GPR7.

FIG. 28 shows a cDNA sequence (SEQ ID NO: 106) of bovine GPR8.

FIG. 29 shows an amino acid sequence (SEQ ID NO: 88) of bovine GPR8.

FIG. 31 shows the results of N-terminal sequencing (residues 1-20 of SEQ ID NO: 1) of GPR7 ligand purified from the culture supernatant of human GPR7 ligand-expressed CHO cells.

BEST MODE FOR CARRYING OUT THE INVENTION

Figure 8:
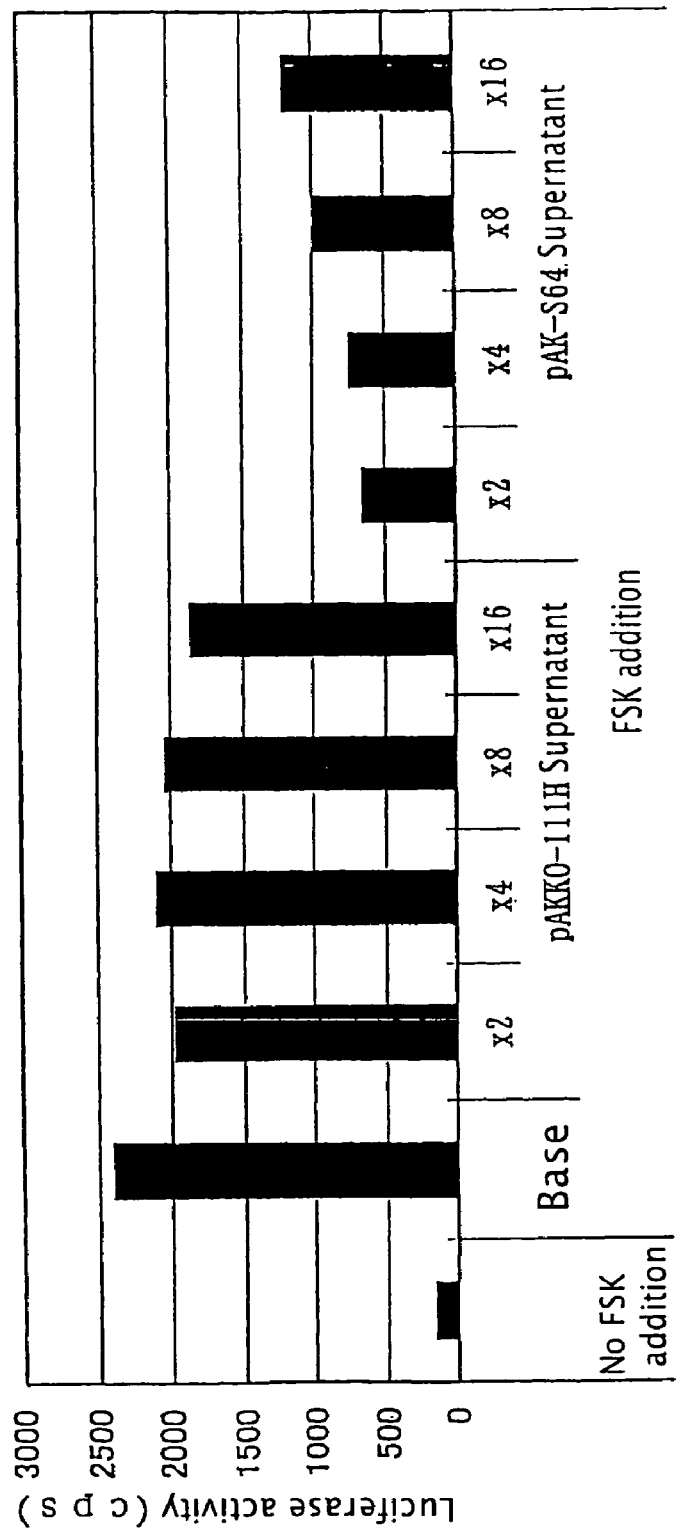
FIG. 8 shows the results of suppression detected on a luciferase activity by ligand stimulation, when the culture supernatants of ligand expression vector pAK-S64 and empty expression vector (pAKKO-111H)-expressed CHO cells were added in the presence of forskolin (FSK) to a medium of CHO cells wherein GPR7 cDNA-inserted plasmid was transiently expressed.

The peptide of the present invention having the same or substantially the same amino acid sequence as the amino acid sequence represented by SEQ ID NO:1, SEQ ID NO:4, SEQ ID NO:7, SEQ ID NO:13 or SEQ ID NO:16 (hereinafter sometimes merely referred to as the peptide of the present invention) may be any peptide derived from any cells of human or other warm-blooded animals, e.g., guinea pigs, rats, mice, chicken, rabbits, swine, sheep, bovine, monkeys, etc. (e.g., retina cells, liver cells, splenocytes, nerve cells, glial cells, β cells of pancreas, bone marrow cells, mesangial cells, Langerhans' cells, epidermic cells, epithelial cells, endothelial cells, fibroblasts, fibrocytes, myocytes, fat cells, immune cells (e.g., macrophages, T cells, B cells, natural killer cells, mast cells, neutrophils, basophils, eosinophils, monocytes), megakaryocyte, synovial cells, chondrocytes, bone cells, osteoblasts, osteoclasts, mammary gland cells, hepatocytes or interstitial cells, the corresponding precursor cells, stem cells, cancer cells, etc., of these cells), or any tissues where such cells are present, e.g., brain or any region of the brain (e.g., retina, olfactory bulb, amygdaloid nucleus, basal ganglia, hippocampus, thalamus, hypothalamus, cerebral cortex, medulla oblongata, cerebellum), spinal cord, hypophysis, stomach, pancreas, kidney, liver, gonad, thyroid, gall-bladder, bone marrow, adrenal gland, skin, muscle, lung, gastrointestinal tract (e.g., large intestine and small intestine), blood vessel, heart, thymus, spleen, submandibular gland, peripheral blood, prostate, testis, ovary, placenta, uterus, bone, joint, skeletal muscle, etc.; or hemocyte type cells or their cultured cells (e.g., MEL, M1, CTLL-2, HT-2, WEHI-3, HL-60, JOSK-1, K562, ML-1, MOLT-3, MOLT-4, MOLT-10, CCRF-CEM, TALL-1, Jurkat, CCRT-HSB-2, KE-37, SKW-3, HUT-78, HUT-102, H9, U937, THP-1, HEL, JK-1, CMK, KO-812, MEG-01, etc.). The peptide may also be a synthetic peptide.

The amino acid sequence which has substantially the same amino acid sequence as that represented by SEQ ID NO:1, SEQ ID NO:4, SEQ ID NO:7, SEQ ID NO:13 or SEQ ID NO:16 includes an amino acid sequence having at least about 70% homology, preferably at least about 80% homology, more preferably at least about 90% homology, and most preferably at least about 95% homology, to the amino acid sequence represented by SEQ ID NO:1.

As the peptide having substantially the same amino acid sequence as the amino acid sequence represented by SEQ ID NO:1, preferred is a peptide having substantially the same amino acid sequence as the amino acid sequence represented by SEQ ID NO:1 and having the activity substantially equivalent to that of the amino acid sequence represented by SEQ ID NO:1, etc.

As the peptide having substantially the same amino acid sequence as the amino acid sequence represented by SEQ ID NO:4, preferred is a peptide having substantially the same amino acid sequence as the amino acid sequence represented by SEQ ID NO:4 and having the activity substantially equivalent to that of the amino acid sequence represented by SEQ ID NO:4, etc.

As the peptide having substantially the same amino acid sequence as the amino acid sequence represented by SEQ ID NO:7, preferred is a peptide having substantially the same amino acid sequence as the amino acid sequence represented by SEQ ID NO:7 and having the activity substantially equivalent to that of the amino acid sequence represented by SEQ ID NO:7, etc.

As the peptide having substantially the same amino acid sequence as the amino acid sequence represented by SEQ ID NO:13, preferred is a peptide having substantially the same amino acid sequence as the amino acid sequence represented by SEQ ID NO:13 and having the activity substantially equivalent to that of the amino acid sequence represented by SEQ ID NO:13, etc.

As the peptide having substantially the same amino acid sequence as the amino acid sequence represented by SEQ ID NO:16, preferred is a peptide having substantially the same amino acid sequence as the amino acid sequence represented by SEQ ID NO:16 and having the activity substantially equivalent to that of the amino acid sequence represented by SEQ ID NO:16, etc.

Specifically, the substantially equivalent activity includes activities that the peptide of the present invention possesses (for example, preventive/therapeutic activities for diseases described below, GPR7 binding activities, cell stimulating activities on the GPR7-expressed cells (e.g., activities that promote arachidonic acid release, acetylcholine release, intracellular $Ca^{2+}$ release, intracellular cAMP production, intracellular cGMP production, inositol phosphate production, change in cell membrane potential, phosphorylation of intracellular proteins, activation of c-fos, pH reduction, GTPγS binding activities, etc.) and the like.

The term substantially equivalent is used to mean that these activities are equivalent in nature (e.g., biochemically or pharmacologically).

Specific examples of the amino acid sequence, which is substantially the same amino acid sequence as the amino acid sequence represented by SEQ ID NO:1, include:

(i) the amino acid sequence represented by SEQ ID NO:1;

(ii) the amino acid sequence represented by SEQ ID NO:2;

(iii) the amino acid sequence represented by SEQ ID NO:3;

(iv) the amino acid sequence represented by SEQ ID NO:66;

(v) the amino acid sequence represented by SEQ ID NO:1, SEQ ID NO:2, SEQ ID NO:3 or SEQ ID NO:66, in which 1 to 5 (preferably 1 to 3, more preferably 1 to 2, and most preferably 1) amino acids are deleted;

(vi) the amino acid sequence represented by SEQ ID NO:1, SEQ ID NO:2, SEQ ID NO:3 or SEQ ID NO:66, to which 1 to 5 (preferably 1 to 3, more preferably 1 to 2, and most preferably 1) amino acids are added;

(vii) the amino acid sequence represented by SEQ ID NO:1, SEQ ID NO:2, SEQ ID NO:3 or SEQ ID NO:66, in which 1 to 5 (preferably 1 to 3, more preferably 1 to 2, and most preferably 1) amino acids are inserted;

(viii) the amino acid sequence represented by SEQ ID NO:1, SEQ ID NO:2, SEQ ID NO:3 or SEQ ID NO:66, in which 1 to 5 (preferably 1 to 3, more preferably 1 to 2, and most preferably 1) amino acids are replaced by other amino acids;

(ix) amino acid sequences in combination of (v) to (viii) above; etc.

Specific examples of the amino acid sequence, which is substantially the same amino acid sequence as the amino acid sequence represented by SEQ ID NO:4, include:

(i) the amino acid sequence represented by SEQ ID NO:4;

(ii) the amino acid sequence represented by SEQ ID NO:5;

(iii) the amino acid sequence represented by SEQ ID NO:6;

(iv) the amino acid sequence represented by SEQ ID NO:67;

(v) the amino acid sequence represented by SEQ ID NO:4, SEQ ID NO:5, SEQ ID NO:6 or SEQ ID NO:67, in which 1 to 5 (preferably 1 to 3, more preferably 1 to 2, and most preferably 1) amino acids are deleted;

(vi) the amino acid sequence represented by SEQ ID NO:4, SEQ ID NO:5, SEQ ID NO:6 or SEQ ID NO:67, to which 1 to 5 (preferably 1 to 3, more preferably 1 to 2, and most preferably 1) amino acids are added;

(vii) the amino acid sequence represented by SEQ ID NO:4, SEQ ID NO:5, SEQ ID NO:6 or SEQ ID NO:67, in which 1 to 5 (preferably 1 to 3, more preferably 1 to 2, and most preferably 1) amino acids are inserted;

(viii) the amino acid sequence represented by SEQ ID NO:4, SEQ ID NO:5, SEQ ID NO:6 or SEQ ID NO:67, in which 1 to 5 (preferably 1 to 3, more preferably 1 to 2, and most preferably 1) amino acids are replaced by other amino acids;

(ix) amino acid sequences in combination of (v) to (viii) above; etc.

Specific examples of the amino acid sequence, which is substantially the same amino acid sequence as the amino acid sequence represented by SEQ ID NO:7, include:

(i) the amino acid sequence represented by SEQ ID NO:7;

(ii) the amino acid sequence represented by SEQ ID NO:8;

(iii) the amino acid sequence represented by SEQ ID NO:9;

(iv) the amino acid sequence represented by SEQ ID NO:10;

(v) the amino acid sequence represented by SEQ ID NO:11;

(vi) the amino acid sequence represented by SEQ ID NO:12;

(vii) the amino acid sequence represented by SEQ ID NO:68;

(viii) the amino acid sequence represented by SEQ ID NO:69;

(ix) the amino acid sequence represented by SEQ ID NO:7, SEQ ID NO:8, SEQ ID NO:9, SEQ ID NO:10, SEQ ID NO:11, SEQ ID NO:12, SEQ ID NO:68 or SEQ ID NO:69, in which 1 to 5 (preferably 1 to 3, more preferably 1 to 2, and most preferably 1) amino acids are deleted;

(x) the amino acid sequence represented by SEQ ID NO:7, SEQ ID NO:8, SEQ ID NO:9, SEQ ID NO:10, SEQ ID NO:11, SEQ ID NO:12, SEQ ID NO:68 or SEQ ID NO:69, to which 1 to 5 (preferably 1 to 3, more preferably 1 to 2, and most preferably 1) amino acids are added;

(xi) the amino acid sequence represented by SEQ ID NO:7, SEQ ID NO:8, SEQ ID NO:9, SEQ ID NO:10, SEQ ID NO:11, SEQ ID NO:12, SEQ ID NO:68 or SEQ ID NO:69, in which 1 to 5 (preferably 1 to 3, more preferably 1 to 2, and most preferably 1) amino acids are inserted;

(xii) the amino acid sequence represented by SEQ ID NO:7, SEQ ID NO:8, SEQ ID NO:9, SEQ ID NO:10, SEQ ID NO:11, SEQ ID NO:12, SEQ ID NO:68 or SEQ ID NO:69, in which 1 to 5 (preferably 1 to 3, more preferably 1 to 2, and most preferably 1) amino acids are replaced by other amino acids;

(xiii) amino acid sequences in combination of (ix) to (xii) above; etc.

Specific examples of the amino acid sequence, which is substantially the same amino acid sequence as the amino acid sequence represented by SEQ ID NO:13, include:

(i) the amino acid sequence represented by SEQ ID NO:13;

(ii) the amino acid sequence represented by SEQ ID NO:14;

(iii) the amino acid sequence represented by SEQ ID NO:15;

(iv) the amino acid sequence represented by SEQ ID NO:70;

(v) the amino acid sequence represented by SEQ ID NO:13, SEQ ID NO:14, SEQ ID NO:15 or SEQ ID NO:70, in which 1 to 5 (preferably 1 to 3, more preferably 1 to 2, and most preferably 1) amino acids are deleted;

(vi) the amino acid sequence represented by SEQ ID NO:13, SEQ ID NO:14, SEQ ID NO:15 or SEQ ID NO:70, to which 1 to 5 (preferably 1 to 3, more preferably 1 to 2, and most preferably 1) amino acids are added;

(vii) the amino acid sequence represented by SEQ ID NO:13, SEQ ID NO:14, SEQ ID NO:15 or SEQ ID NO:70, in which 1 to 5 (preferably 1 to 3, more preferably 1 to 2, and most preferably 0.1) amino acids are inserted;

(viii) the amino acid sequence represented by SEQ ID NO:13, SEQ ID NO:14, SEQ ID NO:15 or SEQ ID NO:70, in which 1 to 5 (preferably 1 to 3, more preferably 1 to 2, and most preferably 1) amino acids are replaced by other amino acids;

(ix) amino acid sequences in combination of (v) to (viii) above; etc.

Specific examples of the amino acid sequence, which is substantially the same amino acid sequence as the amino acid sequence represented by SEQ ID NO:16, include:

(i) the amino acid sequence represented by SEQ ID NO:16;

(ii) the amino acid sequence represented by SEQ ID NO:17;

(iii) the amino acid sequence represented by SEQ ID NO:18;

(iv) the amino acid sequence represented by SEQ ID NO:71;

(v) the amino acid sequence represented by SEQ ID NO:16, SEQ ID NO:17, SEQ ID NO:18 or SEQ ID NO:71, in which 1 to 5 (preferably 1 to 3, more preferably 1 to 2, and most preferably 1) amino acids are deleted;

(vi) the amino acid sequence represented by SEQ ID NO:16, SEQ ID NO:17, SEQ ID NO:18 or SEQ ID NO:71, to which 1 to 5 (preferably 1 to 3, more preferably 1 to 2, and most preferably 1) amino acids are added;

(vii) the amino acid sequence represented by SEQ ID NO:16, SEQ ID NO:17, SEQ ID NO:18 or SEQ ID NO:71, in which 1 to 5 (preferably 1 to 3, more preferably 1 to 2, and most preferably 1) amino acids are inserted;

(viii) the amino acid sequence represented by SEQ ID NO:16, SEQ ID NO:17, SEQ ID NO:18 or SEQ ID NO:71, in which 1 to 5 (preferably 1 to 3, more preferably 1 to 2, and most preferably 1) amino acids are replaced by other amino acids;

(ix) amino acid sequences in combination of (v) to (viii) above; etc.

Specific examples of the peptide of the present invention are, for example:

[Peptide A]
human peptide having the amino acid sequence represented by SEQ ID NO:1;
mouse peptide having the amino acid sequence represented by. SEQ ID NO:2;
rat peptide having the amino acid sequence represented by SEQ ID NO:3;
bovine peptide having the amino acid sequence represented by SEQ ID NO:66;

[Peptide B]
human peptide having the amino acid sequence represented by SEQ ID NO:4;
mouse peptide having the amino acid sequence represented by SEQ ID NO:5;
rat peptide having the amino acid sequence represented by SEQ ID NO:6;
bovine peptide having the amino acid sequence represented by SEQ ID NO:67;

[Peptide C]
human peptide having the amino acid sequence represented by SEQ ID NO:7, or its amide;
mouse peptide having the amino acid sequence represented by SEQ ID NO:9, or its amide;
rat peptide having the amino acid sequence represented by SEQ ID NO:11, or its amide;
bovine peptide having the amino acid sequence represented by SEQ ID NO:68, or its amide;

[Peptide D]
human peptide having the amino acid sequence represented by SEQ ID NO:8;
mouse peptide having the amino acid sequence represented by SEQ ID NO:10;
rat peptide having the amino acid sequence represented by SEQ ID NO:12;
bovine peptide having the amino acid sequence represented by SEQ ID NO:69;

[Peptide E]
human peptide having the amino acid sequence represented by SEQ ID NO:13;

mouse peptide having the amino acid sequence represented by SEQ ID NO:14;

rat peptide having the amino acid sequence represented by SEQ ID NO:15;

bovine peptide having the amino acid sequence represented by SEQ ID NO:70;

[Peptide F]

human peptide having the amino acid sequence represented by SEQ ID NO:16;

mouse peptide having the amino acid sequence represented by SEQ ID NO:17;

rat peptide having the amino acid sequence represented by SEQ ID NO:18;

bovine peptide having the amino acid sequence represented by SEQ ID NO:71; and the like.

The partial peptide of the present invention may be any peptide so long as it is a partial peptide of the peptide of the present invention described above. Normally, peptides composed of at least 5 amino acids, preferably at least 10 amino acids are preferred and those further having activities similar to those of the peptide of the present invention are preferred.

The precursor peptide to the peptide of the present invention may be a polypeptide including the peptide of the present invention described above, which can produce the peptide of the present invention by cleaving with an appropriate peptidase.

Specifically, proteins, etc. having same or substantially the same amino acid sequence as the amino acid sequence represented by SEQ ID NO:19 or SEQ ID NO:22 are employed.

The protein having the same or substantially the same amino acid sequence as the amino acid sequence represented by SEQ ID NO:19 or SEQ ID NO:22 may be any protein derived from any cells of human or other warm-blooded animals, e.g., guinea pigs, rats, mice, chicken, rabbits, swine, sheep, bovine, monkeys, etc. (e.g., retina cells, liver cells, splenocytes, nerve cells, glial cells, cells of pancreas, bone marrow cells, mesangial cells, Langerhans' cells, epidermic cells, epithelial cells, endothelial cells, fibroblasts, fibrocytes, myocytes, fat cells, immune cells (e.g., macrophages, T cells, B cells, natural killer cells, mast cells, neutrophils, basophils, eosinophils, monocytes), megakaryocyte, synovial cells, chondrocytes, bone cells, osteoblasts, osteoclasts, mammary gland cells, hepatocytes or interstitial cells, the corresponding precursor cells, stem cells, cancer cells, etc., of these cells), or any tissues where such cells are present, e.g., brain or any region of the brain (e.g., retina, olfactory bulb, amygdaloid nucleus, basal ganglia, hippocampus, thalamus, hypothalamus, cerebral cortex, medulla oblongata, cerebellum), spinal cord, hypophysis, stomach, pancreas, kidney, liver, gonad, thyroid, gall-bladder, bone marrow, adrenal gland, skin, muscle, lung, gastrointestinal tract (e.g., large intestine and small intestine), blood vessel, heart, thymus, spleen, submandibular gland, peripheral blood, prostate, testis, ovary, placenta, uterus, bone, joint, skeletal muscle, etc.; or hemocyte type cells or their cultured cells (e.g., MEL, M1, CTLL-2, HT-2, WEHI-3, HL-60, JOSK-1, K562, ML-1, MOLT-3, MOLT-4, MOLT-10, CCRF-CEM, TALL-1, Jurkat, CCRT-HSB-2, KE-37, SKW-3, HUT-78, HUT-102, H9, U937, THP-1, HEL, JK-1, CMK, KO-812, MEG-01, etc.). The protein may also be a synthetic protein.

The amino acid sequence which has substantially the same amino acid sequence as that represented by SEQ ID NO:19 or SEQ ID NO:22 includes an amino acid sequence having at least about 70% homology, preferably at least about 80% homology, and more preferably at least about 90% homology, to the amino acid sequence represented by SEQ ID NO:19 or SEQ ID NO:22.

In particular, examples of the amino acid sequence, which has substantially the same amino acid sequence as that represented by SEQ ID NO:19, include:

(i) the amino acid sequence represented by SEQ ID NO:19 (human type);

(ii) the amino acid sequence represented by SEQ ID NO:20 (mouse type);

(iii) the amino acid sequence represented by SEQ ID NO:21 (rat type);

(iv) the amino acid sequence represented by SEQ ID NO:72 (bovine type);

(v) the amino acid sequence represented by SEQ ID NO:19, SEQ ID NO:20, SEQ ID NO:21 or SEQ ID NO:72, in which 1 to 15 (preferably 1 to 10, more preferably 1 to 5, and most preferably 1 to 3) amino acids are deleted;

(vi) the amino acid sequence represented by SEQ ID NO:19, SEQ ID NO:20, SEQ ID NO:21 or SEQ ID NO:72, to which 1 to 15 (preferably 1 to 10, more preferably 1 to 5, and most preferably 1 to 3) amino acids are added;

(vii) the amino acid sequence represented by SEQ ID NO:19, SEQ ID NO:20, SEQ ID NO:21 or SEQ ID NO:72, in which 1 to 15 (preferably 1 to 10, more preferably 1 to 5, and most preferably 1 to 3) amino acids are inserted;

(viii) the amino acid sequence represented by SEQ ID NO:19, SEQ ID NO:20, SEQ ID NO:21 or SEQ ID NO:72, in which 1 to 15 (preferably 1 to 10, more preferably 1 to 5, and most preferably 1 to 3) amino acids are replaced by other amino acids;

(ix) amino acid sequences in combination of (v) to (viii) above; etc.

Examples of the amino acid sequence, which has substantially the same amino acid sequence as that represented by SEQ ID NO:22, include:

(i) the amino acid sequence represented by SEQ ID NO:22 (human type);

(ii) the amino acid sequence represented by SEQ ID NO:23 (mouse type);

(iii) the amino acid sequence represented by SEQ ID NO:24 (rat type);

(iv) the amino acid sequence represented by SEQ ID NO:73 (bovine type);

(v) the amino acid sequence represented by SEQ ID NO:22, SEQ ID NO:23, SEQ ID NO:24 or SEQ ID NO:73, in which 1 to 15 (preferably 1 to 10, more preferably 1 to 5, and most preferably 1 to 3) amino acids are deleted;

(vi) the amino acid sequence represented by SEQ ID NO:22, SEQ ID NO:23, SEQ ID NO:24 or SEQ ID NO:73, to which 1 to 15 (preferably 1 to 10, more preferably 1 to 5, and most preferably 1 to 3) amino acids are added;

(vii) the amino acid sequence represented by SEQ ID NO:22, SEQ ID NO:23 or SEQ ID NO:24, in which 1 to 15 (preferably 1 to 10, more preferably 1 to 5, and most preferably 1 to 3) amino acids are inserted;

(viii) the amino acid sequence represented by SEQ ID NO:22, SEQ ID NO:23, SEQ ID NO:24 or SEQ ID NO:73, in which 1 to 15 (preferably 1 to 10, more preferably 1 to 5, and most preferably 1 to 3) amino acids are replaced by other amino acids;

(ix) amino acid sequences in combination of (v) to (viii) above; etc.

The human precursor peptide G having the amino acid sequence represented by SEQ ID NO:19 is the peptide wherein a secretory signal sequence is removed from the human precursor peptide H having the amino acid sequence represented by SEQ ID NO:22.

The human precursor peptide G having the amino acid sequence represented by SEQ ID NO:20 is the peptide wherein a secretory signal sequence is removed from the human precursor peptide H having the amino acid sequence represented by SEQ ID NO:23.

The human precursor peptide G having the amino acid sequence represented by SEQ ID NO:21 is the peptide wherein a secretory signal sequence is removed from the human precursor peptide H having the amino acid sequence represented by SEQ ID NO:24.

The human precursor peptide G having the amino acid sequence represented by SEQ ID NO:72 is the peptide wherein a secretory signal sequence is removed from the human precursor peptide H having the amino acid sequence represented by SEQ ID NO:73.

The precursor peptide of the present invention may have similar activities to those of the peptide of the present invention.

The protein (human GPR7) having the same or substantially the same amino acid sequence as the amino acid sequence represented by SEQ ID NO:49, the protein (rat TGR26) having the same or substantially the same amino acid sequence as the amino acid sequence represented by SEQ ID NO:59, the protein (human GPR8) having the same or substantially the same amino acid sequence as the amino acid sequence represented by SEQ ID NO:84, the protein (bovine GPR7) having the same or substantially the same amino acid sequence as the amino acid sequence represented by SEQ ID NO:86, the protein (bovine GPR8) having the same or substantially the same amino acid sequence as the amino acid sequence represented by SEQ ID NO:88 may be any protein derived from any cells of human or other warm-blooded animals, e.g., guinea pigs, rats, mice, chicken, rabbits, swine, sheep, bovine, monkeys, etc. (e.g., retina cells, liver cells, splenocytes, nerve cells, glial cells, β cells of pancreas, bone marrow cells, mesangial cells, Langerhans' cells, epidermic cells, epithelial cells, endothelial cells, fibroblasts, fibrocytes, myocytes, fat cells, immune cells (e.g., macrophages, T cells, B cells, natural killer cells, mast cells, neutrophils, basophils, eosinophils, monocytes), megakaryocyte, synovial cells, chondrocytes, bone cells, osteoblasts, osteoclasts, mammary gland cells, hepatocytes or interstitial cells, the corresponding precursor cells, stem cells, cancer cells, etc., of these cells), or any tissues where such cells are present, e.g., brain or any region of the brain (e.g., retina, olfactory bulb, amygdaloid nucleus, basal ganglia, hippocampus, thalamus, hypothalamus, cerebral cortex, medulla oblongata, cerebellum), spinal cord, hypophysis, stomach, pancreas, kidney, liver, gonad, thyroid, gallbladder, bone marrow, adrenal gland, skin, muscle, lung, gastrointestinal tract (e.g., large intestine and small intestine), blood vessel, heart, thymus, spleen, submandibular gland, peripheral blood, prostate, testis, ovary, placenta, uterus, bone, joint, skeletal muscle, etc.; or hemocyte type cells or their cultured cells (e.g., MEL, M1, CTLL-2, HT-2, WEHI-3, HL-60, JOSK-1, K562, ML-1, MOLT-3, MOLT-4, MOLT-10, CCRF-CEM, TALL-1, Jurkat, CCRT-HSB-2, KE-37, SKW-3, HUT-78, HUT-102, H9, U937, THP-1, HEL, JK-1, CMK, KO-812, MEG-01, etc.). The protein may also be a synthetic protein.

The amino acid sequence which has substantially the same amino acid sequence as that represented by SEQ ID NO:49 includes an amino acid sequence having at least about 70% homology, preferably at least about 80% homology, and more preferably at least about 90% homology, to the amino acid sequence represented by SEQ ID NO:49.

In particular, examples of the amino acid sequence, which has substantially the same amino acid sequence as that represented by SEQ ID NO:49, include, in addition to the amino acid sequence described above:

(i) the amino acid sequence represented by SEQ ID NO:49, in which 1 to 15 (preferably 1 to 10, more preferably 1 to 5, and most preferably 1 to 3) amino acids are deleted;

(ii) the amino acid sequence represented by SEQ ID NO:49, to which 1 to 15 (preferably 1 to 10, more preferably 1 to 5, and most preferably 1 to 3) amino acids are added;

(iii) the amino acid sequence represented by SEQ ID NO:49, in which 1 to 15 (preferably 1 to 10, more preferably 1 to 5, and most preferably 1 to 3) amino acids are inserted;

(iv) the amino acid sequence represented by S SEQ ID NO:49, in which 1 to 15 (preferably 1 to 10, more preferably 1 to 5, and most preferably 1 to 3) amino acids are replaced by other amino acids;

(v) amino acid sequences in combination of (i) to (iv) above; etc.

The amino acid sequence which has substantially the same amino acid sequence as that represented by SEQ ID NO:59 includes an amino acid sequence having at least about 70% homology, preferably at least about 80% homology, and more preferably at least about 90% homology, to the amino acid sequence represented by SEQ ID NO:59.

In particular, examples of the amino acid sequence, which has substantially the same amino acid sequence as that represented by SEQ ID NO:59, include, in addition to the amino acid sequence described above:

(i) the amino acid sequence represented by SEQ ID NO:59, in which 1 to 15 (preferably 1 to 10, more preferably 1 to 5, and most preferably 1 to 3) amino acids are deleted;

(ii) the amino acid sequence represented by SEQ ID NO:59, to which 1 to 15 (preferably 1 to 10, more preferably 1 to 5, and most preferably 1 to 3) amino acids are added;

(iii) the amino acid sequence represented by SEQ ID NO:59, in which 1 to 15 (preferably 1 to 10, more preferably 1 to 5, and most preferably 1 to 3) amino acids are inserted;

(iv) the amino acid sequence represented by S SEQ ID NO:59, in which 1 to 15 (preferably 1 to 10, more preferably 1 to 5, and most preferably 1 to 3) amino acids are replaced by other amino acids;

(v) amino acid sequences in combination of (i) to (iv) above; etc.

The amino acid sequence which has substantially the same amino acid sequence as that represented by SEQ ID NO:84 includes an amino acid sequence having at least about 70% homology, preferably at least about 80% homology, and more preferably at least about 90% homology, to the amino acid sequence represented by SEQ ID NO:84.

In particular, examples of the amino acid sequence, which has substantially the same amino acid sequence as that represented by SEQ ID NO:84, include, in addition to the amino acid sequence described above:

(i) the amino acid sequence represented by SEQ ID NO:84, in which 1 to 15 (preferably 1 to 10, more preferably 1 to 5, and most preferably 1 to 3) amino acids are deleted;

(ii) the amino acid sequence represented by SEQ ID NO:84, to which 1 to 15 (preferably 1 to 10, more preferably 1 to 5, and most preferably 1 to 3) amino acids are added;

(iii) the amino acid sequence represented by SEQ ID NO:84, in which 1 to 15 (preferably 1 to 10, more preferably 1 to 5, and most preferably 1 to 3) amino acids are inserted;

(iv) the amino acid sequence represented by S SEQ ID NO:84, in which 1 to 15 (preferably 1 to 10, more preferably 1 to 5, and most preferably 1 to 3) amino acids are replaced by other amino acids;

(v) amino acid sequences in combination of (i) to (iv) above; etc.

The amino acid sequence which has substantially the same amino acid sequence as that represented by SEQ ID NO:86 includes an amino acid sequence having at least about 70% homology, preferably at least about 80% homology, more preferably at least about 90% homology, and most preferably at least about 95% homology, to the amino acid sequence represented by SEQ ID NO:86.

In particular, examples of the amino acid sequence, which has substantially the same amino acid sequence as that represented by SEQ ID NO:86, include, in addition to the amino acid sequence described above:

(i) the amino acid sequence represented by SEQ ID NO:86, in which 1 to 15 (preferably 1 to 10, more preferably 1 to 5, and most preferably 1 to 3) amino acids are deleted;

(ii) the amino acid sequence represented by SEQ ID NO:86, to which 1 to 15 (preferably 1 to 10, more preferably 1 to 5, and most preferably 1 to 3) amino acids are added;

(iii) the amino acid sequence represented by SEQ ID NO:86, in which 1 to 15 (preferably 1 to 10, more preferably 1 to 5, and most preferably 1 to 3) amino acids are inserted;

(iv) the amino acid sequence represented by S SEQ ID NO:86, in which 1 to 15 (preferably 1 to 10, more preferably 1 to 5, and most preferably 1 to 3) amino acids are replaced by other amino acids;

(v) amino acid sequences in combination of (i) to (iv) above; etc.

The amino acid sequence which has substantially the same amino acid sequence as that represented by SEQ ID NO:88 includes an amino acid sequence having at least about 70% homology, preferably at least about 80% homology, more preferably at least about 90% homology, and most preferably at least about 95% homology, to the amino acid sequence represented by SEQ ID NO:88.

In particular, examples of the amino acid sequence, which has substantially the same amino acid sequence as that represented by SEQ ID NO:88, include, in addition to the amino acid sequence described above:

(i) the amino acid sequence represented by SEQ ID NO:88, in which 1 to 15 (preferably 1 to 10, more preferably 1 to 5, and most preferably 1 to 3) amino acids are deleted;

(ii) the amino acid sequence represented by SEQ ID NO:88, to which 1 to 15 (preferably 1 to 10, more preferably 1 to 5, and most preferably 1 to 3) amino acids are added;

(iii) the amino acid sequence represented by SEQ ID NO:88, in which 1 to 15 (preferably 1 to 10, more preferably 1 to 5, and most preferably 1 to 3) amino acids are inserted;

(iv) the amino acid sequence represented by S SEQ ID NO:88, in which 1 to 15 (preferably 1 to 10, more preferably 1 to 5, and most preferably 1 to 3) amino acids are replaced by other amino acids;

(v) amino acid sequences in combination of (i) to (iv) above; etc.

The partial peptide of human GPR7, rat TGR26, human GPR8, bovine GPR7 or bovine GPR8 (hereinafter merely referred to as GPR7 collectively) may be any peptide, so long as it is a partial peptide usable in the methods for screening pharmaceuticals, etc. later described, but, a partial peptide capable of binding to the peptide of the present invention, a partial peptide containing the corresponding amino acid sequence in the area outside the cell membrane, etc. are preferably employed.

The peptide of the present invention, its partial peptide or its precursor peptide, especially the peptide of the present invention also includes a peptide wherein the N-terminal amino acid residue is brominated. Preferred examples of the N-terminal amino acid residue are tryptophan residue (Trp), etc.

Specifically, a peptide containing the amino acid sequence selected from SEQ ID NO:1 to SEQ ID NO:12, SEQ ID NO:19 to SEQ ID NO:21, SEQ ID NO:66 to SEQ ID NO:69 and SEQ ID NO:72, etc., wherein the N-terminal tryptophan residue (Trp) is brominated, is employed. Among these peptides, preferably employed is a peptide containing the amino acid sequence represented by SEQ ID NO:1, SEQ ID NO:2, SEQ ID NO:3, SEQ ID NO:4, SEQ ID NO:5, SEQ ID NO:6, SEQ ID NO:66 or SEQ ID NO:67, wherein the N-terminal tryptophan residue (Trp) is brominated. The position to be brominated is not particularly limited but the tryptophan residue (Trp) at the 6-position is preferred.

More specifically, a peptide containing the amino acid sequence selected from SEQ ID NO:1 to SEQ ID NO:12, SEQ ID NO:19 to SEQ ID NO:21, SEQ ID NO:66 to SEQ ID NO:69 and SEQ ID NO:72, wherein the N-terminal tryptophan residue (Trp) is 6-brominated, is preferably employed. Among them, preferably employed is a peptide containing the amino acid sequence represented by SEQ ID NO:1, SEQ ID NO:2, SEQ ID NO:3, SEQ ID NO:4, SEQ ID NO:5, SEQ ID NO:6, SEQ. ID NO:66 or SEQ ID NO:67, wherein the N-terminal tryptophan residue (Trp) is 6-brominated.

The peptide of the present invention, its partial peptide or its precursor peptide (hereinafter sometimes merely referred to as the peptide of the present invention), and GPR7 or its partial peptide (hereinafter sometimes merely referred to as GPR7) are represented in accordance with the conventional way of describing peptides, that is, the N-terminus (amino terminus) at the left hand and the C-terminus (carboxyl terminus) at the right hand.

In the peptide of the present invention or GPR7, the C-terminus may be any of a carboxyl group (—COOH), a carboxylate (—COO$^-$), an amide (—CONH$_2$) or an ester (—COOR).

Examples of the ester group shown by R include a $C_{1-6}$ alkyl group such as methyl, ethyl, n-propyl, isopropyl, n-butyl, etc.; a $C_{3-8}$ cycloalkyl group such as cyclopentyl, cyclohexyl, etc.; a $C_{6-12}$ aryl group such as phenyl, α-naphthyl, etc.; a $C_{7-14}$ aralkyl group such as a phenyl-$C_{1-2}$-alkyl group, e.g., benzyl, phenethyl, etc., or an α-naphthyl-$C_{1-2}$-alkyl group such as α-naphthylmethyl, etc.; and the like. In addition, pivaloyloxymethyl or the like, which is used widely as an ester for oral administration, may also be used.

Where the peptide of the present invention or GPR7 contains a carboxyl group (or a carboxylate) at a position other than the C-terminus, it may be amidated or esterified and such an amide or ester is also included within the peptide of the present invention. The ester group may be the same group as that described with respect to the C-terminus described above.

Furthermore, the peptide of the present invention or GPR7 includes peptides, wherein the amino group at the N-terminal amino acid residue (e.g., methionine residue) is protected with a protecting group (e.g., a $C_{1-6}$ acyl group such as a $C_{2-6}$ alkanoyl group, e.g., formyl group, acetyl group, etc.); those wherein the N-terminal region is cleaved in vivo and the glutamyl group thus formed is pyroglutaminated; those wherein a substituent (e.g., —OH, —SH, amino group, imidazole group, indole group, guanidino group, etc.) on the side chain of an amino acid in the molecule is protected with a suitable protecting group (e.g., a $C_{1-6}$ acyl group such as a $C_{2-6}$ alkanoyl group, e.g., formyl group, acetyl group, etc.), or conjugated proteins such as glycoproteins bound to sugar chains.

For salts of the peptide of the present invention or GPR7, preferred are salts with physiologically acceptable acids (e.g., inorganic acids or organic acids) or bases (e.g., alkali metal salts), etc., especially physiologically acceptable acid addition salts. Examples of such salts include salts with, for example, inorganic acids (e.g., hydrochloric acid, phosphoric acid, hydrobromic acid, sulfuric acid); salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like. Hereinafter, the peptide of the present invention or GPR7 is used to include these salts as well.

The peptide of the present invention or GPR7 may be manufactured by a publicly known method used to purify a peptide from human or other warm-blooded animal cells or tissues described above, or by culturing a transformant that contains the DNA encoding the peptide, as will be later described. Furthermore, the peptide of the present invention or GPR7 may also be manufactured by the methods for synthesizing peptides or by modifications thereof, which will also be described hereinafter.

Where the peptide of the present invention or GPR7 is manufactured from human or mammalian tissues or cells, human or mammalian tissues or cells are homogenized, then extracted with an acid or the like, and the extract is isolated and purified by a combination of chromatography techniques such as reverse phase chromatography, ion exchange chromatography, and the like.

To synthesize the peptide of the present invention or GPR7 or amides thereof, commercially available resins that are used for peptide synthesis may be used. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmehtylphenyl acetamidomethyl resin, polyacrylamide resin, 4-(2',4'-dimethoxyphenyl-hydroxymethyl)phenoxy resin, 4-(2',4'-dimethoxyphenyl-Fmoc-aminoethyl) phenoxy resin, etc. Using these resins, amino acids in which α-amino groups and functional groups on the side chains are appropriately protected are condensed on the resin in the order of the sequence of the objective peptide according to various condensation methods publicly known in the art. At the end of the reaction, the peptide is cut out from the resin and at the same time, the protecting groups are removed. Then, intramolecular disulfide bond-forming reaction is performed in a highly diluted solution to obtain the objective peptide of the present invention or GPR7, or amides thereof.

For condensation of the protected amino acids described above, a variety of activation reagents for peptide synthesis may be used, and carbodiimides are particularly preferable. Examples of such carbodiimides include DCC, N,N'-diisopropylcarbodiimide, N-ethyl-N'-(3-dimethylaminoprolyl)carbodiimide, etc. For activation by these reagents, the protected amino acids in combination with a racemization inhibitor (e.g., HOBt, HOOBt) are added directly to the resin, or the protected amino acids are previously activated in the form of symmetric acid anhydrides, HOBt esters or HOOBt esters, followed by adding the thus activated protected amino acids to the resin.

Solvents suitable for use to activate the protected amino acids or condense with the resin may be chosen from solvents known to be usable for peptide condensation reactions. Examples of such solvents are acid amides such as N,N-dimethylformamide, N,N-dimethylacetamide, N-methylpyrrolidone, etc.; halogenated hydrocarbons such as methylene chloride, chloroform, etc.; alcohols such as trifluoroethanol, etc.; sulfoxides such as dimethylsulfoxide, etc.; ethers such as pyridine, dioxan, tetrahydrofuran, etc.; nitriles such as acetonitrile, propionitrile, etc.; esters such as methyl acetate, ethyl acetate, etc.; and appropriate mixtures of these solvents. The reaction temperature is appropriately chosen from the range known to be applicable to peptide binding reactions and is usually selected in the range of approximately −20° C. to 50° C. The activated amino acid derivatives are used generally in an excess of 1.5 to 4 times. The condensation is examined by a test using the ninhydrin reaction; when the condensation is insufficient, the condensation can be completed by repeating the condensation reaction without removal of the protecting groups. When the condensation is yet insufficient even after repeating the reaction, unreacted amino acids are acetylated with acetic anhydride or acetylimidazole so as not to affect the following reactions.

Examples of the protecting groups for amino groups of the starting compounds include Z, Boc, t-pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulphenyl, diphenylphosphinothioyl, Fmoc, etc.

A carboxyl group can be protected by, e.g., alkyl esterification (e.g., esterification of linear, branched or cyclic alkyl moiety such as methyl, ethyl, propyl, butyl, t-butyl, cyclopentyl, cyclohexyl, cycloheptyl, cyclooctyl, 2-adamantyl, etc.), aralkyl esterification (e.g., esterification in the form of benzyl ester, 4-nitrobenzyl ester, 4-methoxybenzyl ester, 4-chlorobenzyl ester, benzhydryl ester, etc.), phenacyl esterification, benzyloxycarbonyl hydrazidation, t-butoxycarbonyl hydrazidation, trityl hydrazidation, or the like.

The hydroxyl group of serine can be protected through, for example, its esterification or etherification. Examples of groups appropriately used for the esterification include a lower alkanoyl group, such as acetyl group, an aroyl group such as benzoyl group, and a group derived from carbonic acid such as benzyloxycarbonyl group, ethoxycarbonyl group, etc. Examples of a group appropriately used for the etherification include benzyl group, tetrahydropyranyl group, t-butyl group, etc.

Examples of groups for protecting the phenolic hydroxyl group of tyrosine include Bzl, $Cl_2$-Bzl, 2-nitrobenzyl, Br-Z, t-butyl, etc.

Examples of groups used to protect the imidazole moiety of histidine include Tos, 4-methoxy-2,3,6-trimethylbenzenesulfonyl, DNP, benzyloxymethyl, Bum, Boc, Trt, Fmoc, etc.

Examples of the activated carboxyl groups in the starting compounds include the corresponding acid anhydrides, azides, activated esters (esters with alcohols (e.g., pentachlorophenol, 2,4,5-trichlorophenol, 2,4-dinitrophenol, cyanomethyl alcohol, p-nitrophenol, HONB, N-hydroxysuccimide, N-hydroxyphthalimide, HOBt)). As the activated amino acids, in which the amino groups are activated in the starting material, the corresponding phosphoric amides are employed.

To eliminate (split off) the protecting groups, there are used catalytic reduction under hydrogen gas flow in the presence of a catalyst such as Pd-black or Pd-carbon; an acid treatment with anhydrous hydrogen fluoride, methanesulfonic acid, trifluoromethane-sulfonic acid or trifluoroacetic acid, or a mixture solution of these acids; a treatment with a base such as diisopropylethylamine, triethylamine, piperidine or piperazine; and reduction with sodium in liquid ammonia. The elimination of the protecting group by the acid treatment described above is carried out generally at a temperature of approximately −20° C. to 40° C. In the acid treatment, it is efficient to add a cation scavenger such as anisole, phenol, thioanisole, m-cresol, p-cresol, dimethylsulfide, 1,4-butanedithiol or 1,2-ethanedithiol. Furthermore, 2,4-dinitrophenyl group known as the protecting group for the imidazole of histidine is removed by a treatment with thiophenol. Formyl group used as the protecting group of the indole of tryptophan is eliminated by the aforesaid acid treatment in the presence of 1,2-ethanedithiol or 1,4-butanedithiol, as well as by a treatment with an alkali such as a dilute sodium hydroxide solution, dilute ammonia, etc.

Protection of functional groups that should not be involved in the reaction of the starting materials, protecting groups, elimination of the protecting groups and activation of functional groups involved in the reaction may be appropriately selected from publicly known groups and publicly known means.

In another method for obtaining the amides of the peptide of the present invention or GPR7, for example, the α-carboxyl group of the carboxy terminal amino acid is first protected by amidation; the peptide chain is then extended from the amino group side to a desired length. Thereafter, a peptide in which only the protecting group of the N-terminal α-amino group in the peptide chain has been eliminated from the peptide and a peptide in which only the protecting group of the C-terminal carboxyl group has been eliminated are prepared. The two peptides are condensed in a mixture of the solvents described above. The details of the condensation reaction are the same as described above. After the protected peptide obtained by the condensation is purified, all the protecting groups are eliminated by the method described above to give the desired crude peptide. This crude peptide is purified by various known purification means. Lyophilization of the major fraction gives the amides of the desired peptide of the present invention or GPR7.

To prepare the esterified form of the peptide of the present invention or GPR7, for example, the α-carboxyl group of the carboxy terminal amino acid is condensed with a desired alcohol to prepare the amino acid ester, which is followed by procedure similar to the preparation of the amidated form of the peptide of the present invention or GPR7 to give the desired ester form of the peptide of the present invention or GPR7.

The partial peptide of the peptide of the present invention or GPR7 can be manufactured by publicly known methods for peptide synthesis, or the partial peptide of GPR7 can be manufactured by cleaving GPR7 with an appropriate peptidase. For the methods for peptide synthesis, for example, either solid phase synthesis or liquid phase synthesis may be used. That is, the partial peptide or amino acids that can construct the peptide of the present invention or the partial peptide of GPR7 are condensed with the remaining part. Where the product contains protecting groups, these protecting groups are removed to give the desired peptide. Publicly known methods for condensation and elimination of the protecting groups are described in (1)-(5) below.

(1) M. Bodanszky & M. A. Ondetti: Peptide Synthesis, Interscience Publishers, New York (1966)

(2) Schroeder & Luebke: The Peptide, Academic Press, New York (1965)

(3) Nobuo Izumiya, et al.: *Peptide Gosei-no-Kiso to Jikken* (Basics and experiments of peptide synthesis), published by Maruzen Co. (1975)

(4) Haruaki Yajima & Shunpei Sakakibara: *Seikagaku Jikken Koza* (Biochemical Experiment) 1, *Tanpakushitsu no Kagaku* (Chemistry of Proteins) IV, 205 (1977)

(5) Haruaki Yajima, ed.: *Zoku Iyakuhin no Kaihatsu* (A sequel to Development of Pharmaceuticals), Vol. 14, Peptide Synthesis, published by Hirokawa Shoten After completion of the reaction, the peptide of the present invention, GPR7 or a partial peptide thereof may be purified and isolated by a combination of conventional purification methods such as solvent extraction, distillation, column chromatography, liquid chromatography and recrystallization to give the partial peptide of the present invention. When the peptide of the present invention or the partial peptide of GPR7 obtained by the above methods is in a free form, the peptide can be converted into an appropriate salt by a publicly known method; when the product is obtained in the form of a salt, it can be converted into a free form or other salts by a publicly known method or its modification.

The polynucleotide encoding the peptide of the present invention or GPR7 may be any polynucleotide so long as it contains the base sequence (DNA or RNA, preferably DNA) encoding the peptide of the present invention or GPR7 described above. Such a polynucleotide may also be any one of DNA encoding the peptide of the present invention or GPR7, RNA such as mRNA, etc., and may be double-stranded or single-stranded. Where the polynucleotide is double-stranded, it may be double-stranded DNA, double-stranded RNA or DNA:RNA hybrid. Where the polynucleotide is single-stranded, it may be a sense strand (i.e., a coding strand) or an antisense strand (i.e., a non-coding strand).

Using the polynucleotide encoding the peptide of the present invention or GPR7, mRNA of the peptide of the present invention or GPR7 can be quantified by, for example, the publicly known method published in separate volume of *Jikken Igaku* 15 (7) "New PCR and its application" (1997), or by its modifications.

The DNA encoding the peptide of the present invention or GPR7 may be any DNA, as long as it contains a base sequence encoding the peptide of the present invention or GPR7 described above. The DNA may also be any of genomic DNA, genomic DNA library, cDNA derived from the cells and tissues described above, cDNA library derived from the cells and tissues described above and synthetic DNA.

The vector to be used for the library may be any of bacteriophage, plasmid, cosmid and phagemid. The DNA may also be directly amplified by reverse transcriptase polymerase chain reaction (hereinafter abbreviated as RT-PCR) using the total RNA or mRNA fraction prepared from the cells and tissues described above.

The DNA encoding the peptide of the present invention may be any DNA, so long as it is a DNA having a base sequence hybridizable to the base sequence represented by any sequence identification number of SEQ ID NO:25 to SEQ ID NO:42 and SEQ ID NO:74 to SEQ ID NO:79 under highly stringent conditions and encoding a peptide having the activities substantially equivalent to those of the peptide of the present invention.

Specific examples of the DNA hybridizable to the base sequence represented by any sequence identification number of SEQ ID NO:25 to SEQ ID NO:42 and SEQ ID NO:74 to SEQ ID NO:79 under highly stringent conditions include DNAs containing a base sequence having at least about 70% homology, preferably at least about 80% homology, more preferably at least about 90% homology and the most preferably at least about 95% homology, to the base sequence represented by any sequence identification number of SEQ ID NO:25 to SEQ ID NO:42 and SEQ ID NO:74 to SEQ ID NO:79.

The hybridization can be carried out by publicly known methods or by modifications of these methods, for example, according to the method described in Molecular Cloning, 2nd (J. Sambrook et al., Cold Spring Harbor Lab. Press, 1989). A commercially available library may also be used according to the instructions of the attached manufacturer's protocol. Preferably, the hybridization can be carried out under highly stringent conditions.

The highly stringent conditions used herein are, for example, those in a sodium concentration at about 19 to 40 mM, preferably about 19 to 20 mM at a temperature of about 50 to 70° C., preferably about 60 to 65° C. In particular, hybridization conditions in a sodium concentration of about 19 mM at a temperature of about 65° C. are most preferred.

More specifically, (i) for the DNA encoding human peptide A containing the amino acid sequence represented by SEQ ID NO:1, there are employed a DNA containing the base sequence represented by SEQ ID NO:25, etc.;

(ii) for the DNA encoding mouse peptide A containing the amino acid sequence represented by SEQ ID NO:2, there are employed a DNA containing the base sequence represented by SEQ ID NO:26, etc.;

(iii) for the DNA encoding rat peptide A containing the amino acid sequence represented by SEQ ID NO:3, there are employed a DNA containing the base sequence represented by SEQ ID NO:27, etc.;

(iv) for the DNA encoding human peptide B containing the amino acid sequence represented by SEQ ID NO:4, there are employed a DNA containing the base sequence represented by SEQ ID NO:28, etc.;

(v) for the DNA encoding mouse peptide B containing the amino acid sequence represented by SEQ ID NO:5, there are employed a DNA containing the base sequence represented by SEQ ID NO:29, etc.;

(vi) for the DNA encoding rat peptide B containing the amino acid sequence represented by SEQ ID NO:6, there are employed a DNA containing the base sequence represented by SEQ ID NO:30, etc.;

(vii) for the DNA encoding human peptide C containing the amino acid sequence represented by SEQ ID NO:7, there are employed a DNA containing the base sequence represented by SEQ ID NO:31, etc.;

(viii) for the DNA encoding human peptide D containing the amino acid sequence represented by SEQ ID NO:8, there are employed a DNA containing the base sequence represented by SEQ ID NO:32, etc.;

(ix) for the DNA encoding mouse peptide C containing the amino acid sequence represented by SEQ ID NO:9, there are employed a DNA containing the base sequence represented by SEQ ID NO:33, etc.;

(x) for the DNA encoding mouse peptide D containing the amino acid sequence represented by SEQ ID NO:10, there are employed a DNA containing the base sequence represented by SEQ ID NO:34, etc.;

(xi) for the DNA encoding rat peptide C containing the amino acid sequence represented by SEQ ID NO:11, there are employed a DNA containing the base sequence represented by SEQ ID NO:35, etc.;

(xii) for the DNA encoding rat peptide D containing the amino acid sequence represented by SEQ ID NO:12, there are employed a DNA containing the base sequence represented by SEQ ID NO:36, etc.;

(xiii) for the DNA encoding human peptide E containing the amino acid sequence represented by SEQ ID NO:13, there are employed a DNA containing the base sequence represented by SEQ ID NO:37, etc.;

(xiv) for the DNA encoding mouse peptide E containing the amino acid sequence represented by SEQ ID NO:14, there are employed a DNA containing the base sequence represented by SEQ ID NO:38, etc.;

(xv) for the DNA encoding rat peptide E containing the amino acid sequence represented by SEQ ID NO:15, there are employed a DNA containing the base sequence represented by SEQ ID NO:39, etc.;

(xvi) for the DNA encoding human peptide F containing the amino acid sequence represented by SEQ ID NO:16, there are employed a DNA containing the base sequence represented by SEQ ID NO:40, etc.;

(xvii) for the DNA encoding mouse peptide F containing the amino acid sequence represented by SEQ ID NO:17, there are employed a DNA containing the base sequence represented by SEQ ID NO:41, etc.;

(xviii) for the DNA encoding rat peptide F containing the amino acid sequence represented by SEQ ID NO:18, there are employed a DNA containing the base sequence represented by SEQ ID NO:42, etc.;

(xix) for the DNA encoding bovine peptide A containing the amino acid sequence represented by SEQ ID NO:66, there are employed a DNA containing the base sequence represented by SEQ ID NO:74, etc.;

(xx) for the DNA encoding bovine peptide B containing the amino acid sequence represented by SEQ ID NO:67, there are employed a DNA containing the base sequence represented by SEQ ID NO:75, etc.;

(xxi) for the DNA encoding bovine peptide C containing the amino acid sequence represented by SEQ ID NO:68, there are employed a DNA containing the base sequence represented by SEQ ID NO:76, etc.;

(xxii) for the DNA encoding bovine peptide D containing the amino acid sequence represented by SEQ ID NO:69, there are employed a DNA containing the base sequence represented by SEQ ID NO:77, etc.;

(xxiii) for the DNA encoding bovine peptide E containing the amino acid sequence represented by SEQ ID NO:70, there are employed a DNA containing the base sequence represented by SEQ ID NO:78, etc.;

(xxvi) for the DNA encoding bovine peptide F containing the amino acid sequence represented by SEQ ID NO:71, there are employed a DNA containing the base sequence represented by SEQ ID NO:79; etc.

The DNA encoding the partial peptide of the present invention may be any DNA, as long as it contains a base sequence encoding the partial peptide of the present invention described above. The DNA may also be any of genomic DNA, genomic DNA library, cDNA derived from the cells and tissues described above, cDNA library derived from the cells and tissues described above and synthetic DNA.

The DNA encoding the partial peptide of the present invention is, for example, a DNA having a partial base sequence of the DNA having the base sequence represented by any sequence identification number of SEQ ID NO:25 to SEQ ID NO:42 and SEQ ID NO:74 to SEQ ID NO:79, or a DNA having a base sequence hybridizable to the base sequence represented by any sequence identification number of SEQ ID NO:25 to SEQ ID NO:42 and SEQ ID NO:74 to SEQ ID NO:79 under highly stringent conditions and encoding a peptide having the activities substantially equivalent to those of the peptide of the present invention.

The DNA hybridizable to the base sequence represented by any sequence identification number of SEQ ID NO:25 to SEQ ID NO:42 and SEQ ID NO:74 to SEQ ID NO:79 has the same significance as described above.

With respect to the hybridization under high stringent conditions, the same procedures as described above apply.

The DNA encoding the precursor peptide of the present invention may be any DNA, so long as it is a DNA having a base sequence hybridizable to the base sequence represented by SEQ ID NO:43 or SEQ ID NO:46 under-highly stringent conditions and encoding a peptide having the activities substantially equivalent to those of the precursor of the present invention.

The DNA hybridizable to the base sequence represented by SEQ ID NO:43 or SEQ ID NO:46 under highly stringent conditions includes a DNA containing a base sequence having at least about 70% homology, preferably at least about 80% homology, more preferably at least about 90% homology, and most preferably at least about 95% homology, to a base sequence represented by any sequence identification number of SEQ ID NO:43 or SEQ ID NO:46.

With respect to the hybridization under high stringent conditions, the same procedures the same conditions as described above apply.

More specifically, (i) for the DNA encoding human GPR7 ligand precursor G containing the amino acid sequence represented by SEQ ID NO:19, there are employed a DNA containing the base sequence represented by SEQ ID NO:43, etc.;

(ii) for the DNA encoding mouse GPR7 ligand precursor G containing the amino acid sequence represented by SEQ ID NO:20, there are employed a DNA containing the base sequence represented by SEQ ID NO:44, etc.;

(iii) for the DNA encoding rat GPR7 ligand precursor G containing the amino acid sequence represented by SEQ ID NO:21, there are employed a DNA containing the base sequence represented by SEQ ID NO:45, etc.;

(iv) for the DNA encoding bovine GPR7 ligand precursor G containing the amino acid sequence represented by SEQ ID NO:72, there are employed a DNA containing the base sequence represented by SEQ ID NO:80, etc.;

(v) for the DNA encoding mouse GPR7 ligand precursor H containing the amino acid sequence represented by SEQ ID NO:22, there are employed a DNA containing the base sequence represented by SEQ ID NO:46, etc.;

(vi) for the DNA encoding mouse GPR7 ligand precursor H containing the amino acid sequence represented by SEQ ID NO:23, there are employed a DNA containing the base sequence represented by SEQ ID NO:47, etc.;

(vii) for the DNA encoding rat GPR7 ligand precursor H containing the amino acid sequence represented by SEQ ID NO:24, there are employed a DNA containing the base sequence represented by SEQ ID NO:48, etc.;

(viii) for the DNA encoding bovine GPR7 ligand precursor H containing the amino acid sequence represented by SEQ ID NO:73, there are employed a DNA containing the base sequence represented by SEQ ID NO:81, etc.

The polynucleotide comprising a part of the base sequence of the DNA encoding the peptide or partial peptide of the present invention, or a part of the base sequence complementary to the DNA is used to mean to embrace not only the DNA encoding the partial peptide of the present invention but also RNA.

According to the present invention, antisense polynucleotides (nucleic acids) that can inhibit the replication or expression of genes for the peptide of the present invention can be designed and synthesized based on the base sequence information of the cloned or determined DNA encoding the peptide of the present invention. Such a polynucleotide (nucleic acid) is capable of hybridizing to RNA of genes for the peptide of the present invention to inhibit the synthesis or function of said RNA or capable of modulating or controlling the expression of genes for the peptide of the present invention via interaction with RNA associated with the peptide of the present invention. Polynucleotides complementary to the selected sequences of RNA associated with the peptide of the present invention and polynucleotides specifically hybridizable to the RNA associated with the peptide of the present invention are useful in modulating or controlling the expression of genes for the peptide of the present invention in vivo and in vitro, and useful for the treatment or diagnosis of diseases, etc. The term "corresponding" is used to mean homologous to or complementary to a particular sequence of the nucleotide, base sequence or nucleic acid, including the genes. The term "corresponding" between nucleotides, base sequences or nucleic acids and peptides (proteins) usually refer to amino acids of a peptide (protein) under the order derived from the sequence of nucleotides (nucleic acids) or their complements. In the genes for the peptide of the present invention, the 5' end hairpin loop, 5' end 6-base-pair repeats, 5' end untranslated region, polypeptide translation initiation codon, protein coding region, ORF translation initiation codon, 3' end untranslated region, 3' end palindrome region, and 3' end hairpin loop, may be selected as preferred target regions, though any other region may be selected as a target in the genes for the peptide of the present invention.

The relationship between the targeted nucleic acids and the polynucleotides complementary to at least a part of the target, specifically the relationship between the target and the polynucleotides hybridizable to the target, can be denoted to be "antisense". Examples of the antisense polynucleotides include polynucleotides containing 2-deoxy-D-ribose, polynucleotides containing D-ribose, any other type of polynucleotides which are N-glycosides of a purine or pyrimidine base, or other polymers containing non-nucleotide backbones (e.g., protein nucleic acids and synthetic sequence-specific nucleic acid polymers commercially available) or other polymers containing nonstandard linkages (provided that the polymers contain nucleotides having such a configuration that allows base pairing or base stacking, as is found in DNA or RNA), etc. The antisense polynucleotides may be double-stranded DNA, single-stranded DNA, single-stranded RNA or a DNA:RNA hybrid, and may further include unmodified polynucleotides (or unmodified oligonucleotides), those with publicly known types of modifications, for example, those with labels known in the art, those with caps, methylated polynucleotides, those with substitution of one or more naturally occurring nucleotides by their analogue, those with intramolecular modifications of nucleotides such as those with uncharged linkages (e.g., methyl phosphonates, phosphotriesters, phosphoramidates, carbamates, etc.) and those with charged linkages or sulfur-containing linkages (e.g., phosphorothioates, phosphorodithioates, etc.), those having side chain groups such as proteins (nucleases, nuclease inhibitors, toxins, antibodies, signal peptides, poly-L-lysine, etc.), saccharides (e.g., monosaccharides, etc.), those with intercalators (e.g., acridine, psoralen, etc.), those containing chelators (e.g., metals, radioactive metals, boron, oxidative metals, etc.), those containing alkylating agents, those with modified linkages (e.g., a anomeric nucleic acids, etc.), and the like. Herein the terms "nucleoside", "nucleotide" and "nucleic acid" are used to refer to moieties that contain not only the purine and pyrimidine bases, but also other heterocyclic bases, which have been modified. Such modifications may include methylated purines and pyrimidines, acylated purines and pyrimidines and other heterocyclic rings. Modified nucleotides and modified nucleotides also include modifications on the sugar moiety, wherein, for example, one or more hydroxyl groups may optionally be substituted with a halogen atom(s), an aliphatic group(s), etc., or may be converted into the corresponding functional groups such as ethers, amines, or the like.

The antisense polynucleotide (nucleic acid) of the present invention is RNA, DNA or a modified nucleic acid (RNA, DNA). Specific examples of the modified nucleic acid are, but not limited to, sulfur and thiophosphate derivatives of nucleic acids and those resistant to degradation of polynucleoside amides or oligonucleoside amides. The antisense nucleic acids of the present invention can be modified preferably based on the following design, that is, by increasing the intracellular stability of the antisense nucleic acid, increasing the cellular permeability of the antisense nucleic acid, increasing the affinity of the nucleic acid to the targeted sense strand to a higher level, or minimizing the toxicity, if any, of the antisense nucleic acid.

Many of such modifications are known in the art, as disclosed in J. Kawakami, et al., Pharm. Tech. Japan, Vol. 8, pp. 247, 1992; Vol. 8, pp. 395, 1992; S. T. Crooke, et al. ed., Antisense Research and Applications, CRC Press, 1993; etc.

The antisense nucleic acid of the present invention may contain altered or modified sugars, bases or linkages. The antisense nucleic acid may also be provided in a specialized form such as liposomes, microspheres, or may be applied to gene therapy, or may be provided in combination with attached moieties. Such attached moieties include polycations such as polylysine that act as charge neutralizers of the phosphate backbone, or hydrophobic moieties such as lipids (e.g., phospholipids, cholesterols, etc.) that enhance the interaction with cell membranes or increase uptake of the nucleic acid. Preferred examples of the lipids to be attached are cholesterols or derivatives thereof (e.g., cholesteryl chloroformate, cholic acid, etc.). These moieties may be attached to the nucleic acid at the 3' or 5' ends thereof and may also be attached thereto through a base, sugar, or intramolecular nucleoside linkage. Other moieties may be capping groups specifically placed at the 3' or 5' ends of the nucleic acid to prevent degradation by nucleases such as exonuclease, RNase, etc. Such capping groups include, but are not limited to, hydroxyl protecting groups known in the art, including glycols such as polyethylene glycol, tetraethylene glycol and the like.

The inhibitory action of the antisense nucleic acid can be examined using the transformant of the present invention, the gene expression system of the present invention in vivo and in vitro, or the translation system of the peptide of the present invention in vivo and in vitro. The nucleic acid can be applied to cells by a variety of publicly known methods.

The DNA encoding human GPR7 may be any DNA, as far as it is a DNA containing the base sequence represented by, e.g., SEQ ID NO:50, a DNA having a base sequence hybridizable to the base sequence represented by SEQ ID NO:50 under high stringent conditions and encoding a protein having the activities substantially equivalent to those of human GPR7 having the base sequence represented by SEQ ID NO:49, or the like.

The DNA hybridizable to the base sequence represented by SEQ ID NO:50 under highly stringent conditions includes a DNA containing a base sequence having at least about 70% homology, preferably at least about 80% homology, more preferably at least about 90% homology, and most preferably at least about 95% homology, to a base sequence represented by SEQ ID NO:50, or the like.

The DNA encoding rat TGR26 may be any DNA, as far as it is a DNA containing the base sequence represented by, e.g., SEQ ID NO:60, a DNA having a base sequence hybridizable to the base sequence represented by SEQ ID NO:60 under high stringent conditions and encoding a protein having the activities substantially equivalent to those of rat TGR26 having the base sequence represented by SEQ ID NO:59, or the like.

The DNA hybridizable to the base sequence represented by SEQ ID NO:60 under highly stringent conditions includes a DNA containing a base sequence having at least about 70% homology, preferably at least about 80% homology, more preferably at least about 90% homology, and most preferably at least about 95% homology, to a base sequence represented by SEQ ID NO:60, or the like.

The DNA encoding human GPR8 may be any DNA, as far as it is a DNA containing the base sequence represented by, e.g., SEQ ID NO:85, a DNA having a base sequence hybridizable to the base sequence represented by SEQ ID NO:85 under high stringent conditions and encoding a protein having the activities substantially equivalent to those of human GPR8 having the base sequence represented by SEQ ID NO:66, or the like.

The DNA hybridizable to the base sequence represented by SEQ ID NO:85 under highly stringent conditions includes a DNA containing a base sequence having at least about 70% homology, preferably at least about 80% homology, more preferably at least about 90% homology, and most preferably at least about 95% homology, to a base sequence represented by SEQ ID NO:85, or the like.

The DNA encoding bovine GPR7 may be any DNA, as far as it is a DNA containing the base sequence represented by, e.g., SEQ ID NO:87, a DNA having a base sequence hybridizable to the base sequence represented by SEQ ID NO:87 under high stringent conditions and encoding a protein having the activities substantially equivalent to those of bovine GPR7 having the base sequence represented by SEQ ID NO:86, or the like.

The DNA hybridizable to the base sequence represented by SEQ ID NO:87 under highly stringent conditions includes a DNA containing a base sequence having at least about 70% homology, preferably at least about 80% homology, more preferably at least about 90% homology, and most preferably at least about 95% homology, to a base sequence represented by SEQ ID NO:87, or the like.

The DNA encoding bovine GPR8 may be any DNA, as far as it is a DNA containing the base sequence represented by, e.g., SEQ ID NO:89, a DNA having a base sequence hybridizable to the base sequence represented by SEQ ID NO:89 under high stringent conditions and encoding a protein having the activities substantially equivalent to those of bovine GPR8 having the base sequence represented by SEQ ID NO:88, or the like.

The DNA hybridizable to the base sequence represented by SEQ ID NO:89 under highly stringent conditions includes a DNA containing a base sequence having at least about 70% homology, preferably at least about 80% homology, more preferably at least about 90% homology, and most preferably at least about 95% homology, to a base sequence represented by SEQ ID NO:89, or the like.

The hybridization can be carried out by publicly known methods or by modifications of these methods, for example, according to the method described in Molecular Cloning, 2nd (J. Sambrook et al., Cold Spring Harbor Lab. Press, 1989), etc. A commercially available library may also be used according to the instructions of the attached manufacturer's protocol. Preferably, the hybridization can be carried out under highly stringent conditions.

The highly stringent conditions used herein are, for example, those in a sodium concentration at about 19 to 40 mM, preferably about 19 to 20 mM at a temperature of about 50 to 70° C., preferably about 60 to 65° C. In particular, hybridization conditions in a sodium concentration of about 19 mM at a temperature of about 65° C. are most preferred.

More specifically, for the DNA encoding human GPR7 containing the amino acid sequence represented by SEQ ID NO:49, there are employed a DNA containing the base sequence represented by SEQ ID NO:50, etc.; for the DNA encoding rat TGR26 containing the amino acid sequence represented by SEQ ID NO:59, there are employed a DNA containing the base sequence represented by SEQ ID NO:60, etc.; for the DNA encoding human GPR8 containing the amino acid sequence represented by SEQ ID NO:84, there are employed a DNA containing the base sequence represented by SEQ ID NO:85, etc.; for the DNA encoding bovine GPR7 containing the amino acid sequence represented by SEQ ID NO:86, there are employed a DNA containing the base sequence represented by SEQ ID NO:87, etc.; and, for the DNA encoding bovine GPR8 containing the amino acid sequence represented by SEQ ID NO:88, there are employed a DNA containing the base sequence represented by SEQ ID NO:89, etc.

The DNA encoding the partial peptide of GPR7 may be any DNA, as long as it contains a base sequence encoding the partial peptide of GPR7 described above. The DNA may also be any of genomic DNA, genomic DNA library, cDNA derived from the cells and tissues described above, cDNA library derived from the cells and tissues described above and synthetic DNA.

The DNA encoding the partial peptide of human GPR7 is, for example, a DNA having a partial base sequence of the DNA having the base sequence represented by SEQ ID NO:50, or a DNA having a base sequence hybridizable to the base sequence represented by SEQ ID NO:50 under highly stringent conditions and encoding a peptide having the activities substantially equivalent to those of human GPR7.

The DNA hybridizable to the base sequence represented by SEQ ID NO:50 has the same significance as described above.

The DNA encoding the partial peptide of rat TGR26 is, for example, a DNA having a partial base sequence of the DNA having the base sequence represented by SEQ ID NO:60, or a DNA having a base sequence hybridizable to the base sequence represented by SEQ ID NO:60 under highly stringent conditions and encoding a peptide having the activities substantially equivalent to those of rat TGR26.

The DNA hybridizable to the base sequence represented by SEQ ID NO:60 has the same significance as described above.

The DNA encoding the partial peptide of human GPR8 may be any DNA, as long as it contains a base sequence encoding the partial peptide of human GPR8 described above. The DNA may also be any of genomic DNA, genomic DNA library, cDNA derived from the cells and tissues described above, cDNA library derived from the cells and tissues described above and synthetic DNA.

The DNA encoding the partial peptide of human GPR8 is, for example, a DNA having a partial base sequence of the DNA having the base sequence represented by SEQ ID NO:85, or a DNA having a base sequence hybridizable to the base sequence represented by SEQ ID NO:85 under highly stringent conditions and encoding a peptide having the activities substantially equivalent to those of human GPR8.

The DNA hybridizable to the base sequence represented by SEQ ID NO:85 has the same significance as described above.

The DNA encoding the partial peptide of bovine GPR7 may be any DNA, as long as it contains a base sequence encoding the partial peptide of bovine GPR7 described above. The DNA may also be any of genomic DNA, genomic DNA library, cDNA derived from the cells and tissues described above, cDNA library derived from the cells and tissues described above and synthetic DNA.

The DNA encoding the partial peptide of bovine GPR7 is, for example, a DNA having a partial base sequence of the DNA having the base sequence represented by SEQ ID NO:87, or a DNA having a base sequence hybridizable to the base sequence represented by SEQ ID NO:87 under highly stringent conditions and encoding a peptide having the activities substantially equivalent to those of bovine GPR7.

The DNA hybridizable to the base sequence represented by SEQ ID NO:87 has the same significance as described above.

The DNA encoding the partial peptide of bovine GPR8 may be any DNA, as long as it contains a base sequence encoding the partial peptide of bovine GPR8 described above. The DNA may also be any of genomic DNA, genomic DNA library, cDNA derived from the cells and tissues described above, cDNA library derived from the cells and tissues described above and synthetic DNA.

The DNA encoding the partial peptide of bovine GPR8 is, for example, a DNA having a partial base sequence of the DNA having the base sequence represented by SEQ ID NO:89, or a DNA having a base sequence hybridizable to the base sequence represented by SEQ ID NO:89 under highly stringent conditions and encoding a peptide having the activities substantially equivalent to those of bovine GPR8.

The DNA hybridizable to the base sequence represented by SEQ ID NO:89 has the same significance as described above.

With respect to the hybridization under high stringent conditions, the same procedures as described-above apply.

The DNA encoding the peptide of the present invention or GPR7 may be labeled by publicly known methods. Specific examples include those labeled with an isotope, those labeled with fluorescence (labeling with, e.g., fluorescein, etc.), those biotinated, those labeled with enzyme, etc.

For cloning of the DNA that fully encodes the peptide of the present invention or GPR7, the DNA may be either amplified by publicly known PCR using synthetic DNA primers containing a part of the base sequence of the peptide of the present invention or GPR7, or the DNA inserted into an appropriate vector can be selected by hybridization with a labeled DNA fragment or synthetic DNA that encodes a part or entire region of the peptide of the present invention or GPR7. The hybridization can be carried out, for example, according to the method described in Molecular Cloning, 2nd (J. Sambrook et al., Cold Spring Harbor Lab. Press, 1989), etc. The hybridization may also be performed using commercially available library in accordance with the protocol described in the attached instructions.

Conversion of the base sequence of DNA can be made by publicly known methods such as the ODA-LA PCR method, the Gapped duplex method or the Kunkel method, or modifications thereof, by using a publicly known kit available as Mutan™-super Express Km (manufactured by TaKaRa Shuzo Co., Ltd., trademark), Mutan™-K (manufactured by TaKaRa Shuzo Co., Ltd., trademark), etc.

The cloned peptide-encoding DNA can be used as it is, depending upon purpose or, if desired, after digestion with a restriction enzyme or after addition of a linker thereto. The DNA may contain ATG as a translation initiation codon at the 5' end thereof and TAA, TGA or TAG as a translation termination codon at the 3' end thereof. These translation initiation and termination codons may also be added by using an appropriate synthetic DNA adapter.

The expression vector of the peptide of the present invention or GPR7 can be manufactured, for example, by (a) excising the desired DNA fragment from the DNA encoding the peptide of the present invention or GPR7, (b) and then ligating the DNA fragment with an appropriate expression vector downstream a promoter in the vector.

Examples of the vector include plasmids derived form *E. coli* (e.g., pBR322, pBR325, pUC12, pUC13), plasmids derived from *Bacillus subtilis* (e.g., pUB110, pTP5, pC194), plasmids derived from yeast (e.g., pSH19, pSH15), bacteriophages such as λ phage, etc., animal viruses such as retrovirus, vaccinia virus, baculovirus, etc. as well as pA1-11, pXT1, pRc/CMV, pRc/RSV, pcDNAI/Neo, etc.

The promoter used in the present invention may be any promoter if it matches well with a host to be used for gene expression. In the case of using animal cells as the host, examples of the promoter include SRα promoter, SV40 promoter, HIV•LTR promoter, CMV promoter, HSV-TK promoter, etc.

Among them, CMV (cytomegalovirus) promoter or SRα promoter is preferably used. Where the host is bacteria of the genus *Escherichia*, preferred examples of the promoter include trp promoter, lac promoter, recA promoter, λPL promoter, lpp promoter, T7 promoter, etc. In the case of using bacteria of the genus *Bacillus* as the host, preferred example of the promoter are SPO1 promoter, SPO2 promoter and penP promoter. When yeast is used as the host, preferred examples of the promoter are PHO5 promoter, PGK promoter, GAP promoter and ADH promoter. When insect cells are used as the host, preferred examples of the promoter include polyhedrin promoter, P10 promoter, etc.

In addition to the foregoing examples, the expression vector may further optionally contain an enhancer, a splicing signal, a poly A addition signal, a selection marker, SV40 replication origin (hereinafter sometimes abbreviated as SV40ori) etc. Examples of the selection marker include dihydrofolate reductase (hereinafter sometimes abbreviated as dhfr) gene [methotrexate (MTX) resistance], ampicillin resistant gene (hereinafter sometimes abbreviated as Amp$^r$), neomycin resistant gene (hereinafter sometimes abbreviated as Neo$^r$, G418 resistance), etc. In particular, when dhfr gene is employed as the selection marker using dhfr gene-deficient Chinese hamster cells, selection can also be made on thymidine free media.

If necessary, a signal sequence that matches with a host is added to the N-terminus of the peptide of the present invention. Examples of the signal sequence that can be used are Pho A signal sequence, OmpA signal sequence, etc. in the case of using bacteria of the genus *Escherichia* as the host; α-amylase signal sequence, *subtilisin* signal sequence, etc. in the case of using bacteria of the genus *Bacillus* as the host; MFα signal sequence, SUC2 signal sequence, etc. in the case of using yeast as the host; and insulin signal sequence, α-interferon signal sequence, antibody molecule signal sequence, etc. in the case of using animal cells as the host, respectively.

Using the vector comprising the DNA encoding the peptide of the present invention thus constructed, transformants can be manufactured.

Examples of the host, which may be employed, are bacteria belonging to the genus *Escherichia*, bacteria belonging to the genus *Bacillus*, yeast, insect cells, insects and animal cells, etc.

Specific examples of the bacteria belonging to the genus *Escherichia* include *Escherichia coli* K12 DH1 [Proc. Natl. Acad. Sci. U.S.A., 60, 160 (1968)], JM103 [Nucleic Acids Research, 9, 309 (1981)], JA221 [Journal of Molecular Biology, 120, 517 (1978)], HB101 [Journal of Molecular Biology, 41, 459 (1969)], C600 [Genetics, 39, 440 (1954)], etc.

Examples of the bacteria belonging to the genus *Bacillus* include *Bacillus subtilis* MI114 [Gene, 24, 255 (1983)], 207-21 [Journal of Biochemistry, 95, 87 (1984)], etc.

Examples of yeast include *Saccharomyces cereviseae* AH22, AH22R⁻, NA87-11A, DKD-5D, 20B-12, *Schizosaccharomyces pombe* NCYC1913, NCYC2036, *Pichia pastoris* KM71, etc.

Examples of insect cells include, for the virus AcNPV, *Spodoptera frugiperda* cell (Sf cell), MG1 cell derived from mid-intestine of *Trichoplusia ni*, High Five™ cell derived from egg of *Trichoplusia ni*, cells derived from *Mamestra brassicae*, cells derived from *Estigmena acrea*, etc.; and for the virus BmNPV, *Bombyx mori* N cell (BmN cell), etc. is used. Examples of the Sf cell which can be used are Sf9 cell (ATCC CRL1711), Sf21 cell (both cells are described in Vaughn, J. L. et al., In Vivo, 13, 213-217 (1977)), etc.

As the insect, for example, a larva of *Bombyx mori*, etc. can be used [Maeda et al., Nature, 315, 592 (1985)].

Examples of animal cells include monkey cell COS-7, Vero, Chinese hamster cell CHO (hereinafter referred to as CHO cell), dhfr gene deficient Chinese hamster cell CHO (hereinafter simply referred to as CHO (dhfr⁻) cell), mouse L cell, mouse AtT-20, mouse myeloma cell, rat GH 3, human FL cell, etc.

Bacteria belonging to the genus *Escherichia* can be transformed, for example, by the method described in Proc. Natl. Acad. Sci. U.S.A., 69, 2110 (1972), Gene, 17, 107 (1982), etc.

Bacteria belonging to the genus *Bacillus* can be transformed, for example, by the method described in Molecular & General Genetics, 168, 111 (1979), etc.

Yeast can be transformed, for example, by the method described in Methods in Enzymology, 194, 182-187 (1991), Proc. Natl. Acad. Sci. U.S.A., 75, 1929 (1978), etc.

Insect cells or insects can be transformed, for example, according to the method described in Bio/Technology, 6, 47-55(1988), etc.

Animal cells can be transformed, for example, according to the method described in *Saibo Kogaku* (Cell Engineering), extra issue 8, *Shin Saibo Kogaku Jikken Protocol* (New Cell Engineering Experimental Protocol), 263-267 (1995), published by Shujunsha, or Virology, 52, 456 (1973).

Thus, the transformant transformed with the expression vector containing the DNA encoding the peptide can be obtained.

Where the host is bacteria belonging to the genus *Escherichia* or the genus *Bacillus*, the transformant can be appropriately cultured in a liquid medium which contains materials required for growth of the transformant such as carbon sources, nitrogen sources, inorganic materials, etc. Examples of the carbon sources include glucose, dextrin, soluble starch, sucrose, etc. Examples of the nitrogen sources include inorganic or organic materials such as ammonium salts, nitrate salts, corn steep liquor, peptone, casein, meat extract, soybean cake, potato extract, etc. Examples of the inorganic materials are calcium chloride, sodium dihydrogenphosphate, magnesium chloride, etc. In addition, yeast, vitamins, growth promoting factors etc. may also be added to the medium. Preferably, pH of the medium is adjusted to about 5 to about 8.

A preferred example of the medium for culturing the bacteria belonging to the genus *Escherichia* is M9 medium supplemented with glucose and Casamino acids [Miller, Journal of Experiments in Molecular Genetics, 431-433, Cold Spring Harbor Laboratory, New York, 1972]. If necessary and desired, a chemical such as 3β-indolylacrylic acid can be added to the medium thereby to activate the promoter efficiently.

Where the bacteria belonging to the genus *Escherichia* are used as the host, the transformant is usually cultivated at approximately 15 to 43° C. for approximately 3 to 24 hours. If necessary, the culture may be aerated or agitated.

Where the bacteria belonging to the genus *Bacillus* are used as the host, the transformant is cultivated generally at approximately 30 to 40° C. for approximately 6 to 24 hours. If necessary, the culture can be aerated or agitated.

Where yeast is used as the host, the transformant is cultivated, for example, in Butkholder's minimal medium [Bostian, K. L. et al., Proc. Natl. Acad. Sci. U.S.A., 77, 4505 (1980)] or in SD medium supplemented with 0.5% Casamino acids [Bitter, G. A. et al., Proc. Natl. Acad. Sci. U.S.A., 81, 5330 (1984)]. Preferably, pH of the medium is adjusted to about 5 to about 8. In general, the transformant is cultivated at approximately 20° C. to 35° C. for approximately 24 to 72 hours. If necessary, the culture can be aerated or agitated.

Where insect cells or insects are used as the host, the transformant is cultivated in, for example, Grace's Insect Medium (Grace, T. C. C., Nature, 195, 788 (1962)) to which an appropriate additive such as immobilized 10% bovine serum is added. Preferably, pH of the medium is adjusted to about 6.2 to about 6.4. Normally, the transformant is cultivated at about 27° C. for about 3 days to about 5 days and, if necessary, the culture can be aerated or agitated.

Where animal cells are employed as the host, the transformant is cultivated in, for example, MEM medium containing about 5% to about 20% fetal bovine serum [Science, 122, 501 (1952)], DMEM medium [Virology, 8, 396 (1959)], RPMI 1640 medium [The Journal of the American Medical Association, 199, 519 (1967)], 199 medium [Proceeding of the Society for the Biological Medicine, 73, 1 (1950)], etc. Preferably, pH of the medium is adjusted to about 6 to about 8. The transformant is usually cultivated at about 30° C. to about 40° C. for about 15 hours to about 60 hours and, if necessary, the culture can be aerated or agitated.

As described above, the peptide of the present invention or GPR7 can be produced in the inside, cell membrane or outside of the transformant, etc.

The peptide of the present invention or GPR7 can be separated and purified from the culture described above, e.g., by the following procedures.

When the peptide of the present invention or GPR7 is extracted from the culture or cells, the transformant or cell is collected, after cultivation, by a publicly known method and suspended in an appropriate buffer. The transformant or cell is then disrupted by publicly known methods such as ultrasonication, a treatment with lysozyme and/or freeze-thaw cycling, followed by centrifugation, filtration, etc. Thus, the crude extract of the peptide of the present invention or GPR7 can be obtained. The buffer used for the procedures may contain a protein modifier such as urea or guanidine hydrochloride, or a surfactant such as Triton X-100™, etc. When the peptide is secreted in the culture broth, after completion of the cultivation the supernatant can be separated from the transformant or cell to collect the supernatant by a publicly known method.

The peptide of the present invention or GPR7 contained in the supernatant or in the extract thus obtained can be purified by appropriately combining the publicly known methods for separation and purification. Such publicly known methods for separation and purification include a method utilizing difference in solubility such as salting out, solvent precipitation, etc.; a method mainly utilizing difference in molecular weight such as dialysis, ultrafiltration, gel filtration, SDS-polyacrylamide gel electrophoresis, etc.; a method utilizing difference in electric charge such as ion exchange chromatography, etc.; a method utilizing difference in specific affinity such as affinity chromatography, etc.; a method utilizing difference in hydrophobicity such as reversed phase high performance liquid chromatography, etc.; a method utilizing difference in isoelectric point such as isoelectrofocusing electrophoresis; and the like.

When the peptide of the present invention or GPR7 thus obtained is in a free form, it can be converted into the salt by publicly known methods or modifications thereof. On the other hand, when the peptide is obtained in the form of a salt, it can be converted into the free form or in the form of a different salt by publicly known methods or modifications thereof.

The peptide of the present invention or GPR7 produced by the recombinant can be treated, prior to or after the purification, with an appropriate protein modifying enzyme so that the peptide can be appropriately modified to partially remove a peptide. Examples of the protein-modifying enzyme include trypsin, chymotrypsin, arginyl endopeptidase, protein kinase, glycosidase and the like.

Antibodies to the peptide of the present invention (hereinafter sometimes simply referred to as the antibody(ies) of the present invention) may be any of polyclonal antibodies and monoclonal antibodies, as long as they are capable of recognizing antibodies to the peptide of the present invention.

The antibodies to the peptide of the present invention may be manufactured by publicly known methods for manufacturing antibodies or antisera, using as antigens the peptide of the present invention.

[Production of Monoclonal Antibody]

(a) Production of Monoclonal Antibody-Producing Cells

The peptide of the present invention is administered to warm-blooded animals either solely or together with carriers or diluents to the site where the production of antibody is possible by the administration. In order to potentiate the antibody productivity upon the administration, complete Freund's adjuvants or incomplete Freund's adjuvants may be administered. The administration is usually carried out once every two to six weeks and two to ten times in total. Examples of the applicable warm-blooded animals are monkeys, rabbits, dogs, guinea pigs, rice, rats, sheep, goats and chickens, with the use of mice and rats being preferred.

In the preparation of monoclonal antibody-producing cells, a warm-blooded animal, e.g., mice, immunized with an antigen wherein the antibody titer is noted is selected, then spleen or lymph node is collected after two to five days from the final immunization and antibody-producing cells contained therein are fused with myeloma cells from homozoic or heterozoic animal to give monoclonal antibody-producing hybridomas. Measurement of the antibody titer in antisera may be carried out, for example, by reacting a labeled peptide, which will be described later, with the antiserum followed by assaying the binding activity of the labeling agent bound to the antibody. The fusion may be carried out, for example, by the known method by Koehler and Milstein [Nature, 256, 495 (1975)]. Examples of the fusion promoter are polyethylene glycol (PEG), Sendai virus, etc., of which PEG is preferably employed.

Examples of the myeloma cells are those collected from warm-blooded animals such as NS-1, P3U1, SP2/0, AP-1, etc. In particular, P3U1 is preferably employed. A preferred ratio of the count of the antibody-producing cells used (spleen cells) to the count of myeloma cells is within a range of approximately 1:1 to 20:1. When PEG (preferably, PEG 1000 to PEG 6000) is added in a concentration of approximately 10 to 80% followed by culturing at 20 to 40° C., preferably at 30 to 37° C. for 1 to 10 minutes, an efficient cell fusion can be carried out.

Various methods can be used for screening of a monoclonal antibody-producing hybridoma. Examples of such methods include a method which comprises adding the supernatant of hybridoma to a solid phase (e.g., microplate) adsorbed with the peptide (protein) as an antigen directly or together with a carrier, adding an anti-immunoglobulin antibody (where mouse cells are used for the cell fusion, anti-mouse immunoglobulin antibody is used) labeled with a radioactive substance or an enzyme or Protein A and detecting the monoclonal antibody bound to the solid phase, and a method which comprises adding the supernatant of hybridoma to a solid phase adsorbed with an anti-immunoglobulin antibody or Protein A, adding the peptide labeled with a radioactive substance or an enzyme and detecting the monoclonal antibody bound to the solid phase.

The monoclonal antibody can be selected according to publicly known methods or their modifications. In general, the selection can be effected in a medium for animal cells supplemented with HAT (hypoxanthine, aminopterin and thymidine). Any selection and growth medium can be employed as far as the hybridoma can grow there. For example, RPMI 1640 medium containing 1 to 20%, preferably 10 to 20% fetal bovine serum, GIT medium (Wako Pure Chemical Industries, Ltd.) containing 1 to 10% fetal bovine serum, a serum free medium for cultivation of a hybridoma (SFM-101, Nissui Seiyaku Co., Ltd.) and the like can be used for the selection and growth medium. The cultivation is carried out generally at 20 to 40° C., preferably at 37° C., for about 5 days to about 3 weeks, preferably 1 to 2 weeks, normally in 5% $CO_2$. The antibody titer of the culture supernatant of a hybridoma can be determined as in the assay for the antibody titer in antisera described above.

(b) Purification of Monoclonal Antibody

Separation and purification of a monoclonal antibody can be carried out by publicly known methods, such as separation and purification of immunoglobulins [for example, salting-out, alcohol precipitation, isoelectric point precipitation, electrophoresis, adsorption and desorption with ion exchangers (e.g., DEAE), ultracentrifugation, gel filtration, or a specific purification method which comprises collecting only an antibody with an activated adsorbent such as an antigen-binding solid phase, Protein A or Protein G and dissociating the binding to obtain the antibody].

[Production of Polyclonal Antibody]

The polyclonal antibody of the present invention can be manufactured by publicly known methods or modifications thereof. For example, a warm-blooded animal is immunized with an immunogen (peptide antigen) per se, or a complex of immunogen and a carrier protein is formed and a warm-blooded animal is immunized with the complex in a manner similar to the method described above for the manufacture of monoclonal antibodies. The product containing the antibody to the peptide of the present invention is collected from the immunized animal followed by separation and purification of the antibody.

In the complex of immunogen and carrier protein used to immunize a warm-blooded animal, the type of carrier protein and the mixing ratio of carrier to hapten may be any type and in any ratio, as long as the antibody is efficiently produced to the hapten immunized by crosslinking to the carrier. For example, bovine serum albumin, bovine thyroglobulin, hemocyanin or the like is coupled to hapten in a carrier-to-hapten weight ratio of approximately 0.1 to 20, preferably about 1 to about 5.

A variety of condensation agents can be used for the coupling of carrier to hapten. Glutaraldehyde, carbodiimide, maleimide activated ester and activated ester reagents containing thiol group or dithiopyridyl group are used for the coupling.

The condensation product is administered to warm-blooded animals either solely or together with carriers or diluents to the site that can produce the antibody by the administration. In order to potentiate the antibody productivity upon the administration, complete Freund's adjuvant or incomplete Freund's adjuvant may be administered. The administration is usually made once approximately every 2 to 6 weeks and approximately 3 to 10 times in total.

The polyclonal antibody can be collected from the blood, ascites, etc., preferably from the blood of warm-blooded animal immunized by the method described above.

The polyclonal antibody titer in antiserum can be assayed by the same procedure as that for the determination of serum antibody titer described above. The separation and purification of the polyclonal antibody can be carried out, following the method for the separation and purification of immunoglobulins performed as in the separation and purification of monoclonal antibodies described hereinabove.

Antisense DNAs (hereinafter these DNAs are sometimes merely referred to as the antisense DNA) having a complementary or substantially complementary base sequence to the DNA encoding the peptide of the present invention (hereinafter these DNAs are sometimes merely referred to as the DNA of the present invention) can be any antisense DNA, so long as they possess a base sequence complementary or substantially complementary to that of the DNA of the present invention and capable of suppressing expression of the DNA.

The base sequence substantially complementary to the DNA of the present invention may, for example, be a base sequence having at least about 70% homology, preferably at least about 80% homology, more preferably at least about 90% homology and most preferably at least about 95% homology, to the full-length base sequence or partial base sequence of the base sequence complementary to the DNA of the present invention (i.e., complementary strand to the DNA of the present invention). In the entire base sequence of the complementary strand to the DNA of the present invention, an antisense DNA having at least about 70% homology, preferably at least about 80% homology, more preferably at least about 90% homology and most preferably at least about 95% homology, to the complementary strand of the base sequence which encodes the N-terminal region of the peptide of the present invention (e.g., the base sequence around the initiation codon). These antisense DNAs can be synthesized using a publicly known DNA synthesizer, etc.

Hereinafter, the utilities of (1) the peptide of the present invention; (2) the DNA of the present invention, (3) the antibody of the present invention, and (4) the antisense DNA are explained.

(1) Therapeutic/Preventive Agent for Diseases with which the Peptide of the Present Invention is Associated As shown in EXAMPLE 6 later described, the peptide of the present invention has the cell stimulating activity on GPR7-expressed cells (e.g., the activity that promotes arachidonic acid release, acetylcholine release, intracellular $Ca^{2+}$ release, intracellular cAMP production, intracellular cGMP production, inositol phosphate production, change in cell membrane potential, phosphorylation of intracellular proteins, activation of c-fos, pH reduction, GTPγS binding activity, etc.), and is an endogenous ligand to GPR7. Moreover, the peptide of the present invention has an appetite (eating) stimulating activity, as shown in EXAMPLE 14 later described. Besides, the peptide of the present invention is considered to act as a neuromodulator or neuroendocrine substance or to be associated with memory, learning or stress control.

Therefore, when the peptide of the present invention or the DNA of the present invention involves any abnormality or deficiency, or when GPR7 or the DNA encoding GPR7 involves any abnormality or deficiency, it is highly likely to cause various diseases, including anorexia, hypertension, autoimmune disease, heart failure, cataract, glaucoma, acute bacterial meningitis, acute myocardial infarction, acute pancreatitis, acute viral encephalitis, adult respiratory distress syndrome, alcoholic hepatitis, Alzheimer's disease, asthma, arteriosclerosis, atopic dermatitis, bacterial pneumonia, bladder cancer, fracture, breast cancer, bulimia, polyphagia, burn healing, uterine cervical cancer, chronic lymphocytic leukemia, chronic myelogenous leukemia, chronic pancreatitis, liver cirrhosis, cancer of the colon and rectum (colon cancer/rectal cancer), Crohn's disease, dementia, diabetic complications, diabetic nephropathy, diabetic neuropathy, diabetic retinopathy, gastritis, *Helicobacter pylori* bacterial infectious disease, hepatic insufficiency, hepatitis A, hepatitis B, hepatitis C, hepatitis, herpes simplex virus infectious disease, varicellazoster virus infectious disease, Hodgkin's disease, AIDS infectious disease, human papilloma virus infectious disease, hypercalcemia, hypercholesterolemia, hyperglyceridemia, hyperlipemia, infectious disease, influenza infectious disease, insulin dependent diabetes mellitus (type I), invasive staphylococcal infectious disease, malignant melanoma, cancer metastasis, multiple myeloma, allergic rhinitis, nephritis, nbn-Hodgkin's lymphoma, insulin-independent diabetes mellitus (type II), non-small cell lung cancer, organ transplantation, arthrosteitis, osteomalacia, osteopenia, osteoporosis, ovarian cancer, Behcet's disease of bone, peptic ulcer, peripheral vessel disease, prostatic cancer, reflux esophagitis, renal insufficiency, rheumatoid arthritis, schizophrenia, sepsis, septic shock, severe systemic fungal infectious disease, small cell lung cancer, spinal injury, stomach cancer, systemic lupus erythematosus, transient cerebral ischemia, tuberculosis, cardiac valve failure, vascular/multiple infarction dementia, wound healing, insomnia, arthritis, pituitary hormone secretion disorders [e.g., prolactin secretion disorders (e.g., hypoovarianism, spermatic underdevelopment, menopausal symptoms, hypothyroidism, etc.)], pollakiuria, uremia, neurodegenerative diseases (especially anorexia, etc.), or the like.

Therefore, the peptide of the present invention and the DNA of the present invention can be used as pharmaceuticals (in particular, appetite (eating) stimulants, etc.) for the treatment/prevention of various diseases as described above (especially anorexia, etc.).

When a patient has a reduced level of, or deficient in the peptide of the present invention in his or her body, the peptide of the present invention and the DNA of the present invention can provide the role of the peptide of the present invention sufficiently or properly for the patient, (a) by administering the DNA of the present invention to the patient to express the peptide of the present invention in the body, (b) by inserting the DNA of the present invention into a cell, expressing the peptide of the present invention and then transplanting the cell to the patient, or (c) by administering the peptide of the present invention to the patient, or the like.

When the DNA of the present invention is used as the preventive/therapeutic agents described above, the DNA is administered directly to human or other warm-blooded animal; alternatively, the DNA is inserted into an appropriate vector such as retrovirus vector, adenovirus vector, adenovirus-associated virus vector, etc. and then administered to human or other warm-blooded animal in a conventional manner. The DNA of the present invention may also be administered as an intact DNA, or prepared into pharmaceutical preparations together with a physiologically acceptable carrier such as an adjuvant to assist its uptake and administered by gene gun or through a catheter such as a catheter with a hydrogel.

Where the peptide of the present invention is used as the aforesaid therapeutic/preventive agents, the peptide is advantageously used on a purity level of at least 90%, preferably at least 95%, more preferably at least 98% and most preferably at least 99%.

The peptide of the present invention can be used orally, for example, in the form of tablets which may be sugar coated if necessary, capsules, elixirs, microcapsules etc., or parenterally in the form of injectable preparations such as a sterile solution and a suspension in water or with other pharmaceutically acceptable liquid. These preparations can be manufactured by mixing the peptide of the present invention with a physiologically acceptable known carrier, a flavoring agent, an excipient, a vehicle, an antiseptic agent, a stabilizer, a binder, etc. in a unit dosage form required in a generally accepted manner that is applied to making pharmaceutical preparations. The active ingredient in the preparation is controlled in such a dose that an appropriate dose is obtained within the specified range given.

Additives miscible with tablets, capsules, etc. include a binder such as gelatin, corn starch, tragacanth and gum arabic, an excipient such as crystalline cellulose, a swelling agent such as corn starch, gelatin, alginic acid, etc., a lubricant such as magnesium stearate, a sweetening agent such as sucrose, lactose and saccharin, and a flavoring agent such as peppermint, akamono oil or cherry, etc. When the unit dosage is in the form of capsules, liquid carriers such as oils and fats may further be used together with the additives described above. A sterile composition for injection may be formulated according to a conventional manner used to make pharmaceutical compositions, e.g., by dissolving or suspending the active ingredients in a vehicle such as water for injection with a naturally occurring vegetable oil such as sesame oil and coconut oil, etc. to prepare the pharmaceutical composition.

Examples of an aqueous medium for injection include physiological saline and an isotonic solution containing glucose and other auxiliary agents (e.g., D-sorbitol, D-mannitol, sodium chloride, etc.) and may be used in combination with an appropriate dissolution aid such as an alcohol (e.g., ethanol or the like), a polyalcohol (e.g., propylene glycol and polyethylene glycol), a nonionic surfactant (e.g., polysorbate 80™ and HCO-50), etc. Examples of the oily medium include sesame oil and soybean oil, which may also be used in combination with a dissolution aid such as benzyl benzoate and benzyl alcohol. The prophylactic/therapeutic agent described above may further be formulated with a buffer (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus-prepared liquid for injection is normally filled in an appropriate ampoule.

The vector in which the DNA of the present invention is inserted may also be prepared into pharmaceutical preparations in a manner similar to the procedures above. Such preparations are generally used parenterally.

Since the thus obtained pharmaceutical preparation is safe and low toxic, the preparation can be administered to human or other warm-blooded animals (e.g., rats, mice, guinea pigs, rabbits, chicken, sheep, swine, bovine, horses, cats, dogs, monkeys, etc.).

The dose of the peptide of the present invention varies depending on target disease, subject to be administered, route for administration, etc.; in oral administration, e.g., for the treatment of anorexia, the dose is normally about 0.1 mg to about 100 mg, preferably about 1.0 to about 50 mg, and more preferably about 1.0 to about 20 mg per day for adult (as 60 kg body weight). In parenteral administration, the single dose varies depending on subject to be administered, target disease, etc. but it is advantageous, e.g., for the treatment of anorexia to administer the active ingredient intravenously at a daily dose of about 0.01 to about 30 mg, preferably about 0.1 to about 20 mg, and more preferably about 0.1 to about 10 mg for adult (as 60 kg body weight). For other animal species, the corresponding dose as converted per 60 kg body weight can be administered.

(2) Screening of Drug Candidate Compounds for Diseases (2-1) Screening Method A

Since the peptide of the present invention has the function to act as the ligand to GPR7, the compounds or salts thereof that promote the function of the peptide of the present invention can be used as drugs for the treatment/prevention of diseases such as anorexia, hypertension, autoimmune disease, heart failure, cataract, glaucoma, acute bacterial meningitis, acute myocardial infarction, acute pancreatitis, acute viral encephalitis, adult respiratory distress syndrome, alcoholic hepatitis, Alzheimer's disease, asthma, arteriosclerosis, atopic dermatitis, bacterial pneumonia, bladder cancer, fracture, breast cancer, bulimia, polyphagia, burn healing, uterine cervical cancer, chronic lymphocytic leukemia, chronic myelogenous leukemia, chronic pancreatitis, liver cirrhosis, cancer of the colon and rectum (colon cancer/rectal cancer), Crohn's disease, dementia, diabetic complications, diabetic nephropathy, diabetic neuropathy, diabetic retinopathy, gastritis, *Helicobacter pylori* bacterial infectious disease, hepatic insufficiency, hepatitis A, hepatitis B, hepatitis C, hepatitis, herpes simplex virus infectious disease, varicellazoster virus infectious disease, Hodgkin's disease, AIDS infectious disease, human papilloma virus infectious disease, hypercalcemia, hypercholesterolemia, hyperglyceridemia, hyperlipemia, infectious disease, influenza infectious disease, insulin dependent diabetes mellitus (type I), invasive staphylococcal infectious disease, malignant melanoma, cancer metastasis, multiple myeloma, allergic rhinitis, nephritis, non-Hodgkin's lymphoma, insulin-independent diabetes mellitus (type II), non-small cell lung cancer, organ transplantation, arthrosteitis, osteomalacia, osteopenia, osteoporosis, ovarian cancer, Behcet's disease of bone, peptic ulcer, peripheral vessel disease, prostatic cancer, reflux esophagitis, renal insufficiency, rheumatoid arthritis, schizophrenia, sepsis, septic shock, severe systemic fungal infectious disease, small cell lung cancer, spinal injury, stomach cancer, systemic lupus erythematosus, transient cerebral ischemia, tuberculosis, cardiac valve failure, vascular/multiple infarction dementia, wound healing, insomnia, arthritis, pituitary hormone secretion disorders [e.g., prolactin secretion disorders (e.g., hypoovarianism, spermatic underdevelopment, menopausal symptoms, hypothyroidism, etc.)], pollakiuria, uremia, neurodegenerative disease (especially anorexia, etc.), or the like.

On the other hand, the compounds or salts thereof that inhibit the function of the peptide of the present invention are useful as safe and low-toxic drugs for the prevention/treatment of, e.g., obesity (e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity, etc.), hyperphagia, etc.; as safe and low-toxic drugs for the treatment/prevention (prolactin production suppressing agents) for pituitary tumor, diencephalon tumor, menstrual disorder, autoimmune disease, prolactinoma, sterility, impotence, amenorrhea, lactorrhea, acromegaly, Chiari-Frommel syndrome, Argonz-del Castillo syndrome, Forbes-Albright syndrome, lymphoma or Sheehan's syndrome, spermatogenesis disorder, etc., preferably, as safe and low-toxic drugs for the prevention/treatment of obesity, hyperphagia, etc.

By using the peptide of the present invention, or by constructing the expression system of the recombinant peptide of the present invention and using the receptor-binding assay system via the expression system, compounds that alter the binding property between the peptide of the present invention and GPR7 (compounds that promote or inhibit the activities of the peptide of the present invention) (e.g., peptide, protein, a non-peptide compound, a synthetic compound, fermentation product, etc.), or salts thereof, can be screened. Such compounds include compounds (i.e., GPR7 agonists) that have the cell-stimulating activity of the peptide of the present invention (e.g., the activity that promotes arachidonic acid release, acetylcholine release, intracellular $Ca^{2+}$ release, intracellular cAMP production, intracellular cGMP production, inositol phosphate production, change in cell membrane potential, phosphorylation of intracellular proteins, activation of c-fos, pH reduction, GTPγ S binding activity, etc.) mediated by GPR7; compounds having no such cell-stimulating activity (i.e., GPR7 antagonists); and the like. The term "alters the binding property to the ligand" is used to include both cases where binding to the ligand is inhibited and binding to the ligand is promoted.

Thus, the present invention provides:

a method of screening a compound or its salt that promotes or inhibits the activity of the peptide of the present invention, which comprises using the peptide of the present invention, more specifically:

a method of screening a compound that alters the binding property between the peptide of the present invention and GPR7 (a compound that promotes or inhibits the activity of the peptide of the present invention) or its salt, which comprises comparing (i) the case wherein the peptide of the present invention is brought in contact with GPR7 or its partial peptide (hereinafter they are sometimes merely referred to as GPR7) and (ii) the case wherein the peptide of the present invention and a test compound are brought in contact with GPR7.

According to the screening method of the present invention, the method comprises assaying, for example, the binding amount of the ligand to GPR7, the cell-stimulating activity, etc. (i) in the case wherein the peptide of the present invention is brought in contact with GPR7 and (ii) in the case wherein the peptide of the present invention and a test compound are brought in contact with GPR7, and comparing (i) and (ii).

Specifically, the screening method of the present invention includes:

(1) a method of screening a compound that alters the binding property between the peptide of the present invention and GPR7 (a compound that promotes or inhibits the activity of the peptide of the present invention) or its salt, which comprises assaying the binding amount of a labeled form of the peptide of the present invention to GPR7, (i) in the case wherein a labeled form of the peptide of the present invention is brought in contact with GPR7 and (ii) in the case wherein a labeled form of the peptide of the present invention and a test compound are brought in contact with GPR7, and comparing (i) and (ii);

(2) a method of screening a compound that alters the binding property between the peptide of the present invention and GPR7 (a compound that promotes or inhibits the activity of the peptide of the present invention) or its salt, which comprises assaying the binding amount of a labeled form of the peptide of the present invention to a cell containing GPR7 or its cell membrane, (i) in the case wherein a labeled form of the peptide of the present invention is brought in contact with the cell containing GPR7 or its cell membrane and (ii) in the case wherein a labeled form of the peptide of the present invention and a test compound are brought in contact with the cell containing GPR7 or its cell membrane, and comparing (i) and (ii);

(3) a method of screening a compound that alters the binding property between the peptide of the present invention and GPR7 (a compound that promotes or inhibits the activity of the peptide of the present invention) or its salt, which comprises assaying the binding amount of a labeled form of the peptide of the present invention to GPR7, (i) in the case wherein a labeled form of the peptide of the present invention is brought in contact with GPR7 expressed on a cell membrane by culturing a transformant containing a DNA encoding GPR7 and (ii) in the case wherein a labeled form of the peptide of the present invention and a test compound are brought in contact with GPR7 expressed on a cell membrane by culturing a transformant containing a DNA encoding GPR7, and comparing (i) and (ii);

(4) a method of screening a compound that alters the binding property between the peptide of the present invention and GPR7 (a compound that promotes or inhibits the activity of the peptide of the present invention) or its salt, which comprises assaying the cell-stimulating activity mediated by GPR7 (e.g., the activity that promotes or suppresses arachidonic acid release, acetylcholine release, intracellular $Ca^{2+}$ release, intracellular cAMP production, intracellular cGMP production, inositol phosphate production, change in cell membrane potential, phosphorylation of intracellular proteins, activation of c-fos, pH reduction, $GTP\gamma S$ binding activity, etc.), when a compound that activates GPR7 (e.g., the peptide of the present invention) is brought in contact with a cell containing GPR7 and when the compound that activates GPR7 and a test compound are brought in contact with a cell containing GPR7, and comparing the activity; and, (5) a method of screening a compound that alters the binding property between the peptide of the present invention and GPR7 (a compound that promotes or inhibits the activity of the peptide of the present invention) or its salt, which comprises assaying the cell-stimulating activity mediated by GPR7 (e.g., the activity that promotes or suppresses arachidonic acid release, acetylcholine release, intracellular $Ca^{2+}$ release, intracellular cAMP production, intracellular cGMP production, inositol phosphate production, change in cell membrane potential, phosphorylation of intracellular proteins, activation of c-fos, pH reduction, $GTP\gamma S$ binding activity, etc.), when a compound that activates GPR7 (e.g., the peptide of the present invention, etc.) is brought in contact with GPR7 expressed on a cell membrane by culturing a transformant containing a DNA encoding GPR7 and when the compound that activates GPR7 and a test compound are brought in contact with GPR7 expressed on a cell membrane by culturing a transformant containing a DNA encoding GPR7, and comparing the activity; etc.

The screening method of the present invention will be described below more specifically.

First, the GPR7, which is used for the screening method of the present invention, may be any protein, so long as it recognizes the peptide of the present invention as a ligand, and membrane fractions from human or other warm-blooded animal organs are preferably employed. However, it is very difficult to obtain human-derived organs especially, and the GPR7, etc. expressed abundantly by use of recombinants are suitable for use in the screening. GPR7 may be manufactured by the methods described above.

Where the cell containing GPR7 or its cell membrane fraction is used in the screening method of the present invention, the procedures later described may apply.

When the cell containing GPR7 is used, the cell may be fixed with glutaraldehyde, formalin, etc. The fixation may be carried out by a publicly known method.

The cell containing GPR7 refers to a host cell expressing GPR7. Examples of such a host cell include *Escherichia coli, Bacillus subtilis*, yeast, insect cells, animal cells, etc. Host cells in which GPR7 is expressed may be prepared in a manner similar to the above-stated method for manufacturing transformants transformed by expression vectors containing the peptide of the present invention.

The membrane fraction refers to a fraction that abundantly contains cell membranes prepared by publicly known methods after disrupting cells. Examples of the cell disruption include cell squashing using a Potter-Elvehjem homogenizer, disruption using a Waring blender or Polytron (manufactured by Kinematica Inc.), disruption by ultrasonication, disruption by cell spraying via a thin nozzle under increasing pressure using a French press, etc., and the like. Cell membranes are fractionated mainly by fractionation using a centrifugal force such as for fractionation centrifugation, density gradient centrifugation, etc. For example, cell disruption fluid is centrifuged at a low rate (500 rpm to 3,000 rpm) for a short period of time (normally about 1 minute to about 10 minutes), the resulting supernatant is then centrifuged at a higher rate (15,000 rpm to 30,000 rpm) normally for 30 minutes to 2 hours. The precipitate thus obtained is used as the membrane fraction. The membrane fraction is rich in GPR7 expressed and membrane components such as cell-derived phospholipids, membrane proteins, or the like.

The amount of GPR7 contained in the cells containing GPR7 or in the membrane fraction is preferably $10^3$ to $10^8$ molecules per cell, more preferably $10^5$ to $10^7$ molecules per cell. As the amount of expression increases, the ligand binding activity per unit of membrane fraction (specific activity) increases so that not only the highly sensitive screening system can be constructed but also large quantities of samples can be assayed with the same lot.

To perform the methods (1) through (3) for screening the compound that alters the binding property between the peptide of the present invention and GPR7 (the compound that promotes or inhibits the activity of the peptide of the present invention), an appropriate GPR7 fraction and a labeled form of the peptide of the present invention, etc. are required. The GPR7 fraction is preferably a fraction of a naturally occurring form of GPR7 or a fraction of a recombinant type of GPR7 having an equivalent activity. Herein, the term equivalent activity is intended to mean a ligand binding activity, etc. that is equivalent to the activity possessed by naturally occurring GPR7. As the labeled ligand, there may be used a labeled ligand, a labeled ligand analog compound, etc. For example, there may be used ligands that are labeled with [$^3$H], [$^{125}$I], [$^{14}$C], [$^{35}$S], etc. Of these, [$^{125}$I]-labeled ligand is preferred.

Specifically, the compound that alters the binding property between the peptide of the present invention and GPR7 is screened by the following procedures. First, a receptor preparation is prepared by suspending cells containing GPR7 or the membrane fraction thereof in a buffer appropriate for use in the screening method. Any buffer can be used so long as it does not interfere the ligand-receptor binding, including a phosphate buffer or a Tris-HCl buffer, having pH of 4 to 10 (preferably pH of 6 to 8), etc. For the purpose of minimizing non-specific binding, a surfactant such as CHAPS, Tween-80™ (Kao-Atlas Inc.), digitonin, deoxycholate, etc., may optionally be added to the buffer. Further for the purpose of suppressing the degradation of GPR7 or the peptide of the present invention with a protease, a protease inhibitor such as PMSF, leupeptin, E-64 (manufactured by Peptide Institute, Inc.), pepstatin, etc. may also be added. A given amount (5,000 cpr to 500,000 cpm) of the labeled peptide of the present invention is added to 0.01 ml to 10 ml of the receptor solution, in which $10^{-10}$ M to $10^{-7}$ M of a test compound is co-present. To determine the amount of non-specific binding (NSB), a reaction tube charged with an unlabeled form of the peptide of the present invention in a large excess is also provided. The reaction is carried out at approximately 0° C. to 50° C., preferably 4° C. to 37° C. for 20 minutes to 24 hours, preferably 30 minutes to 3 hours. After completion of the reaction, the reaction mixture is filtrated through glass fiber filter paper, etc. and washed with an appropriate volume of the same buffer. The residual radioactivity on the glass fiber filter paper is then measured by means of a liquid scintillation counter or γ-counter. When nonspecific binding (NSB) is subtracted from the count ($B_0$) where any antagonizing substance is absent and the resulting count ($B_0$ minus NSB) is made 100%, the test compound showing the specific binding amount (B minus NSB) of, e.g., 50% or less may be selected as a candidate compound.

The method (4) or (5) described above for screening the compound that alters the binding property between the peptide of the present invention and GPR7 (the compound that promotes or inhibits the activity of the peptide of the present invention) can be carried out as follows. For example, the cell stimulating activity mediated by GPR7 (e.g., the activity that promotes or suppresses arachidonic acid release, acetylcholine release, intracellular $Ca^{2+}$ release, intracellular cAMP production, intracellular cGMP production, inositol phosphate production, change in cell membrane potential, phosphorylation of intracellular proteins, activation of c-fos, pH reduction, GTPγ S binding activity, etc.) may be determined by a publicly known method, or using an assay kit commercially available. Specifically, the cells containing GPR7 are first cultured on a multiwell plate, etc. Prior to screening, the medium is replaced with fresh medium or with an appropriate non-cytotoxic buffer, followed by incubation for a given period of time in the presence of a test compound, etc. Subsequently, the cells are extracted or the supernatant is recovered and the resulting product is quantified by appropriate procedures. Where it is difficult to detect the production of the cell-stimulating activity indicator (e.g., arachidonic acid, etc.) due to a degrading enzyme contained in the cells, an inhibitor against such as a degrading enzyme may be added prior to the assay. For detecting the activity such as the cAMP production suppression, the baseline production in the cells is increased by forskolin or the like and the suppressing effect on the increased baseline production can be detected.

For screening through the assay of the cell stimulating activity, appropriate cells, in which GPR7 is expressed, are required. Preferred cells, in which GPR7 is expressed, are the aforesaid cell line in which GPR7 is expressed, etc.

Examples of the test compounds include peptides, proteins, non-peptide compounds, synthetic compounds, fermentation products, cell extracts, plant extracts, animal tissue extracts, etc.

The kit for screening the compound or a salt thereof that alters the binding property between the peptide of the present invention (the compound that promotes or inhibits the activity of the peptide of the present invention) and GPR7 comprises GPR7 or its salt, a partial peptide of GPR7 or its salt, cells containing GPR7 or a membrane fraction of the cells containing GPR7, and the peptide of the present invention.

Examples of the screening kit of the present invention are given below:

1. Reagent for Screening (1) Assay Buffer and Wash Buffer

Hanks' Balanced Salt Solution (manufactured by Gibco Co.) supplemented with 0.05% bovine serum albumin (Sigma Co.).

The solution is sterilized by filtration through a 0.45 μm filter and stored at 4° C. Alternatively, the solution may be prepared at use.

(2) GPR7 Preparation

CHO cells on which GPR7 has been expressed are subcultured in a 12-well plate at the rate of $5 \times 10^5$ cells/well and then cultured at 37° C. under 5% $CO_2$ and 95% air for 2 days.

(3) Labeled Ligand

The peptide of the present invention labeled with commercially available [$^3$H], [$^{125}$I], [$^{14}$C], [$^{35}$S], etc. is dissolved in a suitable solvent or buffer. The solution is stored at 4° C. or −20° C., which is diluted to 1 μM with an assay buffer at use.

(4) Standard Ligand Solution

The peptide of the present invention is dissolved in PBS supplemented with 0.1% bovine serum albumin (manufactured by Sigma, Inc.) in a concentration of 1 mM, and the solution is stored at −20° C.

2. Assay Method (1) Cells are cultured in a 12-well tissue culture plate to express GPR7. After washing the cells twice with 1 ml of the assay buffer, 490 µl of the assay buffer is added to each well.

(2) After 5 µl of a test compound solution of $10^{-3}$ to $10^{-10}$ M is added, 5 µl of a labeled form of the peptide of the present invention is added to the system followed by reacting at room temperature for an hour. To determine the amount of the non-specific binding, the peptide of the present invention of $10^{-3}$ M is added in an amount of 5 µl, instead of the test compound.

(3) The reaction mixture is removed and washed 3 times with 1 ml each of the wash buffer. The labeled peptide of the present invention bound to the cells is dissolved in 0.2N NaOH-1% SDS and mixed with 4 ml of a liquid scintillator A (manufactured by Wako Pure Chemical Industries, Ltd.).

(4) Radioactivity is measured using a liquid scintillation counter (manufactured by Beckmann) and PMB (percent of the maximum binding) is calculated in accordance with the following equation 1:

$$PMB = [(B-NSB)/(B_0-NSB)] \times 100$$

wherein:
PMB: percent of the maximum binding
B: value when a sample is added
NSB: non-specific binding
$B_0$: maximum binding The compound or its salt, which can be obtained by the screening method or the screening kit of the present invention, is the compound that alters the binding property between the peptide of the present invention and GPR7 (the compound that promotes or inhibits the activity of the peptide of the present invention). Specifically, these compounds are compounds or salts thereof that exhibit the cell stimulating activity mediated by GPR7 (i.e., GPR7 agonist), or compounds that have no such cell stimulating activity (i.e., GPR7 antagonist). Examples of such compounds include peptides, proteins, non-peptide compounds, synthetic compounds and fermentation products. These compounds may be either novel or publicly known compounds.

In order to evaluate whether the compound is either the GPR7 agonist or antagonist described above, it is determined by (i) or (ii) below.

(i) According to the screening methods (1) to (3), binding assay is carried out to obtain the compound that alters the binding property between the peptide of the present invention and GPR7 (especially, the compound that inhibits the binding). It is then determined if the compound has the above cell-stimulating activity mediated by GPR7. The compound or its salt having the cell-stimulating activity is the GPR7 agonist, whereas the compound or its salt having no such an activity is the GPR7 antagonist.

(ii) (a) A test compound is brought in contact with a cell containing GPR7, whereby the aforesaid cell-stimulating activity mediated by GPR7 is assayed. The compound having the cell-stimulating activity or its salt is the GPR7 agonist.

(b) The cell-stimulating activity mediated by GPR7 is assayed in the case where a compound that activates GPR7 (e.g., the peptide of the present invention or GPR7 agonist, etc.) is brought in contact with cells containing GPR7 and in the case where the compound that activates GPR7 and a test compound are brought in contact with cells containing GPR7, and comparison is made therebetween. The compound or its salt that can reduce the cell-stimulating activity induced by the compound that activates GPR7 is the GPR7 antagonist.

The GPR7 agonists exhibit similar physiological activity of the peptide of the present invention on GPR7, and are thus safe and low-toxic drugs (e.g., preventive/therapeutic drugs for anorexia, appetite (eating) stimulants, preventive/therapeutic drugs for pituitary hormone secretion disorders [e.g., prolactin secretion disorders (e.g., hypoovarianism, spermatic underdevelopment, menopausal symptoms, hypothyroidism, etc.)].

On the contrary, the GPR7 antagonist can suppress the physiological activity that the peptide of the present invention has on GPR7, and are thus useful as safe and low-toxic drugs for the prevention/treatment of, e.g., obesity (e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity, etc.), hyperphagia, etc.; as safe and low-toxic drugs for the treatment/prevention (prolactin production suppressing agents) for pituitary tumor, diencephalon tumor, menstrual disorder, autoimmune disease, prolactinoma, sterility, impotence, amenorrhea, lactorrhea, acromegaly, Chiari-Frommel syndrome, Argonz-del Castillo syndrome, Forbes-Albright syndrome, lymphoma or Sheehan's syndrome, spermatogenesis disorder, etc.; preferably as safe and low-toxic preventive/therapeutic agents for obesity, hyperphagia, etc.

The compound or its salt, which can be obtained by using the screening method A or the screening kit of the present invention, is selected from, e.g., peptides, proteins, non-peptide compounds, synthetic compounds, fermentation products, cell extracts, plant extracts, animal tissue extracts, plasma, etc., and is the compound that promotes or inhibits the function of the peptide of the present invention.

As salts of the compound, those similar to the salts of the peptide of the present invention described above may be used.

When the compound obtained by the screening method A or screening kit of the present invention is used as the therapeutic/preventive agent described above, the compound can be prepared into pharmaceutical preparations in a conventional manner. For example, the compound may be prepared in the form of tablets, capsules, elixir, microcapsule, a sterile solution, a suspension, etc., as in the aforesaid drugs containing the peptide of the present invention.

Since the thus obtained pharmaceutical preparation is safe and low toxic, the preparation may be administered to human or other warm-blooded animals (e.g., mice, rats, rabbits, sheep, swine, bovine, horses, chicken, cats, dogs, monkeys, chimpanzees, etc.).

The dose of the compound or its salt varies depending on its activity, target disease, subject to be administered, route for administration, etc.; where the GPR7 agonist is orally administered, e.g., for the treatment of anorexia, the dose of the compound is normally about 0.1 to about 100 mg, preferably about 1.0 to about 50 mg, and more preferably about 1.0 to about 20 mg per day for adult (as 60 kg body weight). In parenteral administration, a single dose of the compound varies depending on subject to be administered, target disease, etc. When the GPR7 agonist is administered to adult (as 60 kg body weight) in the form of injection, e.g., for the treatment of anorexia, it is advantageous to administer the compound intravenously to adult generally at a daily dose of about 0.01 to about 30 mg, preferably about 0.1 to about 20 mg, and more preferably about 0.1 to about 10 mg. For other animal species, the corresponding dose as converted per 60 kg body weight can be administered.

Also, when the GPR7 antagonist is orally administered to adult (per 60 kg body weight), e.g., for the treatment of obesity, a daily dose of the compound administered is generally approximately 0.1 to 100 mg, preferably approximately 1.0 to 50 mg, and more preferably approximately 1.0 to 20 mg. In parenteral administration, a single dose of the compound varies depending on subject to be administered, target disease, etc. When the GPR7 antagonist is administered to adult (as 60 kg body weight) in the form of injection, e.g., for the treatment of obesity, it is advantageous to administer the compound intravenously to adult (per 60 kg body weight) generally at a daily dose of about 0.01 to about 30 mg, preferably about 0.1 to about 20 mg, and more preferably about 0.1 to about 10 mg. For other animal species, the corresponding dose as converted per 60 kg body weight can be administered.

(2-2) Screening Method B

Next, the method of screening a compound that regulates the expression level of GPR7 ligand is explained below.

The screening method B of the present invention is specifically (i) a method of screening a compound or its salt that increases or decreases the expression level of GPR7 ligand, which comprises assaying the expression level of GPR7 ligand or the amount of mRNA encoding GPR7 ligand in the case that a cell or tissue capable of expressing GPR7 ligand is cultured in the presence or absence of a test compound, and comparing the expression level in each case.

As the cell or tissue capable of expressing GPR7 ligand, there may be used a cell or tissue derived from human or other warm-blooded animals (e.g. guinea pigs, rats, mice, chicken, rabbits, swine, sheep, bovine, monkeys, etc.); any cell (e.g., nerve cells, endocrine cells, neuroendocrine cells, glial cells, β cells of pancreas, bone marrow cells, hepatocytes, splenocytes, mesangial cells, epidermic cells, epithelial cells, endothelial cells, fibroblasts, fibrocytes, myocytes, fat cells, immune cells (e.g., macrophages, T cells, B cells, natural killer cells, mast cells, neutrophils, basophils, eosinophils, monocytes, dendritic cells), megakaryocyte, synovial cells, chondrocytes, bone cells, osteoblasts, osteoclasts, mammary gland cells or interstitial cells, the corresponding precursor cells, stem cells, cancer cells, etc., of these cells), or any tissue where such a cell is present, e.g., brain or any region of the brain (e.g., olfactory bulb, amygdaloid nucleus, basal ganglia, hippocampus, thalamus, hypothalamus, cerebral cortex, medulla oblongata, cerebellum), spinal cord, hypophysis, stomach, pancreas, kidney, liver, gonad, thyroid, gall-bladder, bone marrow, adrenal gland, skin, muscle, lung, gastrointestinal tract (e.g., large intestine and small intestine), blood vessel, heart, thymus, spleen, submandibular gland, peripheral blood, prostate, testis, ovary, placenta, uterus, bone, cartilage, joint, skeletal muscle, etc., wherein established cell line or primary culture system may also be used. Transformants transformed by a recombinant vector bearing a DNA encoding GPR7 ligand described above may also be used.

To cultivate the cells capable of expressing GPR7 ligand, the method given for cultivating transformants above applies.

As the test compound, a DNA library may also be used, in addition to the test compounds described above.

The expression level of GPR7 ligand can be determined by publicly known methods such as immunochemical methods, etc., using an antibody, etc. Alternatively, mRNA encoding GPR7 ligand can be determined by publicly known methods including northern hybridization, RT-PCR or TaqMan PCR.

Comparison of the expression level of mRNA can be made by publicly known methods or a modification thereof, for example, according to the method described in Molecular Cloning, 2nd (J. Sambrook et al., Cold Spring Harbor Lab. Press, 1989).

Specifically, the amount of mRNA encoding GPR7 ligand is determined by contacting RNA extracted from cells according to publicly known methods with the DNA encoding GPR7 ligand or a part thereof or the antisense polynucleotide of the present invention, and assaying the amount of mRNA bound to the DNA encoding GPR7 ligand or a part thereof or the antisense polynucleotide of the present invention. The amount of mRNA bound to the DNA encoding GPR7 ligand or a part thereof or the antisense polynucleotide of the present invention can be readily assayed by labeling the DNA encoding GPR7 ligand or a part thereof or the antisense polynucleotide of the present invention with, e.g., a radioisotope, a dye, etc. Examples of the radioisotope are $^{32}P$, $^3H$, etc. Examples of the dye used are fluorescent dyes such as fluorescein, FAM (Biosystems, Inc.), JOE (PE Biosystems, Inc.), TAMRA (PE Biosystems, Inc.), ROX (PE Biosystems, Inc.), Cy5 (Amersham), Cy3 (Amersham), etc.

The amount of mRNA can also be determined by converting RNA extracted from cells into cDNA by a reverse transcriptase, amplifying the cDNA by PCR using the DNA encoding GPR7 ligand or a part thereof or the antisense polynucleotide of the present invention as a primer, and assaying the amount of cDNA amplified.

As described above, the test compound that increases the amount of mRNA encoding GPR7 ligand can be selected as a compound that increases the expression level of GPR7 ligand. Also, the test compound that decreases the amount of mRNA encoding GPR7 ligand can be selected as a compound that decreases the expression level of GPR7 ligand.

The present invention further provides:

(ii) a method of screening a compound or its salt that promotes or inhibits a reporter activity, which comprises assaying the expression level of GPR7 ligand or the amount of mRNA encoding GPR7 ligand in the case that a cell or tissue capable of expressing GPR7 ligand is cultured in the presence or absence of a test compound, and comparing the expression level in each case.

As the reporter gene, there may be employed, e.g., lacZ (β-galactosidase gene), chloramphenicol acetyltransferase (CAT), luciferase, growth factor, β-glcuronidase, alkaline phosphatase, green fluorescent protein (GFP), β-lactamase, etc.

By determining the level of the reporter gene product (e.g., mRNA, protein) Using publicly known methods, the test compound that increases the level of the reporter gene product can be selected as the compound having the activity of regulating (especially promoting) the promoter or enhancer activity of GPR7 ligand of the present invention, i.e., the compound having the activity of increasing the expression level of GPR7 ligand. To the contrary, the test compound that decreases the level of the reporter gene product can be selected as the compound having the activity of regulating (especially inhibiting) the promoter or enhancer activity of GPR7 ligand, i.e., the compound having the activity of decreasing the expression level of GPR7 ligand.

As the test compounds, those described above are employed.

The transformants can be cultivated as in the transformants described above.

Construction of vectors for the reporter genes and assay can be performed according to publicly known techniques (e.g., Molecular Biotechnology, 13, 29-43, 1999).

The compounds having the activity of increasing the expression level of GPR7 are useful as safe and low-toxic drugs (e.g., preventive/therapeutic agents for anorexia, appetite (eating) stimulants, preventive/therapeutic agents for pituitary hormone secretion disorders [e.g., prolactin secretion disorders (e.g., hypoovarianism, spermatic underdevelopment, menopausal symptoms, hypothyroidism, etc.)].

The compounds having the activity of decreasing the expression level of GPR7 ligand are useful as safe and low-toxic drugs for the prevention/treatment of obesity (e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity, etc.), hyperphagia, etc.; as safe and low-toxic drugs for the prevention/treatment (prolactin production suppressing agents) for pituitary tumor, diencephalon tumor, menstrual disorders, autoimmune disease, prolactinoma, sterility, impotence, amenorrhea, lactorrhea, acromegaly, Chiari-Frommel syndrome, Argonz-del Castillo syndrome, Forbes-Albright syndrome, lymphoma or Sheehan's syndrome, spermatogenesis disorder, etc.; preferably, as safe and low-toxic drugs for the prevention/treatment of obesity, hyperphagia, etc.

The compound or its salt, which can be obtained by using the screening method B or the screening kit of the present invention, is a compound selected from, e.g., peptides, proteins, non-peptide compounds, synthetic compounds, fermentation products, cell extracts, plant extracts, animal tissue extracts, plasma, etc., and is the compound that promotes or inhibits the function of the peptide of the present invention.

For salts of the compound, those as described for the peptide of the present invention are employed.

When the compound obtained by the screening method B or screening kit of the present invention is used as the therapeutic/preventive agent described above, the compound can be prepared into pharmaceutical preparations in a conventional manner. For example, the compound may be prepared in the form of tablets, capsules, elixir, microcapsule, a sterile solution, a suspension, etc., as in the aforesaid drugs containing the peptide of the present invention.

Since the thus obtained pharmaceutical preparation is safe and low toxic, the preparation may be administered to human or other warm-blooded animals (e.g., mice, rats, rabbits, sheep, swine, bovine, horses, chicken, cats, dogs, monkeys, chimpanzees, etc.).

The dose of the compound or its salt varies depending on its activity, target disease, subject to be administered, route for administration, etc.; where the compound that increases the expression level of GPR7 ligand is orally administered, e.g., for the treatment of anorexia, the dose of the compound is normally about 0.1 to about 100 mg, preferably about 1.0 to about 50 mg, and more preferably about 1.0 to about 20 mg per day for adult (as 60 kg body weight). In parenteral administration, a single dose of the compound varies depending on subject to be administered, target disease, etc. When the compound that increases the expression level of GPR7 ligand is administered to adult (as 60 kg body weight) in the form of injection, e.g., for the treatment of anorexia, it is advantageous to administer the compound intravenously to adult generally at a daily dose of about 0.01 to about 30 mg, preferably about 0.1 to about 20 mg, and more preferably about 0.1 to about 10 mg. For other animal species, the corresponding dose as converted per 60 kg body weight can be administered.

Also, when the compound that decreases the expression level of GPR7 ligand is orally administered to adult (per 60 kg body weight), e.g., for the treatment of obesity, a daily dose of the compound administered is generally approximately 0.1 to 100 mg, preferably approximately 1.0 to 50 mg, and more preferably approximately 1.0 to. 20 mg. In parenteral administration, a single dose of the compound varies depending on subject to be administered, target disease, etc. When the compound that decreases the expression level of GPR7 ligand is administered to adult (as 60 kg body weight) in the form of injection, e.g., for the treatment of obesity, it is advantageous to administer the compound intravenously to adult (per 60 kg body weight) generally at a daily dose of about 0.01 to about 30 mg, preferably about 0.1 to about 20 mg, and more preferably about 0.1 to about 10 mg. For other animal species, the corresponding dose as converted per 60 kg body weight can be administered.

(3) Quantification of the Peptide of the Present Invention

The antibody of the present invention is capable of specifically recognizing the peptide of the present invention, and can thus be used for quantification of the peptide of the present invention in a sample fluid, in particular, for quantification by sandwich immunoassay.

That is, the present invention provides:

(i) a method for quantification of the peptide of the present invention in a sample fluid, which comprises competitively reacting the antibody of the present invention with a sample fluid and a labeled form of the peptide of the present invention, and measuring a ratio of the labeled peptide of the present invention bound to the antibody; and, (ii) a method for quantification of the peptide of the present invention in a sample fluid, which comprises simultaneously or continuously reacting the sample fluid with the antibody of the present invention and a labeled form of another antibody of the present invention immobilized on an insoluble carrier, and measuring the activity of the labeling agent on the immobilized carrier.

In the method of quantification (ii) described above, it is preferred that one antibody is capable of recognizing the N-terminal region of the peptide of the present invention, while another antibody is capable of recognizing the C-terminal region of the peptide of the present invention.

The monoclonal antibody to the peptide of the present invention may be used to quantify the peptide of the present invention. Moreover, the peptide of the present invention may also be detected by means of a tissue staining, etc. For these purposes, the antibody molecule per se may be used, or $F(ab')_2$, Fab' or Fab fractions of the antibody molecule may be used as well.

The method of quantifying the peptide of the present invention using the antibody of the present invention is not particularly limited, and any method may be used so far as it relates to a method, in which the amount of an antibody, antigen or antibody-antigen complex can be detected by a chemical or a physical means, depending on or corresponding to the amount of antigen (e.g., the amount of the peptide) in a sample fluid to be assayed, and then calculated using a standard curve prepared by a standard solution containing the known amount of antigen. Advantageously used are, for example, nephrometry, competitive method, immunometric method and sandwich method; in terms of sensitivity and specificity, the sandwich method, which will be described later, is particularly preferred.

Examples of labeling agents, which are employed for the assay method using the same, are radioisotopes, enzymes, fluorescent substances, luminescent substances, etc. Examples of radioisotopes are [$^{125}$I], [$^{131}$I], [$^{3}$H], [$^{14}$C], etc. Preferred examples of enzymes are those that are stable and have a high specific activity, which include β-galactosidase, β-glucosidase, alkaline phosphatase, peroxidase, malate dehydrogenase, etc. Examples of fluorescent substances are fluorescamine, fluorescein isothiocyanate, etc. Examples of luminescent substances are luminol, a luminol derivative, luciferin, lucigenin, etc. Furthermore, a biotin-avidin system may be used as well for binding an antibody or antigen to a labeling agent.

In the immobilization of antigens or antibodies, physical adsorption may be used. Alternatively, chemical binding that is conventionally used for immobilization of proteins, enzymes, etc. may be used as well. Examples of the carrier include insoluble polysaccharides such as agarose, dextran, cellulose, etc.; synthetic resins such as polystyrene, polyacrylamide, silicone, etc.; or glass; and the like.

In the sandwich method, a sample fluid is reacted with an immobilized form of the monoclonal antibody of the present invention (primary reaction), then reacted with a labeled form of the monoclonal antibody of the present invention (secondary reaction) and the activity of the labeling agent on the insoluble carrier is assayed; thus, the amount of the peptide of the present invention in a sample fluid can be determined. The primary and secondary reactions may be carried out in a reversed order, simultaneously or sequentially with intervals. The type of the labeling agent and the method of immobilization may be the same as those described hereinabove. In the immunoassay by the sandwich method, it is not always necessary that the antibody used for the labeled antibody and for the solid phase should be one type or one species but a mixture of two or more antibodies may also be used for the purpose of improving the assay sensitivity, etc.

In the method of assaying the peptide of the present invention by the sandwich method according to the present invention, preferred monoclonal antibodies of the present invention used for the primary and the secondary reactions are antibodies, which binding sites to the peptide of the present invention are different from each other. Thus, the antibodies used in the primary and secondary reactions are those wherein, when the antibody used in the secondary reaction recognizes the C-terminal region of the peptide of the present invention, the antibody recognizing the site other than the C-terminal regions, e.g., recognizing the N-terminal region, is preferably used in the primary reaction.

The monoclonal antibody of the present invention may be used in an assay system other than the sandwich method, such as the competitive method, the immunometric method or the nephrometry.

In the competitive method, an antigen in a sample fluid and a labeled antigen are competitively reacted with an antibody, then an unreacted labeled antigen (F) and a labeled antigen bound to the antibody (B) are separated (i.e., B/F separation) and the labeled amount of either B or F is measured to determine the amount of the antigen in the sample fluid. In the reactions for such a method, there are a liquid phase method in which a soluble antibody is used as the antibody and the B/F separation is effected by polyethylene glycol, while a second antibody to the antibody is used, and a solid phase method in which an immobilized antibody is used as the first antibody or a soluble antibody is used as the first antibody, while an immobilized antibody is used as the second antibody.

In the immunometric method, an antigen in a sample fluid and an immobilized antigen are competitively reacted with a given amount of a labeled antibody followed by separating the solid phase from the liquid phase; or an antigen in a sample fluid and an excess amount of labeled antibody are reacted, then an immobilized antigen is added to bind an unreacted labeled antibody to the solid phase and the solid phase is separated from the liquid phase. Thereafter, the labeled amount of any of the phases is measured to determine the antigen amount in the sample fluid.

In the nephrometry, the amount of insoluble sediment, which is produced as a result of the antigen-antibody reaction in a gel or in a solution, is measured. Even when the amount of an antigen in a sample fluid is small and only a small amount of the sediment is obtained, a laser nephrometry utilizing laser scattering can be suitably used.

In applying each of those immunoassays to the assay method of the present invention, any special conditions, operations, etc. are not required. The assay system for the peptide of the present invention may be constructed in addition to conditions or operations conventionally used for each of the methods, taking technical consideration by one skilled in the art into account. For the details of such conventional technical means, a variety of reviews, reference books, etc. may be referred to:

for example, Hiroshi Irie (ed.): "Radioimmunoassay" (published by Kodansha, 1974); Hiroshi Irie (ed.): "Radioimmunoassay; Second Series" (published by Kodansha, 1979); Eiji Ishikawa, et al. (ed.): "Enzyme Immunoassay" (published by Igaku Shoin, 1978); Eiji Ishikawa, et al. (ed.): "Enzyme Immunoassay" (Second Edition) (published by Igaku Shoin, 1982); Eiji Ishikawa, et al. (ed.): "Enzyme Immunoassay" (Third Edition) (published by Igaku Shoin, 1987); "Methods in Enzymology" Vol. 70 (Immunochemical Techniques (Part A)); ibid., Vol. 73 (Immunochemical Techniques (Part B)); ibid., Vol. 74 (Immunochemical Techniques (Part C)); ibid., Vol. 84 (Immunochemical Techniques (Part D: Selected Immunoassays)); ibid., Vol. 92 (Immunochemical Techniques (Part E: Monoclonal Antibodies and General Immunoassay Methods)); ibid., Vol. 121 (Immunochemical Techniques (Part I: Hybridoma Technology and Monoclonal Antibodies)) (all published by Academic Press); etc.

As described above, the peptide of the present invention can be quantified with high sensitivity, using the antibody of the present invention.

Furthermore, when a reduced level of the peptide of the present invention is detected by quantifying a level of the peptide of the present invention using the antibody of the present invention, it can be diagnosed that one suffers from, e.g., anorexia, hypertension, autoimmune disease, heart failure, cataract, glaucoma, acute bacterial meningitis, acute myocardial infarction, acute pancreatitis, acute viral encephalitis, adult respiratory distress syndrome, alcoholic hepatitis, Alzheimer's disease, asthma, arteriosclerosis, atopic dermatitis, bacterial pneumonia, bladder cancer, fracture, breast cancer, bulimia, polyphagia, burn healing, uterine cervical cancer, chronic lymphocytic leukemia, chronic myelogenous leukemia, chronic pancreatitis, liver cirrhosis, cancer of the colon and rectum (colon cancer/rectal cancer), Crohn's disease, dementia, diabetic complications, diabetic nephropathy, diabetic neuropathy, diabetic retinopathy, gastritis, *Helicobacter pylori* bacterial infectious disease, hepatic insufficiency, hepatitis A, hepatitis B, hepatitis C, hepatitis, herpes simplex virus infectious disease, varicella-zoster virus infectious disease, Hodgkin's disease, AIDS infectious disease, human papilloma virus infectious disease, hypercalcemia, hypercholesterolemia, hyperglyceridemia, hyperlipemia, infectious disease, influenza infectious disease, insulin dependent diabetes mellitus (type I), invasive staphylococcal infectious disease, malignant melanoma, cancer metastasis, multiple myeloma, allergic rhinitis, nephritis, non-Hodgkin's lymphoma, insulin-independent diabetes mellitus (type II), non-small cell lung cancer, organ transplantation, arthrosteitis, osteomalacia, osteopenia, osteoporosis, ovarian cancer, Behcet's disease of bone, peptic ulcer, peripheral vessel disease, prostatic cancer, reflux esophagitis, renal insufficiency, rheumatoid arthritis, schizophrenia, sepsis, septic shock, severe systemic fungal infectious disease, small cell lung cancer, spinal injury, stomach cancer, systemic lupus erythematosus, transient cerebral ischemia, tuberculosis, cardiac valve failure, vascular/multiple infarction dementia, wound healing, insomnia, arthritis, pituitary hormone secretion disorders [e.g., prolactin secretion disorders (e.g., hypoovarianism, spermatic underdevelopment, menopausal symptoms, hypothyroidism, etc.)], pollakiuria, uremia, neurodegenerative disease (especially, anorexia or the like) etc.; or it is highly likely for one to suffer from these disease in the future.

When an increased level of the peptide of the present invention is detected, it can be diagnosed that one suffers from, e.g., obesity (e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity, etc.), hyperphagia, pituitary tumor, diencephalon tumor, menstrual disorder, autoimmune disease, prolactinoma, sterility, impotence, amenorrhea, lactorrhea, acromegaly, Chiari-Frommel syndrome, Argonz-del Castillo syndrome, Forbes-Albright syndrome, lymphoma, Sheehan's syndrome, spermatogenesis disorder (especially, obesity, or the like), etc.; or it is highly likely for one to suffer from these disease in the future.

The antibody of the present invention may also be employed to detect the peptide of the present invention present in a sample fluid such as body fluids, tissues, etc. The antibody may further be used for the preparation of an antibody column to purify the peptide of the present invention, detect the peptide of the present invention in each fraction upon purification, analysis of the behavior of the peptide of the present invention in the cells under investigation.

(4) Gene Diagnostic Agent

By using the DNA of the present invention, e.g., as a probe, abnormality (gene abnormality) of the DNA or mRNA encoding the peptide of the present invention in human or other warm-blooded animal (e.g., rat, mouse, guinea pig, rabbit, chicken, sheep, swine, bovine, horse, cat, dog, monkey, etc.), can be detected. Thus, the DNA of the present invention is useful as a gene diagnostic agent for the damage to the DNA or mRNA, mutation, a decreased expression or an increased expression, or overexpression of the DNA or mRNA.

The gene diagnosis described above using the DNA of the present invention can be performed by, for example, the publicly known northern hybridization assay or the PCR-SSCP assay (Genomics, 5, 874-879 (1989); Proceedings of the National Academy of Sciences of the United States of America, 86, 2766-2770 (1989)).

When a decreased expression of mRNA is detected, e.g., by northern hybridization, it can be diagnosed that one is likely to suffer from, for example, anorexia, hypertension, autoimmune disease, heart failure, cataract, glaucoma, acute bacterial meningitis, acute myocardial infarction, acute pancreatitis, acute viral encephalitis, adult respiratory distress syndrome, alcoholic hepatitis, Alzheimer's disease, asthma, arteriosclerosis, atopic dermatitis, bacterial pneumonia, bladder cancer, fracture, breast cancer, bulimia, polyphagia, burn healing, uterine cervical cancer, chronic lymphocytic leukemia, chronic myelogenous leukemia, chronic pancreatitis, liver cirrhosis, cancer of the colon and rectum (colon cancer/rectal cancer), Crohn's disease, dementia, diabetic complications, diabetic nephropathy, diabetic neuropathy, diabetic retinopathy, gastritis, *Helicobacter pylori* bacterial infectious disease, hepatic insufficiency, hepatitis A, hepatitis B, hepatitis C, hepatitis, herpes simplex virus infectious disease, varicellazoster virus infectious disease, Hodgkin's disease, AIDS infectious disease, human papilloma virus infectious disease, hypercalcemia, hypercholesterolemia, hyperglyceridemia, hyperlipemia, infectious disease, influenza infectious disease, insulin dependent diabetes mellitus (type I), invasive staphylococcal infectious disease, malignant melanoma, cancer metastasis, multiple myeloma, allergic rhinitis, nephritis, non-Hodgkin's lymphoma, insulin-independent diabetes mellitus (type II), non-small cell lung cancer, organ transplantation, arthrosteitis, osteomalacia, osteopenia, osteoporosis, ovarian cancer, Behcet's disease of bone, peptic ulcer, peripheral vessel disease, prostatic cancer, reflux esophagitis, renal insufficiency, rheumatoid arthritis, schizophrenia, sepsis, septic shock, severe systemic fungal infectious disease, small cell lung cancer, spinal injury, stomach cancer, systemic lupus erythematosus, transient cerebral ischemia, tuberculosis, cardiac valve failure, vascular/multiple infarction dementia, wound healing, insomnia, arthritis, pituitary hormone secretion disorders [e.g., prolactin secretion disorders (e.g., hypoovarianism, spermatic underdevelopment, menopausal symptoms, hypothyroidism, etc.)], pollakiuria, uremia, neurodegenerative disease (especially anorexia or the like) etc.; or it is highly likely for one to suffer from diseases in the future.

When overexpression of mRNA is detected by northern hybridization, it can be diagnosed that one is likely to suffer from, for example, obesity (e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity, etc.), hyperphagia, pituitary tumor, diencephalon tumor, menstrual disorder, autoimmune disease, prolactinoma, sterility, impotence, amenorrhea, lactorrhea, acromegaly, Chiari-Frommel syndrome, Argonz-del Castillo syndrome, Forbes-Albright syndrome, lymphoma or Sheehan's syndrome, spermatogenesis disorder, etc. (especially, obesity or the like); or it is highly likely for one to suffer from diseases in the future.

(5) Pharmaceutical Composition Comprising Antisense DNA

The antisense DNA that binds complementarily to the DNA of the present invention to inhibit expression of the DNA can be used as preventive/therapeutic agents for diseases, for example, obesity (e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity, etc.), hyperphagia, pituitary tumor, diencephalon tumor, menstrual disorder, autoimmune disease, prolactinoma, sterility, impotence, amenorrhea, lactorrhea, acromegaly, Chiari-Frommel syndrome, Argonz-del Castillo syndrome, Forbes-Albright syndrome, lymphoma or Sheehan's syndrome, spermatogenesis disorder, etc. (especially, obesity or the like), etc.

For example, when the antisense DNA is used, the antisense DNA may be administered directly, or the DNA is inserted into an appropriate vector such as retrovirus vector, adenovirus vector, adenovirus-associated virus vector, etc. and then administered in a conventional manner. The antisense DNA may also be administered as an intact DNA, or prepared into pharmaceutical preparations together with a physiologically acceptable carrier such as an adjuvant to assist its uptake and administered by gene gun or through a catheter such as a catheter with a hydrogel.

In addition, the antisense DNA may also be employed as an oligonucleotide probe for diagnosis to examine the presence of the DNA of the present invention in tissues or cells and states of its expression.

(6) Pharmaceutical Composition Comprising the Antibody of the Present Invention

The antibody of the present invention having the effect to neutralize the activity of the peptide of the present invention can be used as drugs for the prevention/treatment of diseases, for example, obesity (e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity, etc.), hyperphagia, pituitary tumor, diencephalon tumor, menstrual disorder, autoimmune disease, prolactinoma, sterility, impotence, amenorrhea, lactorrhea, acromegaly, Chiari-Frommel syndrome, Argonz-del Castillo syndrome, Forbes-Albright syndrome, lymphoma or Sheehan's syndrome, spermatogenesis disorder, etc. (especially, obesity, or the like), etc.

The therapeutic/preventive agents for diseases described above comprising the antibody of the present invention can be administered to human or mammals (e.g., rats, rabbits, sheep, swine, bovine, cats, dogs, monkeys, etc.) orally or parenterally directly as a liquid preparation, or as a pharmaceutical composition in an appropriate preparation form. The dose varies depending on subject to be administered, target disease, conditions, route for administration, etc.; when it is used for the treatment/prevention of the adult patient with, e.g., obesity, the agent is advantageously administered to the patient through intravenous injection, normally in a single dose of approximately 0.01 to 20 mg/kg body weight, preferably about 0.1 to about 10 mg/kg body weight, and more preferably about 0.1 to about 5 mg/kg body weight, approximately 1 to 5 times, preferably approximately 1 to 3 times, per day. For other parenteral administration and oral administration, the corresponding dose may be administered. When the conditions are extremely serious, the dose may be increased depending on the conditions.

The antibody of the present invention may be administered directly as it is or as an appropriate pharmaceutical composition. The pharmaceutical composition used for the administration described above contains a pharmacologically acceptable carrier with the aforesaid compounds or salts thereof, a diluent or excipient. Such a composition is provided in the preparation suitable for oral or parenteral administration.

That is, examples of the composition for oral administration include solid or liquid preparations, specifically, tablets (including dragees and film-coated tablets), pills, granules, powdery preparations, capsules (including soft capsules), syrup, emulsions, suspensions, etc. Such a composition is manufactured by publicly known methods and contains a vehicle, a diluent or excipient conventionally used in the field of pharmaceutical preparations. Examples of the vehicle or excipient for tablets are lactose, starch, sucrose, magnesium stearate, etc.

Examples of the composition for parenteral administration that can be used are injections, suppositories, etc. and the injections include the form of intravenous, subcutaneous, transcutaneous, intramuscular and drip injections, etc. Such injections are prepared by publicly known methods, e.g., by dissolving, suspending or emulsifying the aforesaid antibody or its salts in a sterile aqueous or oily liquid medium. For the aqueous medium for injection, for example, physiological saline and isotonic solutions containing glucose and other adjuvant, etc. are used. Appropriate dissolution aids, for example, alcohol (e.g., ethanol), polyalcohol (e.g., propylene glycol or polyethylene glycol), nonionic surfactant [e.g., polysorbate 80, HCO-50 (polyoxyethylene (50 mol) adduct of hydrogenated castor oil)] may be used in combination. For the oily solution, for example, sesame oil, soybean oil and the like are used, and dissolution aids such as benzyl benzoate, benzyl alcohol, etc. may be used in combination. The thus-prepared liquid for injection is normally filled in an appropriate ampoule. The suppository used for rectal administration is prepared by mixing the aforesaid antibody or its salts with conventional suppository base.

The oral or parenteral pharmaceutical composition described above is advantageously prepared in a unit dosage form suitable for the dose of the active ingredient. Examples of such unit dosage form include tablets, pills, capsules, injections (ampoules), suppositories, etc. It is preferred that the antibody described above is contained generally in a dose of 5 to 500 mg per unit dosage form, 5 to 100 mg especially for injections and 10 to 250 mg for other preparations.

Each composition described above may further contain other active components unless formulation with the antibody causes any adverse interaction.

(7) DNA Transgenic Animal

The present invention provides a non-human mammal bearing an exogenous DNA encoding the peptide of the present invention (hereinafter merely referred to as the exogenous DNA of the present invention) or its variant DNA (sometimes simply referred to as the exogenous variant DNA of the present invention).

Thus, the present invention provides:
(i) a non-human mammal bearing the exogenous DNA or its variant DNA;
(ii) the mammal according to (i), wherein the non-human mammal is a rodent;

(iii) the mammal according to (ii), wherein the rodent is mouse or rat; and, (iv) a recombinant vector bearing the exogenous DNA of the present invention or its variant DNA and capable of expressing in a mammal.

The non-human mammal bearing the exogenous DNA of the present invention or its variant DNA (hereinafter simply referred to as the DNA transgenic animal of the present invention) can be prepared by transfecting a desired DNA into an unfertilized egg, a fertilized egg, a spermatozoon, a germinal cell containing a primordial germinal cell thereof, or the like, preferably in the embryogenic stage in the development of a non-human mammal (more preferably in the single cell or fertilized cell stage and generally before the 8-cell phase), by standard means, such as the calcium phosphate method, the electric pulse method, the lipofection method, the agglutination method, the microinjection method, the particle gun method, the DEAE-dextran method etc. Also, it is possible to transfect the exogenous DNA of the present invention into a somatic cell, a living organ, a tissue cell, or the like by the DNA transfection methods, and utilize the transformant for cell culture, tissue culture, etc. In addition, these cells may be fused with the above-described germinal cell by a publicly known cell fusion method to create the transgenic animal of the present invention.

Examples of the non-human mammal that can be used include bovine, swine, sheep, goats, rabbits, dogs, cats, guinea pigs, hamsters, mice, rats, and the like. Above all, preferred are rodents, especially mice (e.g., C57BL/6 strain, DBA2 strain, etc. for a pure line and for a cross line, B6C3F$_1$ strain, BDF$_1$ strain B6D2F$_1$ strain, BALB/c strain, ICR strain, etc.) or rats (Wistar, SD, etc.), since they are relatively short in ontogeny and life cycle from a standpoint of creating model animals for human disease.

"Mammals" in a recombinant vector that can be expressed in the mammals include the aforesaid non-human mammals and human.

The exogenous DNA of the present invention refers to the DNA of the present invention that is once isolated/extracted from mammals, not the DNA of the present invention inherently possessed by the non-human mammals.

The variant DNA of the present invention includes variants resulting from variation (e.g., mutation, etc.) in the base sequence of the original DNA of the present invention, specifically DNAs resulting from base addition, deletion, substitution with other bases, etc. and further including abnormal DNA.

The abnormal DNA is intended to mean such a DNA that expresses the abnormal peptide of the present invention and exemplified by the DNA that expresses a peptide to suppress the functions of the normal peptide of the present invention, or the like.

The exogenous DNA of the present invention may be any one of those derived from a mammal of the same species as, or a different species from, the mammal as the target animal. In transfecting the DNA of the present invention, it is generally advantageous to use the DNA as a DNA construct in which the DNA is ligated downstream a promoter capable of expressing the DNA in the target animal. For example, in the case of transfecting the human DNA of the present invention, a DNA transgenic mammal that expresses the DNA of the present invention to a high level, can be prepared by microinjecting a DNA construct (e.g., vector, etc.) ligated with the human DNA of the present invention into a fertilized egg of the target non-human mammal downstream various promoters, which are capable of expressing the DNA derived from various mammals (e.g., rabbits, dogs, cats, guinea pigs, hamsters, rats, mice, etc.) bearing the DNA of the present invention highly homologous to the human DNA.

As expression vectors for the peptide of the present invention, there are *Escherichia coli*-derived plasmids, *Bacillus subtilis*-derived plasmids, yeast-derived plasmids, bacteriophages such as λ phage, retroviruses such as Moloney leukemia virus, etc., and animal viruses such as vaccinia virus, baculovirus, etc. Of these vectors, *Escherichia coli*-derived plasmids, *Bacillus subtilis*-derived plasmids, or yeast-derived plasmids, etc. are preferably used.

Examples of these promoters for regulating the DNA expression described above include (1) promoters for the DNA derived from viruses (e.g., simian virus, cytomegalovirus, Moloney leukemia virus, JC virus, breast cancer virus, poliovirus, etc.), and (2) promoters derived from various mammals (human, rabbits, dogs, cats, guinea pigs, hamsters, rats, mice, etc.), for example, promoters of albumin, insulin II, uroplakin II, elastase, erythropoietin, endothelin, muscular creatine kinase, glial fibrillary acidic protein, glutathione S-transferase, platelet-derived growth factor, keratins K1, K10 and K14, collagen types I and II, cyclic AMP-dependent protein kinase βI subunit, dystrophin, tartarate-resistant alkaline phosphatase, atrial natriuretic factor, endothelial receptor tyrosine kinase (generally abbreviated as Tie2), sodium-potassium adenosine triphosphorylase (Na,K-ATPase), neurofilament light chain, metallothioneins I and IIA, metalloproteinase I tissue inhibitor, MHC class I antigen (H-2L), H-ras, renin, dopamine β-hydroxylase, thyroid peroxidase (TPO), peptide chain elongation factor 1α (EF-1α), β actin, α and β myosin heavy chains, myosin light chains 1 and 2, myelin base protein, thyroglobulins, Thy-1, immunoglobulins, H-chain variable region (VNP), serum amyloid component P, myoglobin, troponin C, smooth muscle a actin, preproencephalin A, vasopressin, etc. Among others them, cytomegalovirus promoters, human peptide elongation factor 1α (EF-1α) promoters, human and chicken β actin promoters etc., which protein can highly express in the whole body are preferred.

It is preferred that the vectors described above have a sequence for terminating the transcription of the desired messenger RNA in the DNA transgenic animal (generally called a terminator); for example, a sequence of each DNA derived from viruses and various mammals. SV40 terminator of simian virus, etc. are preferably used.

In addition, for the purpose of increasing the expression of the desired exogenous DNA to a higher level, the splicing signal and enhancer region of each DNA, a portion of the intron of an eukaryotic DNA may also be ligated at the 5' upstream of the promoter region, or between the promoter region and the translational region, or at the 3' downstream of the translational region, depending upon purpose.

The normal translational region for the peptide of the present invention can be obtained using as a starting material the entire genomic DNA or its portion of liver, kidney, thyroid cell or fibroblast origin from human or various mammals (e.g., rabbits, dogs, cats, guinea pigs, hamsters, rats, mice, etc.) or of various commercially available genomic DNA libraries, or using complementary DNA prepared by a publicly known method from RNA of liver, kidney, thyroid cell or fibroblast origin as a starting material. Also, an exogenous abnormal DNA can produce a translational region, which is obtained by point mutagenesis variation of the normal translational region for a peptide obtained from the cells or tissues described above.

The said translational region can be prepared by a conventional DNA engineering technique, in which the DNA is ligated downstream the aforesaid promoter and if desired, upstream the translation termination site, as a DNA construct capable of being expressed in the transgenic animal.

The exogenous DNA of the present invention is transfected at the fertilized egg cell stage in a manner such that the DNA is certainly present in all the germinal cells and somatic cells of the target mammal. The fact that the exogenous DNA of the present invention is present in the germinal cells of the animal prepared by DNA transfection means that all offspring of the prepared animal will maintain the exogenous DNA of the present invention in all of the germinal cells and somatic cells thereof. The offspring of the animal that inherits the exogenous DNA of the present invention also have the exogenous DNA in all of the germinal cells and somatic cells thereof.

The non-human mammal, in which the normal exogenous DNA of the present invention has been transfected, can be passaged as the DNA-bearing animal under ordinary rearing environment, by confirming that the exogenous DNA is stably retained by mating.

By the transfection of the exogenous DNA of the present invention at the fertilized egg cell stage, the DNA is retained to be excess in all of the germinal and somatic cells. The fact that the exogenous DNA of the present invention is excessively present in the germinal cells of the prepared animal after transfection means that the exogenous DNA of the present invention is excessively present in all of the germinal cells and somatic cells thereof. The offspring of the animal that inherits the exogenous DNA of the present invention have excessively the exogenous DNA of the present invention in all of the germinal cells and somatic cells thereof.

By obtaining a homozygotic animal having the transfected DNA in both of homologous chromosomes and mating a male and female of the animal, all offspring can be passaged to retain the DNA.

In a non-human mammal bearing the normal DNA of the present invention, the normal DNA of the present invention has expressed to a high level, and may eventually develop the hyperfunction of the peptide of the present invention by promoting the function of endogenous normal DNA. Therefore, the animal can be utilized as a pathologic model animal for such a disease. Specifically, using the normal DNA transgenic animal of the present invention, it is possible to elucidate the mechanism of the hyperfunction of the peptide of the present invention and the pathological mechanism of the disease associated with the peptide of the present invention and to determine how to treat the disease.

Furthermore, since a mammal wherein the exogenous normal DNA of the present invention is transfected exhibits an increasing symptom of the peptide of the present invention librated, the animal is usable for screening therapeutic agents for the disease associated with the peptide of the present invention.

On the other hand, a non-human mammal having the exogenous abnormal DNA of the present invention can be passaged under normal breeding conditions as the DNA-bearing animal by confirming the stable retaining of the exogenous DNA via crossing. Further, the exogenous DNA to be subjected can be utilized as a starting material by inserting the DNA into the plasmid described above. The DNA construct with promoter can be prepared by conventional DNA engineering techniques. The transfection of the abnormal DNA of the present invention at the fertilized egg cell stage is preserved to be present in all of the germinal and somatic cells of the mammals to be subjected. The fact that the abnormal DNA of the present invention is present in the germinal cells of the animal after DNA transfection means that all of the offspring of the prepared animal have the abnormal DNA of the present invention in all of the germinal and somatic cells. Such an offspring passaged the exogenous DNA of the present invention contains the abnormal DNA of the present invention in all of the germinal and somatic cells. A homozygous animal having the introduced DNA on both of homologous chromosomes can be acquired and then by mating these male and female animals, all the offspring can be bled to have the DNA.

Since a non-human mammal having the abnormal DNA of the present invention may express the abnormal DNA of the present invention at a high level, the animal may be the function inactivation type inadaptability of the peptide of the present invention by inhibiting the function of the endogenous normal DNA and can be utilized as its disease model animal. For example, using the abnormal DNA-transgenic animal of the present invention, it is possible to elucidate the mechanism of inadaptability of the peptide of the present invention and to perform to study a method for treatment of this disease.

More specifically, the transgenic animal of the present invention expressing the abnormal DNA of the present invention to a high level is also expected to serve as an experimental model for the elucidation of the mechanism of the functional inhibition (dominant negative effect) of normal peptide by the abnormal peptide of the present invention in the function inactive type inadaptability of the peptide of the present invention.

A mammal bearing the abnormal exogenous DNA of the present invention is also expected to serve for screening a candidate drug for the treatment of the function inactive type inadaptability of the peptide of the present invention, since the peptide of the present invention is increased in such an animal in its free form.

Other potential applications of two kinds of the transgenic animals described above include:

(1) use as a cell source for tissue culture;

(2) elucidation of the relation to a peptide that is specifically expressed or activated by the peptide of the present invention, by direct analysis of DNA or RNA in tissue of the DNA transgenic animal of the present invention or by analysis of the peptide tissue expressed by the DNA;

(3) research in the function of cells derived from tissues that are cultured usually only with difficulty, using cells of tissue bearing the DNA cultured by a standard tissue culture technique;

(4) screening of a drug that enhances the functions of cells using the cells described in (3) above; and, (5) isolation and purification of the variant peptide of the present invention and preparation of an antibody thereto.

Furthermore, clinical conditions of a disease associated with the peptide of the present invention, including the function inactive type inadaptability of the peptide of the present invention can be determined using the DNA transgenic animal of the present invention. Also, pathological findings on each organ in a disease model associated with the peptide of the present invention can be obtained in more detail, leading to the development of a new method for treatment as well as the research and therapy of any secondary diseases associated with the disease.

It is also possible to obtain a free DNA-transfected cell by withdrawing each organ from the DNA transgenic animal of the present invention, mincing the organ and degrading with a proteinase such as trypsin, etc., followed by establishing the line of culturing or cultured cells. Furthermore, the DNA transgenic animal of the present invention can serve as identification of cells capable of producing the peptide of the present invention, and as studies on association with apoptosis, differentiation or propagation or on the mechanism of signal transduction in these properties to inspect any abnormality therein. Thus, the DNA transgenic animal of the present invention can provide an effective research material for the peptide of the present invention and for elucidating the function and effect thereof.

To develop a therapeutic drug for the treatment of diseases associated with the peptide of the present invention, including the function inactive type inadaptability of the peptide of the present invention, using the DNA transgenic animal of the present invention, an effective and rapid method for screening can be provided by using the method for inspection and the method for quantification, etc. described above. It is also possible to investigate and develop a method for DNA therapy for the treatment of diseases associated with the peptide of the present invention, using the DNA transgenic animal of the present invention or a vector capable of expressing the exogenous DNA of the present invention.

(8) Knockout Animal

The present invention provides a non-human mammal embryonic stem cell bearing the DNA of the present invention inactivated and a non-human mammal deficient in expressing the DNA of the present invention.

Thus, the present invention provides:

(i) a non-human embryonic stem cell in which the DNA of the present invention is inactivated;

(ii) an embryonic stem cell according to (i), wherein the DNA is inactivated by introducing a reporter gene (e.g., β-galactosidase gene derived from *Escherichia coli*);

(iii) an embryonic stem cell according to (i), which is resistant to neomycin;

(iv) an embryonic stem cell according to (i), wherein the non-human mammal is a rodent;

(v) an embryonic stem cell according to (iv), wherein the rodent is mouse;

(vi) a non-human mammal deficient in expressing the DNA of the present invention, wherein the DNA of the present invention is inactivated;

(vii) a non-human mammal according to (vi), wherein the DNA is inactivated by inserting a reporter gene (e.g., β-galactosidase derived from *Escherichia coli*) therein and the reporter gene is capable of being expressed under control of a promoter for the DNA of the present invention;

(viii) a non-human mammal according to (vi), which is a rodent;

(ix) a non-human mammal according to (viii), wherein the rodent is mouse; and, (x) a method of screening a compound or its salt that promotes or inhibits the promoter activity for the DNA of the present invention, which comprises administering a test compound to the mammal of (vii) and detecting expression of the reporter gene.

The non-human mammal embryonic stem cell in which the DNA of the present invention is inactivated refers to a non-human mammal embryonic stem cell that suppresses the ability of the non-human mammal to express the DNA by artificially mutating the DNA of the present invention, or the DNA has no substantial ability to express the peptide of the present invention (hereinafter sometimes referred to as the knockout DNA of the present invention) by substantially inactivating the activity of the peptide of the present invention encoded by the DNA (hereinafter merely referred to as ES cell).

As the non-human mammal, the same examples as described above apply.

Techniques for artificially mutating the DNA of the present invention include deletion of a part or all of the DNA sequence and insertion of or substitution with other DNA, by genetic engineering. By these variations, the knockout DNA of the present invention may be prepared, for example, by shifting the reading frame of a codon or by disrupting the function of a promoter or exon.

Specifically, the non-human mammal embryonic stem cell in which the DNA of the present invention is inactivated (hereinafter merely referred to as the ES cell with the DNA of the present invention inactivated or the knockout ES cell of the present invention) can be obtained by, for example, isolating the DNA of the present invention that the desired non-human mammal possesses, inserting a DNA fragment having a DNA sequence constructed by inserting a drug resistant gene such as a neomycin resistant gene or a hygromycin resistant gene, or a reporter gene such as lacZ (β-galactosidase gene) or cat (chloramphenicol acetyltransferase gene), etc. into its exon site thereby to disable the functions of exon, or integrating to a chromosome of the subject animal by, e.g., homologous recombination, a DNA sequence which terminates gene transcription (e.g., polyA additional signal, etc.) in the intron between exons, thus inhibiting the synthesis of complete messenger RNA to eventually destroy the gene (hereinafter simply referred to as targeting vector). The thus obtained ES cells are subjected to Southern hybridization analysis using a DNA sequence on or near the DNA of the present invention as a probe, or to PCR analysis using a DNA sequence on the targeting vector and another DNA sequence near the DNA of the present invention, which is not included in the targeting vector as primers, thereby to select the knockout ES cell of the present invention.

The parent ES cells to inactivate the DNA of the present invention by homologous recombination, etc. may be of a strain already established as described above, or may be originally established in accordance with a modification of the known method by Evans and Kaufman supra. For example, in the case of mouse ES cells, currently it is common practice to use ES cells of the 129 strain. However, since their immunological background is obscure, the C57BL/6 mouse or the $BDF_1$ mouse ($F_1$ hybrid between C57BL/16 and DBA/2), wherein the low ovum availability per C57BL/6 in the C57B116 mouse has been improved by crossing with DBA/2, may be preferably used, instead of obtaining a pure line of ES cells with the clear immunological genetic background and for other purposes. The $BDF_1$ mouse is advantageous in that, when a pathologic model mouse is generated using ES cells obtained therefrom, the genetic background can be changed to that of the C57BL/6 mouse by back-crossing with the C57BL/6 mouse, since its background is of the C57BL/6 mouse, as well as being advantageous in that ovum availability per animal is high and ova are robust.

In establishing ES cells, blastocytes at 3.5 days after fertilization are commonly used. In the present invention, embryos are preferably collected at the 8-cell stage, after culturing until the blastocyte stage, the embryos are used to efficiently obtain a large number of early stage embryos.

Although the ES cells used may be of either sex, male ES cells are generally more convenient for generation of a germ cell line chimera and are therefore preferred. It is also desirable that sexes are identified as soon as possible to save painstaking culture time.

Methods for sex identification of the ES cell include the method in which a gene in the sex-determining region on the Y-chromosome is amplified by the PCR process and detected. When this method is used, one colony of ES cells (about 50 cells) is sufficient for sex-determination analysis, which karyotype analysis, for example G-banding method, requires about $10^6$ cells; therefore, the first selection of ES cells at the early stage of culture can be based on sex identification, and male cells can be selected early, which saves a significant amount of time at the early stage of culture.

Second selection can be achieved by, for example, number of chromosome confirmation by the G-banding method. It is usually desirable that the chromosome number of the obtained ES cells be 100% of the normal number. However, when it is difficult to obtain the cells having the normal number of chromosomes due to physical operation etc. in cell establishment, it is desirable that the ES cell be again cloned to a normal cell (e.g., in mouse cells having the number of chromosomes being 2n=40) after the gene of the ES cells is rendered knockout.

Although the embryonic stem cell line thus obtained shows a very high growth potential, it must be subcultured with great care, since it tends to lose its ontogenic capability. For example, the embryonic stem cell line is cultured at about 37° C. in a carbon dioxide incubator (preferably about 5% carbon dioxide and about 95% air, or about 5% oxygen, about 5% carbon dioxide and 90% air) in the presence of LIF (1-10000 U/ml) on appropriate feeder cells such as STO fibroblasts, treated with a trypsin/EDTA solution (normally about 0.001 to about 0.5% trypsin/about 0.1 to about 5 mM EDTA, preferably about 0.1% trypsin/1 mM EDTA) at the time of passage to obtain separate single cells, which are then seeded on freshly prepared feeder cells. This passage is normally conducted every 1 to 3 days; it is desirable that cells are observed at passage and cells found to be morphologically abnormal in culture, if any, should be abandoned.

Where ES cells are allowed to reach a high density in mono-layers or to form cell aggregates in suspension under appropriate conditions, they will spontaneously differentiate to various cell types, for example, pariental and visceral muscles, cardiac muscle or the like (M. J. Evans and M. H. Kaufman, Nature, 292, 154, 1981; G. R. Martin, Proc. Natl. Acad. Sci. U.S.A., 78, 7634, 1981; T. C. Doetschman et al., Journal of Embryology Experimental Morphology, 87, 27, 1985). The cells deficient in expressing the DNA of the present invention, which are obtainable from the differentiated ES cells of the present invention, are useful for studying the peptide of the present invention or the receptor protein of the present invention from an aspect of cell biology.

The non-human mammal deficient in expressing the DNA of the present invention can be identified from a normal animal by measuring the mRNA amount in the subject animal by a publicly known method, and indirectly comparing the levels of expression.

As the non-human mammal, the same examples as described above apply.

With respect to the non-human mammal deficient in expressing the DNA of the present invention, the DNA of the present invention can be rendered knockout by transfecting a targeting vector, prepared as described above, to non-human mammal embryonic stem cells or oocytes thereof, and conducting homologous recombination in which a targeting vector DNA sequence, wherein the DNA of the present invention is inactivated by the transfection, is replaced with the DNA of the present invention on a chromosome of a non-human mammal embryonic stem cell or embryo thereof.

The cells with the DNA of the present invention knockout can be identified by Southern hybridization analysis using a DNA sequence on or near the DNA of the present invention as a probe, or by PCR analysis using as primers a DNA sequence on the targeting vector and another DNA sequence, which is not included in the targeting vector. When non-human mammalian embryonic stem cells are used, a cell line wherein the DNA, of the present invention is inactivated by homologous recombination is cloned; the resulting cloned cell line is injected to, e.g., a non-human mammalian embryo or blastocyte, at an appropriate stage such as the 8-cell stage. The resulting chimeric embryos are transplanted to the uterus of the pseudopregnant non-human mammal. The resulting animal is a chimeric animal composed of both cells having the normal locus of the DNA of the present invention and those having an artificially mutated locus of the DNA of the present invention.

When some germ cells of the chimeric animal have a mutated locus of the DNA of the present invention, an individual, which entire tissue is composed of cells having a mutated locus of the DNA of the present invention can be selected from a series of offspring obtained by crossing between such a chimeric animal and a normal animal, e.g., by coat color identification, etc. The individuals thus obtained are normally deficient in heterozygous expression of the peptide of the present invention. The individuals deficient in homozygous expression of the peptide of the present invention or the receptor protein of the present invention can be obtained from offspring of the intercross between the heterozygotes of the peptide of the present invention or the receptor protein of the present invention.

When an oocyte or egg cell is used, a DNA solution may be injected, e.g., to the prenucleus by microinjection thereby to obtain a transgenic non-human mammal having a targeting vector introduced in a chromosome thereof. From such transgenic non-human mammals, those having a mutation at the locus of the DNA of the present invention can be obtained by selection based on homologous recombination.

As described above, individuals in which the DNA of the present invention is rendered knockout permit passage rearing under ordinary rearing conditions, after the individuals obtained by their crossing have proven to have been knockout.

Furthermore, the genital system may be obtained and maintained by conventional methods. That is, by crossing male and female animals each having the inactivated DNA, homozygote animals having the inactivated DNA in both loci can be obtained. The homozygotes thus obtained may be reared so that one normal animal and two or more homozygotes are produced from a mother animal to efficiently obtain such homozygotes. By crossing male and female heterozygotes, homozygotes and heterozygotes having the inactivated DNA are proliferated and passaged.

The non-human mammal embryonic stem cell, in which the DNA of the present invention is inactivated, is very useful for preparing a non-human mammal deficient in expressing the DNA of the present invention.

Since the non-human mammal deficient in expressing the DNA of the present invention lacks various biological activities derived from the peptide of the present invention, such an animal can be a disease model suspected of inactivated biological activities of the peptide of the present invention and thus, offers an effective study to investigate causes for and therapy for these diseases.

(8a) Method of Screening Compounds having Therapeutic/Preventive Effects on Diseases caused by Deficiency, Damages, etc. of the DNA of the Present Invention The non-human mammal deficient in expressing the DNA of the present invention can be employed for screening of compounds having therapeutic/prophylactic effects on diseases caused by deficiency, damages, etc. of the DNA of the present invention.

That is, the present invention provides a method for screening of a compound or its salt having therapeutic/preventive effects on diseases caused by deficiency, damages, etc. of the DNA of the present invention, which comprises administering a test compound to the non-human mammal deficient in expressing the DNA of the present invention and observing/measuring a change occurred in the animal.

As the non-human mammal deficient in expressing the DNA of the present invention which can be employed for the screening method, the same examples as given hereinabove apply.

Examples of the test compounds include peptides, proteins, non-peptide compounds, synthetic compounds, fermentation products, cell extracts, vegetable extracts, animal tissue extracts, blood plasma, etc. These compounds may be novel compounds or publicly known compounds.

Specifically, the non-human mammal deficient in expressing the DNA of the present invention is treated with a test compound, comparison is made with an intact animal for control and a change in each organ, tissue, disease conditions, etc. of the animal is used as an indicator to assess the therapeutic/prophylactic effects of the test compound.

For treating an animal to be test with a test compound, for example, oral administration, intravenous injection, etc. are applied and the treatment is appropriately selected depending upon conditions of the test animal, properties of the test compound, etc. Furthermore, a dose of test compound to be administered can be appropriately chosen depending on method for administration, nature of the test compound, etc.

In screening compounds having the therapeutic/preventive effect on, e.g., anorexia, hypertension, autoimmune disease, heart failure, cataract, glaucoma, acute bacterial meningitis, acute myocardial infarction, acute pancreatitis, acute viral encephalitis, adult respiratory distress-syndrome, alcoholic hepatitis, Alzheimer's disease, asthma, arteriosclerosis, atopic dermatitis, bacterial pneumonia, bladder cancer, fracture, breast cancer, bulimia, polyphagia, burn healing, uterine cervical cancer, chronic lymphocytic leukemia, chronic myelogenous leukemia, chronic pancreatitis, liver cirrhosis, cancer of the colon and rectum (colon cancer/rectal cancer), Crohn's disease, dementia, diabetic complications, diabetic nephropathy, diabetic neuropathy, diabetic retinopathy, gastritis, *Helicobacter pylori* bacterial infectious disease, hepatic insufficiency, hepatitis A, hepatitis B, hepatitis C, hepatitis, herpes simplex virus infectious disease, varicellazoster virus infectious disease, Hodgkin's disease, AIDS infectious disease, human papilloma virus infectious disease, hypercalcemia, hypercholesterolemia, hyperglyceridemia, hyperlipemia, infectious disease, influenza infectious disease, insulin dependent diabetes mellitus (type I), invasive staphylococcal infectious disease, malignant melanoma, cancer metastasis, multiple myeloma, allergic rhinitis, nephritis, non-Hodgkin's lymphoma, insulin-independent diabetes mellitus (type II), non-small cell lung cancer, organ transplantation, arthrosteitis, osteomalacia, osteopenia, osteoporosis, ovarian cancer, Behcet's disease of bone, peptic ulcer, peripheral vessel disease, prostatic cancer, reflux esophagitis, renal insufficiency, rheumatoid arthritis, schizophrenia, sepsis, septic shock, severe systemic fungal infectious disease, small cell lung cancer, spinal injury, stomach cancer, systemic lupus erythematosus, transient cerebral ischemia, tuberculosis, cardiac valve failure, vascular/multiple infarction dementia, wound healing, insomnia, arthritis, pituitary hormone secretion disorders [e.g., prolactin secretion disorders (e.g., hypoovarianism, spermatic underdevelopment, menopausal symptoms, hypothyroidism, etc.)], pollakiuria, uremia, neurodegenerative disease, etc. (especially, anorexia, or the like), the non-human mammal deficient in expressing the DNA of the present invention is subjected to a sugar loading treatment, a test compound is administered before or after the sugar loading treatment and, blood sugar level, body weight change, etc. of the animal is measured with passage of time.

In the screening method described above, when a test compound is administered to a test animal and found to reduce the blood sugar level of the animal to at least about 10%, preferably at least about 30% and more preferably at least 25 about 50%, the test compound can be selected to be a compound having a therapeutic/preventive effect on the diseases above.

The compound obtained using the screening method above is a compound selected from the test compounds described, above and exhibits a therapeutic/preventive effect on the diseases caused by deficiencies, damages, etc. of the peptide of the present invention. Therefore, the compound can be employed as a safe and low toxic drug for the treatment and prevention of these diseases. Furthermore, compounds derived from such a compound obtained by the screening described above can be similarly employed.

The compound obtained by the screening method above may be in the form of salts. As such salts, there may be used salts with physiologically acceptable acids (e.g., inorganic acids, organic acids, etc.) or bases (e.g., alkali metal salts, etc.), preferably in the form of physiologically acceptable acid addition salts. Examples of such salts are salts with inorganic acids (e.g., hydrochloric acid, phosphoric acid, hydrobromic acid, sulfuric acid, etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.) and the like.

A pharmaceutical composition comprising the compound or its salt, obtained by the above screening method, may be manufactured in a manner similar to the method for preparing the pharmaceutical composition comprising the peptide of the present invention described hereinabove.

Since the pharmaceutical composition thus obtained is safe and low toxic, it can be administered to human or mammals (e.g., rats, mice, guinea pigs, rabbits, sheep, swine, bovine, horses, cats, dogs, monkeys, etc.).

A dose of the compound or its salt to be administered varies depending upon particular disease, subject to be administered, route of administration, etc., and in oral administration to an adult patient with anorexia (as 60 kg body weight), the compound is administered generally in a dose of approximately 0.1 to 100 mg, preferably approximately 1.0 to 50 mg, more preferably approximately 1.0 to 20 mg per day. For parenteral administration to an adult patient with anorexia (as 60 kg body weight), it is advantageous to administer the compound intravenously in the form of an injectable preparation in a dose of approximately 0.01 to 30 mg, preferably approximately 0.1 to 20 mg, more preferably approximately 0.1 to 10 mg per day, though the single dosage varies depending upon particular subject, particular disease, etc. For other animals, the compound can (8b) Method of Screening a Compound that Promotes or Inhibits the Activity of a Promoter to the DNA of the Present Invention be administered in the corresponding dose with converting it into that for the 60 kg body weight.

The present invention provides a method of screening a compound or its salt that promotes or inhibits the activity of a promoter to the DNA of the present invention, which comprises administering a test compound to a non-human mammal deficient in expressing the DNA of the present invention and detecting expression of the reporter gene.

In the screening method described above, the non-human mammal deficient in expressing the DNA of the present invention is selected from the aforesaid non-human mammal deficient in expressing the DNA of the present invention, as an animal in which the DNA of the present invention is inactivated by introducing a reporter gene and the reporter gene is expressed under control of a promoter to the DNA of the present invention.

The same examples of the test compound apply to those given above.

As the reporter gene, the same specific examples apply. Preferably employed are β-galactosidase (lacZ), soluble alkaline phosphatase gene, luciferase gene and the like.

Since the reporter gene is present under control of a promoter to the DNA of the present invention in the non-human mammal deficient in expressing the DNA of the present invention wherein the DNA of the present invention is substituted with the reporter gene, the activity of the promoter can be detected by tracing expression of a substance encoded by the reporter gene.

For example, when a part of the DNA region encoding the peptide of the present invention is substituted with, e.g., β-galactosidase gene (lacZ) derived from *Escherichia coli*, β-galactosidase is expressed in a tissue where the peptide of the present invention should originally be expressed, instead of the peptide of the present invention. Thus, the state of expression condition of the peptide of the present invention can be readily observed in vivo of an animal by staining with a reagent, e.g., 5-bromo-4-chloro-3-indolyl-β-galactopyranoside (X-gal) which is substrate for β-galactosidase. Specifically, a mouse deficient in the peptide of the present invention, or its tissue slice section is fixed with glutaraldehyde, etc. After washing with phosphate buffered saline (PBS), the system is reacted with a staining solution containing X-gal at room temperature or about 37° C. for approximately 30 minutes to an hour. After the β-galactosidase reaction is terminated by washing the tissue preparation with 1 mM EDTA/PBS solution, the color formed is observed. Alternatively, mRNA encoding lacZ may be detected in a conventional manner.

The compound or salts thereof obtained using the aforesaid screening method are compounds that are selected from the test compounds described above and the compounds that promote or inhibit the activity of a promoter to the DNA of the present invention.

The compound obtained by the screening method above may form salts. As salts of the compound, there may be used salts with physiologically acceptable acids (e.g., inorganic acids, etc.) or bases (e.g., organic acids, etc.), and especially preferred are physiologically acceptable acid addition salts. Examples of such salts are salts with inorganic acids (e.g., hydrochloric acid, phosphoric acid, hydrobromic acid, sulfuric acid, etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.) and the like.

The compound or its salt that promotes the promoter activity to the DNA of the present invention can promote expression of the peptide of the present invention thereby to promote the function of the peptide. Thus, these compounds are useful as safe and low-toxic drugs for the treatment/prevention of diseases, e.g., anorexia, hypertension, autoimmune disease, heart failure, cataract, glaucoma, acute bacterial meningitis, acute myocardial infarction, acute pancreatitis, acute viral encephalitis, adult respiratory distress syndrome, alcoholic hepatitis, Alzheimer's disease, asthma, arteriosclerosis, atopic dermatitis, bacterial pneumonia, bladder cancer, fracture, breast cancer, bulimia, polyphagia, burn healing, uterine cervical cancer, chronic lymphocytic leukemia, chronic myelogenous leukemia, chronic pancreatitis, liver cirrhosis, cancer of the colon and rectum (colon cancer/rectal cancer), Crohn's disease, dementia, diabetic complications, diabetic nephropathy, diabetic neuropathy, diabetic retinopathy, gastritis, *Helicobacter pylori* bacterial infectious disease, hepatic insufficiency, hepatitis A, hepatitis B, hepatitis C, hepatitis, herpes simplex virus infectious disease, varicellazoster virus infectious disease, Hodgkin's disease, AIDS infectious disease, human papilloma virus infectious disease, hypercalcemia, hypercholesterolemia, hyperglyceridemia, hyperlipemia, infectious disease, influenza infectious disease, insulin dependent diabetes mellitus (type I), invasive staphylococcal infectious disease, malignant melanoma, cancer metastasis, multiple myeloma, allergic rhinitis, nephritis, non-Hodgkin's lymphoma, insulin-independent diabetes mellitus (type II), non-small cell lung cancer, organ transplantation, arthrosteitis, osteomalacia, osteopenia, osteoporosis, ovarian cancer, Behcet's disease of bone, peptic ulcer, peripheral vessel disease, prostatic cancer, reflux esophagitis, renal insufficiency, rheumatoid arthritis, schizophrenia, sepsis, septic shock, severe systemic fungal infectious disease, small cell lung cancer, spinal injury, stomach cancer, systemic lupus erythematosus, transient cerebral ischemia, tuberculosis, cardiac valve failure, vascular/multiple infarction dementia, wound healing, insomnia, arthritis, pituitary hormone secretion disorders [e.g., prolactin secretion disorders (e.g., hypoovarianism, spermatic underdevelopment, menopausal symptoms, hypothyroidism, etc.)], pollakiuria, uremia, neurodegenerative disease, etc. (especially, anorexia or the like) or the like (especially, appetite (eating) stimulant).

The compound or its salt that inhibits the activity of a promoter to the DNA of the present invention can inhibit expression of the peptide of the present invention thereby to inhibit the function of the peptide. Thus, these compounds are useful as drugs, including preventive/therapeutic drugs (prolactin production inhibitors) for diseases, for example, obesity (e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity, etc.), hyperphagia, pituitary tumor, diencephalon tumor, menstrual disorder, autoimmune disease, prolactinoma, sterility, impotence, amenorrhea, lactorrhea, acromegaly, Chiari-Frommel syndrome, Argonz-del Castillo syndrome, Forbes-Albright syndrome, lymphoma or Sheehan's syndrome, spermatogenesis disorders, etc.; preferably as preventive/therapeutic agents for obesity, hyperphagia, etc.

Furthermore, compounds derived from the compounds obtained by the screening described above may be likewise used.

The pharmaceuticals comprising the compound or its salt obtained by the screening method may be manufactured as in the aforesaid pharmaceuticals comprising the peptide of the present invention or its salt.

Since the pharmaceutical preparation thus obtained is safe and low toxic, it can be administered to human or mammals (e.g., rats, mice, guinea pigs, rabbits, sheep, swine, bovine, horses, cats, dogs, monkeys, etc.).

A dose of the compound or its salt to be administered varies depending upon target disease, subject to be administered, route of administration, etc.; when the compound that promotes the promoter activity to the DNA of the present invention is orally administered to an adult patient with, e.g., anorexia (as 60 kg body weight), the compound is administered generally in a dose of approximately 0.1 to 100 mg, preferably approximately 1.0 to 50 mg, more preferably approximately 1.0 to 20 mg per day. In parenteral administration, a single dose of the compound varies depending upon subject to be administered, target disease, etc. When the compound that promotes the promoter activity to the DNA of the present invention is administered to an adult patient with, e.g., anorexia (as 60 kg body weight) in the form of an injectable preparation, it is advantageous to administer the compound, intravenously in a dose of approximately 0.01 to 30 mg, preferably approximately 0.1 to 20 mg, more preferably approximately 0.1 to 10 mg per day. For other animals, the compound can be administered in the corresponding dose with converting it into that for the 60 kg body weight.

On the other hand, when a compound that inhibits the promoter activity to the DNA of the present invention is orally administered, the compound is orally administered to an adult patient with, e.g., obesity (as 60 kg body weight) generally in a dose of approximately 0.1 to 100 mg, preferably approximately 1.0 to 50 mg, more preferably approximately 1.0 to 20 mg per day. In parenteral administration, a single dose of the compound varies depending upon subject to be administered, target disease, etc. When the compound that inhibits the promoter activity to the DNA of the present invention is administered to an adult patient with, e.g., obesity (as 60 kg body weight) in the form of an injectable preparation, it is advantageous to administer the compound intravenously in a dose of approximately 0.01 to 30 mg, preferably approximately 0.1 to 20 mg, more preferably approximately 0.1 to 10 mg per day. For other animals, the compound can be administered in the corresponding dose with converting it into that for the 60 kg body weight.

As described above, the non-human mammal deficient in expressing the DNA of the present invention is extremely useful for screening a compound or its salt that promotes or inhibits the activity of a promoter to the DNA of the present invention, and can thus greatly contribute to investigations of causes for various diseases caused by failure to express the DNA of the present invention or to development of preventive/therapeutic agents for these diseases.

Moreover, when a so-called transgenic animal (gene-transfected animal) is prepared by using a DNA containing the promoter region of the peptide of the present invention, ligating genes encoding various proteins downstream the same and injecting the genes into animal oocyte, the peptide can be specifically synthesized by the animal so that it becomes possible to investigate the activity in vivo. Furthermore, when an appropriate reporter gene is ligated to the promoter region described above to establish a cell line so as to express the gene, such can be used as a survey system of low molecular weight compounds that specifically promotes or suppresses the ability of producing the peptide itself of the present invention in vivo.

The utilities of bovine GPR7 and bovine GPR8 (hereinafter merely referred to as the bovine GPR7/8) of the present invention are explained below.

Antibodies to the bovine GPR7/8 of the present invention (hereinafter sometimes simply referred to as the bovine GPR7/8 antibody) may be any of polyclonal antibodies and monoclonal antibodies, as long as they are capable of recognizing antibodies to the bovine GPR7/8 of the present invention.

The antibody of the present invention may be manufactured by publicly known methods for manufacturing antibodies or antisera, using the bovine GPR7/8 of the present invention as an antigen.

The antisense DNA (hereinafter sometimes merely referred to as the bovine GPR7/8 antisense DNA) having a complementary or substantially complementary base sequence to the DNA (hereinafter sometimes merely referred to as the bovine GPR7/8 DNA) encoding the bovine GPR7/8 of the present invention can be any antisense DNA, so long as it has a base sequence complementary or substantially complementary to that of the bovine GPR7/8 DNA of the present invention and capable of suppressing expression of the DNA.

The base sequence substantially complementary to the bovine GPR7/8 DNA of the present invention may, for example, be a base sequence having at least about 70% homology, preferably at least about 80% homology, more preferably at least about 90% homology and most preferably at least about 95% homology, to the full-length base sequence or partial base sequence of the base sequence complementary to the bovine GPR7/8 DNA of the present invention (i.e., complementary strand to the DNA of the present invention). In the entire base sequence of the complementary strand to the bovine GPR7/8 DNA of the present invention, an antisense DNA having at least about 70% homology, preferably at least about 80% homology, more preferably at least about 90% homology and most preferably at least about 95% homology, to the complementary strand of the base sequence which encodes the N-terminal region of the bovine GPR7/8 of the present invention (e.g., the base sequence around the initiation codon) is particularly preferred. These antisense DNAs can be synthesized using a publicly known DNA synthesizer, etc.

The utilities of (1) the bovine GPR7/8 of the present invention, (2) the bovine GPR7/8 DNA of the present invention, (3) the bovine GPR7/8 antibody of the present invention, and (4) the bovine GPR7/8 antisense DNA are explained below.

(1) Therapeutic/Preventive Agent for Diseases with which the Bovine GPR7/8 of the Present Invention is Associated As shown in EXAMPLE 25 later described, the bovine GPR7/8 of the present invention is a receptor to the peptide of the present invention.

Accordingly, when the bovine GPR7/8 of the present invention or the bovine GPR7/8 DNA of the present invention involves any abnormality or deficiency, it is highly likely to cause various diseases, including anorexia, hypertension, autoimmune disease, heart failure, cataract, glaucoma, acute bacterial meningitis, acute myocardial infarction, acute pancreatitis, acute viral encephalitis, adult respiratory distress syndrome, alcoholic hepatitis, Alzheimer's disease, asthma, arteriosclerosis, atopic dermatitis, bacterial pneumonia, bladder cancer, fracture, breast cancer, bulimia, polyphagia, burn healing, uterine cervical cancer, chronic lymphocytic leukemia, chronic myelogenous leukemia, chronic pancreatitis, liver cirrhosis, cancer of the colon and rectum (colon cancer/rectal cancer), Crohn's disease, dementia, diabetic complications, diabetic nephropathy, diabetic neuropathy, diabetic retinopathy, gastritis, *Helicobacter pylori* bacterial infectious disease, hepatic insufficiency, hepatitis A, hepatitis B, hepatitis C, hepatitis, herpes simplex virus infectious disease, varicellazoster virus infectious disease, Hodgkin's disease, AIDS infectious disease, human papilloma virus infectious disease, hypercalcemia, hypercholesterolemia, hyperglyceridemia, hyperlipemia, infectious disease, influenza infectious disease, insulin dependent diabetes mellitus (type I), invasive staphylococcal infectious disease, malignant melanoma, cancer metastasis, multiple myeloma, allergic rhinitis, nephritis, non-Hodgkin's lymphoma, insulin-independent diabetes mellitus (type I), non-small cell lung cancer, organ transplantation, arthrosteitis, osteomalacia, osteopenia, osteoporosis, ovarian cancer, Behcet's disease of bone, peptic ulcer, peripheral vessel disease, prostatic cancer, reflux esophagitis, renal insufficiency, rheumatoid arthritis, schizophrenia, sepsis, septic shock, severe systemic fungal infectious disease, small cell lung cancer, spinal injury, stomach cancer, systemic lupus erythematosus, transient cerebral ischemia, tuberculosis, cardiac valve failure, vascular/multiple infarction dementia, wound healing, insomnia, arthritis, pituitary hormone secretion disorders [e.g., prolactin secretion disorders (e.g., hypoovarianism, spermatic underdevelopment, menopausal symptoms, hypothyroidism, etc.)], pollakiuria, uremia, neurodegenerative diseases (especially anorexia, etc.), or the like.

Therefore, the bovine GPR7/8 of the present invention and the bovine GPR7/8 DNA of the present invention can be used as pharmaceuticals (in particular, appetite (eating) stimulants, etc.) for the treatment/prevention of various diseases as described above (especially anorexia, etc.).

When a patient has a reduced level of, or deficient in the bovine GPR7/8 of the present invention in his or her body, the bovine GPR7/8 of the present invention and the bovine GPR7/8 DNA of the present invention can exhibit the role of the bovine GPR7/8 of the present invention sufficiently or properly for the patient, (a) by administering the bovine GPR7/8 DNA of the present invention to the patient to express the bovine GPR7/8 of the present invention in the body, (b) by inserting the bovine GPR7/8 DNA of the present invention into a cell, expressing the bovine GPR7/8 of the present invention and then transplanting the cell to the patient, or (c) by administering the bovine GPR7/8 of the present invention to the patient, or the like.

Where the bovine GPR7/8 of the present invention or the bovine GPR7/8 DNA of the present invention is used as drugs for the treatment/prevention described above, these drugs can be manufactured and used similarly to the pharmaceuticals comprising the peptide of the present invention or the DNA of the present invention described above.

(2) Screening of Drug Candidate Compounds for Diseases (2-1) Screening Method A

The method of screening a compound or its salt that alters the binding of the bovine GPR7/8 of the present invention to the peptide of the present invention is carried out as described hereinabove.

(2-2) Screening Method B

Next, the method of screening a compound that regulates the expression level of bovine GPR7/8 is explained below.

The screening method B of the present invention is specifically (i) a method of screening a compound or its salt that increases or decreases the expression level of bovine GPR7/8, which comprises assaying the expression level of bovine GPR7/8 or the level of mRNA encoding the bovine GPR7/8 in the case that a cell or tissue capable of expressing the bovine GPR7/8 is cultured in the presence or absence of a test compound, and comparing the expression level in each case.

As the cell or tissue capable of expressing the bovine GPR7/8, there may be used a cell or tissue derived from human or other warm-blooded animals (e.g., guinea pigs, rats, mice, chicken, rabbits, swine, sheep, bovine, monkeys, etc.); any cell (e.g., nerve cells, endocrine cells, neuroendocrine cells, glial cells, β cells of pancreas, bone marrow cells, hepatocytes, splenocytes, mesangial cells, epidermic cells, epithelial cells, endothelial cells, fibroblasts, fibrocytes, myocytes, fat cells, immune cells (e.g., macrophages, T cells, B cells, natural killer cells, mast cells, neutrophils, basophils, eosinophils, monocytes, dendritic, cells), megakaryocyte, synovial cells, chondrocytes, bone cells, osteoblasts, osteoclasts, mammary gland cells or interstitial cells, the corresponding precursor cells, stem cells, cancer cells, etc., of these cells), or any tissue where such a cell is present, e.g., brain or any region of the brain (e.g., olfactory bulb, amygdaloid nucleus, basal ganglia, hippocampus, thalamus, hypothalamus, cerebral cortex, medulla oblongata, cerebellum), spinal cord, hypophysis, stomach, pancreas, kidney, liver, gonad, thyroid, gall-bladder, bone marrow, adrenal gland, skin, muscle, lung, gastrointestinal tract (e.g., large intestine and small intestine), blood vessel, heart, thymus, spleen, submandibular gland, peripheral blood, prostate, testis, ovary, placenta, uterus, bone, cartilage, joint, skeletal muscle, etc., wherein established cell line or primary culture system may also be used. Transformants transformed by a recombinant vector bearing a DNA encoding the bovine GPR7/8 described above may also be used.

To cultivate the cells capable of expressing the bovine GPR7/8, the method given for cultivating transformants above applies.

As the test compound, a DNA library may also be used, in addition to the test compounds described above.

The expression level of bovine GPR7/8 can be determined by publicly known methods such as immunochemical methods, etc., using an antibody, etc. Alternatively, mRNA encoding the bovine GPR7/8 can be determined by publicly known methods including northern hybridization, RT-PCR or TaqMan PCR.

Comparison of the expression level of mRNA can be made by publicly known methods or a modification thereof, for example, according to the method described in Molecular Cloning, 2nd (J. Sambrook et al., Cold Spring Harbor Lab. Press, 1989), etc.

Specifically, the level of mRNA encoding the bovine GPR7/8 is determined by contacting RNA extracted from cells according to publicly known methods with the DNA encoding the bovine GPR7/8 or a part thereof or the bovine GPR7/8 antisense polynucleotide of the present invention, and assaying the level of mRNA bound to the DNA encoding the bovine GPR7/8 or a part thereof or the antisense polynucleotide of the present invention. The level of mRNA bound to the DNA encoding the bovine GPR7/8 or a part thereof or the bovine GPR7/8 antisense polynucleotide of the present invention can be readily assayed by labeling the DNA encoding the bovine GPR7/8 or a part thereof or the bovine GPR7/8 antisense polynucleotide of the present invention with, e.g., a radioisotope, a dye, etc. Examples of the radioisotope are $^{32}$P, $^{3}$H, etc. Examples of the dye used are fluorescent dyes such as fluorescein, FAM (Biosystems, Inc.), JOE (PE Biosystems, Inc.), TAMRA (PE Biosystems, Inc.), ROX (PE Biosystems, Inc.), Cy5 (Amersham), Cy3 (Amersham), etc.

The level of mRNA can also be determined by converting RNA extracted from cells into cDNA by a reverse transcriptase, amplifying the cDNA by PCR using the DNA encoding the bovine GPR7/8 or a part thereof or the bovine GPR7/8 antisense polynucleotide of the present invention as a primer, and assaying the amount of cDNA amplified.

As described above, the test compound that increases the level of mRNA encoding the bovine GPR7/8 can be selected as a compound that increases the expression level of bovine GPR7/8. Also, the test compound that decreases the level of mRNA encoding the bovine GPR7/8 can be selected as a compound that decreases the expression level of bovine GPR7/8.

The present invention further provides:

(ii) a method of screening a compound that promotes or inhibits a promoter activity, which comprises assaying the reporter activity in the case that a transformant transformed by a recombinant DNA ligated with a reporter gene downstream the promoter region or enhancer region of a gene encoding the bovine GPR7/8 is cultured in the presence or absence of a test compound, and comparing the activity in each case.

As the reporter gene, there may be employed, e.g., lacZ (β-galactosidase gene), chloramphenicol acetyltransferase (CAT), luciferase, growth factor, β-glcuronidase, alkaline phosphatase, green fluorescent protein (GFP), β-lactamase, etc.

By determining the level of the reporter gene product (e.g., mRNA, protein) using publicly known methods, the test compound that increases the level of the reporter gene product can be selected as the compound having the activity of regulating (especially promoting) the promoter or enhancer activity of bovine GPR7/8 of the present invention, i.e., the compound having the activity of increasing the expression level of bovine GPR7/8. To the contrary, the test compound that decreases the level of the reporter gene product can be selected as the compound having the activity of regulating (especially inhibiting) the promoter or enhancer activity of bovine GPR7/8, i.e., the compound having the activity of decreasing the expression level of bovine GPR7/8.

As the test compounds, those described above are employed.

The transformants can be cultivated as given for the transformants described above.

Construction of vectors for the reporter genes and assay can be performed according to publicly known techniques (e.g., Molecular Biotechnology, 13, 29-43, 1999).

The compounds having the activity of increasing the expression level of bovine GPR7/8 are useful-as safe and low-toxic drugs (e.g., preventive/therapeutic agents for anorexia, appetite (eating) stimulants, preventive/therapeutic agents for pituitary hormone secretion disorders [e.g., prolactin secretion disorders (e.g., hypoovarianism, spermatic underdevelopment, menopausal symptoms, hypothyroidism, etc.)].

The compounds having the activity of decreasing the expression level of bovine GPR7/8 are useful as safe and low-toxic drugs for the prevention/treatment of obesity (e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity, etc.), hyperphagia, etc.; as safe and low-toxic drugs for the prevention/treatment (prolactin production suppressing agents) for pituitary tumor, diencephalon tumor, menstrual disorders, autoimmune disease, prolactinoma, sterility, impotence, amenorrhea, lactorrhea, acromegaly, Chiari-Frommel syndrome, Argonz-del Castillo syndrome, Forbes-Albright syndrome, lymphoma or Sheehan's syndrome, spermatogenesis disorder, etc.; preferably, as safe and low-toxic drugs for the prevention/treatment of obesity, hyperphagia, etc.

The compound or its salt, which can be obtained by using the screening method B or the screening kit of the present invention, is a compound selected from, e.g., peptides, proteins, non-peptide compounds, synthetic compounds, fermentation products, cell extracts, plant extracts, animal tissue extracts, plasma, etc., and is the compound that promotes or inhibits the function of the peptide of the present invention.

For salts of the compound, those as described for the peptide of the present invention are employed.

When the compound obtained by the screening method B or screening kit of the present invention is used as the therapeutic/preventive agent described above, the compound can be prepared into pharmaceutical preparations and provided for use, in a similar manner to the aforesaid pharmaceuticals comprising the compound or its salt that alters the expression level of the peptide of the present invention described above.

(3) Quantification of the Bovine GPR7/8 of the Present Invention

The antibody of the present invention is capable of specifically recognizing the bovine GPR7/8 of the present invention, and can thus be used for quantification of the bovine GPR7/8 of the present invention in a sample fluid, in particular, for quantification by sandwich immunoassay.

That is, the present invention provides:

(i) a method for quantification of the bovine GPR7/8 of the present invention in a sample fluid, which comprises competitively reacting the bovine GPR7/8 antibody of the present invention with a sample fluid and a labeled form of the bovine GPR7/8 of the present invention, and measuring a ratio of the labeled bovine GPR7/8 of the present invention bound to the antibody; and, (ii) a method for quantification of the bovine GPR7/8 of the present invention in a sample fluid, which comprises simultaneously or continuously reacting the sample fluid with the antibody of the present invention and a labeled form of another antibody of the present invention immobilized on an insoluble carrier, and measuring the activity of the labeling agent on the immobilized carrier.

In the method of quantification (ii) described above, it is preferred that one antibody is capable of recognizing the N-terminal region of the bovine GPR7/8 of the present invention, while another antibody is capable of recognizing the C-terminal region of the bovine GPR7/8 of the present invention.

The monoclonal antibody to the bovine GPR7/8 of the present invention may be used to quantify the bovine GPR7/8 of the present invention, and may further be used to detect the same by means of a tissue staining, etc. For these purposes, the antibody molecule per se may be used, or F(ab')$_2$, Fab' or Fab fractions of the antibody molecule may be used as well.

The method of quantifying the bovine GPR7/8 of the present invention using the bovine GPR7/8 antibody of the present invention is not particularly limited, and any method may be used so far as it relates to a method, in which the amount of an antibody, antigen or antibody-antigen complex can be detected by a chemical or a physical means, depending on or corresponding to the amount of antigen (e.g., the amount of the peptide) in a sample fluid to be assayed, and then calculated using a standard curve prepared by a standard solution containing the known amount of antigen. Advantageously used are, for example, nephrometry, competitive method, immunometric method and sandwich method; in terms of sensitivity and specificity, the sandwich method, which will be described later, is particularly preferred.

Examples of labeling agents, which are employed for the assay method using the same, are radioisotopes, enzymes, fluorescent substances, luminescent substances, etc. Examples of radioisotopes are [$^{125}$I], [$^{131}$I], [$^{3}$H], [$^{14}$C], etc. Preferred examples of enzymes are those that are stable and have a high specific activity, which include β-galactosidase, β-glucosidase, alkaline phosphatase, peroxidase, malate dehydrogenase, etc. Examples of fluorescent substances are fluorescamine, fluorescein isothiocyanate, etc. Examples of luminescent substances are luminol, a luminol derivative, luciferin, lucigenin, etc. Furthermore, a biotin-avidin system may be used as well for binding an antibody or antigen to a labeling agent.

In the immobilization of antigens or antibodies, physical adsorption may be used. Alternatively, chemical binding that is conventionally used for immobilization of proteins, enzymes, etc. may be used as well. Examples of the carrier include insoluble polysaccharides such as ag arose, dextran, cellulose, etc.; synthetic resins such as polystyrene, polyacrylamide, silicone, etc.; or glass; and the like.

In the sandwich method, a sample fluid is reacted with an immobilized form of the bovine GPR7/8 monoclonal antibody of the present invention (primary reaction), then reacted with a labeled form of the bovine GPR7/8 monoclonal antibody of the present invention (secondary reaction) and the activity of the labeling agent on the insoluble carrier is assayed; thus, the amount of the bovine GPR7/8 of the present invention in a sample fluid can be determined. The primary and secondary reactions may be carried out in a reversed order, simultaneously or sequentially with intervals. The type of the labeling agent and the method of immobilization may be the same as those described hereinabove. In the immunoassay by the sandwich method, it is not always necessary that the antibody used for the labeled antibody and for the solid phase should be one type or one species but a mixture of two or more antibodies may also be used for the purpose of improving the assay sensitivity, etc.

In the method of assaying the bovine GPR7/8 of the present invention by the sandwich method according to the present invention, the bovine GPR7/8 monoclonal antibodies of the present invention used for the primary and the secondary reactions are preferably antibodies, which binding sites to the bovine GPR7/8 of the present invention are different from each other. Thus, the antibodies used in the primary and secondary reactions are those wherein, when the antibody used in the secondary reaction recognizes the C-terminal region of the bovine GPR7/8 of the present invention, the antibody recognizing the site other than the C-terminal regions, e.g., recognizing the N-terminal region, is preferably used in the primary reaction.

The bovine GPR7/8 antibody of the present invention may be used in an assay system other than the sandwich method, such as the competitive method, the immunometric method or the nephrometry.

In the competitive method, an antigen in a sample fluid and a labeled antigen are competitively reacted with an antibody, then an unreacted labeled antigen (F) and a labeled antigen bound to the antibody (B) are separated (i.e., B/F separation) and the labeled amount of either B or F is measured to determine the amount of the antigen in the sample fluid. In the reactions for such a method, there are a liquid phase method in which a soluble antibody is used as the antibody and the B/F separation is effected by polyethylene glycol, while a second antibody to the antibody is used, and a solid phase method in which an immobilized antibody is used as the first antibody or a soluble antibody is used as the first antibody, while an immobilized antibody is used as the second antibody.

In the immunometric method, an antigen in a sample fluid and an immobilized antigen are competitively reacted with a given amount of a labeled antibody followed by separating the solid phase from the liquid phase; or an antigen in a sample fluid and an excess amount of labeled antibody are reacted, then an immobilized antigen is added to bind an unreacted labeled antibody to the solid phase and the solid phase is separated from the liquid phase. Thereafter, the labeled amount of any of the phases is measured to determine the antigen amount in the sample fluid.

In the nephrometry, the amount of insoluble sediment, which is produced as a result of the antigen-antibody reaction in a gel or in a solution, is measured. Even when the amount of an antigen in a sample fluid is small and only a small amount of the sediment is obtained, a laser nephrometry utilizing laser scattering can be suitably used.

In applying each of those immunoassays to the assay method of the present invention, any special conditions, operations, etc. are not required. The assay system for the bovine GPR7/8 of the present invention may be constructed in addition to conditions or operations conventionally used for each of the methods, taking technical consideration by one skilled in the art into account. For the details of such conventional technical means, a variety of reviews, reference books, etc. may be referred to:

for example, Hiroshi Irie (ed.): "Radioimmunoassay" (published by Kodansha, 1974); Hiroshi Irie (ed:): "Radioimmunoassay; Second Series" (published by Kodansha, 1979); Eiji Ishikawa, et al. (ed.): "Enzyme Immunoassay" (published by Igaku Shoin, 1978); Eiji Ishikawa, et al. (ed.): "Enzyme lhmunoassay" (Second Edition) (published by Igaku Shoin, 1982); Eiji Ishikawa, et al. (ed.): "Enzyme Immunoassay" (Third Edition) (published by Igaku Shoin, 1987); "Methods in Enzymology" Vol. 70 (Immunochemical Techniques (Part A)); ibid., Vol. 73 (Immunochemical Techniques (Part B)); ibid., Vol. 74 (Immunochemical Techniques (Part C)); ibid., Vol. 84 (Immunochemical Techniques (Part. D: Selected Immunoassays)); ibid., Vol. 92 (Immunochemical Techniques (Part E: Monoclonal Antibodies and General Immunoassay Methods)); ibid., Vol. 121 (Immunochemical Techniques (Part I: Hybridoma Technology and Monoclonal Antibodies)) (all published by Academic Press); etc.

As described above, the bovine GPR7/8 of the present invention can be quantified with high sensitivity, using the bovine GPR7/8 antibody of the present invention.

Furthermore, when a reduced level of the bovine GPR7/8 of the present invention is detected by quantifying a level of the bovine GPR7/8 of the present invention using, the bovine GPR7/8 antibody of the present invention, it can be diagnosed that one suffers from, e.g., anorexia, hypertension, autoimmune disease, heart failure, cataract, glaucoma, acute bacterial meningitis, acute myocardial infarction, acute pancreatitis, acute viral encephalitis, adult respiratory distress syndrome, alcoholic hepatitis, Alzheimer's disease, asthma, arteriosclerosis, atopic dermatitis, bacterial pneumonia, bladder cancer, fracture, breast cancer, bulimia, polyphagia, burn healing, uterine cervical cancer, chronic lymphocytic leukemia, chronic myelogenous leukemia, chronic pancreatitis, liver cirrhosis, cancer of the colon and rectum (colon cancer/rectal cancer), Crohn's disease, dementia, diabetic complications, diabetic nephropathy, diabetic neuropathy, diabetic retinopathy, gastritis, *Helicobacter pylori* bacterial infectious disease, hepatic insufficiency, hepatitis A, hepatitis B, hepatitis C, hepatitis, herpes simplex virus infectious disease, varicellazoster virus infectious disease, Hodgkin's disease, AIDS infectious disease, human papilloma virus infectious disease, hypercalcemia, hypercholesterolemia, hyperglyceridemia, hyperlipemia, infectious disease, influenza infectious disease, insulin dependent diabetes mellitus (type I), invasive staphylococcal infectious disease, malignant melanoma, cancer metastasis, multiple myeloma, allergic rhinitis, nephritis, non-Hodgkin's lymphoma, insulin-independent diabetes mellitus (type II), non-small cell lung cancer, organ transplantation, arthrosteitis, osteomalacia, osteopenia, osteoporosis, ovarian cancer, Behcet's disease of bone, peptic ulcer, peripheral vessel disease, prostatic cancer, reflux esophagitis, renal insufficiency, rheumatoid arthritis, schizophrenia, sepsis, septic shock, severe systemic fungal infectious disease, small cell lung cancer, spinal injury, stomach cancer, systemic lupus erythematosus, transient cerebral ischemia, tuberculosis, cardiac valve failure, vascular/multiple infarction dementia, wound healing, insomnia, arthritis, pituitary hormone secretion disorders [e.g., prolactin secretion disorders (e.g., hypoovarianism, spermatic underdevelopment, menopausal symptoms, hypothyroidism, etc.)], pollakiuria, uremia, neurodegenerative disease (especially, anorexia or the like) etc.; or it is highly likely for one to suffer from these disease in the future.

When an increased level of the bovine GPR7/8 of the present invention is detected, it can be diagnosed that one suffers from, e.g., obesity (e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity, etc.), hyperphagia, pituitary tumor, diencephalon tumor, menstrual disorder, autoimmune disease, prolactinoma, sterility, impotence, amenorrhea, lactorrhea, acromegaly, Chiari-Frommel syndrome, Argonz-del Castillo syndrome, Forbes-Albright syndrome, lymphoma, Sheehan's syndrome, spermatogenesis disorder (especially, obesity, or the like), etc.; or it is highly likely for one to suffer from these disease in the future.

The bovine GPR7/8 antibody of the present invention may also be employed to detect the bovine GPR7/8 of the present invention present in a sample fluid such as body fluids, tissues, etc. The antibody may further be used for the preparation of an antibody column to purify the bovine GPR7/8 of the present invention, detect the bovine GPR7/8, of the present invention in each fraction upon purification, analysis of the behavior of the bovine GPR7/8 of the present invention in the cells under investigation.

(4) Gene Diagnostic Agent

By using the bovine GPR7/8 DNA of the present invention, e.g., as a probe, abnormality (gene abnormality) of the DNA or mRNA encoding the bovine GPR7/8 of the present invention in human or other warm-blooded animals (e.g., rats, mice, guinea pigs, rabbits, chicken, sheep, swine, bovine, horses, cats, dogs, monkeys, etc.) can be detected. Thus, the bovine GPR7/8 DNA of the present invention is useful as a gene diagnostic agent for the damage to the DNA or mRNA, mutation, a decreased expression or an increased expression, or overexpression of the DNA or mRNA.

The gene diagnosis described above using the bovine GPR7/8 DNA of the present invention can be performed by, for example, the publicly known northern hybridization assay, or the PCR-SSCP assay (Genomics, 5, 874-879 (1989); Proceedings of the National Academy of Sciences of the United States of America, 86, 2766-2770 (1989)), etc.

When a decreased expression of mRNA is detected, e.g., by northern hybridization, it can be diagnosed that one is likely to suffer from, for example, anorexia, hypertension, autoimmune disease, heart failure, cataract, glaucoma, acute bacterial meningitis, acute myocardial infarction, acute pancreatitis, acute viral encephalitis, adult respiratory distress syndrome, alcoholic hepatitis, Alzheimer's disease, asthma, arteriosclerosis, atopic dermatitis, bacterial pneumonia, bladder cancer, fracture, breast cancer, bulimia, polyphagia, burn healing, uterine cervical cancer, chronic lymphocytic leukemia, chronic myelogenous leukemia, chronic pancreatitis, liver cirrhosis, cancer of the colon and rectum (colon cancer/rectal cancer), Crohn's disease, dementia, diabetic complications, diabetic nephropathy, diabetic neuropathy, diabetic retinopathy, gastritis, *Helicobacter pylori* bacterial infectious disease, hepatic insufficiency, hepatitis A, hepatitis B, hepatitis C, hepatitis, herpes simplex virus infectious disease, varicellazoster virus infectious disease, Hodgkin's disease, AIDS infectious disease, human papilloma virus infectious disease, hypercalcemia, hypercholesterolemia, hyperglyceridemia, hyperlipemia, infectious disease, influenza infectious disease, insulin dependent diabetes mellitus (type I), invasive staphylococcal infectious disease, malignant melanoma, cancer metastasis, multiple myeloma, allergic rhinitis, nephritis, non-Hodgkin's lymphoma, insulin-independent diabetes mellitus (type II), non-small cell lung cancer, organ transplantation; arthrosteitis, osteomalacia, osteopenia, osteoporosis, ovarian cancer, Behcet's disease of bone, peptic ulcer, peripheral vessel disease, prostatic cancer, reflux esophagitis, renal insufficiency, rheumatoid arthritis, schizophrenia, sepsis, septic shock, severe systemic fungal infectious disease, small cell lung cancer, spinal injury, stomach cancer, systemic lupus erythematosus, transient cerebral ischemia, tuberculosis, cardiac valve failure, vascular/multiple infarction dementia, wound healing, insomnia, arthritis, pituitary hormone secretion disorders [e.g., prolactin secretion disorders (e.g., hypoovarianism, spermatic underdevelopment, menopausal symptoms, hypothyroidism, etc.)], pollakiuria, uremia, neurodegenerative disease (especially anorexia or the like) etc.; or it is highly likely for one to suffer from diseases in the future.

When overexpression of mRNA is detected by northern hybridization, it can be diagnosed that one is likely to suffer from, for example, obesity (e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity, etc.), hyperphagia, pituitary tumor, diencephalon tumor, menstrual disorder, autoimmune disease, prolactinoma, sterility, impotence, amenorrhea, lactorrhea, acromegaly, Chiari-Frommel syndrome, Argonz-del Castillo syndrome, Forbes-Albright syndrome, lymphoma or Sheehan's syndrome, spermatogenesis disorder, etc. (especially, obesity or the like); or it is highly likely for one to suffer from diseases in the future.

(5) Pharmaceutical Composition Comprising Bovine GPR7/8 Antisense DNA

The antisense DNA that binds complementarily to the bovine GPR7/8 DNA of the present invention to inhibit expression of the DNA can be used as preventive/therapeutic agents, for example, for obesity (e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity, etc.), hyperphagia, pituitary tumor, diencephalon tumor, menstrual disorder, autoimmune disease, prolactinoma, sterility, impotence, amenorrhea, lactorrhea, acromegaly, Chiari-Frommel syndrome, Argonz-del Castillo syndrome, Forbes-Albright syndrome, lymphoma or Sheehan's syndrome, spermatogenesis disorder, etc. (especially, obesity or the like), etc.

For example, when the antisense DNA is used, the antisense DNA may be administered directly, or the DNA is inserted into an appropriate vector such as retrovirus vector, adenovirus vector, adenovirus-associated virus vector, etc. and then administered in a conventional manner. The antisense DNA may also be administered as an intact DNA, or prepared into pharmaceutical preparations together with a physiologically acceptable carrier such as an adjuvant to assist its uptake and administered by gene gun or through a catheter such as a catheter with a hydrogel.

In addition, the antisense DNA may also be employed as an oligonucleotide probe for diagnosis to examine the presence of the bovine GPR7/8 DNA of the present invention in tissues or cells and states of its expression.

(6) Pharmaceutical Composition Comprising the Bovine GPR7/8 Antibody of the Present Invention The bovine GPR7/8 antibody of the present invention having an effect to neutralize the activity of the bovine GPR7/8 of the present invention can be used as drugs for the prevention/treatment of, for example, obesity (e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity, etc.), hyperphagia, pituitary tumor, diencephalon tumor, menstrual disorder, autoimmune disease, prolactinoma, sterility, impotence, amenorrhea, lactorrhea, acromegaly, Chiari-Frommel syndrome, Argonz-del Castillo syndrome, Forbes-Albright syndrome, lymphoma or Sheehan's syndrome, spermatogenesis disorder, etc. (especially, obesity, or the like), etc.

The therapeutic/preventive agent comprising the bovine GPR7/8 antibody of the present invention can be manufactured in a similar manner to the pharmaceuticals comprising the antibody to the peptide of the present invention described above and provided for use.

(7) Bovine GPR7/8 DNA Transgenic Animal

The present invention provides a non-human mammal bearing an exogenous DNA encoding the bovine GPR7/8 of the present invention (hereinafter merely referred to as the exogenous bovine GPR7/8 DNA of the present invention) or its variant DNA (sometimes simply referred to as the exogenous variant bovine GPR7/8 DNA of the present invention).

Thus, the present invention provides:

(i) a non-human mammal bearing the exogenous bovine GPR7/8 DNA or its variant DNA;

(ii) the mammal according to (i), wherein the non-human mammal is a rodent;

(iii) the mammal according to (ii), wherein the rodent is mouse or rat; and, (iv) a recombinant vector bearing the exogenous bovine GPR7/8 DNA of the present invention or its variant DNA and capable of expressing in a mammal.

The bovine GPR7/8 DNA transgenic animals of the present invention can be prepared in a manner similar to the DNA transgenic animals of the present invention described above.

In a non-human mammal bearing the normal bovine GPR7/8 DNA of the present invention, the normal bovine GPR7/8 DNA of the present invention is expressed to a high level, and may eventually develop the hyperfunction of the bovine GPR7/8 of the present invention by promoting the function of endogenous normal bovine GPR7/8 DNA. Therefore, the animal can be utilized as a pathologic model animal for such a disease. Specifically, using the normal bovine GPR7/8 DNA transgenic animal of the present invention, it is possible to elucidate the mechanism of the hyperfunction of the bovine GPR7/8 of the present invention and the pathological mechanism of the disease associated with the bovine GPR7/8 of the present invention and to determine how to treat the disease.

Furthermore, since a mammal wherein the exogenous normal bovine GPR7/8 DNA of the present invention is transfected exhibits an increasing symptom of the bovine GPR7/8 of the present invention librated, the animal is usable for screening therapeutic agents for the disease associated with the bovine GPR7/8 of the present invention.

On the other hand, in a non-human mammal bearing the abnormal bovine GPR7/8 DNA of the present invention, the abnormal bovine GPR7/8 DNA of the present invention is expressed at a high level, the animal may be the function inactivation type in adaptability of the bovine GPR7/8 of the present invention by inhibiting the function of the endogenous normal bovine GPR7/8 DNA and can be utilized as its disease model animal. For example, using the abnormal bovine GPR7/8 DNA-transonic animal of the present invention, it is possible to elucidate the mechanism of in adaptability of the bovine GPR7/8 of the present invention and to perform to study a method for treatment of this disease.

More specifically, the transonic animal of the present invention expressing the abnormal bovine GPR7/8 DNA of the present invention to a high level is also expected to serve as an experimental model for the elucidation of the mechanism of the functional inhibition (dominant negative effect) of normal bovine GPR7/8 by the abnormal bovine GPR7/8 of the present invention in the function inactive type in adaptability of the bovine GPR7/8 of the present invention.

The abnormal exogenous bovine GPR7/8 DNA transonic mammal of the present invention is also expected to serve for screening a candidate drug for the treatment of the function inactive type in adaptability of the bovine GPR7/8 of the present invention, since the bovine GPR7/8 of the present invention is increased in such an animal in its free form.

Other potential applications of two kinds of the bovine GPR7/8 DNA transonic animals described above include:

(1) use as a cell source for tissue culture;

(2) elucidation of the relation to a peptide that is specifically expressed or activated by the bovine GPR7/8 of the present invention, by direct analysis of DNA or RNA in tissues of the bovine GPR7/8 DNA transonic animal of the present invention or by analysis of a peptide tissue expressed by the DNA;

(3) research in the function of cells derived from tissues that are cultured usually only with difficulty, using cells of tissue bearing the DNA cultured by a standard tissue culture technique;

(4) screening of a drug that enhances the functions of cells using the cells described in (3) above; and, (5) isolation and purification of the variant bovine GPR7/8 of the present invention and preparation of an antibody thereto.

Furthermore, clinical conditions of a disease associated with the bovine GPR7/8 of the present invention, including the function inactive type in adaptability of the bovine GPR7/8 of the present invention can be determined using the bovine GPR7/8 DNA transonic animal of the present invention. Also, pathological findings on each organ in a disease model associated with the bovine GPR7/8 of the present invention can be obtained in more detail, leading to the development of a new method for treatment as well as the research and therapy of any secondary diseases associated with the disease.

It is also possible to obtain a free DNA-transfected cell by withdrawing each organ from the bovine GPR7/8 DNA transonic animal of the present invention, mincing the organ and degrading with a proteinase such as trying, etc., followed by establishing the line of culturing or cultured cells. Furthermore, the transonic animal can serve as identification of cells capable of producing the bovine GPR7/8 of the present invention, and as studies on association with apropos, differentiation or propagation or on the mechanism of signal transduction in these properties to inspect any abnormality therein. Thus, the transonic animal can provide an effective research material for the bovine GPR7/8 of the present invention and for elucidating the function and effect thereof.

To develop a therapeutic drug for the treatment of diseases associated with the bovine GPR7/8 of the present invention, including the function inactive type in adaptability of the bovine GPR7/8 of the present invention, using the bovine GPR7/8 DNA transonic animal of the present invention, an effective and rapid method for screening can be provided by using the method for inspection and the method for quantification, etc. Described above. It is also possible to investigate and develop a method for DNA therapy for the treatment of diseases associated with the bovine GPR7/8 of the present invention, using the bovine GPR7/8 DNA transonic animal of the present invention or a vector capable of expressing the exogenous bovine GPR7/8 DNA of the present invention.

(8) Knockout Animal

The present invention provides a non-human mammal embryonic stem cell bearing the bovine GPR7/8 DNA of the present invention inactivated and a non-human mammal deficient in expressing the bovine GPR7/8 DNA of the present invention.

Thus, the present invention provides:

(i) a non-human embryonic stem cell in which the bovine GPR7/8 DNA of the present invention is inactivated;

(ii) an embryonic stem cell according to (i), wherein the DNA is inactivated by introducing a reporter gene (e.g., β-galactosidase gene derived from *Escherichia coli*);

(iii) an embryonic stem cell according to (i), which is resistant to neomycin;

(iv) an embryonic stem cell according to (i), wherein the non-human mammal is a rodent;

(v) an embryonic stem cell according to (iv), wherein the rodent is mouse;

(vi) a non-human mammal deficient in expressing the bovine GPR7/8 DNA of the present invention, wherein the DNA is inactivated;

(vii) a non-human mammal according to (vi), wherein the DNA is inactivated by inserting a reporter gene (e.g., β-galactosidase derived from *Escherichia coli*) therein and the reporter gene is capable of being expressed under control of a promoter for the DNA of the present invention;

(viii) a non-human mammal according to (vi), which is a rodent;

(ix) a non-human mammal according to (viii), wherein the rodent is mouse; and, (x) a method of screening a compound or its salt that promotes or inhibits the promoter activity for the bovine GPR7/8 DNA of the present invention, which comprises administering a test compound to the mammal of (vii) and detecting expression of the reporter gene.

The non-human mammal embryonic stem cell wherein the bovine GPR7/8 DNA of the present invention is inactivated, and the non-human mammal deficient in expressing the bovine GPR7/8 DNA of the present invention wherein the DNA is inactivated can be prepared as in the non-human mammal embryonic stem cell of the present invention and the non-human mammal deficient in expressing the DNA of the present invention described above.

The non-human mammal embryonic stem cell, in which the bovine GPR7/8 DNA of the present invention is inactivated, is very useful for preparing a non-human mammal deficient in expressing the bovine GPR7/8 DNA of the present invention.

Since the non-human mammal deficient in expressing the bovine GPR7/8 DNA of the present invention lacks various biological activities derived from the bovine GPR7/8 of the present invention, such an animal can be a disease model suspected of inactivated biological activities of the bovine GPR7/8 of the present invention and thus, offers an effective study to investigate causes for and therapy for these diseases.

(8a) Method of Screening Compounds having Therapeutic/Preventive Effects on Diseases Caused by Deficiency, Damages, etc. of the Bovine GPR7/8 DNA of the Present Invention The non-human mammal deficient in expressing the bovine GPR7/8 DNA of the present invention can be employed for screening of compounds having therapeutic/prophylactic effects on diseases caused by deficiency, damages, etc. of the bovine GPR7/8 DNA of the present invention.

That is, the present invention provides a method for screening of a compound or its salt having therapeutic/preventive effects on diseases caused by deficiency, damages, etc. of the bovine GPR7/8 DNA of the present invention, which comprises administering a test compound to the non-human mammal deficient in expressing the bovine GPR7/8 DNA of the present invention and observing/measuring a change occurred in the animal.

As the non-human mammal deficient in expressing the bovine GPR7/8-DNA of the present invention which can be employed for the screening method, the same examples as given hereinabove apply.

Examples of the test compounds include peptides, proteins, non peptide compounds, synthetic compounds, fermentation products, cell extracts, vegetable extracts, animal tissue extracts, blood plasma, etc. These compounds may be novel compounds or publicly known compounds.

Specifically, the non-human mammal deficient in expressing the bovine GPR7/8 DNA of the present invention is treated with a test compound, comparison is made with an intact animal for control and a change in each organ, tissue, disease conditions, etc. of the animal is used as an indicator to assess the therapeutic/prophylactic effects of the test compound.

For treating an animal to be test with a test compound, for example, oral administration, intravenous injection, etc. are applied and the treatment is appropriately selected depending upon conditions of the test animal, properties of the test compound, etc. Furthermore, a dose of test compound to be administered can be appropriately chosen depending on method for administration, nature of the test compound, etc.

In screening compounds having the therapeutic/preventive effect on, e.g., anorexia, hypertension, autoimmune disease, heart failure, cataract, glaucoma, acute bacterial meningitis, acute myocardial infarction, acute pancreatitis, acute viral encephalitis, adult respiratory distress syndrome, alcoholic hepatitis, Alzheimer's disease, asthma, arteriosclerosis, atopic dermatitis, bacterial pneumonia, bladder cancer, fracture, breast cancer, bulimia, polyphagia, burn healing, uterine cervical cancer, chronic lymphocytic leukemia, chronic myelogenous leukemia, chronic pancreatitis, liver cirrhosis, cancer of the colon and rectum (colon cancer/rectal cancer), Crohn's disease, dementia, diabetic complications, diabetic nephropathy, diabetic neuropathy, diabetic retinopathy, gastritis, *Helicobacter pylori* bacterial infectious disease, hepatic insufficiency, hepatitis A, hepatitis B, hepatitis C, hepatitis, herpes simplex virus infectious disease, varicellazoster virus infectious disease, Hodgkin's disease, AIDS infectious disease, human papilloma virus infectious disease, hypercalcemia, hypercholesterolemia, hyperglyceridemia, hyperlipemia, infectious disease, influenza infectious disease, insulin dependent diabetes mellitus (type I), invasive staphylococcal infectious disease, malignant melanoma, cancer metastasis, multiple myeloma, allergic rhinitis, nephritis, non-Hodgkin's lymphoma, insulin-independent diabetes mellitus (type II), non-small cell lung cancer, organ transplantation, arthrosteitis, osteomalacia, osteopenia, osteoporosis, ovarian cancer, Behcet's disease of bone, peptic ulcer, peripheral vessel disease, prostatic cancer, reflux esophagitis, renal insufficiency, rheumatoid arthritis, schizophrenia, sepsis, septic shock, severe systemic fungal infectious disease, small cell lung cancer, spinal injury, stomach cancer, systemic lupus erythematosus, transient cerebral ischemia, tuberculosis, cardiac valve failure, vascular/multiple infarction dementia, wound healing, insomnia, arthritis, pituitary hormone secretion disorders [e.g., prolactin secretion disorders (e.g., hypoovarianism, spermatic underdevelopment, menopausal symptoms, hypothyroidism, etc.)], pollakiuria, uremia, neurodegenerative disease, etc. (especially, anorexia, or the like), the non-human mammal deficient in expressing the bovine GPR7/8 DNA of the present invention is subjected to a sugar loading treatment, a test compound is administered before or after the sugar loading treatment and, blood sugar level, body weight change, etc. of the animal is measured with passage of time.

In the screening method described above, when a test compound is administered to a test animal and found to reduce the blood sugar level of the animal to at least about 10%, preferably at least about 30% and more preferably at least about 50%, the test compound can be selected to be a compound having a therapeutic/preventive effect on the diseases above.

The compound obtained using the screening method above is a compound selected from the test compounds described above and exhibits a therapeutic/preventive effect on the diseases caused by deficiencies, damages, etc. of the bovine GPR7/8 of the present invention. Therefore, the compound can be employed as a safe and low toxic drug for the treatment and prevention of these diseases. Furthermore, compounds derived from such a compound obtained by the screening described above can be similarly employed.

The compound obtained by the screening method above may be in the form of salts. As such salts, there may be used salts with physiologically acceptable acids (e.g., inorganic acids, organic acids, etc.) or bases (e.g., alkali metal salts, etc.), preferably in the form of physiologically acceptable acid addition salts. Examples of such salts are salts with inorganic acids (e.g., hydrochloric acid, phosphoric acid, hydrobromic acid, sulfuric acid, etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.) and the like.

A pharmaceutical composition comprising the compound or its salt, obtained by the above screening method, may be manufactured in a manner similar to the method for preparing the pharmaceutical composition comprising the peptide of the present invention described hereinabove.

Since the pharmaceutical composition thus obtained is safe and low toxic, it can be administered to human or mammals (e.g., rats, mice, guinea pigs, rabbits, sheep, swine, bovine, horses, cats, dogs, monkeys, etc.).

A dose of the compound or its salt to be administered varies depending upon particular disease, subject to be administered, route of administration, etc., and in oral administration to an adult patient with anorexia (as 60 kg body weight), the compound is administered generally in a dose of approximately 0.1 to. 100 mg, preferably approximately 1.0 to 50 mg, more preferably approximately 1.0 to 20 mg per day. For parenteral administration to an adult patient with anorexia (as 60 kg body weight), it is advantageous to administer the compound intravenously in the form of an injectable preparation in a dose of approximately 0.01 to 30 mg, preferably approximately 0.1 to 20 mg, more preferably approximately 0.1 to 10 mg per day, though the single dosage varies depending upon particular subject, particular disease, etc. For other animals, the compound can be administered in the corresponding dose with converting it into that for the 60 kg body weight.

(8b) Method of Screening a Compound that Promotes or Inhibits the Activity of a Promoter to the Bovine GPR7/8 DNA of the Present Invention The present invention provides a method of screening a compound or its salt that promotes or inhibits the activity of a promoter to the bovine GPR7/8 DNA of the present invention, which comprises administering a test compound to a non-human mammal deficient in expressing the bovine GPR7/8 DNA of the present invention and detecting expression of the reporter gene.

In the screening method described above, the non-human mammal deficient in expressing the bovine GPR7/8 DNA of the present invention is selected from the aforesaid non-human mammal deficient in expressing the bovine GPR7/8 DNA of the present invention, as an animal in which the bovine GPR7/8 DNA of the present invention is inactivated by introducing a reporter gene and the reporter gene is expressed under control of a promoter to the bovine GPR7/8 DNA of the present invention.

The same examples of the test compound apply to those given above.

As the reporter gene, the same specific examples apply. Preferably employed are β-galactosidase (lacZ), soluble alkaline phosphatase gene, luciferase gene and the like.

Since the reporter gene is present under control of a promoter to the bovine GPR7/8 DNA of the present invention in the non-human mammal deficient in expressing the bovine GPR7/8 DNA of the present invention wherein the bovine GPR7/8 DNA of the present invention is substituted with the reporter gene, the activity of the promoter can be detected by tracing expression of a substance encoded by the reporter gene.

For example, when a part of the DNA region encoding the bovine GPR7/8 of the present invention is substituted with, e.g., β-galactosidase gene (lacZ) derived from *Escherichia coli*, β-galactosidase is expressed in a tissue where the bovine GPR7/8 of the present invention should originally be expressed, instead of the bovine GPR7/8 of the present invention. Thus, the state of expression condition of the bovine GPR7/8 of the present invention can be readily observed in vivo of an animal by staining with a reagent, e.g., 5-bromo-4-chloro-3-indolyl-β-galactopyranoside (X-gal) which is substrate for β-galactosidase. Specifically, a mouse deficient in the bovine GPR7/8 of the present invention, or its tissue slice section is fixed with glutaraldehyde, etc. After washing with phosphate buffered saline (PBS), the system is reacted with a staining solution containing X-gal at room temperature or about 37° C. for approximately 30 minutes to an hour. After the β-galactosidase reaction is terminated by washing the tissue preparation with 1 mM EDTA/PBS solution, the color formed is observed. Alternatively, mRNA encoding lacZ may be detected in a conventional manner.

The compound or salts thereof obtained using the aforesaid screening method are compounds that are selected from the test compounds described above and the compounds that promote or inhibit the activity of a promoter to the bovine GPR7/8 DNA of the present invention.

The compound obtained by the screening method above may form salts. As salts of the compound, there may be used salts with physiologically acceptable acids (e.g., inorganic acids, etc.) or bases (e.g., organic acids, etc.), and especially preferred are physiologically acceptable acid addition salts. Examples of such salts are salts with inorganic acids (e.g., hydrochloric acid, phosphoric acid, hydrobromic acid, sulfuric acid, etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.) and the like.

The compound or its salt that promotes the promoter activity to the bovine GPR7/8 DNA of the present invention can promote expression of the bovine GPR7/8 of the present invention thereby to promote the function of the bovine GPR7/8. Thus, these compounds are useful as safe and low-toxic drugs for the treatment/prevention of diseases, e.g., anorexia, hypertension, autoimmune disease, heart failure, cataract, glaucoma, acute bacterial meningitis, acute myocardial infarction, acute pancreatitis, acute viral encephalitis, adult respiratory distress syndrome, alcoholic hepatitis, Alzheimer's disease, asthma, arteriosclerosis, atopic dermatitis, bacterial pneumonia, bladder cancer, fracture, breast cancer, bulimia, polyphagia, burn healing, uterine cervical cancer, chronic lymphocytic leukemia, chronic myelogenous leukemia, chronic pancreatitis, liver cirrhosis, cancer of the colon and rectum (colon cancer/rectal cancer), Crohn's disease, dementia, diabetic complications, diabetic nephropathy, diabetic neuropathy, diabetic retinopathy, gastritis, *Helicobacter pylori* bacterial infectious disease, hepatic insufficiency, hepatitis A, hepatitis B, hepatitis C, hepatitis, herpes simplex virus infectious disease, varicella-zoster virus infectious disease, Hodgkin's disease, AIDS infectious disease, human papilloma virus infectious disease, hypercalcemia, hypercholesterolemia, hyperglyceridemia, hyperlipemia, infectious disease, influenza infectious disease, insulin dependent diabetes mellitus (type I), invasive staphylococcal infectious disease, malignant melanoma, cancer metastasis, multiple myeloma, allergic rhinitis, nephritis, non-Hodgkin's lymphoma, insulin-independent diabetes mellitus (type II), non-small cell lung cancer, organ transplantation, arthrosteitis osteomalacia, osteopenia, osteoporosis, ovarian cancer, Behcet's disease of bone, peptic ulcer, peripheral vessel disease, prostatic cancer, reflux esophagitis, renal insufficiency, rheumatoid arthritis, schizophrenia, sepsis, septic shock, severe systemic fungal infectious disease, small cell lung cancer, spinal injury, stomach cancer, systemic lupus erythematosus, transient cerebral ischemia, tuberculosis, cardiac valve failure, vascular/multiple infarction dementia, wound healing, insomnia, arthritis, pituitary hormone secretion disorders [e.g., prolactin secretion disorders (e.g., hypoovarianism, spermatic underdevelopment, menopausal symptoms, hypothyroidism, etc.)], pollakiuria, uremia, neurodegenerative disease, etc. (especially, anorexia or the like) or the like (especially, appetite (eating) stimulant).

The compound or its salt that inhibits the activity of a promoter to the bovine GPR7/8 DNA of the present invention can inhibit expression of the bovine GPR7/8 of the present invention thereby to inhibit the function of the bovine GPR7/8. Thus, these compounds are useful as drugs, including preventive/therapeutic drugs (prolactin production inhibitors) for diseases, for example, obesity (e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity, etc.), hyperphagia, pituitary tumor, diencephalon tumor, menstrual disorder, autoimmune disease, prolactinoma, sterility, impotence, amenorrhea, lactorrhea, acromegaly, Chiari-Frommel syndrome, Argonz-del Castillo syndrome, Forbes-Albright syndrome, lymphoma or Sheehan's syndrome, spermatogenesis disorders, etc.; preferably as preventive/therapeutic agents for obesity, hyperphagia, etc.

Furthermore, compounds derived from the compounds obtained by the screening described above may be likewise used.

The pharmaceuticals comprising the compound or its salt obtained by the screening method may be manufactured as in the aforesaid pharmaceuticals comprising the peptide of the present invention or its salt.

Since the pharmaceutical preparation thus obtained is safe and low toxic; it can be administered to human or mammals (e.g., rats, mice, guinea pigs, rabbits, sheep, swine, bovine, horses, cats, dogs, monkeys, etc.).

A dose of the compound or its salt to be administered varies depending upon target disease, subject to be administered, route of administration, etc.; when the compound that promotes the promoter activity to the bovine GPR7/8 DNA of the present invention is orally administered to an adult patient, e.g., with anorexia (as 60 kg body weight), the compound is administered generally in a dose of approximately 0.1 to 100 mg, preferably approximately 1.0 to 50 mg, more preferably approximately 1.0 to 20 mg per day. In parenteral administration, a single dose of the compound varies depending upon subject to be administered, target disease, etc. When the compound that promotes the promoter activity to the bovine GPR7/8 DNA of the present invention is administered to an adult patient with, e.g., anorexia (as 60 kg body weight) in the form of an injectable preparation, it is advantageous to administer the compound intravenously in a dose of approximately 0.01 to 30 mg, preferably approximately 0.1 to 20 mg, more preferably approximately 0.1 to 10 mg per day. For other animals, the compound can be administered in the corresponding dose with converting it into that for the 60 kg body weight.

On the other hand, when a compound that inhibits the promoter activity to the bovine GPR7/8 DNA of the present invention is orally administered, the compound is orally administered to an adult patient with obesity (as 60 kg body weight) generally in a dose of approximately 0.1 to 100 mg, preferably approximately 1.0 to 50 mg, more preferably approximately 1.0 to 20 mg per day. In parenteral administration, a single dose of the compound varies depending upon subject to be administered, target disease, etc. For example, when the compound that inhibits the promoter activity to the bovine GPR7/8 DNA of the present invention is administered to an adult patient with obesity (as 60 kg body weight) in the form of an injectable preparation, it is advantageous to administer the compound intravenously in a dose of approximately 0.01 to 30 mg, preferably approximately 0.1 to 20 mg, more preferably approximately 0.1 to 10 mg per day. For other animals, the compound can be administered in the corresponding dose with converting it into that for the 60 kg body weight.

As described above, the non-human mammal deficient in expressing the bovine GPR7/8 DNA of the present invention is extremely useful for screening a compound or its salt that promotes or inhibits the activity of a promoter to the bovine GPR7/8 DNA of the present invention, and can thus greatly contribute to investigations of causes for various diseases caused by failure to express the bovine GPR7/8 DNA of the present invention or to development of preventive/therapeutic agents for these diseases.

Moreover, when a so-called transonic animal (gene-transfected animal) is prepared by using the bovine GPR7/8 DNA containing the promoter region of the bovine GPR7/8 of the present invention, ligating genes encoding various proteins downstream the same and injecting the genes into animal oocyte, the peptide can be specifically synthesized by the animal so that it becomes possible to investigate the activity in vivo. Furthermore, when an appropriate reporter gene is ligated to the promoter region described above to establish a cell line so as to express the gene, such can be used as a survey system of low molecular weight compounds that specifically promotes or suppresses the ability of producing the bovine GPR7/8 itself of the present invention in vivo.

In the specification and drawings, the codes of bases and amino acids are shown by abbreviations and in this case, they are denoted in accordance with the IUPAC-IUB Commission on Biochemical Nomenclature or by the common codes in the art, examples of which are shown below. For amino acids that may have the optical isomer, L form is presented unless otherwise indicated.

| | |
|---|---|
| DNA | deoxyribonucleic acid |
| cDNA | complementary deoxyribonucleic acid |
| A | adenine |
| T | thymine |
| G | guanine |
| C | cytosine |
| I | inosine |
| R | adenine (A) or guanine (G) |
| Y | thymine (T) or cytosine (C) |
| M | adenine (A) or cytosine (C) |
| K | guanine (G) or thymine (T) |
| S | guanine (G) or cytosine (C) |
| W | adenine (A) or thymine (T) |
| B | guanine (G), guanine (G) or thymine (T) |
| D | adenine (A), guanine (G) or thymine (T) |
| V | adenine (A), guanine (G) or cytosine (C) |
| N | adenine (A), guanine (G), cytosine (C) or thymine (T), or unknown or other base |
| RNA | ribonucleic acid |
| mRNA | messenger ribonucleic acid |
| dATP | deoxyadenosine triphosphate |
| dTTP | deoxythymidine triphosphate |
| dGTP | deoxyguanosine triphosphate |
| dCTP | deoxycytidine triphosphate |
| ATP | adenosine triphosphate |
| EDTA | ethylenediaminetetraacetic acid |
| SDS | sodium dodecyl sulfate |
| BHA | benzhydrylamine |
| pMBHA | p-methyobenzhydrylamine |
| Tos | p-toluenesulfonyl |
| Bzl | benzyl |
| Bom | benzyloxymethyl |
| Boc | t-butyloxycarbonyl |
| DCM | dichloromethane |
| HOBt | 1-hydroxybenztriazole |
| DCC | N,N'-dicyclohexylcarbodiimide |
| TFA | trifluoroacetic acid |
| DIEA | diisopropylethylamine |
| Gly or G | glycine |
| Ala or A | alanine |
| Val or V | valine |
| Leu or L | leucine |
| Ile or I | isoleucine |
| Ser or S | serine |
| Thr or T | threonine |
| Cys or C | cysteine |
| Met or M | methionine |
| Glu or E | glutamic acid |
| Asp or D | aspartic acid |
| Lys or K | lysine |
| Arg or R | arginine |
| His or H | histidine |
| Phe or F | phenylalanine |
| Tyr or Y | tyrosine |
| Trp or W | tryptophan |
| Pro or P | proline |
| Asn or N | asparagine |
| Gln or Q | glutamine |
| pGlu | pyroglutamic acid |
| Tyr (I) | 3-iodotyrosine |
| DMF | N,N-dimethylformamide |
| Fmoc | N-9-fluorenylmethoxycarbonyl |
| Trt | trityl |
| Pbf | 2,2,4,6,7-pentamethyldihydrobenzofuran-5-sulfonyl |
| Clt | 2-chlorotrityl |
| $Bu^t$ | t-butyl |
| Met (O) | methionine sulfoxide |

The sequence identification numbers in the sequence listing of the specification indicates the following sequences, respectively.

[SEQ ID NO:1]
This shows the amino acid sequence of human GPR7 ligand A.

[SEQ ID NO:2]
This shows the amino acid sequence of mouse GPR7 ligand A.

[SEQ ID NO:3]
This shows the amino acid sequence of rat GPR7 ligand A.

[SEQ ID NO:4]
This shows the amino acid sequence of human GPR7 ligand B.

[SEQ ID NO:5]
This shows the amino acid sequence of mouse GPR7 ligand B.

[SEQ ID NO:6]
This shows the amino acid sequence of rat GPR7 ligand B.

[SEQ ID NO:7]
This shows the amino acid sequence of human GPR7 ligand C.

[SEQ ID NO:8]
This shows the amino acid sequence of human GPR7 ligand D.

[SEQ ID NO:9]
This shows the amino acid sequence of mouse GPR7 ligand C.

[SEQ ID NO:10]
This shows the amino acid sequence of mouse GPR7 ligand D.

[SEQ ID NO:11]
This shows the amino acid sequence of rat GPR7 ligand C.

[SEQ ID NO:12]
This shows the amino acid sequence of rat GPR7 ligand D.

[SEQ ID NO:13]
This shows the amino acid sequence of human GPR7 ligand E.

[SEQ ID NO:14]
This shows the amino acid sequence of mouse GPR7 ligand E.

[SEQ ID NO:15]
This shows the amino acid sequence of rat GPR7 ligand E.

[SEQ ID NO:16]
This shows the amino acid sequence of human GPR7 ligand F.

[SEQ ID NO:17]
This shows the amino acid sequence of mouse GPR7 ligand F.

[SEQ ID NO:18]
This shows the amino acid sequence of rat GPR7 ligand F.

[SEQ ID NO:19]
This shows the amino acid sequence of human GPR7 ligand precursor G containing no secretory signal.

[SEQ ID NO:20]
This shows the amino acid sequence of mouse GPR7 ligand precursor G containing no secretory signal.

[SEQ ID NO:21]
This shows the amino acid sequence of rat GPR7 ligand precursor G containing no secretory signal.

[SEQ ID NO:22]
This shows the amino acid sequence of human GPR7 ligand precursor H containing a secretory signal.

[SEQ ID NO:23]
This shows the amino acid sequence of mouse GPR7 ligand precursor H containing a secretory signal.

[SEQ ID NO:24]
This shows the amino acid sequence of rat GPR7 ligand precursor H containing a secretory signal.

[SEQ ID NO:25]
This shows the base sequence of DNA encoding human GPR7 ligand A.

[SEQ ID NO:26]
This shows the base sequence of DNA encoding mouse GPR7 ligand A.

[SEQ ID NO:27]
This shows the base sequence of DNA encoding rat GPR7 ligand A.

[SEQ ID NO:28]
This shows the base sequence of DNA encoding human GPR7 ligand B.

[SEQ ID NO:29]
This shows the base sequence of DNA encoding mouse GPR7 ligand B.

[SEQ ID NO:30]
This shows the base sequence of DNA encoding rat GPR7 ligand B.

[SEQ ID NO:31]
This shows the base sequence of DNA encoding human GPR7 ligand C.

[SEQ ID NO:32]
This shows the base sequence of DNA encoding human GPR7 ligand D.

[SEQ ID NO:33]
This shows the base sequence of DNA encoding mouse GPR7 ligand C.

[SEQ ID NO:34]
This shows the base sequence of DNA encoding mouse GPR7 ligand D.

[SEQ ID NO:35]
This shows the base sequence of DNA encoding rat GPR7 ligand C.

[SEQ ID NO:36]
This shows the base sequence of DNA encoding rat GPR7 ligand D.

[SEQ ID NO:37]
This shows the base sequence of DNA encoding human GPR7 ligand E.

[SEQ ID NO:38]
This shows the base sequence of DNA encoding mouse GPR7 ligand E.

[SEQ ID NO:39]
This shows the base sequence of DNA encoding rat GPR7 ligand E.

[SEQ ID NO:40]
This shows the base sequence of DNA encoding human GPR7 ligand F.

[SEQ ID NO:41]
This shows the base sequence of DNA encoding mouse GPR7 ligand F.

[SEQ ID NO:42]
This shows the base sequence of DNA encoding rat GPR7 ligand F.

[SEQ ID NO:43]
This shows the base sequence of DNA encoding human GPR7 ligand precursor G containing no secretory signal.

[SEQ ID NO:44]
This shows the base sequence of DNA encoding mouse GPR7 ligand precursor G containing no secretory signal.

[SEQ ID NO:45]
This shows the base sequence of DNA encoding rat GPR1 ligand precursor G containing no secretory signal.

[SEQ ID NO:46]
This shows the base sequence of DNA encoding human GPR7 ligand precursor H containing a secretory signal.

[SEQ ID NO:47]
This shows the base sequence of DNA encoding mouse GPR7 ligand precursor H containing a secretory signal.

[SEQ ID NO:48]
This shows the base sequence of DNA encoding rat GPR7 ligand precursor H containing a secretory signal.

[SEQ ID NO:49]
This shows the amino acid sequence of human GPR7.

[SEQ ID NO:50]
This shows the base sequence of a DNA containing the DNA encoding human GPR7.

[SEQ ID NO:51]
This shows a synthetic DNA used in EXAMPLE 1 to screen cDNA encoding human GPR7 ligand precursor H.

[SEQ ID NO:52]
This shows a synthetic DNA used in EXAMPLE 1 to screen cDNA encoding human GPR7 ligand precursor H.

[SEQ ID NO:53]
This shows a synthetic DNA used in EXAMPLE 2 to screen cDNA encoding mouse GPR7 ligand precursor H.

[SEQ ID NO:54]
This shows a synthetic DNA used in EXAMPLE 2 to screen cDNA encoding mouse GPR7 ligand precursor H.

[SEQ ID NO:55]
This shows a synthetic DNA used in EXAMPLE. 3 to screen cDNA encoding rat GPR7 ligand precursor H.

[SEQ ID NO:56]
This shows a synthetic DNA used in EXAMPLE 3 to screen cDNA encoding rat GPR7 ligand precursor H.

[SEQ ID NO:57]
This shows the base sequence of a primer used in REFERENCE EXAMPLE 1.

[SEQ ID NO:58]
This shows the base sequence of a primer used in REFERENCE EXAMPLE 1.

[SEQ ID NO:59]
This shows the amino acid sequence of rat TGR26.

[SEQ ID NO:60]
This shows the base sequence of DNA encoding rat TGR26.

[SEQ ID NO:61]
This shows the base sequence of Primer 1 used for PCR in REFERENCE EXAMPLE 3.

[SEQ ID NO:62]
This shows the base sequence of Primer 2 used for PCR in REFERENCE EXAMPLE 3.

[SEQ ID NO:63]
This shows the base sequence of a primer used in EXAMPLE 9.

[SEQ ID NO:64]
This shows the base sequence of a primer used in EXAMPLE 9.

[SEQ ID NO:65]
This shows the base sequence of a primer used in EXAMPLE 9.

[SEQ ID NO:66]
This shows the amino acid sequence of bovine GPR7 ligand A.

[SEQ ID NO:67]
This shows the amino acid sequence of bovine GPR7 ligand B.

[SEQ ID NO:68]
This shows the amino acid sequence of bovine GPR7 ligand C.

[SEQ ID NO:69]
This shows the amino acid sequence of bovine GPR7 ligand D.

[SEQ ID NO:70]
This shows the amino acid sequence of bovine GPR7 ligand E.

[SEQ ID NO:71]
This shows the amino acid sequence of bovine GPR7 ligand F.

[SEQ ID NO:72]
This shows the amino acid sequence of bovine GPR7 ligand precursor G containing no secretory signal.

[SEQ ID NO:73]
This shows the amino acid sequence of bovine GPR7 ligand precursor H containing a secretory signal.

[SEQ ID NO:74]
This shows the base sequence of DNA encoding bovine GPR7 ligand A.

[SEQ ID NO:75]
This shows the base sequence of DNA encoding bovine GPR7 ligand B.

[SEQ ID NO:76]
This shows the base sequence of DNA encoding bovine GPR7 ligand C.

[SEQ ID NO:77]
This shows the base sequence of DNA encoding bovine GPR7 ligand D.

[SEQ ID NO:78]
This shows the base sequence of DNA encoding bovine GPR7 ligand E.

[SEQ ID NO:79]
This shows the base sequence of DNA encoding bovine GPR7 ligand F.

[SEQ ID NO:80]
This shows the base sequence of DNA encoding bovine GPR7 ligand precursor G containing no secretory signal.

[SEQ ID NO:81]
This shows the base sequence of DNA encoding bovine GPR7 ligand precursor H containing a secretory signal.

[SEQ ID NO:82]
This shows the base sequence of a primer used in EXAMPLE 12.

[SEQ ID NO:83]
This shows the base sequence of a primer used in EXAMPLE 12.

[SEQ ID NO:84]
This shows the amino acid sequence of human GPR8.

[SEQ ID NO:85]
This shows the base sequence of a DNA containing the DNA encoding human GPR8.

[SEQ ID NO:86]
This shows the amino acid sequence of bovine GPR7.

[SEQ ID NO:87]
This shows the base sequence of a DNA containing the DNA encoding bovine GPR7.

[SEQ ID NO:88]
This shows the amino acid sequence of bovine GPR8.

[SEQ ID NO:89]
This shows the base sequence of a DNA containing the DNA encoding bovine GPR8.

[SEQ ID NO:90]
This shows the base sequence of a primer used in EXAMPLE 16.

[SEQ ID NO:91]
This shows the base sequence of a primer used in EXAMPLE 16.

[SEQ ID NO:92]
This shows the base sequence of a primer used in EXAMPLE 16.

[SEQ ID NO:93]
This shows the base sequence of a primer used in EXAMPLE 17.

[SEQ ID NO:94]
This shows the base sequence of a primer used in EXAMPLE 17.

[SEQ ID NO:95]
This shows the base sequence of a primer used in EXAMPLE 17.

[SEQ ID NO:96]
This shows the base sequence of a primer used in EXAMPLE 18.

[SEQ ID NO:97]
This shows the base sequence of a primer used in EXAMPLE 18.

[SEQ ID NO:98]
This shows the base sequence of a primer used in EXAMPLE 19.

[SEQ ID NO:99]
This shows the base sequence of a primer used in EXAMPLE 19.

[SEQ ID NO:100]
This shows the amino acid sequence of human GPR8 ligand (1-23).

[SEQ ID NO:101]
This shows the complete DNA sequence, including stop codon, from FIG. 1.

[SEQ ID NO:102]
This shows the complete DNA sequence, including stop codon, from FIG. 3.

[SEQ ID NO:103]
This shows the complete DNA sequence, including stop codon, from FIG. 5.

[SEQ ID NO:104]
This shows the complete DNA sequence, including stop codon, from FIG. 20.

[SEQ ID NO:105]
This shows the complete DNA sequence, including stop codon, from FIG. 26.

[SEQ ID NO:106]
This shows the complete DNA sequence, including stop codon, from FIG. 28.

[SEQ ID NO:107]
This shows an embodiment of SEQ ID NO:4, wherein the N-terminal Trp is of a brominated D-form.

[SEQ ID NO:108]
This shows an embodiment of SEQ ID NO:4, wherein the N-terminal Trp is of a brominated D-form.

Transformant *Escherichia ccli* JM109/pTAhGPR7-1, which was obtained in EXAMPLE 1 later described, has been deposited as JM109/pTAhGPR7L-1 since Jun. 27, 2001 on the National Institute of Advanced Industrial Science and Technology, International Patent Organism Depositary, located at Central 6, 1-1-1 Higashi, Tsukuba, Ibaraki, Japan (postal code 305-8566), under the Accession Number FERM BP-7640.

Transformant *Escherichia coli* JM109/pTAmGPR7-1, which was obtained in EXAMPLE 2 later described, has been deposited as JM109/pTAmGPR7L-1 since Jun. 27, 2001 on the National Institute of Advanced Industrial Science and Technology, International Patent Organism Depositary under the Accession Number FERM BP-7641, and since on Jun. 19, 2001 on the Institute for Fermentation (IFO) under the Accession Number IFO 16656, respectively.

Transformant *Escherichia coli* JM109/pTArGPR7-1, which was obtained in EXAMPLE 3 later described, has been deposited as JM109/pTArGPR7L-1 since Jun. 27, 2001 on the National Institute of Advanced Industrial Science and Technology, International Patent Organism Depositary under the Accession Number FERM BP-7642, and since on Jun. 19, 2001 on the Institute for Fermentation (IFO) under the Accession Number IFO 16657, respectively.

Transformant *Escherichia coli* JM109/pTAbGPR7L-1, which was obtained in EXAMPLE 12 later described, has been deposited since Dec. 17, 2001 on the National Institute of Advanced. Industrial Science and Technology, International Patent Organism Depositary under the Accession Number FERM BP-7829, and since on Dec. 6, 2001 on the Institute for Fermentation (IFO) under the Accession Number IFO. 16736, respectively.

Transformant *Escherichia coli* JM109/pTAbGPR7, which was obtained in EXAMPLE 18 later described, has been deposited since May 24, 2002 on the National Institute of Advanced Industrial Science and Technology, International Patent Organism Depositary under the Accession Number FERM BP-8050.

Transformant *Escherichia coli* JM109/pTAbGPR8, which was obtained in EXAMPLE 19 later described, has been deposited since May 24, 2002 on the National Institute of Advanced Industrial Science and Technology, International Patent Organism Depositary under the Accession Number FERM BP-8051.

Transformant *Escherichia coli* DH10B/pAK-rGPR7, which was obtained in REFERENCE EXAMPLE 3 later described, has been deposited since Oct. 31, 2000 on the Institute for Fermentation (IFO), located at 2-17-85, Juso Honcho, Yodogawa-ku, Osaka-shi, Osaka, Japan, under the Accession Number IFO 16496 and since on Nov. 13, 2000 on the Ministry of International Trade and Industry, Agency of Industrial Science and Technology, National Institute of Bioscience and Human Technology (NIBH), located at 1-1-3 Higashi, Tsukuba, Ibaraki, Japan, under the Accession Number FERM BP-7365, respectively.

EXAMPLES

The present invention will be described in more detail below, with reference to REFERENCE EXAMPLES and EXAMPLES, but is not deemed to limit the scope of the present invention thereto.

Reference Example 1

Amplification of Human GPR7 DNA by PCR using Human Chromosomal DNA

By use of human chromosomal DNA as a template, amplification of DNA was carried out by PCR using two synthetic primers (SEQ ID NO:57 and SEQ ID NO:58). The synthetic primers were constructed so as to amplify the gene in the region to be translated to its receptor protein was amplified. In this case, the recognition sequences for restriction enzymes were added at the 5' and 3' ends, respectively, so that the base sequences recognized by restriction enzymes ClaI and SpeI were added to the gene at the 5' and 3' ends, respectively. The reaction solution was composed of 0.5 µl of human chromosomal DNA (TaKaRa Shuzo Co., Ltd.), 1 µM each of the synthetic DNA primers, 0.8 mM dNTPs, 1 mM $MgCl_2$ and 1 µl of KOD polymerase (Toyobo Co., Ltd.), to which the buffer attached to the enzymes was added to make the total reaction volume of 50 µl. For amplification, after heating at 94° C. for 60 seconds, the cycle set to include 98° C. for 15 seconds, 65° C. for 2 seconds and 72° C. for 30 seconds was repeated 35 times, using Thermal Cycler (TaKaRa Shuzo Co., Ltd.). The amplified product was confirmed by 0.8% agarose gel electrophoresis followed by staining with ethidium bromide.

Reference Example 2

Subcloning of the PCR Product into a Plasmid Vector and Confirmation of the Amplified DNA Sequence by Decoding the Base Sequence of the Inserted DNA Part The reaction solution of PCR performed in REFERENCE EXAMPLE 1 was separated by 0.8% low melting point agarose gel electrophoresis. The band part was excised with a razor blade, ground into small pieces, extracted with phenol and then with phenol/chloroform and precipitated in ethanol to recover DNAs. According to the protocol attached to PCR-Script™ Amp SK(+) Cloning Kit (Stratagene Co.), the recovered DNAs were subcloned to plasmid vector pCR-Script Amp SK(+). The recombinant vector was introduced into *Escherichia coli* DH5α competent cells (Toyobo Co., Ltd.) to produce transformants. The clones bearing the DNA-inserted fragment were selected in an LB agar medium supplemented with ampicillin, IPTG and X-gal. Only the clones exhibiting white color were picked up with a sterilized toothpick to obtain transformant *E. coli* DH5α/GPR7. The individual clones were cultured overnight in an LB medium containing ampicillin. Plasmid DNAs were prepared using QIAwell 8 Plasmid Kit (QIAGEN, Inc.). An aliquot of the DNAs thus prepared was cleaved by restriction enzymes ClaI and SpeI to confirm the size of the receptor cDNA fragment inserted. The reaction for base sequencing was carried out by using a DyeDeoxy Terminator Cycle Sequence Kit (Applied Biosystems, Inc.), followed by decoding with a fluorescent automatic sequencer (SEQ ID NO:50). The pCR-Script Amp SK(+) plasmid bearing the DNA having the base sequence represented by SEQ ID NO:50 was named pCR-Script human GPR7. The amino acid sequence of human GPR7 encoded by the DNA having the base sequence represented by SEQ ID NO:50 is presented in SEQ ID NO:49. The DNA sequence of human GPR7 sequenced herein differed by 2 bases from the DNA sequence reported by O'Dowd et al. (O'Dowd, B. F. et al., Genomics, 28, 84-91, 1995). These bases corresponding to 893rd and 894th bases in SEQ ID NO:50 were reportedly C and G in the report by O'Dowd et al., whereas they were found to be G and C in this REFERENCE EXAMPLE. Based on the findings, the 296th amino acid of SEQ ID NO:49 in the translated amino acid sequence is Ser in this EXAMPLE, which was reportedly Thr in O'Dowd et al.

Reference Example 3

Cloning of cDNA Encoding Rat Whole Brain-Derived G Protein-Coupled Receptor Protein and Base Sequencing By use of rat whole brain cDNA (CLONTECH Labs. Inc.), PCR was carried out using two primers, Primer 1 (SEQ ID NO:61) and Primer 2 (SEQ ID NO:62) designed from the base sequence of DNA encoding human GPR8. The reaction solution for PCR wherein 1/10 volume of the above cDNA was used as a template, was composed of 1/50 volume of Advantage-2 cDNA Polymerase Mix (CLONTECH Labs. Inc.), 0.2 µM of Primer 3, 0.2 µM of Primer 2 and 200 µM of dNTPs, to which the buffer attached to the enzymes was added to make the total volume of 25 µl. PCR was carried out, (1) after heating at 94° C. for 2 minutes, by repeating (2) the cycle set to include 94° C. for 20 seconds and 72° C. for 2 minutes 3 times, (3) the cycle set to include 94° C. for 20 seconds, 66° C. for 20 seconds and 68° C. for 2 minutes 3 times and (4) the cycle set to include 94° C. for 20 seconds, 60° C. for 20 seconds and 68° C. for 2 minutes 36 times, finally followed by extension at 68° C. for 7 minutes. The reaction product after the PCR was subcloned to pCR2.1-TOPO (Invitrogen, Inc.) in accordance with the protocol of TA Cloning Kit vector using TA cloning kit (Invitrogen, Inc.). After introducing into *Escherichia coli* DH5α, clones bearing cDNA were selected in LB agar medium supplemented with ampicillin. Individual clones were sequenced to acquire the base sequence (SEQ ID NO:60) of cDNA encoding novel G protein-coupled receptor protein. The novel G protein-coupled receptor protein containing the amino acid sequence (SEQ ID NO:59) encoded by the base sequence of this DNA was named TGR26.

The amino acid sequence represented by SEQ ID NO:59 had 84.8% homology to GPR7 (Genomics, 28, 84-91, 1995), which is known human G protein-coupled receptor protein.

From the above transformants bearing the plasmid inserted with the TGR26-encoding DNA, one clone was selected and shake cultured in LB medium supplemented with ampicillin to acquire plasmid. The plasmid was treated with restriction enzymes ClaI and SpeI to excise the insert encoding TGR26. Using pAKKO-1.11H, which was similarly treated with restriction enzymes ClaI and SpeI, and Ligation Express Kit (CLONTECH, Inc.), ligation was performed and the ligated product was transfected to *Escherichia coli* DH10B by electroporation. With respect to the clone thus obtained, the structure of the plasmid for expression cell construction was confirmed by the treatment with restriction enzymes and sequencing. The clone was then named *Escherichia coli* DH10B/pAK-rGPR7.

Reference Example 4

Preparation of TGR26-Expressing CHO Cells

After *Escherichia coli* DH5α (Toyobo Co., Ltd.) transformed by the expression plasmid pAK-rGPR7 described in REFERENCE EXAMPLE 3 was cultured, pAK-rGPR7 plasmid DNA was prepared. The plasmid DNA was transfected to CHO dhfr⁻ cells by using CellPhect Transfection Kit (Amersham Pharmacia Biotech), according to the protocol attached. A co-precipitated suspension of 5 μg of DNA and calcium phosphate was added to 2 Petri dishes of 6 cm diameter, on which 3×10⁵ CHO dhfr⁻ cells had been plated 48 hours before. After cultivation for a day in MEM a medium containing 10% fetal cow serum, the cells were passaged and cultured in nucleic acid-free MEM a medium containing 10% dialysis fetal cow serum as a selection medium. From the colony of the transformant which was TGR26-expressing CHO cells grown in the selection medium, 44 clones were selected.

Example 1

Acquisition of GPR7 Ligand Precursor Gene from Human Whole Brain cDNA by PCR and Construction of Expression Plasmid Using human whole brain cDNA purchased from CLONTECH as a template, amplification was performed by PCR using the following two synthetic DNAs.

```
                                    (SEQ ID NO:51)
GSF1:  5'-GTCGACATGGCCCGGTCCGCGACACTGGCGGCC-3'

(SEQ ID NO:52)
GSR2:  5'-GCTAGCAGCGGTGCCAGGAGAGGTCCGGGCTCA-3'
```

The reaction solution for PCR contained 1 μl of cDNA solution, 0.5 μl of GSF1 (10 μM), 0.5 μl of GSR2 (10 μM), 2.5 μl of 10× reaction solution attached, 2.5 μl of dNTP (10 mM) and 0.5 μl of KlenTaq (CLONTECH, Inc.), to which 17.5 μl of Otsuka distilled water was added to make 25 μl in total. The reaction solution was applied to PCR using Thermal Cycler 9600. The conditions for PCR were set forth: after denaturation at 95° C. for 2 minutes, the cycle set to include 98° C. for 10 seconds, 60° C. for 20 seconds and 72° C. for 20 seconds was repeated 35 times. After it was confirmed by electrophoresis using an aliquot of the PCR product that the PCR product of about 400 bp was amplified, the PCR product was purified using Quiagen PCR purification Kit and directly sequenced to obtain the sequence shown by FIG. 1. The amino acid sequence deduced from the DNA sequence of FIG. 1 was the sequence shown in FIG. 2. Next, the PCR product recovered from the gel was subcloned to *Escherichia coli* JM109 using TA Cloning Kit (Invitrogen, Inc.), to acquire *Escherichia coli* JM109/pTAh-GPR7-1. Plasmid pTAhGPR7-1 was extracted from *Escherichia coli* obtained by the subcloning, using a plasmid extractor (Kurabo Co., Ltd.) to identify the base sequence of the inserted fragment. It was confirmed that the sequence was the same as that of human GPR7 ligand cDNA shown in FIG. 1. Next, after digestion with restriction enzymes SalI and NheI, human GPR7 ligand cDNA fragment of about 0.4 kb was obtained from the plasmid. Furthermore, expression vector pAKKO-111H for animal cells was digested by restriction enzymes sites SalI and NheI of the multi-cloning sites, and electrophoresed to recover the vector portion. The human GPR7 ligand cDNA fragment prepared by the foregoing procedures was ligated through ligation and *Escherichia coli* JM109 was transformed to obtain *Escherichia coli* JM109 to acquire *E. coli* JM109/pAK-S64.

Transformant *E. coli* JM109/pAK-S64 was cultured to prepare the DNA of plasmid pAK-S64 in large quantities.

Example 2

Acquisition of GPR7 Ligand Precursor Gene from Mouse Whole Brain cDNA by PCR

Using mouse whole brain cDNA as a template, amplification was performed by PCR using the following two synthetic DNAs.

```
                                    (SEQ ID NO:53)
MFSAL1:  5'-GTCGACAGCTCCATGGCCCGGTGTAGGACGCTG-3'

(SEQ ID NO:54)
MRNHE1:  5'-GCTAGCTCAGGTGCTCTGGCAATCAGTCTCGTG-3'
```

The reaction solution for PCR contained 1 μl of cDNA solution, 0.5 μl of MFSAL1 (10 μM), 0.5 μl of MRNHE1 (10 μM), 2.5 μl of 10× reaction solution attached, 2.5 μl of dNTP (10 mM) and 0.5 μl of KlenTaq (CLONTECH, Inc.), to which 17.5 μl of Otsuka distilled water was added to make 25 μl in total. The reaction solution was applied to PCR using Thermal Cycler 9600. The conditions for PCR were set forth: after denaturation at 95° C. for 2 minutes, the cycle set to include 98° C. for 10 seconds, 60° C. for 20 seconds and 72° C. for 20 seconds was repeated 35 times. After it was confirmed by electrophoresis using an aliquot of the PCR product that the PCR product of about 400 bp was amplified, the PCR product was purified using Quiagen PCR purification Kit and directly sequenced to obtain the sequence shown by FIG. 3. The amino acid sequence deduced from the DNA sequence of FIG. 3 was the sequence shown in FIG. 4. Next, the PCR product recovered from the gel was subcloned to *Escherichia coli* JM109 using TA Cloning Kit (Invitrogen, Inc.) to acquire *Escherichia coli* JM109/pTAmGPR7-1. Plasmid pTAmGPR7-1 was extracted from *Escherichia coli* obtained by the subcloning, using a plasmid extractor (Kurabo Co., Ltd.) to identify the base sequence of the inserted fragment. It was confirmed that the sequence was the same as that of mouse GPR7 ligand cDNA shown in FIG. 3.

Example 3

Acquisition of GPR7 Ligand Precursor Gene from Rat Whole Brain cDNA by PCR

Using rat whole brain cDNA as a template, amplification was performed by PCR using the following two synthetic DNAs.

```
                                      (SEQ ID NO:55)
RF:     5'-CACGGCTCCATGGTCCGGTGTAGGACG-3'

(SEQ ID NO:56)
RR:     5'-CAGCGTCGAGGTTTGGGTTGGGGTTCA-3'
```

The reaction solution for PCR contained 1 µl of cDNA solution, 0.5 µl of RF (10 µM), 0.5 µl of RR (10 µM), 2.5 µl of 10× reaction solution attached, 2.5 µl of dNTP (10 mM) and 0.5 µl of KlenTaq (CLONTECH, Inc.), to which 17.5 µl of Otsuka distilled water was added to make 25 µl in total. The reaction solution was applied to PCR using Thermal Cycler 9600. The conditions for PCR were set forth: after denaturation at 95° C. for 2 minutes, the cycle set to include 98° C. for 10 seconds, 60° C. for 20 seconds and 72° C. for 20 seconds was repeated 35 times. After it was confirmed by electrophoresis using an aliquot of the PCR product that the PCR product of about 400 bp was amplified, the PCR product was purified using Quiagen PCR purification Kit and directly sequenced to obtain the sequence shown by FIG. 5. The amino acid sequence deduced from the DNA sequence of FIG. 5 was the sequence shown in FIG. 6. Next, the PCR product recovered from the gel was subcloned to *Escherichia coli* JM109 using TA Cloning Kit (Invitrogen, Inc.) to acquire *Escherichia coli* JM109/pTArGPR7-1. Plasmid pTArGPR7-1 was extracted from *Escherichia coli* obtained by the subcloning, using a plasmid extractor (Kurabo Co., Ltd.) to identify the base sequence of the inserted fragment. It was confirmed that the sequence was the same as that of mouse GPR7 ligand cDNA shown in FIG. 5.

Example 4

Transient Expression of GPR7 Expression Plasmid and Reporter Plasmid in Chinese Hamster Ovary (CHO) Cells

*Escherichia coli* JM109 was transformed using a plasmid prepared by inserting human GPR7 DNA obtained in REFERENCE EXAMPLE 2 into expression plasmid pAKKO-111H for animal cells by a publicly known method. After the colony obtained was isolated and cultured, GPR7 expression plasmid DNA was prepared using QUIAGEN Plasmid Maxi Kit (QIAGEN, Inc.). Also, plasmid DNA of pCRE-Luc (CLONTECH, Inc.), in which luciferase gene was ligated as a reporter at the downstream of cAMP response element (CRE), was prepared in a similar manner.

GPR7 expression plasmid and pCRE-Luc were transiently expressed in CHO cells, to which the expression vector inserted with no receptor gene was transfected. The CHO cells were plated on a 96-well plate (Corning Costar, Inc.) in 40,000 cells/well in a medium volume of 100 µl, followed by incubation overnight at 37° C. For incubation on the plate, DMEM (Dulbecco's modified Eagle's medium, Gibco BRL, Inc.) supplemented with 10% fetal cow serum only was used as medium.

Each plasmid was diluted to a concentration of 240 ng/µl and added to 240 µl of Opti-MEM-I (Gibco BRL, Inc.) in a ratio of 9 µl of GPR7 expression plasmid to 1 µl of pCRE-Luc. The mixture was mixed with an equal volume of a mixture obtained by adding 10 µl of Lipofectamine 2000 (Gibco BRL, Inc.) to 240 µl of Opti-MEM-I (Gibco BRL, Inc.) in a similar manner to produce the liposome-plasmid complex in accordance with the instruction manual attached to Lipofectamine 2000. The complex was added in 25 µl each/well to the culture medium of CHO cells. Four hours later, the culture medium was replaced by an assay buffer (DMEM supplemented with 0.1% bovine serum albumin) to make the medium serum-free, followed by incubation overnight at 37° C.

Example 5

Expression of Ligand Gene in CHO Cells

The human ligand cDNA-inserted expression plasmid pAK-S64 for animal cells prepared in EXAMPLE 1 was transiently expressed in CHO cells in a manner similar to EXAMPLE 4, except that the cells were plated on a 6-well plate (Falcon Corp.) in 600,000 cells/well and incubated overnight, and then the ligand gene plasmid was introduced. The plasmid was diluted to a concentration of 240 ng/µl and an aliquot of 10 µl was added to 240 µl of Opti-MEM-I. The mixture was mixed with an equal volume of a mixture obtained in a similar manner by adding 10 µl of Lipofectamine 2000 to 240 µl of Opti-MEM-I to produce the liposome-plasmid complex in accordance with the method described in the instruction manual attached to Lipofectamine 2000. Each of them was added in 500 µl each/well to the culture medium of CHO cells. Four hours later, the culture medium was replaced by the assay buffer to make the medium serum-free. The medium of each well was recovered 18 hours after the medium exchange to obtain the CHO cell culture supernatant containing the ligand peptide.

Example 6

Detection of Luciferase Activity Suppression by S64 Expression Cell Supernatant in CHO Cells with Transient Expression of GPR7

The pAK-S64 expression culture supernatant prepared in EXAMPLE 5 and forskolin in the final concentration of 2 µM were added to the culture medium of CHO cells wherein GPR7 was transiently expressed according to the procedures of EXAMPLE 4. The culture supernatant of CHO cells wherein a ligand gene-free empty expression vector (pA-KKO-111H) was transiently expressed according to the procedures of EXAMPLE 5 was added as well. At this stage, the expression supernatant was diluted to 2-, 4-, 8- and 16-fold with the assay buffer. After the addition of the supernatant, incubation was carried out for 4 hours at 37° C. to cause the promotion or suppression of transcription/translation of the reporter (luciferase) gene via intracellular signal transduction induced by the agonist activity of ligand mediated by the receptor. After completion of the incubation, the assay buffer was removed from each well and 50 µl each of PicaGene LT2.0 (Toyo Ink Mfg. Co., Ltd.) as a luminescent substrate was added to the well. After the cells were lysed and thoroughly mixed with the substrate, the luminescence amount associated with the expression induction level of the reporter gene in each well was assayed by using a plate reader (ARVOsx Multi-label Counter, Perkin Elmer, Inc.). As the result, the expression suppression of the reporter gene was detected as a decreased luciferase activity only when the culture supernatant of pAK-S64 was added (FIG. 8). Moreover, the degree of this suppression was dependent on the concentration of the pAK-S64 culture-supernatant. This indicates that the product expressed by the total plasmid inserted into pAK-S64 transduced the intracellular signal mediated by GPR7, i.e., acted as a ligand to GPR7.

Example 7

Detection of Luciferase Activity Suppression by S64 Expression Cell Supernatant in CHO Cells with Transient Expression of TGR26

Figure 9:
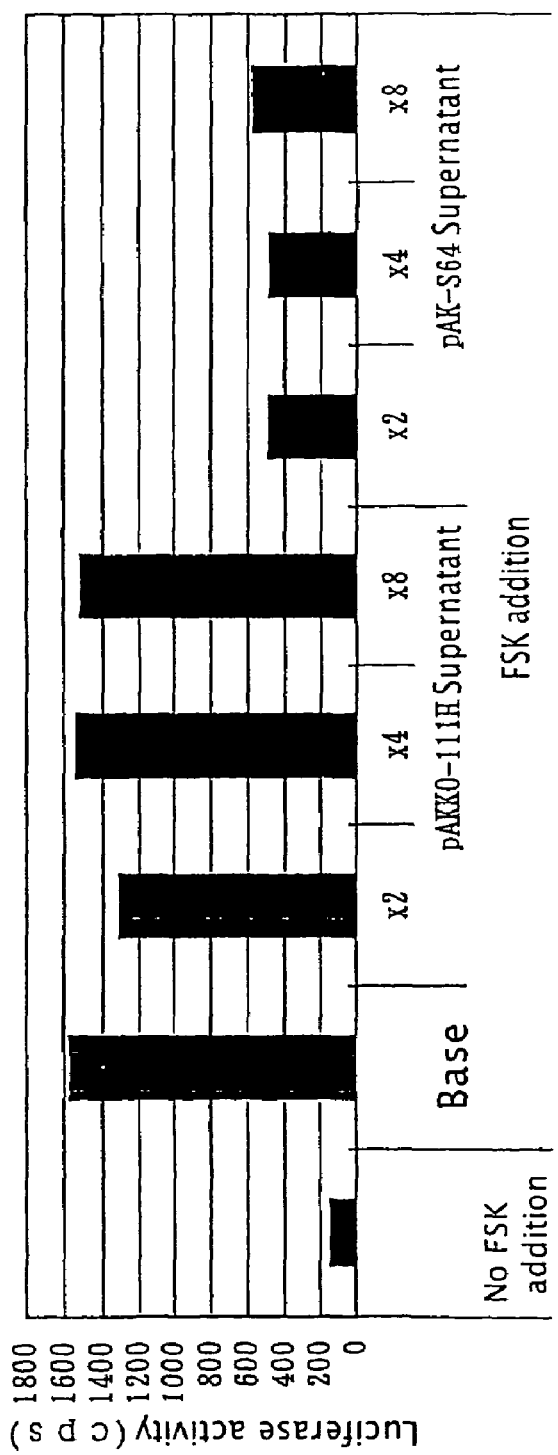
FIG. 9 shows the results of suppression detected on a luciferase activity, when he culture supernatant of CHO cells wherein S64 was transiently expressed was added in the presence of forskolin (FSK) to a medium of CHO cells wherein TGR26 was transiently expressed.

The TGR26 expression plasmid DNA was prepared in a manner similar to EXAMPLE 4, using expression plasmid pAKKO-111H for animal cells in which TGR26 DNA obtained in REFERENCE EXAMPLE 3 was inserted by publicly known methods. The plasmid DNA and the luciferase gene were likewise expressed transiently in the CHO cells according to the procedures of EXAMPLE 4. To the cells, the pAK-S64 expression culture supernatant prepared in EXAMPLE 5 and the culture supernatant of cells wherein the empty expression vector alone was expressed, were added and after forskolin was further added thereto in the final concentration of 2 μM, it was attempted to detect the ligand activity in a manner similar to EXAMPLE 6. As the result, the pAK-S64 supernatant decreased concentration-dependently the luciferase activity increased by forskolin (FIG. 9).

Example 8

Figure 10:
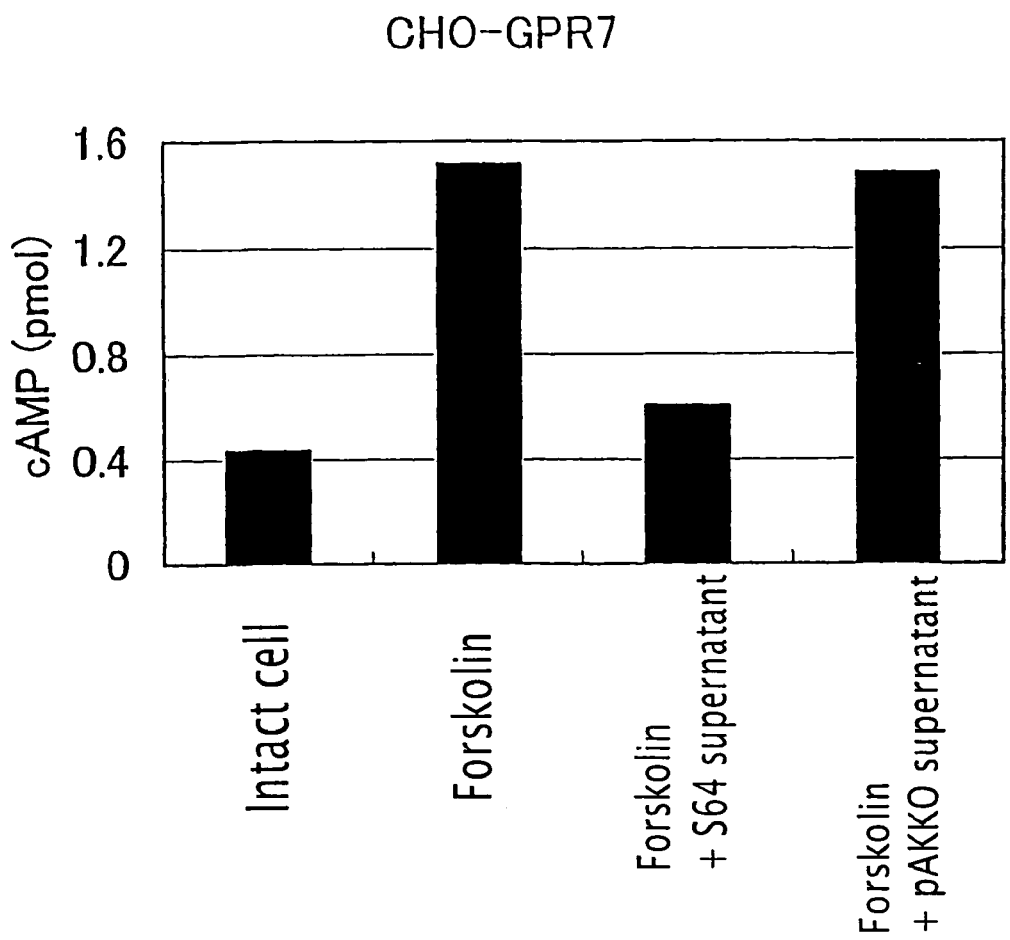
FIG. 10 shows the results of GPR7-expressed CHO cell-specific cAMP production level suppression caused by the supernatant of cells wherein S64 was transiently expressed.
Figure 11:
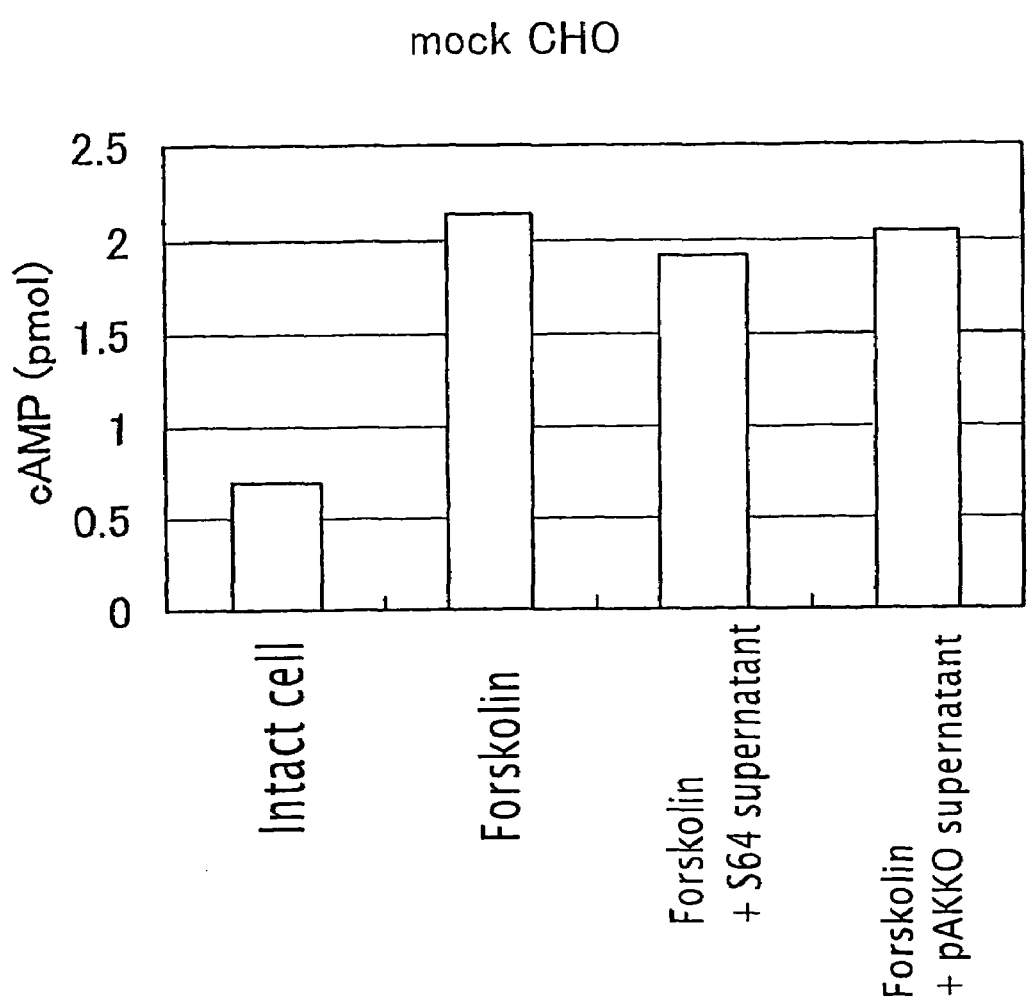
FIG. 11 shows the results of cAMP production level suppression of mock CHO caused by the supernatant of cells wherein S64 was transiently expressed.

Suppression of cAMP Production Level in GPR7-Expressed CHO Cells by S64 Expression Cell Supernatant Using the plasmid for GPR7 expression prepared in EXAMPLE 4, CHO-GPR7 as CHO cells capable of stably expressing GPR7 was prepared by publicly known methods. Mock CHO cells were plated on a 96-well plate (Beckton-Dickinson, Inc.) in 20,000 cells/well. After incubation overnight at 37° C. under 5% $CO_2$, the culture medium was used for the assay. The sample buffer used was Dulbecco's modified Eagle's medium (DMEM, Gibco BRL, Inc.) supplemented with 0.1% bovine serum albumin (Sigma) and 0.2 mM IBMX (Sigma). The cells were washed twice with the sample buffer. After pre-incubation at 37° C. for 30 minutes under 5% $CO_2$, the cells were further washed twice and the sample was added thereto followed by incubation at 37° C. for 30 minutes under 5% $CO_2$. The cells were further washed twice and the sample was added thereto at 37° C. for 30 minutes. Four kinds of the samples were the sample buffer alone (intact), 1 μM of forskolin (Wako Pure Chemical Industries, Ltd.) as a reagent to stimulate an increase of cAMP production, simultaneous addition of the CHO cell culture supernatant obtained in EXAMPLE 5 prepared by transient expression of pAK-S64 (S64 supernatant) and forskolin, and simultaneous addition of the culture supernatant of pAKKO-111H-expressed CHO cells (pAKKO supernatant) and forskolin. After incubation in the presence of the sample, the intracellular cAMP production level was assayed by using cAMP Screen System (ABI). The results revealed that the intracellular cAMP production level was CHO-GPR7-specifically suppressed by adding the S64 supernatant (FIG. 10) and no suppression of the intracellular cAMP production level was noted in the mock CHO cells (FIG. 11).

Example 9

Study of Tissue Distribution of GPR7 Ligand mRNA in Rat by RT-PCR

Figure 12:
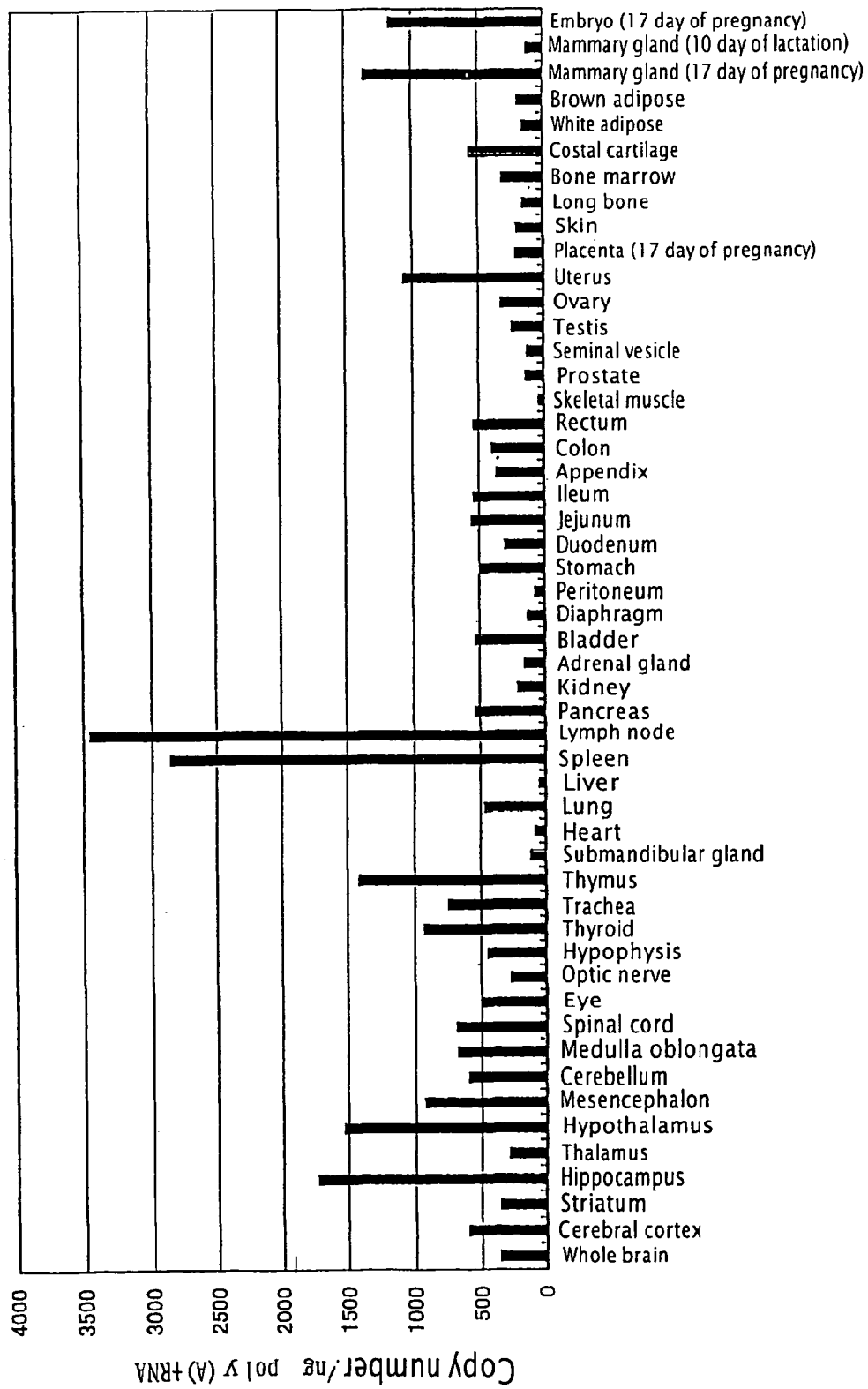
FIG. 12 shows the tissue distribution of GPR7 ligand mRNA in rat and the results of its expression level as determined by RT-PCR.

Various organs were withdrawn from Wistar rat. The total RNA and poly(A)+ RNA were prepared using Isogen (Nippon Gene Co., Ltd.) and mRNA purification kit (Pharmacia), respectively, according to the respective instruction manuals. After 1 μg of poly(A)+ RNA was digested with DnaseI (Amplification Grade, Gibco BRL, Inc.), a 160 ng aliquot was treated at 42° C. using RNA PCR Kit (TaKaRa Shuzo Co., Ltd.) according to the instruction manual to synthesize cDNA. The cDNA synthesized was made a solution of 4 ng/μl when calculated as poly(A)+ RNA and used as a template for RT-PCR thereafter. Using Sequence Detection System Prism 7700 (PE Biosystems), RT-PCR was carried out, wherein primers: 5'-CTGTCGAGTTTCCACAGGT-TCC-3' (SEQ ID NO:63) and 5'-TTGCGCAGAGGTACG-GTTCC-3' (SEQ ID NO:64) were used for amplification and detection, and 5'-(Fam)-CGTGCCAAGAAACGCGTGAC-CTTGTT-(Tamra)-3' (SEQ ID NO:65) was used as TaqMan probe. In the reaction solution for RT-PCR, 0.05 μl each of 100 μM primer solution, 0.5 μl of 5 μM TaqMan probe, 2.5 μl of 10× reaction solution attached, 2.5 μl of dNTP (10 mM) and 0.5 μl of the cDNA solution prepared above were added to 12.5 μl of TaqMan Universal PCR Master Mix (PE Biosystems), to which distilled water was added to make the total solution volume 25 μl. The reaction solution was applied to PCR using Thermal Cycler 9600. After denaturation at 50° C. for 2 minutes and 95° C. for 10 minutes, PCR was carried out by repeating 40 times the cycle set to include 95° C. for 15 seconds and 60° C. for 1 minute. The expression level of GPR7 ligand mRNA in the various tissues in rat was assessed in terms of the copy number per 1 ng of poly(A)+ RNA (FIG. 12).

Example 10

Purification of Endogenous GPR7 Ligand from Bovine Hypothalamus.

Since it was found that human GPR7 ligand precursor mRNA was abundantly expressed in hypothalamus and spinal cord, the endogenous GPR7 ligand was purified from bovine hypothalamus as the starting material, using human GPR7-expressed CHO cells. The purification was performed using as an indicator the intracellular cAMP production suppressing activity (as determined using cAMP-Screen System (ABI)).

Figure 13:
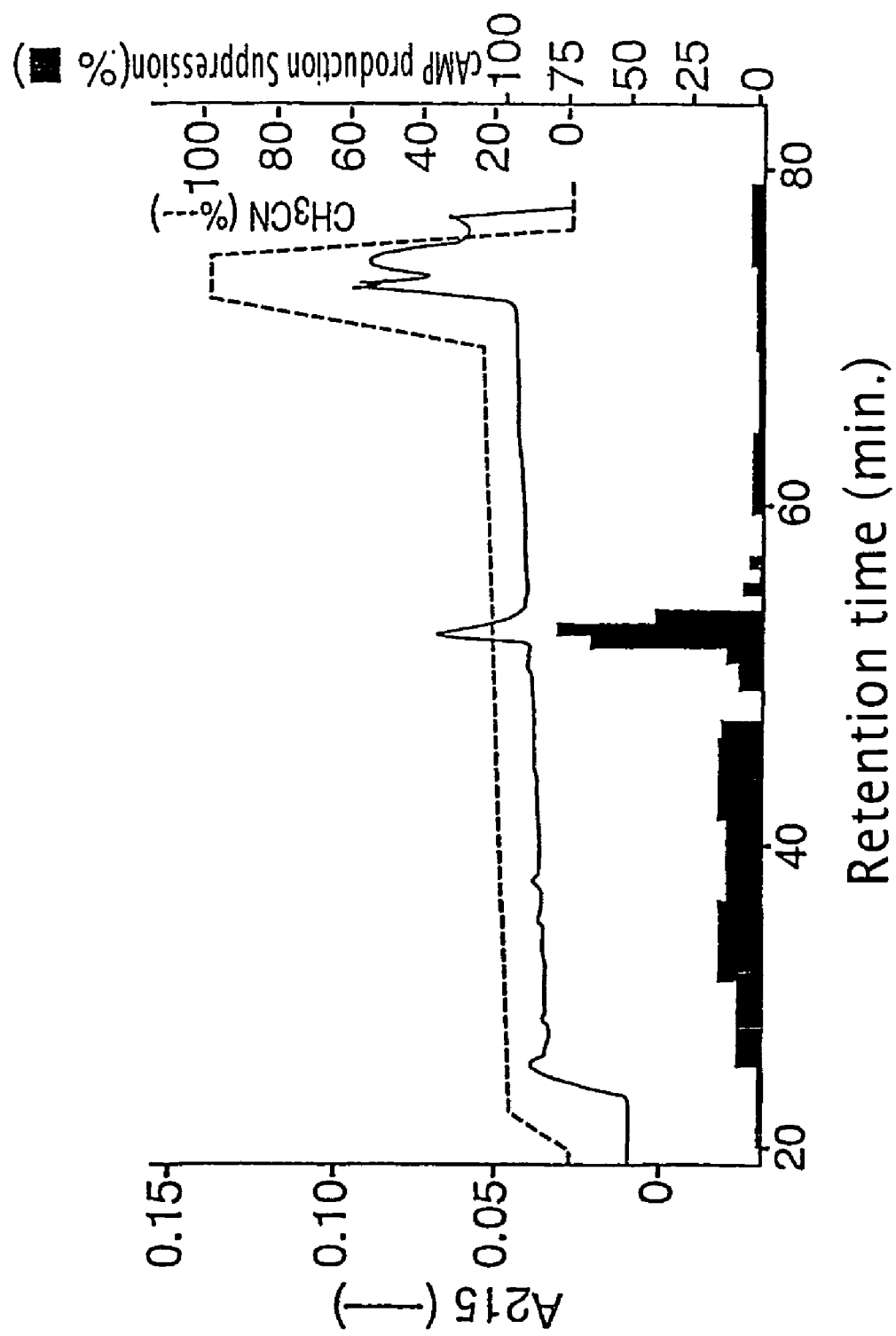
FIG. 13 shows a chromatogram of endogenous GPR7 ligand finally purified from bovine hypothalamus, which indicates the chromatographic pattern on μRPC C2/C18 SC 2.1/10 at the final step of purification and the cAMP production level assayed using the cAMP-screen system (ABI) after reacting each fraction with human GPR7-expressed CHO cells. The chromatographic pattern shows the absorbance at 215 nm and the elution concentration of acetonitrile.

First, 1.0 kg of bovine hypothalamus in a frozen state was boiled in Milli-Q Water. After cooling, acetic acid was added to become 1M, which was then homogenized with a polytron. After agitation overnight, the homogenate was centrifuged to give the supernatant. Trifluoroacetic acid (TFA) was added to the supernatant in 0.05% and the mixture was applied to C18 Column (Prep C18 125 Å; Waters). The peptide bound to the column was stepwise eluted with 10%, 40% and 60% acetonitrile containing 0.5% TFA. A 2-fold volume of 20 mM ammonium acetate (pH 4.7) was added to the 40% acetonitrile fraction for dilution. The mixture was applied to ion exchange column HiPrep CM-Sepharose FF (Pharmacia). The peptide bound to the ion exchange column was eluted on a concentration gradient of 0 to 0.5 M NaCl in 20 mM ammonium acetate (pH 4.7) containing 10% acetonitrile. A 2-fold volume of cold acetone was added to the NaCl fraction (0.3 to 0.35 M) containing the active substance most abundantly. The precipitates were removed by centrifugation and the supernatant was concentrated through an evaporator. TFA was added to the concentrated supernatant in 0.1%. The mixture was applied to reverse phase HPLC column RESOURCE RPC (Pharmacia) to effect further separation. The separation from RESOURCE RPC was performed on a concentration gradient of 20 to 30% acetonitrile, whereby the main activity was eluted on about 22% acetonitrile. A 3-fold volume of cold acetone was added to the active fraction. The precipitates were removed by centrifugation and the supernatant was concentrated through the evaporator. TFA was added to the concentrated supernatant in 0.1%. The mixture was applied to reverse phase HPLC column Vydac C18 218TP5415 (Vydac) to effect further separation. The separation from Vydac C18 218TP5415 was performed on a concentration gradient of 20 to 30% acetonitrile, whereby the main activity was eluted on about 25% acetonitrile. The active fraction was separated through cation exchange column TSK-gel CM-2SW (Toso Co., Ltd.) on a concentration gradient of 0.3 to 0.5 M NaCl in 20 mM ammonium acetate (pH 4.7) containing 10% acetonitrile, whereby the main activity was eluted on about 0.5 M NaCl. TFA was added to the activity-containing fraction from CM-2SW column in 0.1%. The final purification was made through reverse phase HPLC column μRPC C2/C18 SC2.1/10 on a concentration gradient of 16 to 24% acetonitrile. Thus, a single peak which coincided with the activity was obtained (FIG. 13).

Example 11

N-Terminal Amino Acid Sequencing of the Finally Purified Product and Determination of its Molecular Weight by Mass Spectrum With respect to the finally purified product obtained in EXAMPLE 10, approximately a half was analyzed with a protein sequencer (model 491cLC; Applied Biosystems) for the N-terminal amino acid and the other half was analyzed by ESIMS (Thermoquest).

Figure 14:
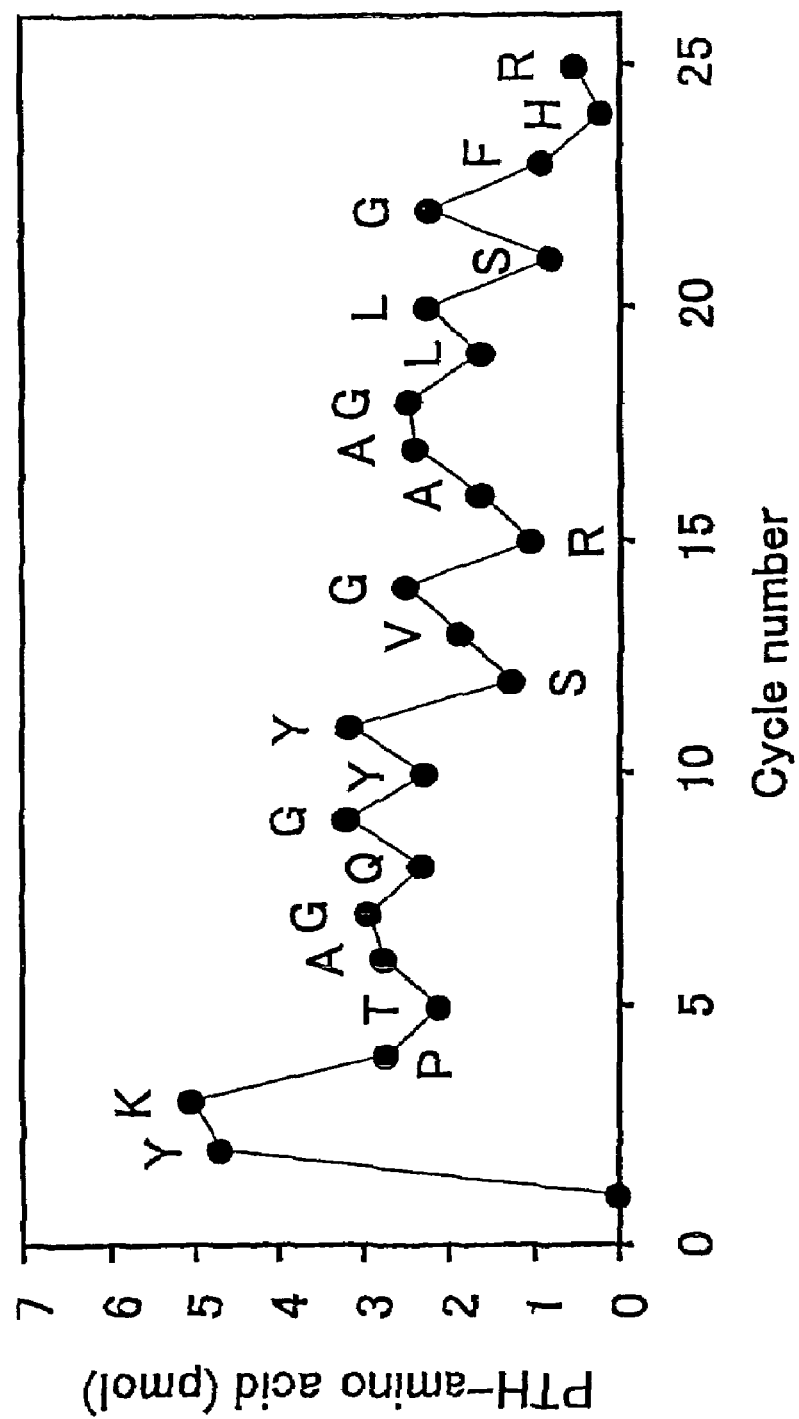
FIG. 14 shows the results of N-terminal sequencing of the endogenous GPR7 ligand purified from bovine hypothalamus.

As a result of the N-terminal sequencing, the sequence corresponding to the positions 26 to 49 of bovine GPR7 ligand precursor could be read in cycles 2 to 25 (FIG. 14). Since cycle 1 could not be identified (x), the product was presumed to undergo a post-translational modification. The sequence after cycle 2 was identified clearly to be the sequence described above.

Figure 15:
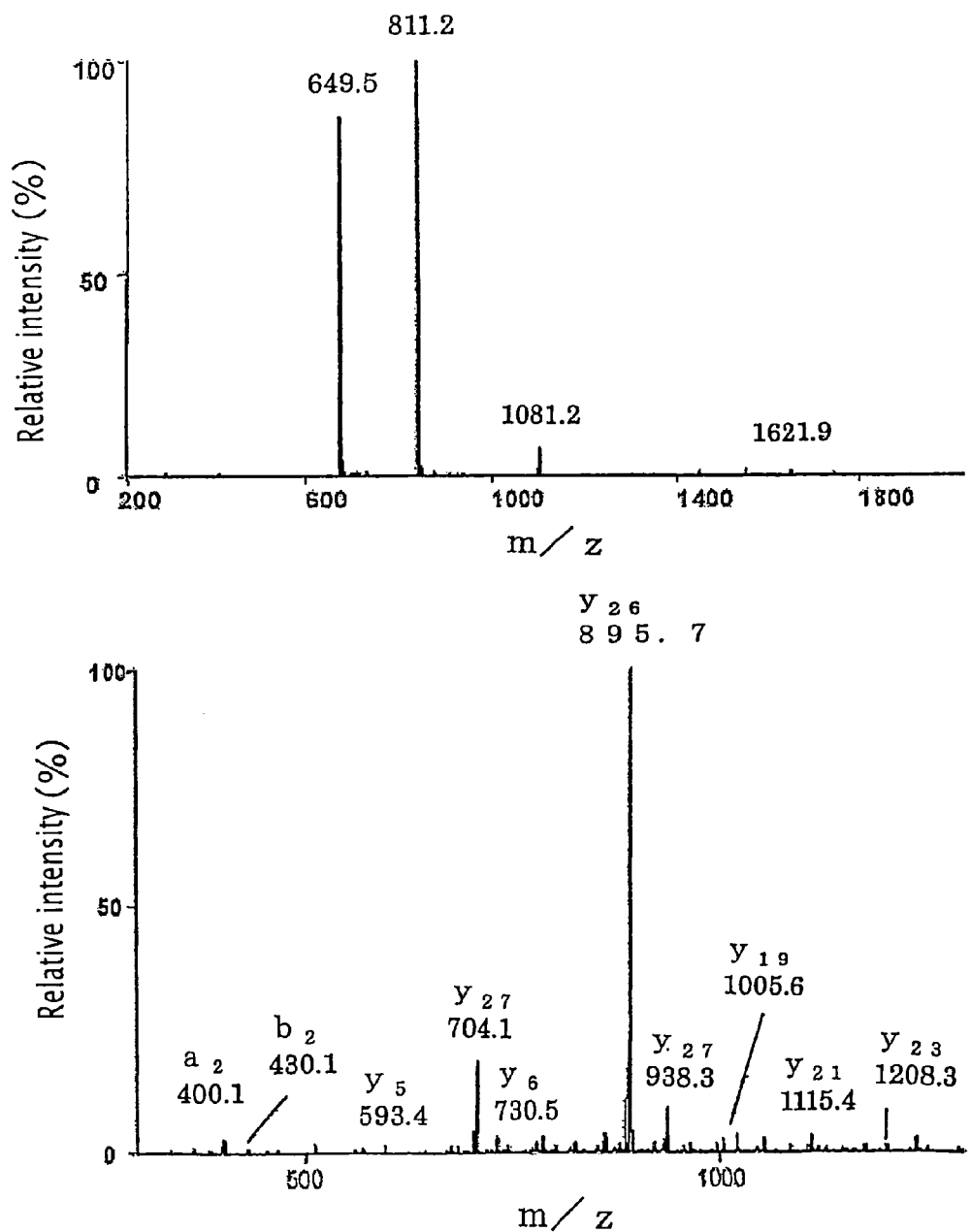
FIG. 15 shows an ESIMS spectrum (upper column) and a MS/MS spectrum (lower column) of the endogenous GPR7 ligand purified from bovine hypothalamus.

In ESIMS (FIG. 15, upper column), the value of 3241.5 was obtained in a full mass scan mode. Based on the molecular weight calculated from the mass spectrum and the analysis results of MS/MS spectrum (FIG. 15, lower column), it was presumed that either one of the N-terminal two residues would undergo a post-translational modification. Taking into account the N-terminal sequencing results together, it was presumed that Trp at position 1 would be modified.

Figure 16:
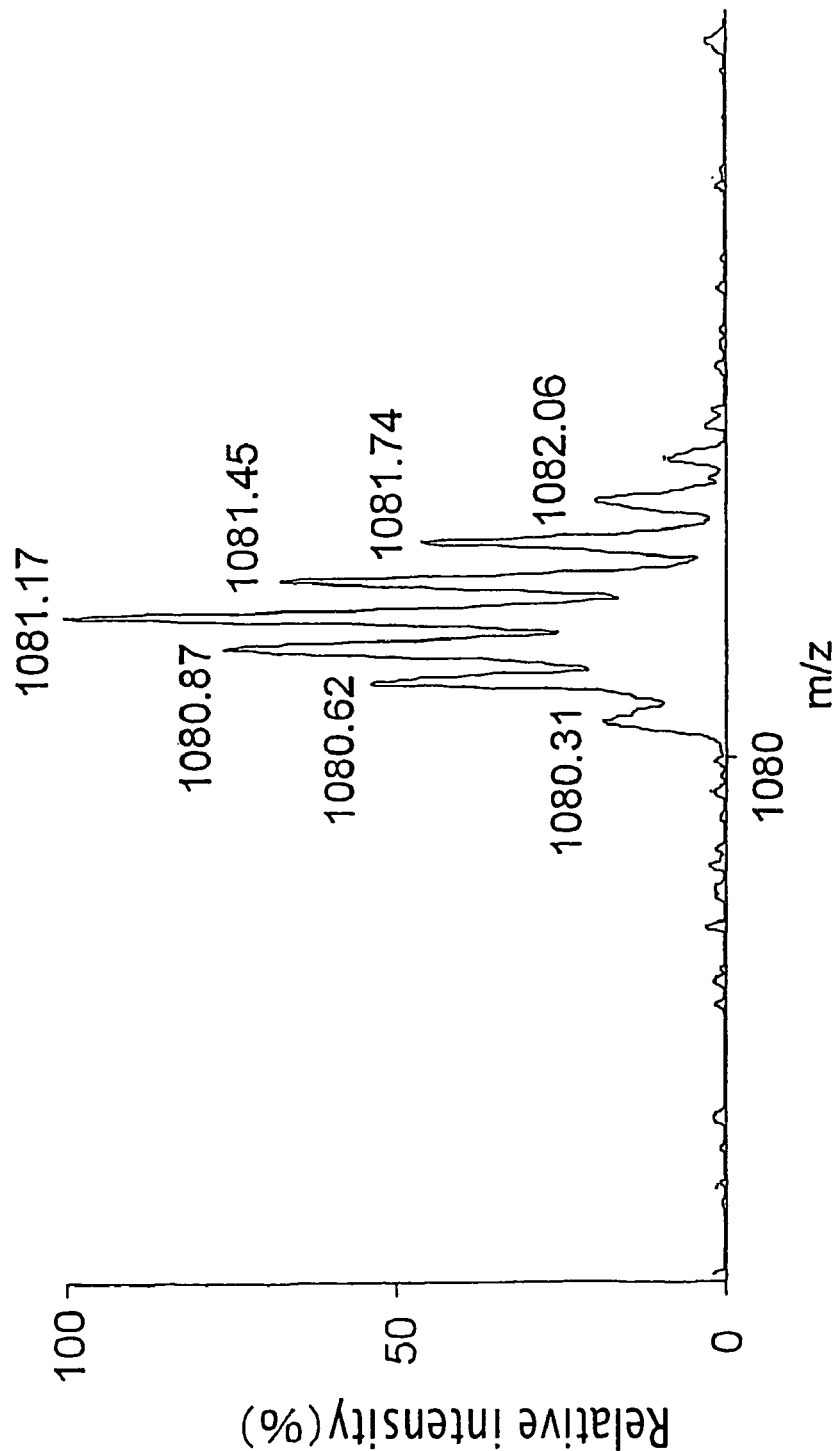
FIG. 16 shows a zoom scanning spectrum of trivalent molecular ions.

Putting the isotonic profile (FIG. 16) of trivalent molecular ions determined in a zoom scan mode together, the substance was presumed to be a GPR7 ligand of 29 residues, which would be brominated on the tryptophan residue at the 1-position.

To confirm the presumption, PTH standard was prepared from DL-5-bromotryptophan (Aldrich) and DL-6-bromotryptophan (Biosynth), followed by sequencing.

Figure 17:
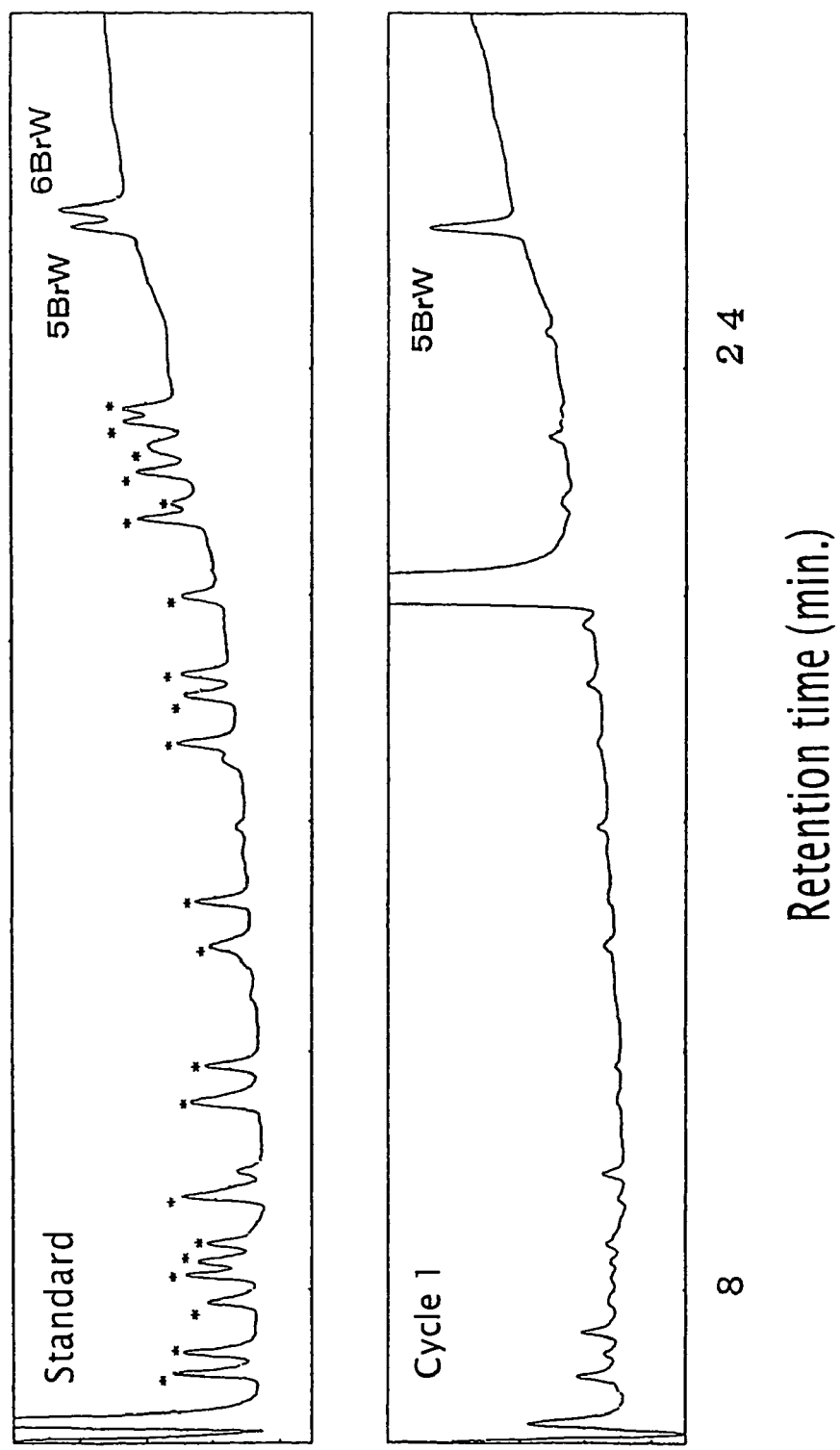
FIG. 17 shows the results of standard analysis performed by mixing PTH-5-bromotryptophan (5BrW) and PTH-6-bromotryptophan (6BrW) with 20 amino acid PTH standards (peaks shown by asterisk*), whereby it was confirmed that the peaks of standard 5BrW overlapped with those of 5BrW in an unknown sample.
Figure 18:
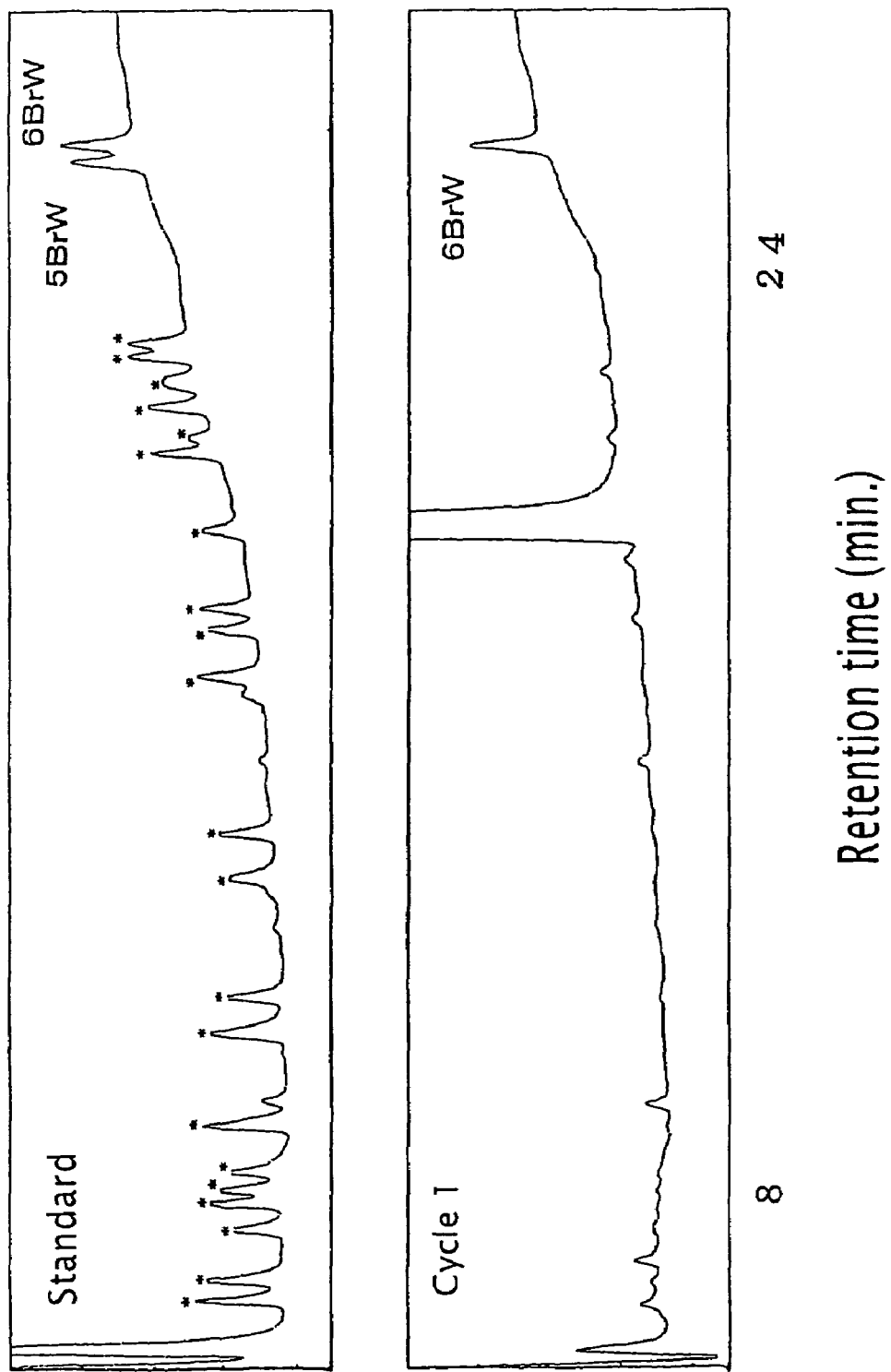
FIG. 18 shows the results of standard analysis performed by mixing PTH-5-bromotryptophan (5BrW) and PTH-6-bromotryptophan (6BrW) with 20 amino acid PTH standards (peaks shown by asterisk*), whereby it was confirmed that the peaks of standard 6BrW overlapped with those of 6BrW in an unknown sample.
Figure 19:
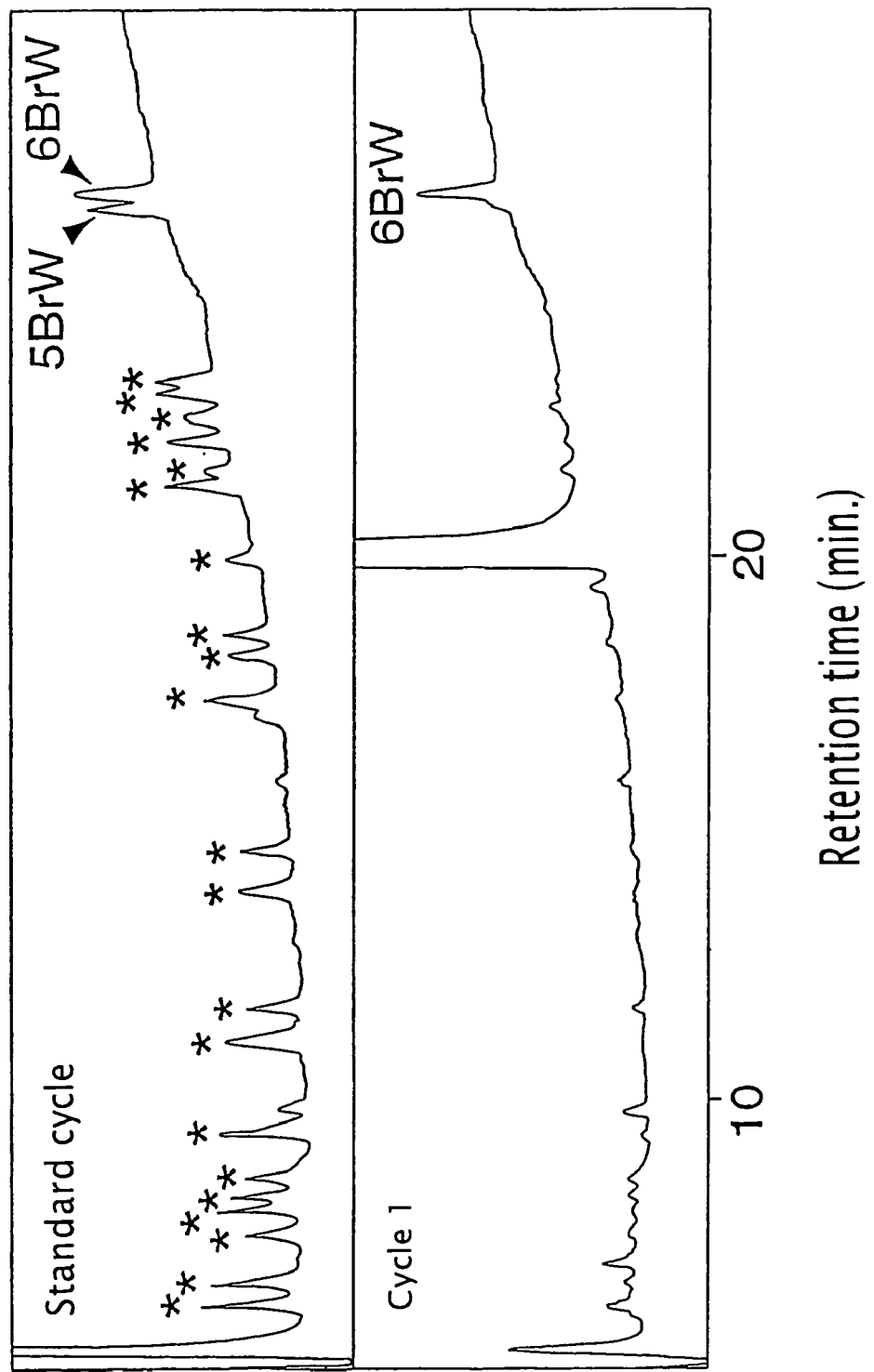
FIG. 19 shows the results of N-terminal sequencing of GPR7L purified from bovine hypothalamus, wherein the amino acids by standard analysis and at cycle 1 on the chromatogram up to cycle 2 coincided with the peaks of 6-bromotryptophan.

To 200 nmols of DL-5-bromotryptophan or DL-6-bromotryptophan, 20 μl of ethanol:triethylamine:DW:phenyl isothiocyanate (sigma)=7:1:1:1 was added. The mixture was reacted at room temperature for 20 minutes. After drying, 50 μl of TFA was added thereto. The mixture was reacted at 50° C. for 10 minutes. After during, 50 μl of HCl: methanol=1:1 was added thereto, followed by reacting at 50° C. for 10 minutes. The reaction mixture was purified on reverse phase HPLC to give the PTH derivative of 5-bromotryptophan or 6-bromotryptophan. The final product was identified on a protein sequencer (FIGS. 17 and 18). These PTH derivatives were mixed with 20 amino acid PTH standard (ABI), and a protocol was prepared to separate the derivatives (TABLES 1 and 2). When the endogenous bovine GPR7 ligand was analyzed, the amino acid at the 1-position coincided with the peak of PTH-6-bromotryptophan (FIG. 19).

Based on the results of analysis, the finally purified product from bovine hypothalamus was found to be a peptide of 29 amino acids (SEQ ID NO:67) corresponding to the 25th Trp to. 53rd Ala of bovine GPR7 ligand precursor, in which Trp at position 1 was 6-brominated by a post-translational modification.

TABLE 1

| Cycle # | Cartridge cycle | Flask cycle | Gradient |
|---|---|---|---|
| Pulsed-Liquid cLC: | | | |
| Default | Cart-PL 6mmGFF cLC | Flask Normal cLC | Normal 1 cLC |
| 1 | None | Prepare Pump cLC | Prepare Pump cLC |
| 2 | None | Flask Blank cLC | Normal 1 cLC |
| 3 | Cart Begin cLC | Flask Standard cLC | Normal 1 cLC |
| BrTrp-liquid cLC: | | | |
| Default | Cart-PL 6mmGFF cLC | Flask Normal cLC | Normal for BrW cLC |
| 1 | Sample wash | Prepare Pump cLC | Prepare Pump cLC |
| 2 | None | Flask Blank cLC | BrTrp cLC |
| 3 | Cart Begin cLC | Flask Standard cLC | BrTrp cLC |
| 4 | Cart-PL 6mmGFF cLC | Flask Normal cLC | BrTrp cLC |
| 5 | Cart-PL 6mmGFF cLC | Flask Normal cLC | BrTrp cLC |

TABLE 1 shows a comparison in cycle and gradient between a method for normal peptide (Pulsed-Liquid cLC) and a method for bromotryptophan (BrTrp-liquid cLC).

TABLE 2

| | | Time (min) | | | | | | | |
|---|---|---|---|---|---|---|---|---|---|
| | | 0 | 0.4 | 4 | 22 | | 22.6 | 29 | 33 |
| Normal 1 cLC | % B | 8 | 10 | 20 | 47 | | 90 | 90 | 70 |
| Normal for BrW cLC | % B | 8 | 10 | 20 | 44 | | 90 | 90 | 70 |
| | | 0.0 | 0.4 | 4 | 22.0 | 28.0 | 28.6 | 32.0 | 33.0 |
| BrTrp cLC | % B | 8 | 10 | 20 | 44 | 44 | 90 | 90 | 70 |

TABLE 2 shows a comparison in gradients prepared for the analysis of a normal peptide (Normal 1 cLC) and bromotryptophan (Normal for BrW cLC, BrTrp cLC), on 491cLC protein sequencer (ABI).

The N-terminal sequencing was performed on 491cLC protein sequencer (ABI) by the analysis method for normal peptide (Normal 1cLC) with a modification (BrTrp-liquid cLC) for bromotryptophan analysis. Other conditions than those described above were set as instructed in the manual provided by the manufacturer. When a modified gradient (BrTrp cLC) is used, 5- and 6-bromotryptophans, which have different positions for Br added, can be discriminated from each other.

When the analysis is made by the modified method or BrTrp-liquid cLC, the gradient for analysis of 5-/6-bromotryptophan is adapted only to blank, standard and up to cycle 2, and a different gradient (Normal for BrW cLC) is adapted to and after cycle 3.

Example 12

Acquisition of Bovine GPR7 Ligand Precursor Gene from Bovine Hypothalamus cDNA by PCR Using bovine hypothalamus cDNA as a template, PCR was performed for amplification, using two synthetic DNAs below.

```
                                              (SEQ ID NO:82)
BF1:     5'-CCCATGGCCGGGCCCGCGATGCTGGTCGCC-3'

(SEQ ID NO:83)
BR1:     5'-TCACTTGCGACAGTCCGAGGCGCTGAGCGA-3"
```

The reaction solution for PCR contained 1 µl of cDNA solution, 0.5 µl of BF1 (10 µM), 0.5 µl of BF2 (10 µM), 2.5 µl of 10× reaction solution attached, 2.5 µl of dNTP (10 mM) and 0.5 µl of KlenTaq (CLONTECH, Inc.), to which 17.5 µl of Otsuka distilled water was added to make the total volume 25 µl. The reaction solution was applied to PCR using Thermal Cycler 9600. The conditions for PCR were set forth: after denaturation at 95° C. for 2 minutes, the cycle set to include 98° C. for 10 seconds, 60° C. for 20 seconds and 72° C. for 20 seconds was repeated 35 times. After it was confirmed by electrophoresis using an aliquot of the PCR product that the PCR product of about 400 bp was amplified, the PCR product was purified using Quiagen PCR purification Kit and directly sequenced to obtain the sequence shown by FIG. 20. The amino acid sequence deduced from the DNA sequence of FIG. 20 was the sequence shown in FIG. 21. Next, the PCR product recovered from the gel was subcloned to *Escherichia coli* JM109 using TA Cloning Kit (Invitrogen, Inc.) to acquire *Escherichia coli* JM109/ pTAbGPR7L-1. Plasmid pTAbGPR7L-1 was extracted from *Escherichia coli* obtained by the subcloning, using a plasmid extractor (Kurabo Co., Ltd.) to identify the base sequence of the inserted fragment. It was confirmed that the sequence was the same as that of bovine GPR7 ligand cDNA.

Example 13

Synthesis of GPR7 Ligand

GPR7 ligand (GPR7L) and GPR8 ligand (GPR8L) were synthesized by the Fmoc/DCC/HOBt protocol, using ABI 433 peptide synthesizer. DL-6-Bromotryptophan (Biosynth) was changed to Boc-DL-6-bromotryptophan-OMe and then subjected to chiral resolution, which was used for peptide synthesis, respectively.

(1) DTrp (6Br)1-human GPR7L (29) (wherein N-terminal D-tryptophan in the amino acid sequence represented by SEQ ID NO: 4 was brominated at the 6-position): (D-Trp (6Br)-Tyr-Lys-Pro-Ala-Ala-Gly-His-Ser-Ser-Tyr-Ser-Val-Gly-Arg-Ala-Ala-Gly-Leu-Leu-Ser-Gly-Leu-Arg-Arg-Ser-Pro-Try-Ala) (SEQ ID NO: 107)

(2) LTrp(6Br)1-human GPR7L (29) (wherein N-terminal L-tryptophanin the amino acid sequence represented by SEQ ID NO:4):
(Trp(6Br)-Try-Lyr-Lys-Pro-Ala-Ala-Gly-His-Ser-Ser-Tyr-Ser-Val-Gly-Arg-Ala-Gly-Leu-Leu-Ser-Gly-Arg-Arg-Ser-Pro-Try-Ala)

(3)Trp1-human GPR7L (29) (SEQ ID NO:4):
(Trp-Try-Lys-Pro-Ala-Ala-Gly-His-Ser-Ser-Tyr-Ser-Val-Gly-Arg-Ala-Ala-Gly-Leu-Leu-Ser-Gly-Arg-Arg-Ser-Pro-Try-Ala)

(4) Trp1-human GPR7L (23) (SEQ ID NO:1):
(Trp-Try-Lys-Pro-Ala-Ala-Gly-His-Ser-Ser-Tyr-Ser-Val-Gly-Arg-Ala-Ala-Gly-Leu-Leu-Ser-Gly-Leu)

(5) DTrp(6Br)1-bovine GPR7L (29) (wherein N-terminal D-tryptophan in the amino acid sequence represented by SEQ ID NO: 67 was brominated at the 6-position): (D-Trp (6Br)-Tyr-Lys-Pro-Thr-Ala-Gly-Gln-Gly-Tyr-Tyr-Ser-Val-Gly-Arg-Ala-Ala-Gly-Leu-Leu-Ser-Gly-Phe-His-Arg-Ser-Pro-Tyr-Ala) (SEQ ID NO: 108)

(6) LTrp(6Br)1-bovine GPR7L (29) (wherein N-terminal L-tryptophanin the amino acid sequence represented by SEQ ID NO:67 was brominated at the 6-position):
(Trp(6Br)-Tyr-Lys-Pro-Thr-Ala-Gly-Gin-Gly-Tyr-Tyr-Ser-Val-Gly-Arg-Ala-Ala-Gly-Leu-Leu-Ser-Gly-Phe-His-Arg-Ser-Pro-Try-Ala)

(7) Trp1-bovine GPR7L (29) SEQ ID NO:67):
(Trp-Tyr-Lys-Pro-Thr-Ala-Gly-Gin-Gly-Tyr-Tyr-Ser-Val-Gly-Arg-Ala-Ala-Gly-Leu-Leu-Ser-Gly-Phe-His-Arg-Ser-Pro-Try-Ala)

(8) Trp1-rat GPR7L(29)(SEQ ID NO:67):
(Trp-Tyr-Lys-Pro-Ala-Ala-Gly-Ser-HisI-His-Tyr-Ser-Val-Gly-Arg-Ala-Ala-Gly-Leu-Leu-Ser-Gly-Phe-His-Arg-Phe-Pro-Ser-Thr)

(9) Trp1-rat GPR7L (24) (SEQ ID NO:3):
(Trp-Try-Lys-Pro-Ala-Ala-Gly-Ser-His-His-Tyr-Ser-Val-Gly-Arg-Ala-Ala-Gly-Leu-Leu-Ser-Ser-Phe-His)

(10) Trp1-human GPR8L (23) (SEQ ID NO:100):
(Trp-Try-Lys-His-Val-Ala-Ser-Pro-Arg-Tyr-His-Thr-Val-Gly-Arg-Ala-Ala-Gly-Leu-Leu-Met-Gly-Leu) (WO 01/98494)

Example 14

Effect of GPR7 Ligand on Feed Uptake in Rat by Lateral Ventricular Injection

The effect of GPR7 ligand (GPR7L) on feed uptake in rat by lateral ventricular injection was examined. Rat was caged at room temperature of 25° C. while lighting for 8 to 20 o'clock. Mature Wistar male rats (300-320 g body weight upon surgery) were anesthetized with an intraperitoneal injection of 50 mg/kg pentobarbital and placed in a rat brain stereotaxic instrument. The level of incisor bar was 3.3 mm below the interaural line. The skull was exposed, and using a dental drill a hole was made on the bone for implantation of guide cannula AG-8 (inner diameter of 0.4 mm, outer diameter of 0.5 mm, EICOM Corporation). In addition, an anchor screw was buried at 3 positions around the hole. A stainless-steel guide cannula, AG-8, was inserted in such a manner that the tip was situated at the upper part of the lateral ventricle. Stereotaxic coordinates were taken from the atlas according to the atlas of Paxinos & Watson (1986) from bregma AP: −0.8 mm, L:1.5 mm and H:−4.5 mm. The guide cannula was secured to the skull using a dental cement and an anchor screw. A stainless-steel dummy cannula AD-8 (outer diameter of 0.35 mm, EICOM Corporation) was then passed through the guide cannula and locked in position with a cap nut (EICOM Corporation). After the surgery, rats were housed in individual cages.

Figure 22:
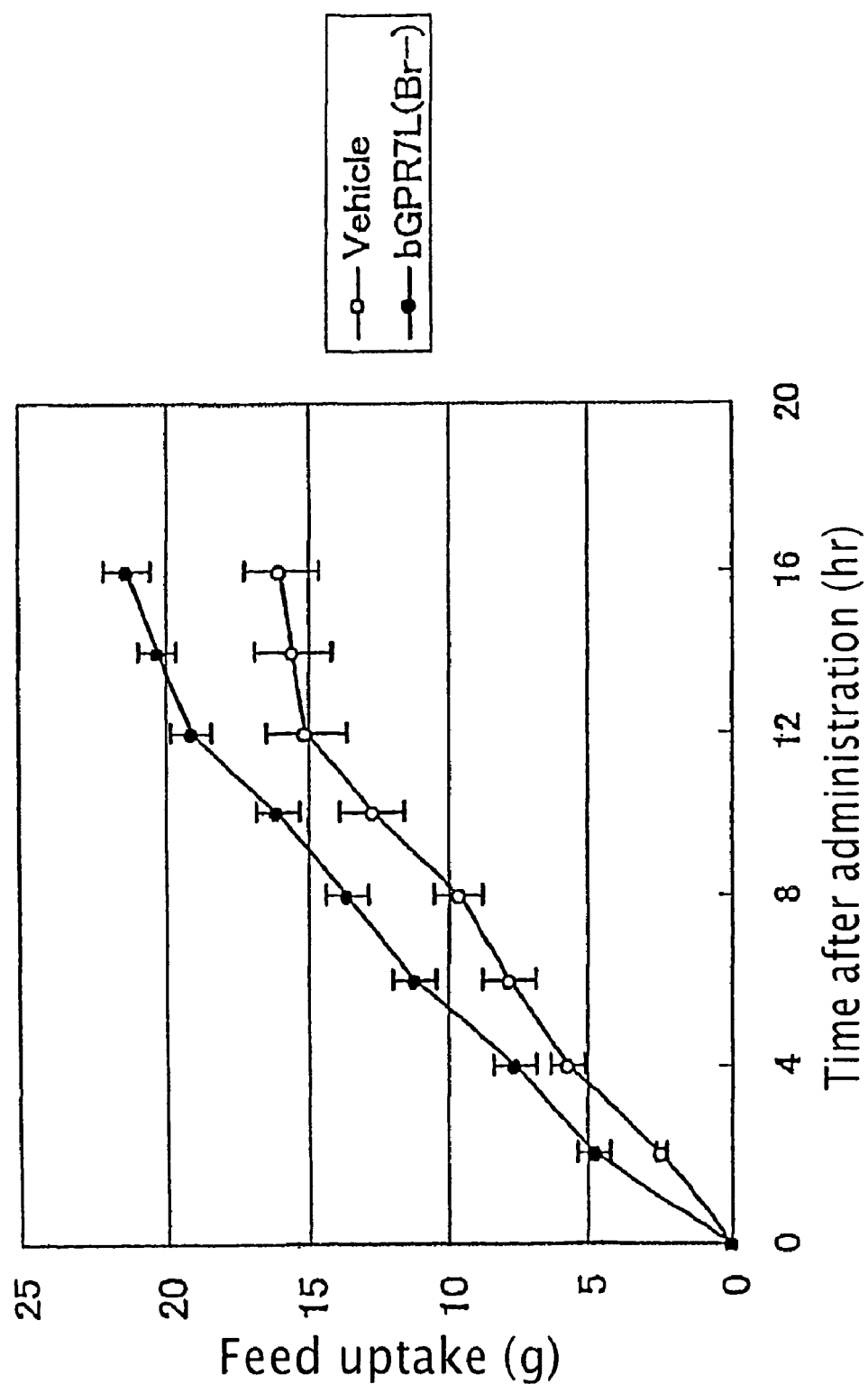
FIG. 22 shows change in feed uptake with passage of time every 2 hours after non-brominated GPR7L or distilled water was administered to rat into the lateral ventricle, wherein Vehicle and bGPR7L (Br—) indicate distilled water and non-brominated bovine GPR7 ligand, respectively.

After the guide cannula was implanted, rats were caged for about a week to recover from surgical operation. The cap nut and dummy cannula inserted into the rat skull were disconnected and instead, a stainless-steel microinjection cannula AMI-9 (inner diameter of 0.17 mm, outer diameter of 0.35 mm, EICOM Corporation) connected to a Teflon (registered trademark) tube (length of 50 cm, inner diameter of 0.1 mm, outer diameter of 0.35 mm, EICOM Corporation) was inserted into the skull. The length of the microinjection cannula was adjusted beforehand to expose the tip from the guide cannula by 1 mm. One end of the Teflon (registered trademark) tube was connected to a microsyringe pump and either sterile distilled water (Otsuka Pharmaceutical Co., Ltd.) or non-brominated GPR7L (Trp1-bovine GPR7L (29), SEQ ID NO:67) synthesized in EXAMPLE 13 dissolved in distilled-water was infused, in a total volume of 10 µl (10 nmols/rat), into the lateral ventricle at a flow rate of 5 µl/min. After a 2 minute standby time following the infusion, the microinjection cannula was disconnected and the dummy cannula was locked in position again with a cap nut. The infusion was continued from 19:00 to 20:00 o'clock, and the feed uptake thereafter was measured with passage of time, using a feed uptake measuring device Feed-Scale (Columbus, Inc.). As shown in FIG. 22, a significant increase in feed uptake from 2 hours after the administration was noted in the group administered with non-brominated GPR7L, as compared to the control group.

Example 15

Assay for Bovine Endogenous GPR7 Ligand by FTMS

Figure 23:
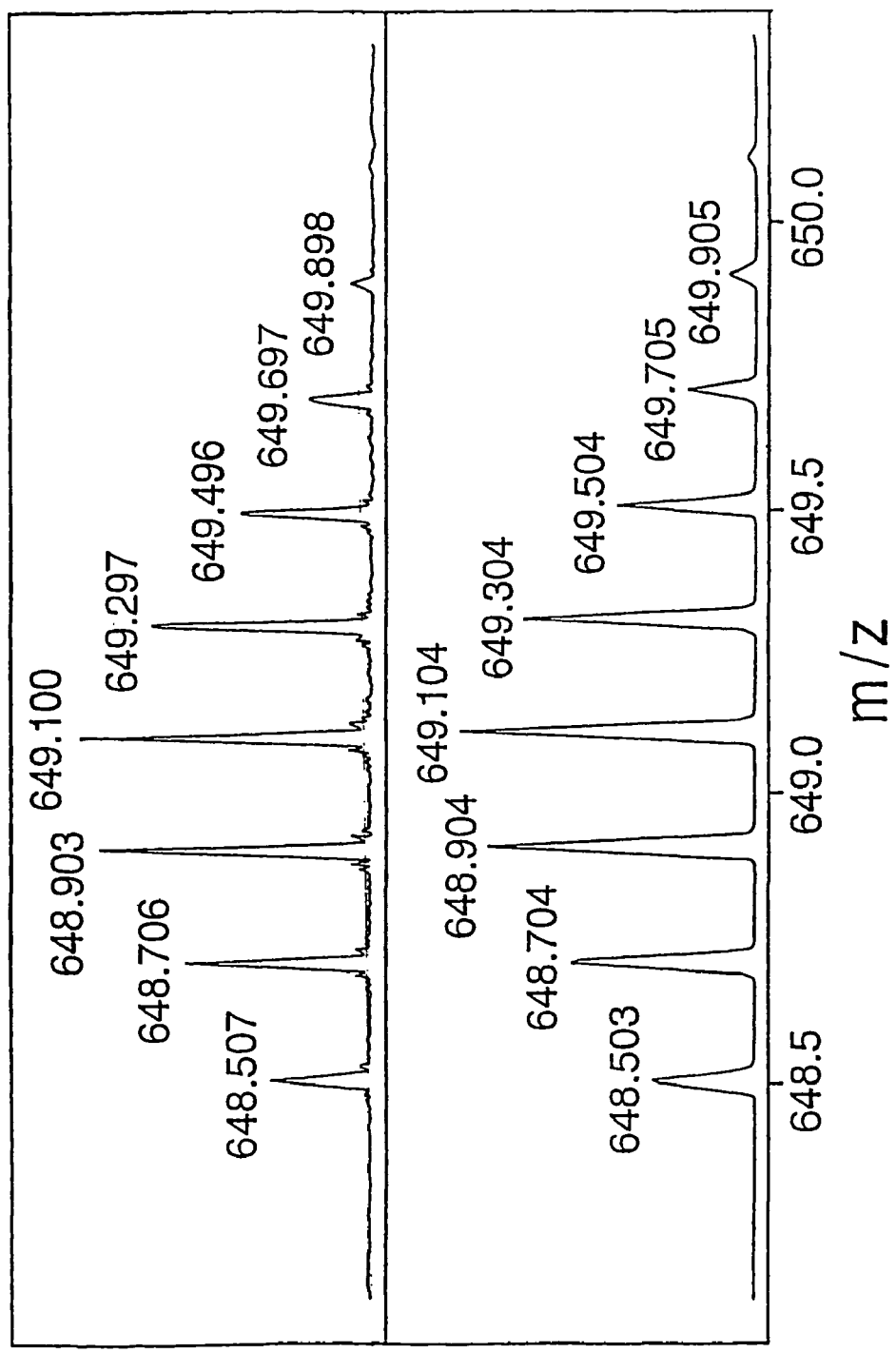
FIG. 23 shows a FMS spectrum of endogenous GPR7 ligand.

Bovine endogenous GPR7 was analyzed on Apex II (Burker Daltonics) by ESIFTMS (FIG. 23, upper). In FIG. 23, $[M+5H]^{5+}$ ions are shown in an enlarged drawing and the $[M+5H]^{5+}$ ion isotope theoretical profile of 1Br-added bovine GPR7L is shown at the lower column. The modified product was identified to be Br, since the isotope profile and mass spectral data matched well.

Example 16

Study of Tissue Distribution of GPR7 Ligand mRNA in Human by RT-PCR

The expression level of mRNA was assayed in a manner similar to EXAMPLE 9, except that cDNAs used as templates were prepared from polyA+ RNA (CLONTECH) derived from various human organs by the following procedures. Using reverse transcriptase or SuperScript II as a random primer and reverse transcriptase, cDNA was prepared from 1 µg of RNA and the reaction was carried out at 42° C. in accordance with the instruction manual attached. After completion of the reaction, the precipitates in ethanol were dissolved in 100 µl. Also, the expression level was quantified in a manner similar to EXAMPLE 9 using Sequence Detection System Prism 7700, except that the following were used for amplification and detection: 5'-CGCTCCCAGCCCTACAGA-3' (SEQ ID NO:90) and 5'-TCGCCTTGCACTGGTAGGTC-3' (SEQ ID NO:91) as primers and as TaqMan probe, 5'-(Fam) AGCCTCGCTGT-GTGCGTCCAGGAC-(Tamra)-3' (SEQ ID NO:92).

Figure 24:
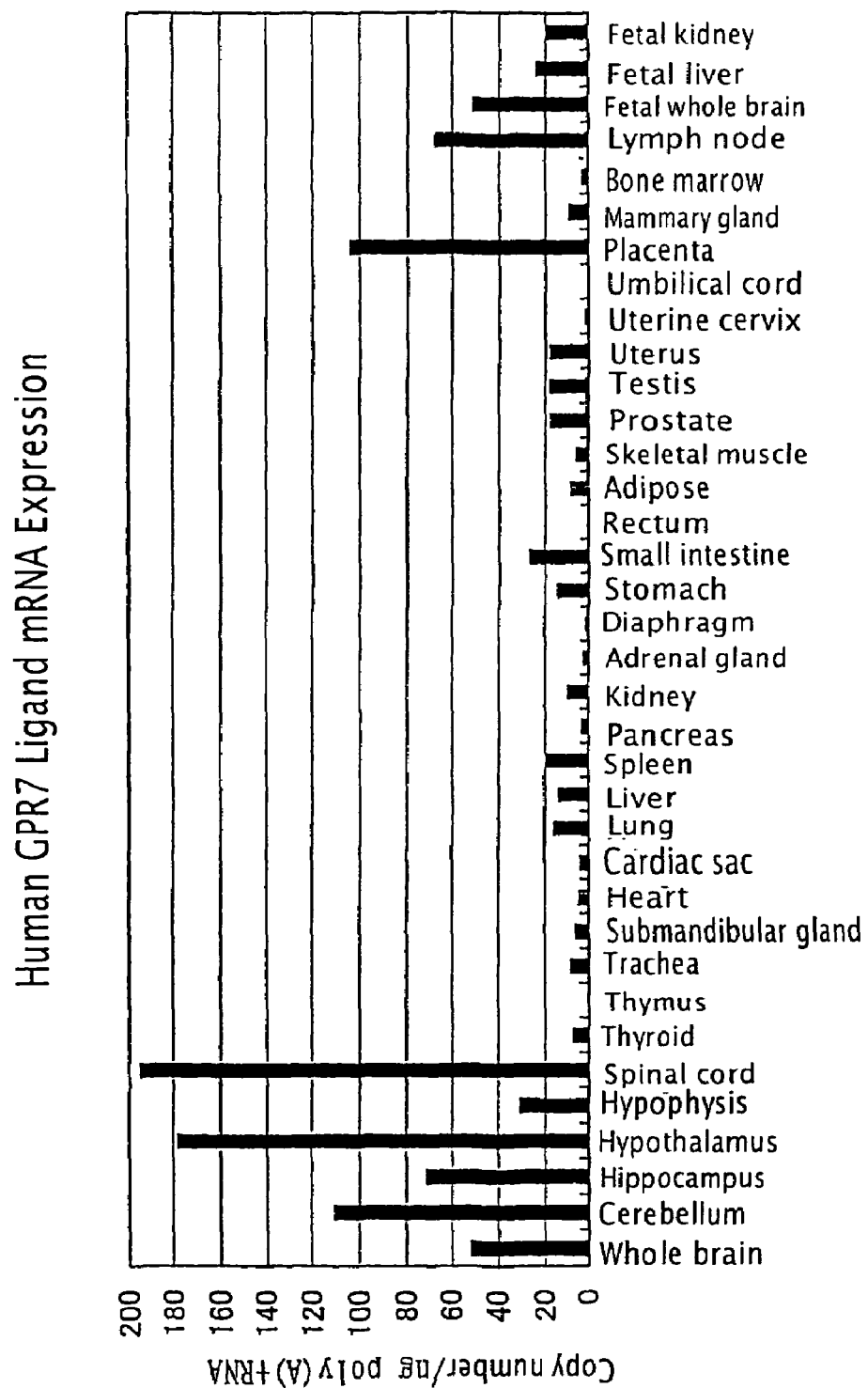
FIG. 24 shows the results of the tissue distribution and expression level of GPR7 ligand mRNA in human as determined by RT-PCR.

The expression level of GPR7 mRNA in various human tissues obtained was assessed in terms of a copy number per 1 ng of poly(A)$^+$ RNA (FIG. 24).

Example 17

Study of Tissue Distribution of Rat GPR7 (rat TGR26) mRNA by RT-PCR

The expression level of mRNA was assayed in a manner similar to EXAMPLE 9. Using the cDNAs derived from various organs of rat used in EXAMPLE 9, the expression level of rat GPR7 mRNA was determined, except that except that the following were used for amplification and detection: 5'-TGCGTGCTATCCAGCTAGACAG-3' (SEQ ID NO:93) and 5'-AGAGGAGGCACACAGCCAGAAT-3' (SEQ ID NO:94) as primers and 5'-(Fam)CGTGCCAA-GAAACGCGTGACCTTGTT-(Tamra)-3' (SEQ ID NO:95) as TaqMan probe.

Figure 25:
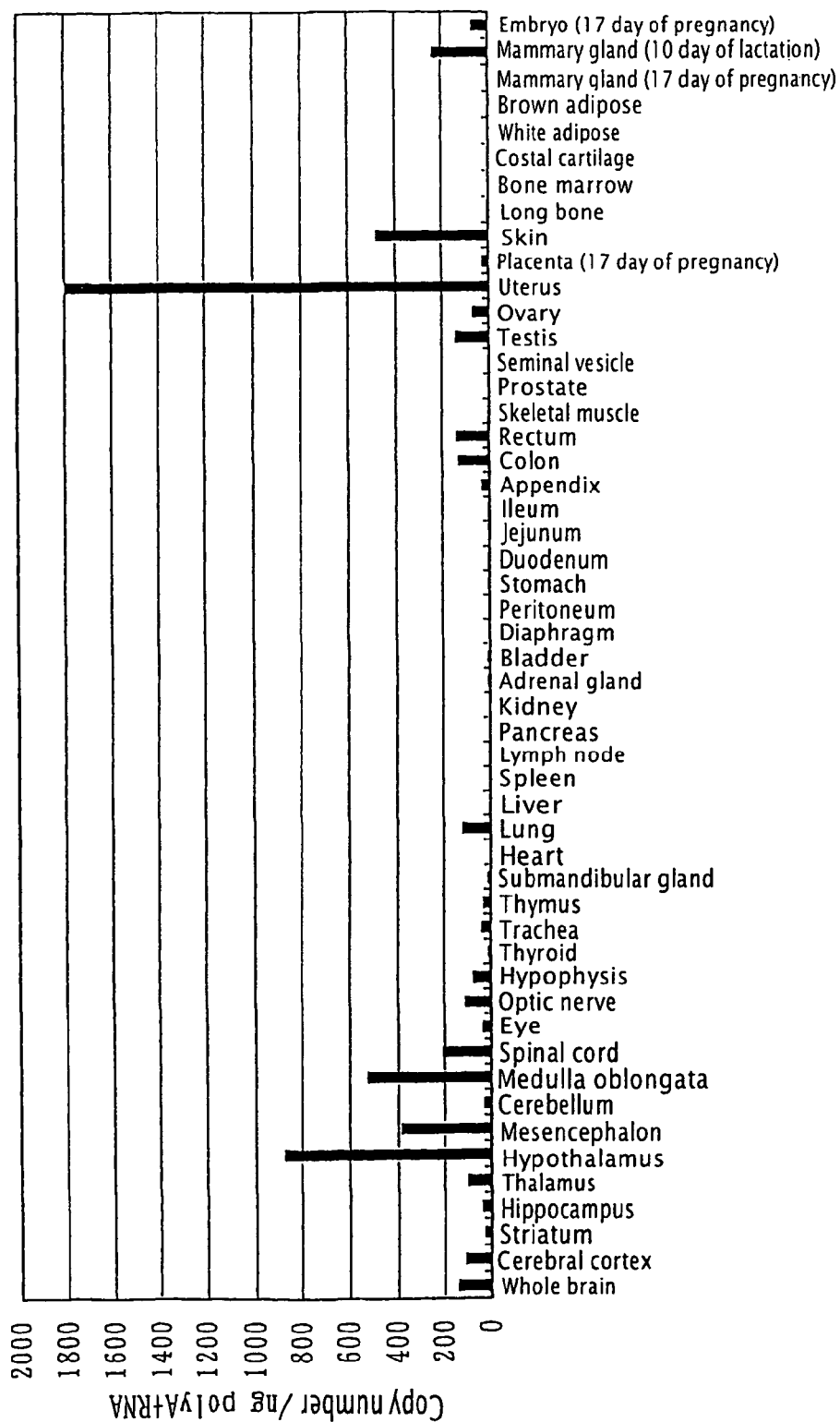
FIG. 25 shows the results of the tissue distribution and expression level of rat GPR7 (rat TGR26) mRNA as determined by RT-PCR.

The expression level of GPR7 mRNA in various tissues of rat obtained was assessed in terms of a copy number per 1 ng of poly(A)$^+$ RNA (FIG. 25).

Example 18

Acquisition of Bovine GPR7 Gene from Bovine Hypothalamus cDNA by PCR

Using bovine hypothalamus cDNA as a template, amplification was performed by PCR using the following two synthetic DNAs.

```
                                          (SEQ ID NO:96)
BGPR7F:    5'-GTCGACCGAGTGTCTGTCCTCGCCAGGATG-3'

(SEQ ID NO:97)
BGPR7R:    5'-GCTAGCTCCTTGTTATCGGGCTCAGGAGGTGGT-3'
```

The reaction solution for PCR contained 1 µl of cDNA solution, 0.5 µl of BGPR7F (10 µM), 0.5 µl of BGPR7R (10 µM), 2.5 µl of 10× reaction solution attached, 2.5 µl of dNTP (10 mM) and 0.5 µl of KlenTaq (CLONTECH, Inc.), to which 17.5 µl of Otsuka distilled water was added to make the total volume 25 µl. The reaction solution was applied to PCR using Thermal Cycler 9600. The conditions for PCR were set forth: after denaturation at 95° C. for 2 minutes, the cycle set to include 98° C. for 10 seconds, 60° C. for 20 seconds and 72° C. for 60 seconds was repeated 40 times. It was confirmed by electrophoresis using an aliquot of the PCR product that the PCR product of about 1000 bp was amplified. The PCR product was then purified using Quiagen PCR purification Kit (QIAGEN, Inc.) and directly sequenced to obtain the sequence shown by FIG. 26. The amino acid sequence deduced from the DNA sequence of FIG. 26 was the sequence shown in FIG. 27. Next, the PCR product recovered from the gel was subcloned to *Escherichia coli* JM109, using TA Cloning Kit (Invitrogen, Inc.), to acquire *Escherichia coli* JM109/pTAbGPR7. Plasmid pTAbGPR7 was extracted from *Escherichia coli* obtained by the subcloning, using a plasmid extractor (Kurabo Co., Ltd.) to identify the base sequence of the inserted fragment. It was confirmed that the sequence was the same as that of bovine GPR7 receptor cDNA.

Example 19

Acquisition of Bovine GPR8 Gene from Bovine Hypothalamus cDNA by PCR

Using bovine hypothalamus cDNA as a template, amplification was performed by PCR using the following two synthetic DNAs.

```
                                   (SEQ ID NO:98)
BGPR8F:   5'-GTCGACCATGATGGAGGCCACTGGGCTGGAAGG-3'

(SEQ ID NO:99)
BGPR8R:   5'-GCTAGCTTATGCCCCCTGGCACCGACATGCGGT-3'
```

PCR was carried out in a manner similar to EXAMPLE 18. The PCR product obtained was purified using Quiagen PCR purification Kit and directly sequenced to obtain the sequence shown by FIG. 28. The amino acid sequence deduced from the DNA sequence of FIG. 28 was the sequence shown in FIG. 29. Next, the PCR product recovered from the gel was subcloned to *Escherichia coli* JM109, using TA Cloning Kit (Invitrogen, Inc.), to acquire *Escherichia coli* JM109/pTAbGPR8. Plasmid pTAbGPR8 was extracted from *Escherichia coli* obtained by the subcloning, using a plasmid extractor to identify the base sequence of the inserted fragment. It was confirmed that the sequence was the same as that of bovine GPR8 cDNA.

Example 20

Figure 30:
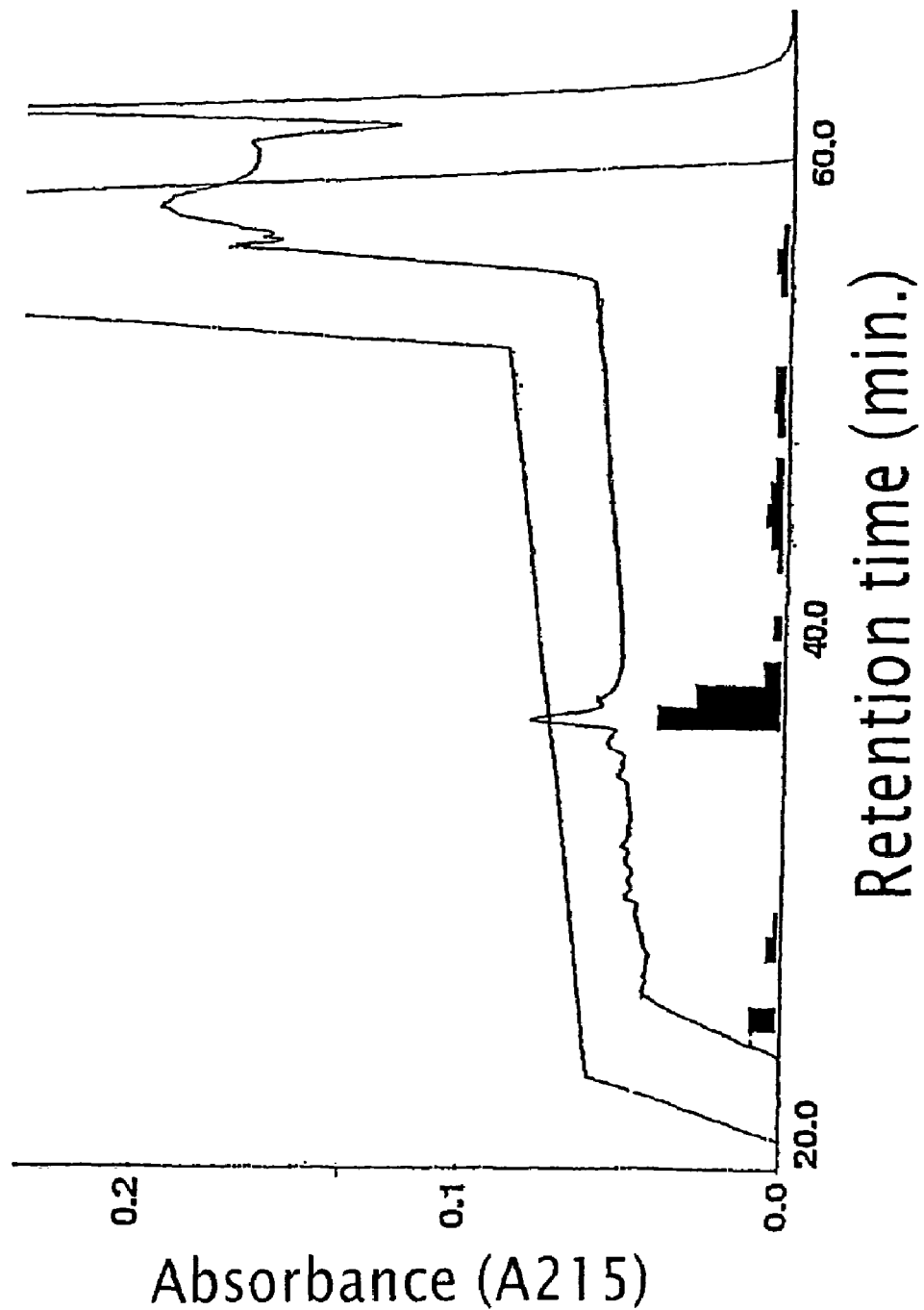
FIG. 30 shows the results of final purification of human GPR7 ligand from the culture supernatant of human GPR7 ligand-expressed CHO cells, wherein chromatographic pattern of μRPC C2C18 SC2.1/10 at the final purification step and the specific intracellular cAMP production suppression activity obtained by recating each fraction with human GPR7-expressed CHO cells are shown. On the chromatogram, absorbance at 215 nm and the elution concentration of acetonitrile are shown.

Purification of GPR7 Ligand from the Culture Supernatant of Human GPR7 Ligand-Expressed CHO Cells The culture supernatant of human GPR7 ligand-expressed CHO cells constructed in EXAMPLE 5 was collected to make the volume 2 liters and stored at −80° C. The culture supernatant was thawed, boiled in hot water and then centrifuged to obtain the supernatant. Trifluoroacetic acid (TFA) was added in 0.05% to the supernatant and the mixture was applied to C18 Column (Prep C18 125 Å; Waters, Inc.). The peptide bound to the column was stepwise eluted with 10, 40 and 60% acetonitrile containing 0.5% TFA. The 30% acetonitrile fraction was diluted with a 3-fold volume of 20 mM ammonium acetate (pH 4.7) and the dilution was applied to ion exchange column HiPrep CM-Sepharose FF (Pharmacia). The peptide bound to the column was eluted in a concentration gradient of 0 M to 0.5 M NaCl in 20 mM ammonium acetate (pH 4.7) containing 10% acetonitrile. An aliquot of each fraction was desalted using Sep-Pak plus C18 Cartridge (Waters, Inc.), the intracellular cAMP production suppression activity specific to human GPR7-expressed CHO cells was assayed. TFA was added in 0.1% to the CM-Sepharose fraction found to have a specific activity to human GPR7-expressed CHO cells, which was separated by passing through reverse phase HPLC column RESOURCE RPC (Pharmacia). The separation through RESOURCE RPC was carried out in a concentration gradient of 15-30% acetonitrile. The main intracellular cAMP production suppression activity specific to the human GPR7-expressed CHO cells was eluted on about 22% acetonitrile. This active fraction was separated by passing through cationic ion exchange column TSK gel CM-SW (Toso Co., Ltd.) in a concentration gradient of 0.2-0.5 M NaCl in 20 mM ammonium acetate (pH 4.7) containing 10% acetonitrile. The main intracellular cAMP production suppression activity was eluted on about 0.3 M NaCl. TFA was added in 0.1% to the fraction from the CM-2SW column. Final purification of the mixture on reverse phase column μRPC C2/C18 SC2.1/10 gave a single peak, which coincided with the intracellular cAMP production suppression activity specific to the human GPR7-expressed CHO cells (FIG. 30).

Figure 31:
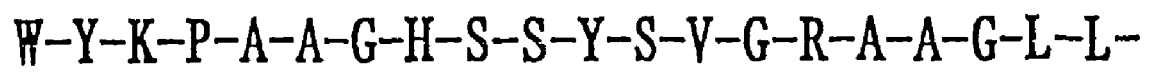

Analysis of the N-terminal amino acids in the finally purified product using a protein sequencer (model 492; Applied Biosystems, Inc.) gave the amino acid sequence shown in FIG. 31.

Figure 32:
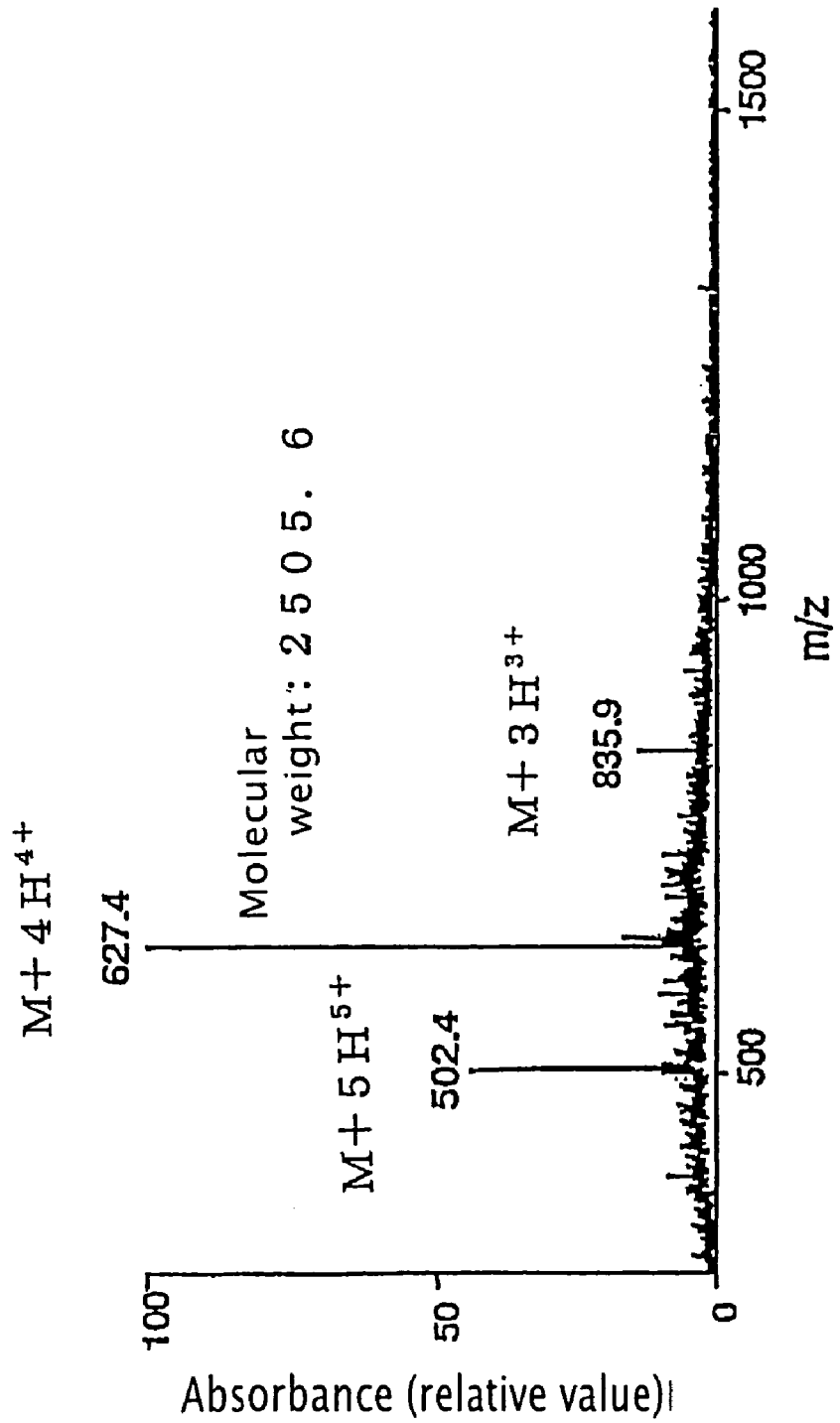
FIG. 32 shows an ESI-MS spectrum of GPR7 ligand purified from the culture supernatant of human GPR7 ligand-expressed CHO cells.

Also, the molecular weight of the finally purified product was determined using ESI-MS (Thermoquest, Inc.) and found to be 2505.6 (FIG. 32).

Based on these analytical results, the finally purified product was found to be a peptide of 24 amino acids corresponding to Trp25 to Arg48 in the precursor.

Example 21

Preparation of Iodine-Labeled Human GPR7 Ligand

A mixture of 20 μl of hGPR7L-23 (SEQ ID NO:1) (0.1 mM or 1 mM), 20 μl of lactoperoxidase (Sigma; prepared using 10 μg/ml and 0.1M HEPES-NaOH pH7.0), 20 μl of Idoine-125 (manufactured by Amersham, MS-30, 74 MBq), 20 μl of 0.005% hydrogen peroxide (manufactured by Wako Pure Chemical Industries, Ltd.) was allowed to stand at room temperature for 20 to 30 minutes. Then, 600 μl of 0.1% TFA was added to the mixture. The mixture was applied to reverse phase HPLC for separation and the peaks of the two'labeled products were fractionated in a tube charged with 1 mL of DMSO. Immediately, the fraction was stored on ice and an aliquot was provided for measurement of the radioactivity with a γ-counter. The remaining preparation was dispensed and stored at −30° C.

Example 22

Preparation of Human GPR7-Expressed CHO Cell Membrane Fraction

Human GPR7-expressed CHO cells were cultured in a flask. The flask was washed with 5 mM EDTA/PBS to strip the cells off. The cells were stripped off with 5 mM EDTA/PBS and centrifuged for recovery. The recovered cells were suspended in 25 mL of a buffer for preparing membrane fraction (50 mM Tris-HCl, pH7.5, 5 mM EDTA, 0.1% bovine serum albumin (manufactured by Sigma), 0.5 mM PMSF (manufactured by Wako Pure Chemical Industries, Ltd.), 20 μg/mL leupeptin (manufactured by Peptide Research Institute), 0.1 μg/mL pepstatin A (manufactured by Peptide Research Institute) and 4 μg/mL E-64 (manufactured by Peptide Research Institute)), followed by homogenization on ice using a polytron (12,000 rpm, 15 seconds×3 times). The homogenate was centrifuged at 4° C. under 1,000 g for 10 minutes with a high speed cooling centrifuge to recover the supernatant. After 25 mL of the buffer for preparing membrane fraction was added to the precipitates, the supernatant was recovered by the same procedures. These supernatants were combined, applied to a cell strainer, dispensed in a super centrifuge tube and centrifuged at 4° C. under 100,000 g for an hour. The pellets were recovered and suspended in a small quantity of the buffer for preparing membrane fractions. After further suspending with a Teflon (registered trademark) homogenizer, an aliquot of the suspension was used to determine a protein level. The remaining suspension was dispensed and stored at −80° C.

Example 23

Scatchard Analysis Using Human GPR7-Expressed CHO Cell Membrane Fraction

Scatchard analysis was performed using human GPR7-expressed CHO cell membrane fraction and [Tyr ($^{125}$I)$^{11}$]-hGPR7L-23 (SEQ ID NO:1). The membrane fraction was diluted in a final concentration of 1 µg/well with an assay buffer (50 mM Tris-HCl, pH7.5, 5 mM EDTA, 0.1% bovine serum albumin (manufactured by Sigma), 0.5 mM PMSF (manufactured by Wako Pure Chemical Industries, Ltd.), 20 µg/mL leupeptin (manufactured by Peptide Research Institute), 0.1 µg/mL pepstatin A (manufactured by Peptide Research Institute) and 4 µg/mL E-64 (manufactured by Peptide Research Institute)), and the labeled product was diluted in 400 µM, 200 µM, 100 µM, 50 µM, 25 µM and 10 µM. Using a polyproprene-made 96-well plate, 50 µl each of the assay buffer alone (total) and hGPR7L-23 (NSB) in a final concentration of 2 µM were dispensed in each well. To each well, 25 µl of the solution of the labeled product was added. After agitation, 25 µl of the diluted membrane fraction was added/mixed, followed by incubation at room temperature for 1.5 hour. Using a cell harvester for the 96-well plate, adsorption was made onto a filter unit (GF/C, treated with polyethyleneimine), which had previously been made wet with an assay buffer (50 mM Tris-HCl, pH7.5). After washing 5 times with the assay buffer, the filter unit was thoroughly dried. As an input, the dilution of the labeled product was directly added to a filter unit (GF/C, treated with polyethyleneimine) and dried. After 50 µl of a liquid scintillator was dispensed thereto, the radioactivity was counted on a Top Count (Packard) and the data was analyzed in triplet (FIG. 33), thereby to obtain the values of Bmax=1.28 pmol/mg protein and Kd=35.5 µM.

Example 24

Figure 33:
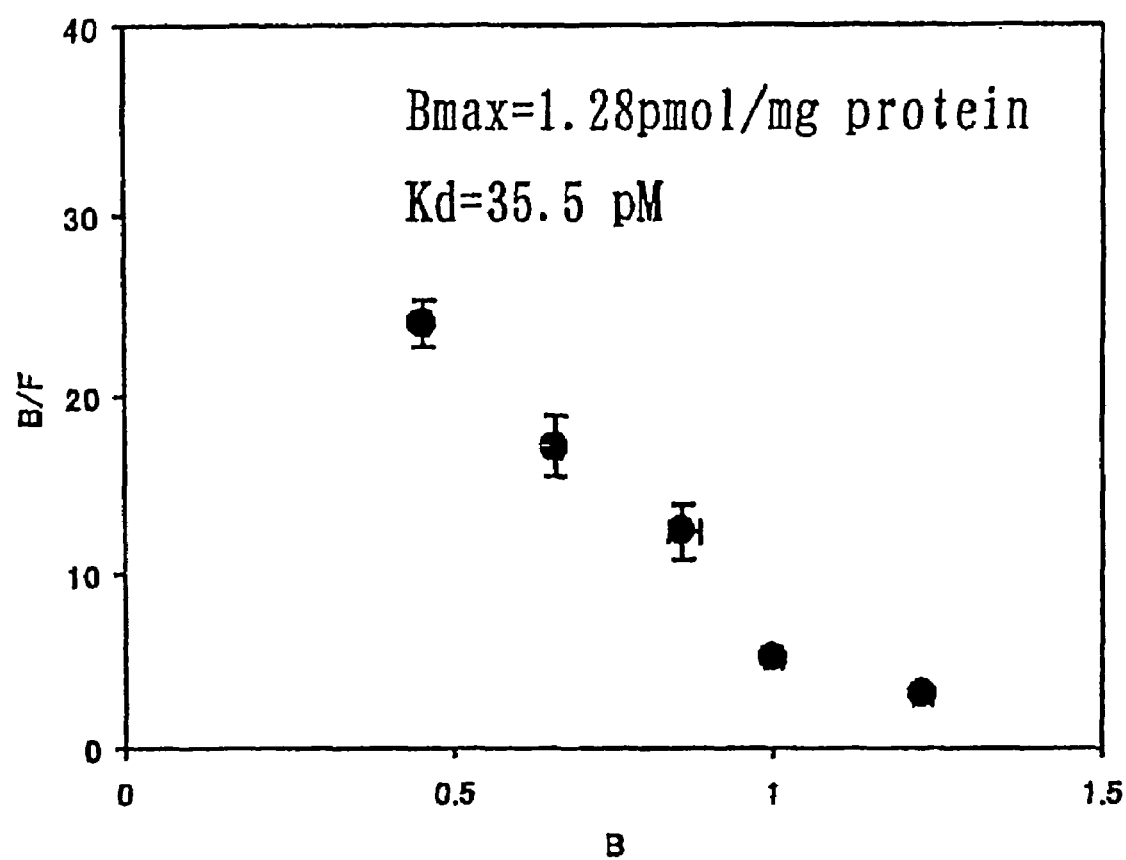
FIG. 33 shows the results of Scatchard analysis using human GPR7 ligand-expressed CHO cells.

Test on Binding Inhibition of Various Peptides Against Human GPR7-Expressed CHO Cells Using the assay buffer, the human GPR7-expressed CHO cell membrane fraction was diluted in a final concentration of 1 µg/well and iodine-labeled hGPR7L-23 (SEQ ID NO:1) was diluted in a final concentration of 100 µM. The peptides shown in TABLE 3 are those obtained by diluting the stock solution of 10 M or $10^{-3}$ M with the assay buffer in $10^{-5}$ M, $10^{-6}$ M, $10^{-7}$ M, $10^{-8}$ M, $10^{-9}$ M, $10^{-10}$ M and $10^{-11}$ M. As NBS, hGPR7L-23 was prepared in a final concentration of $10^{-5}$ M. The sample solution and NSB prepared were dispensed on a polypropylene-made 96-well plate, the assay buffer was dispensed thereto to make the total volume 50 µl, and 25 µl of the iodine-labeled product dilution was added thereto. After agitation, 25 µl of the solution of human GPR7-expressed CHO cell membrane fraction were dispensed thereto and agitated, followed by incubation at room temperature for 1.5 hour. Using a cell harvester for the 96-well plate, the culture medium was adsorbed onto a filter unit, which had previously been wetted with an assay buffer (50 mM Tris-HCl, pH7.5). After washing 5 times with the assay buffer, the filter unit was thoroughly dried. After 50 µl of a liquid scintillator was dispensed thereto, the radioactivity was counted on a Top Count (Packard) and the data was analyzed in triplet (FIG. 33). The results obtained by the test on binding inhibition of various peptides against human GPR7-expressed CHO cell membrane fraction are shown in terms of IC$_{50}$ values in TABLE 3.

TABLE 3

| Peptide | IC50 (nM) |
|---|---|
| DTrp(6Br)1-human GPR7L(29) | 13 |
| LTrp(6Br)1-human GPR7L(29) | 0.32 |
| Trp1-human GPR7L(29) | 0.33 |
| Trp1-human GPR7L(23) | 1.6 |
| Trp1-human GPR8L(23) | 0.4 |
| DTrp(6Br)1-bovine GPR7L(29) | 6.1 |
| LTrp(6Br)1-bovine GPR7L(29) | 0.34 |
| Trp1-bovine GPR7L(29) | 0.31 |
| Trp1-rat GPR7L(29) | 0.34 |
| Trp1-rat GPR7L(24) | 0.30 |

Example 25

Comparison in Agonist Activity of Various Peptides on GPR7 and GPR8-Expressed CHO Cells The intracellular cAMP production suppression activity of peptides associated with various GPR7 ligands on CHO cells, in which human GPR7, bovine GPR8, human GPR8, human GPR8, bovine GPR8 and rat GPR7 were expressed, was examined. Each of the receptor-expressed cells was passaged on a 96-well plate in 4×10$^4$ cells/well, followed by incubation for 1 day at 37° C. under 5% CO$_2$ and 95% air. An assay buffer was prepared by adding 20 mM HEPES, pH7.4, 0.1% bovine serum albumin and 0.2 mM 3-isobutyl-1-methylxanthine (Sigma) to Hanks' Balanced Salt Solution (Gibco BRL). The plate incubated overnight was first washed twice with 150 µl of the assay buffer, and then exchanged with 150 µl of the assay buffer, followed by incubation for 30 minutes at 37° C. in 100% air. By adding 4 µM forskolin to the assay buffer, a buffer for sample dilution was prepared and the stock solution ($10^{-2}$ M of $10^{-3}$ M) was diluted with the buffer thus obtained to prepare sample solutions in final concentrations of $10^{-6}$ M, $10^{-7}$ M, $10^{-8}$ M, $10^{-9}$ M and $10^{-10}$ M. The plate incubated with the assay buffer for 30 minutes was taken out. After washing twice with the assay buffer, 50 µl of the assay buffer and then 50 µl of the sample solution were added thereto. Each sample was assayed in triplet. Furthermore, the assay buffer of the same volume for assaying the basal level and a buffer supplemented with forskolin for assaying the maximum level were added. After the plate was incubated for 30 minutes at 37° C. in 100% air, the intracellular cAMP level was assayed using cAMP-Screen™ System (ABI, Inc.) according to the protocol attached to the kit. A difference between the maximum cAMP level and the cAMP level when each sample was added was calculated and the percentage of cAMP production level promoted by forskolin was worked out, which was made the cAMP production inhibition rate. The IC$_{50}$ values of respective samples are shown in TABLE 4.

TABLE 4

| ペプチド | IC50 (nM) | | | | |
| --- | --- | --- | --- | --- | --- |
| | human GPR7 | human GPR8 | bovine GPR7 | bovine GPR8 | rat GPR7 |
| DTrp(6Br)1-human GPR7L(29) | 106 | 770 | 360 | 424 | 49 |
| LTrp(6Br)1-human GPR7L(29) | 0.44 | 32 | 1.8 | 51 | 0.47 |
| Trp1-human GPR7L(29) | 0.45 | 49 | 2.6 | 52 | 0.29 |
| Trp1-human GPR7L(23) | 0.58 | 44 | 3.5 | 47 | 0.28 |
| Trp1-human GPR8L(23) | 0.82 | 3.7 | 2.4 | 4.8 | 0.32 |
| DTrp(6Br)1-bovine GPR7L(29) | 35 | 198 | 77 | 34 | 2.5 |
| LTrp(6Br)1-bovine GPR7L(29) | 0.58 | 9.7 | 1.9 | 4.0 | 0.21 |
| Trp1-bovine GPR7L(29) | 0.43 | 8.1 | 1.2 | 5.4 | 0.25 |
| Trp1-rat GPR7L(29) | 0.86 | 8.8 | 1.2 | 14 | 0.30 |
| Trp1-rat GPR7L(24) | 0.31 | 2.8 | 0.51 | 3.5 | 0.18 |

Example 9

Study of Expression Distribution of GPR7 Ligand mRNA in Rat Brain by In Situ Hybridization Wistar rat was laparotomized under anesthesia with Nembutal and 250 ml of 0.9% aqueous sodium chloride solution was infused through the left ventricle and then with 250 ml of 4% p-formaldehyde solution. After the brain withdrawn was immersed in the solution for 4 hours at 4° C., the solution was replaced by 20% sucrose solution. The brain was immersed for further 3 days at 4° C. to obtain the brain sample provided for analysis.

GPR7 ligand, antisense and sense probe were prepared by the following method.

First, rat GPR7 ligand cDNA was inserted into plasmid vector pBluescript II KS+ (Stratagene) by publicly known methods. This plasmid was inactivated by treating with restriction enzyme BamHI or XbaI, which was dissolved in TE, respectively, in 0.52 μg/ml and 0.47 μg/ml. To 2 μl of the BamHI-treated product, 40 U of T3 RNA polymerase (Roche), 2 μl of the supplied 10× buffer, 20U of RNase inhibitor (Roche) and 2 μl of DIG RNA Labeling Mix, 10× (Roche), water was added to make the final volume 20 μl. After the mixture was reacted at 37° C. for 2 hours, the reaction was terminated by adding 2 μl of 0.2 M EDTA, and the riboprobe formed by ethanol precipitation was recovered and used as an antisense probe. Also, to 2 μl of the XbaI-treated product, 40 U of T3 RNA polymerase (Roche), 2 μl of the supplied 10× buffer, 20U of RNase inhibitor (Roche) and 2 μl of DIG RNA Labelling Mix, 10× (Roche), water was added to make the final volume 20 μl. The mixture was reacted at 37° C. for 2 hours. After the reaction was terminated by adding 2 μl of 0.2 M EDTA, the riboprobe formed by ethanol precipitation was recovered and used as a sense probe. The respective concentrations were measured and the probes were dissolved in RNase free water to set the concentrations of antisense and sense probes at 0.29 μg/ml and 0.27 μg/ml, respectively.

In situ hybridization was carried out by the following method. The brain sample prepared as described above was sliced on Cryostat CM3050 (Leica) at 25 μm thick in the frontal plane. The slice formed was washed twice with 10 ml of 4×SSC for 5 minutes. Then, Protenase K (Sigma) was added to 10 ml of PK buffer (pH7.4, 10 mM Tris-HCl, 10 mM EDTA) in a final concentration of 2.5 mg/ml, followed by reacting them at 37° C. for 10 minutes. The reaction mixture was washed twice with 10 ml of 4×SSC for 5 minutes. Acetic anhydride was added to 10 ml of an acetylation buffer (pH 7.5, 100 mM triethanolamine) in 0.25%, followed by reaction at room temperature for 10 minutes. The mixture was washed with 10 ml of 4×SSC for 5 minutes. After this operation was repeated twice, the slice was added to 1 ml of a hybrid buffer (pH 7.4, 60% formamide, 10 mM Tris-HCl, 200 μg/ml yeast t-RNA, 1× Denhardt's reagent, 10% dextran sulfate, 600 mM NaCl, 0.25% SDS, 1 mM EDTA) supplemented with 0.2 μg/ml each of the antisense and the sense probe. Hybridization was performed at 55° C. for 13 hours, followed by washing at 55° C. for 15 minutes twice with 10 ml of a wash buffer (2×SSC, 50% formamide). RNaseA (Sigma) was added to RNase buffer (pH8.0, 10 mM Tris-HCl, 1 mM EDTA, 0.5M NaCl) in 2.5 μg/ml and the slice was transferred thereto followed by reacting them at 37° C. for 30 minutes. The reaction mixture was washed at 55° C. for 15 minutes with 10 ml of the wash buffer. After this operation was repeated twice, the mixture was washed with 0.4×SSC at 55° C. for 15 minutes. The slice was transferred to a solution mixture of 0.1 g of a blocking solution (Roche) and Buffer A (pH 7.5, 100 mM Tris-HCl, 150 mM NaCl) to react them at room temperature for an hour. The slice was transferred to 1 ml of Buffer A containing Triton X-100 and supplemented with 0;75U of anti-digoxygenin-AP, Fab fragments (Roche), followed by reacting them at 4° C. for 16 hours. The reaction mixture was then washed with 10 ml of Buffer A at room temperature for 15 minutes. After this operation was repeated twice, the mixture was washed with 10 ml of Buffer B (pH 9.5, 100 mM Tris-HCl, 100 mM NaCl, and 50 mM $MgCl_2$) at room temperature for 15 minutes. To 10 ml of Buffer B, 40 oil of NBT solution (Roche) and 30 μl of X-phosphate solution were added, and the slice was transferred to the mixture to perform a color-forming reaction. After reacting at room temperature for 24 hours, the slice was transferred to 50 ml of TE. The slice was applied onto MAS-coated slide glass (Matsunami Glass Ind. Ltd.). After air-drying, a cover glass was applied thereon with a sealant (50% glycerol, 5% gelatin). The areas where the color was developed specifically to the antisense probe were the medial and lateral preoptic areas of hypothalamus, the lateral hypothalamic field, the CA1-CA3 areas of hippocampal pyramidal cells, the mesencephalic aqueduct ventral division of the midbrain, etc. In these areas, any color formation was not detected by the sense probe.

INDUSTRIAL APPLICABILITY

The peptide of the present invention and its DNA, the bovine GPR7 of the present invention and its DNA, as well as the bovine GPR8 of the present invention and its DNA are useful as pharmaceuticals for the prevention/treatment of, e.g., anorexia, appetite (eating) stimulants, etc.

In addition, the peptide, etc. of the present invention are also useful for screening GPR7 agonists or antagonists, etc.

---

What is claimed is:

1. An isolated peptide comprising the amino acid sequence of SEQ ID NO:4, which may optionally be brominated at the N-terminal amino acid residue, or its amide or ester, or a salt thereof.

2. The peptide or its amide or ester, or a salt thereof, according to claim 1, which comprises the amino acid sequence of SEQ ID NO:4.

3. The peptide or its amide or ester, or a salt thereof, according to claim 1, which consists of the amino acid sequence of SEQ ID NO:4.

4. The peptide or its amide or ester, or a salt thereof, according to claim 1, which consists of the amino acid sequence of SEQ ID NO:4 and which is 6-brominated at the N-terminal tryptophan residue.

5. An isolated peptide or its amide or ester, or a salt thereof, which comprises the amino acid sequence of SEQ ID NO:19.

6. An isolated peptide or its amide or ester, or a salt thereof, which comprises the amino acid sequence of SEQ ID NO:22.

* * * * *

SEQUENCE LISTING

<160> NUMBER OF SEQ ID NOS: 108

<210> SEQ ID NO 1
<211> LENGTH: 23
<212> TYPE: PRT
<213> ORGANISM: Homo sapiens

<400> SEQUENCE: 1

Trp Tyr Lys Pro Ala Ala Gly His Ser Ser Tyr Ser Val Gly Arg Ala
                 5                  10                  15

Ala Gly Leu Leu Ser Gly Leu
            20

<210> SEQ ID NO 2
<211> LENGTH: 24
<212> TYPE: PRT
<213> ORGANISM: Mus sp.

<400> SEQUENCE: 2

Trp Tyr Lys Pro Ala Ala Gly Pro His His Tyr Ser Val Gly Arg Ala
                 5                  10                  15

Ser Gly Leu Leu Ser Ser Phe His
            20

<210> SEQ ID NO 3
<211> LENGTH: 24
<212> TYPE: PRT
<213> ORGANISM: Rattus sp.

<400> SEQUENCE: 3

Trp Tyr Lys Pro Ala Ala Gly Ser His His Tyr Ser Val Gly Arg Ala
                 5                  10                  15

Ala Gly Leu Leu Ser Ser Phe His
            20

<210> SEQ ID NO 4
<211> LENGTH: 29
<212> TYPE: PRT
<213> ORGANISM: Homo sapiens

<400> SEQUENCE: 4

Trp Tyr Lys Pro Ala Ala Gly His Ser Ser Tyr Ser Val Gly Arg Ala
                 5                  10                  15

Ala Gly Leu Leu Ser Gly Leu Arg Arg Ser Pro Tyr Ala
            20                  25

<210> SEQ ID NO 5
<211> LENGTH: 29
<212> TYPE: PRT
<213> ORGANISM: Mus sp.

<400> SEQUENCE: 5

Trp Tyr Lys Pro Ala Ala Gly Pro His His Tyr Ser Val Gly Arg Ala
                 5                  10                  15

Ser Gly Leu Leu Ser Ser Phe His Arg Phe Pro Ser Thr
            20                  25

```
<210> SEQ ID NO 6
<211> LENGTH: 29
<212> TYPE: PRT
<213> ORGANISM: Rattus sp.

<400> SEQUENCE: 6

Trp Tyr Lys Pro Ala Ala Gly Ser His His Tyr Ser Val Gly Arg Ala
                5                   10                  15

Ala Gly Leu Leu Ser Ser Phe His Arg Phe Pro Ser Thr
            20                  25

<210> SEQ ID NO 7
<211> LENGTH: 13
<212> TYPE: PRT
<213> ORGANISM: Homo sapiens

<400> SEQUENCE: 7

Trp Tyr Lys Pro Ala Ala Gly His Ser Ser Tyr Ser Val
                5                   10

<210> SEQ ID NO 8
<211> LENGTH: 14
<212> TYPE: PRT
<213> ORGANISM: Homo sapiens

<400> SEQUENCE: 8

Trp Tyr Lys Pro Ala Ala Gly His Ser Ser Tyr Ser Val Gly
                5                   10

<210> SEQ ID NO 9
<211> LENGTH: 13
<212> TYPE: PRT
<213> ORGANISM: Mus sp.

<400> SEQUENCE: 9

Trp Tyr Lys Pro Ala Ala Gly Pro His His Tyr Ser Val
                5                   10

<210> SEQ ID NO 10
<211> LENGTH: 14
<212> TYPE: PRT
<213> ORGANISM: Mus sp.

<400> SEQUENCE: 10

Trp Tyr Lys Pro Ala Ala Gly Pro His His Tyr Ser Val Gly
                5                   10

<210> SEQ ID NO 11
<211> LENGTH: 13
<212> TYPE: PRT
<213> ORGANISM: Rattus sp.

<400> SEQUENCE: 11

Trp Tyr Lys Pro Ala Ala Gly Ser His His Tyr Ser Val
                5                   10

<210> SEQ ID NO 12
<211> LENGTH: 14
<212> TYPE: PRT
<213> ORGANISM: Rattus sp.

<400> SEQUENCE: 12

Trp Tyr Lys Pro Ala Ala Gly Ser His His Tyr Ser Val Gly
                5                   10
```

<210> SEQ ID NO 13
<211> LENGTH: 70
<212> TYPE: PRT
<213> ORGANISM: Homo sapiens

<400> SEQUENCE: 13

Ser Gln Pro Tyr Arg Gly Ala Glu Pro Pro Gly Gly Ala Gly Ala Ser
                 5                  10                  15

Pro Glu Leu Gln Leu His Pro Arg Leu Arg Ser Leu Ala Val Cys Val
             20                  25                  30

Gln Asp Val Ala Pro Asn Leu Gln Arg Cys Glu Arg Leu Pro Asp Gly
         35                  40                  45

Arg Gly Thr Tyr Gln Cys Lys Ala Asn Val Phe Leu Ser Leu Arg Ala
     50                  55                  60

Ala Asp Cys Leu Ala Ala
 65                  70

<210> SEQ ID NO 14
<211> LENGTH: 67
<212> TYPE: PRT
<213> ORGANISM: Mus sp.

<400> SEQUENCE: 14

Ser Glu Ser Pro Ala Leu Arg Val Gly Thr Gly Pro Leu Arg Asn Leu
                 5                  10                  15

Glu Met Arg Pro Ser Val Arg Ser Leu Ala Leu Cys Val Lys Asp Val
             20                  25                  30

Thr Pro Asn Leu Gln Ser Cys Gln Arg Gln Leu Asn Ser Arg Gly Thr
         35                  40                  45

Phe Gln Cys Lys Ala Asp Val Phe Leu Ser Leu His Glu Thr Asp Cys
     50                  55                  60

Gln Ser Thr
 65

<210> SEQ ID NO 15
<211> LENGTH: 67
<212> TYPE: PRT
<213> ORGANISM: Rattus sp.

<400> SEQUENCE: 15

Ser Glu Ser Pro Ala Leu Arg Val Gly Thr Val Pro Leu Arg Asn Leu
                 5                  10                  15

Glu Met Arg Pro Ser Val Arg Ser Leu Ala Leu Cys Val Lys Asp Val
             20                  25                  30

Thr Pro Asn Leu Gln Ser Cys Gln Arg Gln Leu Asn Ser Arg Gly Thr
         35                  40                  45

Phe Gln Cys Lys Ala Asp Val Phe Leu Ser Leu His Lys Ala Glu Cys
     50                  55                  60

Gln Ser Ala
 65

<210> SEQ ID NO 16
<211> LENGTH: 44
<212> TYPE: PRT
<213> ORGANISM: Homo sapiens

<400> SEQUENCE: 16

Ser Leu Ala Val Cys Val Gln Asp Val Ala Pro Asn Leu Gln Arg Cys
                 5                  10                  15

```
Glu Arg Leu Pro Asp Gly Arg Gly Thr Tyr Gln Cys Lys Ala Asn Val
             20                  25                  30

Phe Leu Ser Leu Arg Ala Ala Asp Cys Leu Ala Ala
         35                  40

<210> SEQ ID NO 17
<211> LENGTH: 44
<212> TYPE: PRT
<213> ORGANISM: Mus sp.

<400> SEQUENCE: 17

Ser Leu Ala Leu Cys Val Lys Asp Val Thr Pro Asn Leu Gln Ser Cys
 1               5                  10                  15

Gln Arg Gln Leu Asn Ser Arg Gly Thr Phe Gln Cys Lys Ala Asp Val
             20                  25                  30

Phe Leu Ser Leu His Glu Thr Asp Cys Gln Ser Thr
         35                  40

<210> SEQ ID NO 18
<211> LENGTH: 44
<212> TYPE: PRT
<213> ORGANISM: Rattus sp.

<400> SEQUENCE: 18

Ser Leu Ala Leu Cys Val Lys Asp Val Thr Pro Asn Leu Gln Ser Cys
 1               5                  10                  15

Gln Arg Gln Leu Asn Ser Arg Gly Thr Phe Gln Cys Lys Ala Asp Val
             20                  25                  30

Phe Leu Ser Leu His Lys Ala Glu Cys Gln Ser Ala
         35                  40

<210> SEQ ID NO 19
<211> LENGTH: 101
<212> TYPE: PRT
<213> ORGANISM: Homo sapiens

<400> SEQUENCE: 19

Trp Tyr Lys Pro Ala Ala Gly His Ser Ser Tyr Ser Val Gly Arg Ala
 1               5                  10                  15

Ala Gly Leu Leu Ser Gly Leu Arg Arg Ser Pro Tyr Ala Arg Arg Ser
             20                  25                  30

Gln Pro Tyr Arg Gly Ala Glu Pro Gly Gly Ala Gly Ala Ser Pro
             35                  40                  45

Glu Leu Gln Leu His Pro Arg Leu Arg Ser Leu Ala Val Cys Val Gln
 50                  55                  60

Asp Val Ala Pro Asn Leu Gln Arg Cys Glu Arg Leu Pro Asp Gly Arg
 65                  70                  75                  80

Gly Thr Tyr Gln Cys Lys Ala Asn Val Phe Leu Ser Leu Arg Ala Ala
                 85                  90                  95

Asp Cys Leu Ala Ala
            100

<210> SEQ ID NO 20
<211> LENGTH: 98
<212> TYPE: PRT
<213> ORGANISM: Mus sp.

<400> SEQUENCE: 20

Trp Tyr Lys Pro Ala Ala Gly Pro His His Tyr Ser Val Gly Arg Ala
 1               5                  10                  15
```

```
            5                   10                  15
Ser Gly Leu Leu Ser Ser Phe His Arg Phe Pro Ser Thr Arg Arg Ser
                20                  25                  30

Glu Ser Pro Ala Leu Arg Val Gly Thr Gly Pro Leu Arg Asn Leu Glu
            35                  40                  45

Met Arg Pro Ser Val Arg Ser Leu Ala Leu Cys Val Lys Asp Val Thr
        50                  55                  60

Pro Asn Leu Gln Ser Cys Gln Arg Gln Leu Asn Ser Arg Gly Thr Phe
 65                 70                  75                  80

Gln Cys Lys Ala Asp Val Phe Leu Ser Leu His Glu Thr Asp Cys Gln
                85                  90                  95

Ser Thr

<210> SEQ ID NO 21
<211> LENGTH: 98
<212> TYPE: PRT
<213> ORGANISM: Rattus sp.

<400> SEQUENCE: 21

Trp Tyr Lys Pro Ala Ala Gly Ser His His Tyr Ser Val Gly Arg Ala
            5                   10                  15

Ala Gly Leu Leu Ser Ser Phe His Arg Phe Pro Ser Thr Arg Arg Ser
                20                  25                  30

Glu Ser Pro Ala Leu Arg Val Gly Thr Val Pro Leu Arg Asn Leu Glu
            35                  40                  45

Met Arg Pro Ser Val Arg Ser Leu Ala Leu Cys Val Lys Asp Val Thr
        50                  55                  60

Pro Asn Leu Gln Ser Cys Gln Arg Gln Leu Asn Ser Arg Gly Thr Phe
 65                 70                  75                  80

Gln Cys Lys Ala Asp Val Phe Leu Ser Leu His Lys Ala Glu Cys Gln
                85                  90                  95

Ser Ala

<210> SEQ ID NO 22
<211> LENGTH: 125
<212> TYPE: PRT
<213> ORGANISM: Homo sapiens

<400> SEQUENCE: 22

Met Ala Arg Ser Ala Thr Leu Ala Ala Ala Leu Ala Leu Cys Leu
            5                   10                  15

Leu Leu Ala Pro Pro Gly Leu Ala Trp Tyr Lys Pro Ala Ala Gly His
                20                  25                  30

Ser Ser Tyr Ser Val Gly Arg Ala Ala Gly Leu Leu Ser Gly Leu Arg
            35                  40                  45

Arg Ser Pro Tyr Ala Arg Arg Ser Gln Pro Tyr Arg Gly Ala Glu Pro
        50                  55                  60

Pro Gly Gly Ala Gly Ala Ser Pro Glu Leu Gln Leu His Pro Arg Leu
 65                 70                  75                  80

Arg Ser Leu Ala Val Cys Val Gln Asp Val Ala Pro Asn Leu Gln Arg
                85                  90                  95

Cys Glu Arg Leu Pro Asp Gly Arg Gly Thr Tyr Gln Cys Lys Ala Asn
            100                 105                 110

Val Phe Leu Ser Leu Arg Ala Ala Asp Cys Leu Ala Ala
        115                 120                 125
```

-continued

```
<210> SEQ ID NO 23
<211> LENGTH: 119
<212> TYPE: PRT
<213> ORGANISM: Mus sp.

<400> SEQUENCE: 23

Met Ala Arg Cys Arg Thr Leu Val Ala Ala Ala Leu Ala Leu Leu Leu
                 5                  10                  15

Pro Pro Ala Leu Ala Trp Tyr Lys Pro Ala Ala Gly Pro His His Tyr
             20                  25                  30

Ser Val Gly Arg Ala Ser Gly Leu Leu Ser Ser Phe His Arg Phe Pro
         35                  40                  45

Ser Thr Arg Arg Ser Glu Ser Pro Ala Leu Arg Val Gly Thr Gly Pro
     50                  55                  60

Leu Arg Asn Leu Glu Met Arg Pro Ser Val Arg Ser Leu Ala Leu Cys
 65                  70                  75                  80

Val Lys Asp Val Thr Pro Asn Leu Gln Ser Cys Gln Arg Gln Leu Asn
                 85                  90                  95

Ser Arg Gly Thr Phe Gln Cys Lys Ala Asp Val Phe Leu Ser Leu His
            100                 105                 110

Glu Thr Asp Cys Gln Ser Thr
        115

<210> SEQ ID NO 24
<211> LENGTH: 119
<212> TYPE: PRT
<213> ORGANISM: Rattus sp.

<400> SEQUENCE: 24

Met Val Arg Cys Arg Thr Leu Val Ala Ala Ala Leu Ala Leu Leu Leu
                 5                  10                  15

Thr Pro Ala Leu Ala Trp Tyr Lys Pro Ala Ala Gly Ser His His Tyr
             20                  25                  30

Ser Val Gly Arg Ala Ala Gly Leu Leu Ser Ser Phe His Arg Phe Pro
         35                  40                  45

Ser Thr Arg Arg Ser Glu Ser Pro Ala Leu Arg Val Gly Thr Val Pro
     50                  55                  60

Leu Arg Asn Leu Glu Met Arg Pro Ser Val Arg Ser Leu Ala Leu Cys
 65                  70                  75                  80

Val Lys Asp Val Thr Pro Asn Leu Gln Ser Cys Gln Arg Gln Leu Asn
                 85                  90                  95

Ser Arg Gly Thr Phe Gln Cys Lys Ala Asp Val Phe Leu Ser Leu His
            100                 105                 110

Lys Ala Glu Cys Gln Ser Ala
        115

<210> SEQ ID NO 25
<211> LENGTH: 69
<212> TYPE: DNA
<213> ORGANISM: Homo sapiens

<400> SEQUENCE: 25
tggtacaagc cagcggcggg gcacagctcc tactcggtgg ccgcgccgc ggggctgctg      60 tccggcctc                                                             69

<210> SEQ ID NO 26
<211> LENGTH: 72
```

```
<212> TYPE: DNA
<213> ORGANISM: Mus sp.

<400> SEQUENCE: 26
tggtacaagc ccgcggcggg accccaccac tactcggtgg gccgcgcctc ggggctactg      60
tcgagtttcc ac                                                        72

<210> SEQ ID NO 27
<211> LENGTH: 72
<212> TYPE: DNA
<213> ORGANISM: Rattus sp.

<400> SEQUENCE: 27
tggtacaagc ccgcggcggg atcccaccac tactcggtgg gccgcgctgc ggggctactg      60
tcgagtttcc ac                                                        72

<210> SEQ ID NO 28
<211> LENGTH: 87
<212> TYPE: DNA
<213> ORGANISM: Homo sapiens

<400> SEQUENCE: 28
tggtacaagc cagcggcggg gcacagctcc tactcggtgg gccgcgccgc ggggctgctg      60
tccggcctcc gcaggtcccc gtacgcg                                        87

<210> SEQ ID NO 29
<211> LENGTH: 87
<212> TYPE: DNA
<213> ORGANISM: Mus sp.

<400> SEQUENCE: 29
tggtacaagc ccgcggcggg accccaccac tactcggtgg gccgcgcctc ggggctactg      60
tcgagtttcc acaggttccc gtccacg                                        87

<210> SEQ ID NO 30
<211> LENGTH: 87
<212> TYPE: DNA
<213> ORGANISM: Rattus sp.

<400> SEQUENCE: 30
tggtacaagc ccgcggcggg atcccaccac tactcggtgg gccgcgctgc ggggctactg      60
tcgagtttcc acaggttccc atccacg                                        87

<210> SEQ ID NO 31
<211> LENGTH: 39
<212> TYPE: DNA
<213> ORGANISM: Homo sapiens

<400> SEQUENCE: 31
tggtacaagc cagcggcggg gcacagctcc tactcggtg                            39

<210> SEQ ID NO 32
<211> LENGTH: 42
<212> TYPE: DNA
<213> ORGANISM: Homo sapiens

<400> SEQUENCE: 32
tggtacaagc cagcggcggg gcacagctcc tactcggtgg gc                        42

<210> SEQ ID NO 33
```

```
<211> LENGTH: 39
<212> TYPE: DNA
<213> ORGANISM: Mus sp.

<400> SEQUENCE: 33
tggtacaagc ccgcggcggg accccaccac tactcggtg                          39

<210> SEQ ID NO 34
<211> LENGTH: 42
<212> TYPE: DNA
<213> ORGANISM: Mus sp.

<400> SEQUENCE: 34
tggtacaagc ccgcggcggg accccaccac tactcggtgg gc                      42

<210> SEQ ID NO 35
<211> LENGTH: 39
<212> TYPE: DNA
<213> ORGANISM: Rattus sp.

<400> SEQUENCE: 35
tggtacaagc ccgcggcggg atcccaccac tactcggtg                          39

<210> SEQ ID NO 36
<211> LENGTH: 42
<212> TYPE: DNA
<213> ORGANISM: Rattus sp.

<400> SEQUENCE: 36
tggtacaagc ccgcggcggg atcccaccac tactcggtgg gc                      42

<210> SEQ ID NO 37
<211> LENGTH: 210
<212> TYPE: DNA
<213> ORGANISM: Homo sapiens

<400> SEQUENCE: 37
tcccagccct acagaggggc ggaaccccccg ggcggggccg cgcctcccc ggagctgcaa    60 ctgcacccca ggctgcggag cctcgctgtg tgcgtccagg acgtcgcccc aaacctgcag  120
aggtgcgagc ggctcccccga cggccgcggg acctaccagt gcaaggcgaa cgtcttcctg  180
tccctgcgcg cagccgactg cctcgccgcc                                    210

<210> SEQ ID NO 38
<211> LENGTH: 201
<212> TYPE: DNA
<213> ORGANISM: Mus sp.

<400> SEQUENCE: 38
tccgagtctc cagcactccg ggtgggaacc ggacctctgc gcaatttaga gatgcgcccc    60
agcgtaagga gccttgccct gtgtgtcaaa gatgtgaccc cgaacctgca gagctgccag  120
cggcaactca acagccgagg gactttccag tgtaaagcgg acgtcttctt gtcgctgcac  180
gagactgatt gccagagcac c                                             201

<210> SEQ ID NO 39
<211> LENGTH: 201
<212> TYPE: DNA
<213> ORGANISM: Rattus sp.

<400> SEQUENCE: 39
tccgagtctc cagcactccg ggtgggaacc gtacctctgc gcaacttgga gatgcgccca    60
```
agcgtaagaa gccttgccct gtgtgtcaaa gatgtgaccc cgaacctgca gagctgccag    120
cggcaactca acagccgagg gactttccag tgtaaggcgg acgtcttctt gtcgctgcac    180
aaggctgaat gccaaagcgc c    201

<210> SEQ ID NO 40
<211> LENGTH: 132
<212> TYPE: DNA
<213> ORGANISM: Homo sapiens

<400> SEQUENCE: 40
agcctcgctg tgtgcgtcca ggacgtcgcc ccaaacctgc agaggtgcga gcggctcccc    60
gacggccgcg ggacctacca gtgcaaggcg aacgtcttcc tgtccctgcg cgcagccgac    120
tgcctcgccg cc    132

<210> SEQ ID NO 41
<211> LENGTH: 132
<212> TYPE: DNA
<213> ORGANISM: Mus sp.

<400> SEQUENCE: 41
agccttgccc tgtgtgtcaa agatgtgacc ccgaacctgc agagctgcca gcggcaactc    60
aacagccgag ggactttcca gtgtaaagcg gacgtcttct tgtcgctgca cgagactgat    120
tgccagagca cc    132

<210> SEQ ID NO 42
<211> LENGTH: 132
<212> TYPE: DNA
<213> ORGANISM: Rattus sp.

<400> SEQUENCE: 42
agccttgccc tgtgtgtcaa agatgtgacc ccgaacctgc agagctgcca gcggcaactc    60
aacagccgag ggactttcca gtgtaaggcg gacgtcttct tgtcgctgca caaggctgaa    120
tgccaaagcg cc    132

<210> SEQ ID NO 43
<211> LENGTH: 303
<212> TYPE: DNA
<213> ORGANISM: Homo sapiens

<400> SEQUENCE: 43
tggtacaagc cagcggcggg gcacagctcc tactcggtgg gccgcgccgc ggggctgctg    60
tccggcctcc gcaggtcccc gtacgcgcgg cgctcccagc cctacagagg ggcggaaccc    120
ccgggcgggg ccggcgcctc cccggagctg caactgcacc ccaggctgcg gagcctcgct    180
gtgtgcgtcc aggacgtcgc cccaaacctg cagaggtgcg agcggctccc cgacggccgc    240
gggacctacc agtgcaaggc gaacgtcttc ctgtccctgc gcgcagccga ctgcctcgcc    300
gcc    303

<210> SEQ ID NO 44
<211> LENGTH: 294
<212> TYPE: DNA
<213> ORGANISM: Mus sp.

<400> SEQUENCE: 44
tggtacaagc ccgcggcggg accccaccac tactcggtgg gccgcgcctc ggggctactg    60

```
tcgagtttcc acaggttccc gtccacgcga cgctccgagt ctccagcact ccgggtggga    120
accggacctc tgcgcaattt agagatgcgc cccagcgtaa ggagccttgc cctgtgtgtc    180
aaagatgtga ccccgaacct gcagagctgc cagcggcaac tcaacagccg agggactttc    240
cagtgtaaag cggacgtctt cttgtcgctg cacgagactg attgccagag cacc          294

<210> SEQ ID NO 45
<211> LENGTH: 294
<212> TYPE: DNA
<213> ORGANISM: Rattus sp.

<400> SEQUENCE: 45
tggtacaagc ccgcggcggg atcccaccac tactcggtgg gccgcgctgc ggggctactg     60
tcgagtttcc acaggttccc atccacgcga cgttccgagt ctccagcact ccgggtggga   120
accgtacctc tgcgcaactt ggagatgcgc ccaagcgtaa gaagccttgc cctgtgtgtc   180
aaagatgtga ccccgaacct gcagagctgc cagcggcaac tcaacagccg agggactttc   240
cagtgtaagg cggacgtctt cttgtcgctg cacaaggctg aatgccaaag cgcc         294

<210> SEQ ID NO 46
<211> LENGTH: 375
<212> TYPE: DNA
<213> ORGANISM: Homo sapiens

<400> SEQUENCE: 46
atggcccggt ccgcgacact ggcggccgcc gccctggcgc tgtgcctgct gctggcgccg    60
cctggcctcg cgtggtacaa gccagcggcg gggcacagct cctactcggt gggccgcgcc   120
gcggggctgc tgtccggcct ccgcaggtcc cgtacgcgc ggcgctccca gccctacaga   180
ggggcggaac cccgggcgg ggccggcgcc tccccggagc tgcaactgca ccccaggctg    240
cggagcctcg ctgtgtgcgt ccaggacgtc gccccaaacc tgcagaggtg cgagcggctc   300
cccgacggcc gcgggaccta ccagtgcaag gcgaacgtct tcctgtccct gcgcgcagcc   360
gactgcctcg ccgcc                                                   375

<210> SEQ ID NO 47
<211> LENGTH: 357
<212> TYPE: DNA
<213> ORGANISM: Mus sp.

<400> SEQUENCE: 47
atggcccggt gtaggacgct ggtggccgct gccctggcgc tgctcctgcc gccagccctc    60
gcgtggtaca agcccgcggc gggacccac cactactcgg tgggccgcgc ctcgggcta    120 ctgtcgagtt tccacaggtt cccgtccacg cgacgctccg agtctccagc actccgggtg   180
ggaaccggac ctctgcgcaa tttagagatg cgccccagcg taaggagcct tgccctgtgt   240
gtcaaagatg tgaccccgaa cctgcagagc tgccagcggc aactcaacag ccgagggact   300
ttccagtgta aagcggacgt cttcttgtcg ctgcacgaga ctgattgcca gagcacc      357

<210> SEQ ID NO 48
<211> LENGTH: 357
<212> TYPE: DNA
<213> ORGANISM: Rattus sp.

<400> SEQUENCE: 48
atggtccggt gtaggacgct ggtggccgcc gccctggcgc tgctcctgac gccagccctc    60
gcgtggtaca agcccgcggc gggatcccac cactactcgg tgggccgcgc tgcggggcta   120
```

```
ctgtcgagtt tccacaggtt cccatccacg cgacgttccg agtctccagc actccgggtg    180
ggaaccgtac ctctgcgcaa cttggagatg cgcccaagcg taagaagcct tgccctgtgt    240
gtcaaagatg tgaccccgaa cctgcagagc tgccagcggc aactcaacag ccgagggact    300
ttccagtgta aggcggacgt cttcttgtcg ctgcacaagg ctgaatgcca aagcgcc       357
```

<210> SEQ ID NO 49
<211> LENGTH: 328
<212> TYPE: PRT
<213> ORGANISM: Homo sapiens
<400> SEQUENCE: 49

```
Met Asp Asn Ala Ser Phe Ser Glu Pro Trp Pro Ala Asn Ala Ser Gly
1               5                   10                  15

Pro Asp Pro Ala Leu Ser Cys Ser Asn Ala Ser Thr Leu Ala Pro Leu
            20                  25                  30

Pro Ala Pro Leu Ala Val Ala Val Pro Val Val Tyr Ala Val Ile Cys
        35                  40                  45

Ala Val Gly Leu Ala Gly Asn Ser Ala Val Leu Tyr Val Leu Leu Arg
    50                  55                  60

Ala Pro Arg Met Lys Thr Val Thr Asn Leu Phe Ile Leu Asn Leu Ala
65                  70                  75                  80

Ile Ala Asp Glu Leu Phe Thr Leu Val Leu Pro Ile Asn Ile Ala Asp
                85                  90                  95

Phe Leu Leu Arg Gln Trp Pro Phe Gly Glu Leu Met Cys Lys Leu Ile
            100                 105                 110

Val Ala Ile Asp Gln Tyr Asn Thr Phe Ser Ser Leu Tyr Phe Leu Thr
        115                 120                 125

Val Met Ser Ala Asp Arg Tyr Leu Val Val Leu Ala Thr Ala Glu Ser
    130                 135                 140

Arg Arg Val Ala Gly Arg Thr Tyr Ser Ala Ala Arg Ala Val Ser Leu
145                 150                 155                 160

Ala Val Trp Gly Ile Val Thr Leu Val Val Leu Pro Phe Ala Val Phe
                165                 170                 175

Ala Arg Leu Asp Asp Glu Gln Gly Arg Arg Gln Cys Val Leu Val Phe
            180                 185                 190

Pro Gln Pro Glu Ala Phe Trp Trp Arg Ala Ser Arg Leu Tyr Thr Leu
        195                 200                 205

Val Leu Gly Phe Ala Ile Pro Val Ser Thr Ile Cys Val Leu Tyr Thr
    210                 215                 220

Thr Leu Leu Cys Arg Leu His Ala Met Arg Leu Asp Ser His Ala Lys
225                 230                 235                 240

Ala Leu Glu Arg Ala Lys Lys Arg Val Thr Phe Leu Val Val Ala Ile
                245                 250                 255

Leu Ala Val Cys Leu Leu Cys Trp Thr Pro Tyr His Leu Ser Thr Val
            260                 265                 270

Val Ala Leu Thr Thr Asp Leu Pro Gln Thr Pro Leu Val Ile Ala Ile
        275                 280                 285

Ser Tyr Phe Ile Thr Ser Leu Ser Tyr Ala Asn Ser Cys Leu Asn Pro
    290                 295                 300

Phe Leu Tyr Ala Phe Leu Asp Ala Ser Phe Arg Arg Asn Leu Arg Gln
305                 310                 315                 320

Leu Ile Thr Cys Arg Ala Ala Ala
                325
```

<210> SEQ ID NO 50
<211> LENGTH: 1000
<212> TYPE: DNA
<213> ORGANISM: Homo sapiens

<400> SEQUENCE: 50

| | | | | | |
|---|---|---|---|---|---|
| atcgatatgg | acaacgcctc | gttctcggag | ccctggcccg | ccaacgcatc | gggcccggac | 60 |
| ccggcgctga | gctgctccaa | cgcgtcgact | ctggcgccgc | tgccggcgcc | gctggcggtg | 120 |
| gctgtaccag | ttgtctacgc | ggtgatctgc | gccgtgggtc | tggcgggcaa | ctccgccgtg | 180 |
| ctgtacgtgt | tgctgcgggc | gccccgcatg | aagaccgtca | ccaacctgtt | catcctcaac | 240 |
| ctggccatcg | ccgacgagct | cttcacgctg | gtgctgccca | tcaacatcgc | cgacttcctg | 300 |
| ctgcggcagt | ggcccttcgg | ggagctcatg | tgcaagctca | tcgtggctat | cgaccagtac | 360 |
| aacaccttct | ccagcctcta | cttcctcacc | gtcatgagcg | ccgaccgcta | cctggtggtg | 420 |
| ttggccactg | cggagtcgcg | ccgggtggcc | ggccgcacct | acagcgccgc | gcgcgcggtg | 480 |
| agcctggccg | tgtgggggat | cgtcacactc | gtcgtgctgc | ccttcgcagt | cttcgcccgg | 540 |
| ctagacgacg | agcagggccg | gcgccagtgc | gtgctagtct | ttccgcagcc | cgaggccttc | 600 |
| tggtggcgcg | cgagccgcct | ctacacgctc | gtgctgggct | tcgccatccc | cgtgtccacc | 660 |
| atctgtgtcc | tctataccac | cctgctgtgc | cggctgcatg | ccatgcggct | ggacagccac | 720 |
| gccaaggccc | tggagcgcgc | caagaagcgg | gtgaccttcc | tggtggtggc | aatcctggcg | 780 |
| gtgtgcctcc | tctgctggac | gccctaccac | ctgagcaccg | tggtggcgct | caccaccgac | 840 |
| ctcccgcaga | cgccgctggt | catcgctatc | tcctacttca | tcaccagcct | gagctacgcc | 900 |
| aacagctgcc | tcaaccccTT | cctctacgcc | ttcctggacg | ccagcttccg | caggaacctc | 960 |
| cgccagctga | taacttgccg | cgcggcagcc | tgacactagt | | | 1000 |

<210> SEQ ID NO 51
<211> LENGTH: 33
<212> TYPE: DNA
<213> ORGANISM: Artificial Sequence
<220> FEATURE:
<223> OTHER INFORMATION: Primer

<400> SEQUENCE: 51
gtcgacatgg cccggtccgc gacactggcg gcc                                33

<210> SEQ ID NO 52
<211> LENGTH: 33
<212> TYPE: DNA
<213> ORGANISM: Artificial Sequence
<220> FEATURE:
<223> OTHER INFORMATION: Primer

<400> SEQUENCE: 52
gctagcagcg gtgccaggag aggtccgggc tca                                33

<210> SEQ ID NO 53
<211> LENGTH: 33
<212> TYPE: DNA
<213> ORGANISM: Artificial Sequence
<220> FEATURE:
<223> OTHER INFORMATION: Primer

<400> SEQUENCE: 53
gtcgacagct ccatggcccg gtgtaggacg ctg                                33

<210> SEQ ID NO 54
<211> LENGTH: 33
<212> TYPE: DNA
<213> ORGANISM: Artificial Sequence
<220> FEATURE:
<223> OTHER INFORMATION: Primer

<400> SEQUENCE: 54
gctagctcag gtgctctggc aatcagtctc gtg                         33

<210> SEQ ID NO 55
<211> LENGTH: 27
<212> TYPE: DNA
<213> ORGANISM: Artificial Sequence
<220> FEATURE:
<223> OTHER INFORMATION: Primer

<400> SEQUENCE: 55
cacggctcca tggtccggtg taggacg                                27

<210> SEQ ID NO 56
<211> LENGTH: 27
<212> TYPE: DNA
<213> ORGANISM: Artificial Sequence
<220> FEATURE:
<223> OTHER INFORMATION: Primer

<400> SEQUENCE: 56
cagcgtcgag gtttgggttg gggttca                                27

<210> SEQ ID NO 57
<211> LENGTH: 32
<212> TYPE: DNA
<213> ORGANISM: Artificial Sequence
<220> FEATURE:
<223> OTHER INFORMATION: Primer

<400> SEQUENCE: 57
atcgatatgg acaacgcctc gttctcggag cc                          32

<210> SEQ ID NO 58
<211> LENGTH: 32
<212> TYPE: DNA
<213> ORGANISM: Artificial Sequence
<220> FEATURE:
<223> OTHER INFORMATION: Primer

<400> SEQUENCE: 58
actagtgtca ggctgccgcg cggcaagtta tc                          32

<210> SEQ ID NO 59
<211> LENGTH: 329
<212> TYPE: PRT
<213> ORGANISM: Rattus sp.

<400> SEQUENCE: 59

Met His Asn Leu Ser Leu Phe Glu Pro Gly Arg Gly Asn Val Ser Cys
              5                   10                  15

Gly Gly Pro Phe Leu Gly Cys Pro Asn Glu Ser Asn Pro Ala Pro Leu
             20                  25                  30

Pro Leu Pro Gln Pro Leu Ala Val Ala Val Pro Val Val Tyr Gly Val
         35                  40                  45

Ile Cys Ala Val Gly Leu Ala Gly Asn Ser Ala Val Leu Tyr Val Leu
     50                  55                  60

```
Leu Arg Thr Pro Arg Met Lys Thr Val Thr Asn Val Phe Ile Leu Asn
 65                  70                  75                  80

Leu Ala Ile Ala Asp Glu Leu Phe Thr Leu Val Leu Pro Ile Asn Ile
                 85                  90                  95

Ala Asp Phe Leu Leu Arg Arg Trp Pro Phe Gly Glu Val Met Cys Lys
            100                 105                 110

Leu Ile Val Ala Val Asp Gln Tyr Asn Thr Phe Ser Ser Leu Tyr Phe
        115                 120                 125

Leu Ala Val Met Ser Ala Asp Arg Tyr Leu Val Leu Ala Thr Ala
    130                 135                 140

Glu Ser Arg Arg Val Ser Gly Arg Thr Tyr Gly Ala Ala Arg Ala Val
145                 150                 155                 160

Ser Leu Ala Val Trp Ala Leu Val Thr Leu Val Leu Pro Phe Ala
                165                 170                 175

Val Phe Ala Arg Leu Asp Glu Glu Gln Gly Arg Arg Gln Cys Val Leu
            180                 185                 190

Val Phe Pro Gln Pro Glu Ala Phe Trp Trp Arg Ala Ser Arg Leu Tyr
        195                 200                 205

Thr Leu Val Leu Gly Phe Ala Ile Pro Val Ser Thr Ile Cys Ala Leu
    210                 215                 220

Tyr Ile Thr Leu Leu Cys Arg Leu Arg Ala Ile Gln Leu Asp Ser His
225                 230                 235                 240

Ala Lys Ala Leu Asp Arg Ala Lys Lys Arg Val Thr Leu Leu Val Val
                245                 250                 255

Ala Ile Leu Ala Val Cys Leu Leu Cys Trp Thr Pro Tyr His Leu Ser
            260                 265                 270

Thr Ile Val Ala Leu Thr Thr Asp Leu Pro Gln Thr Pro Leu Val Ile
        275                 280                 285

Gly Ile Ser Tyr Phe Ile Thr Ser Leu Ser Tyr Ala Asn Ser Cys Leu
    290                 295                 300

Asn Pro Phe Leu Tyr Ala Phe Leu Asp Asp Ser Phe Arg Arg Ser Leu
305                 310                 315                 320

Arg Gln Leu Val Ser Cys Arg Thr Ala
                325

<210> SEQ ID NO 60
<211> LENGTH: 987
<212> TYPE: DNA
<213> ORGANISM: Rattus sp.

<400> SEQUENCE: 60
atgcacaact tgtcgctctt cgagcctggc aggggcaatg tgtcttgcgg cggcccattt      60
ttgggctgtc ctaacgagtc gaacccagcg cctctgccac tgccgcagcc tctgcggta     120 gcagtgcctg tggtctacgg ggtgatctgc gcggtgggac tggcgggcaa ctccgcggtg    180
ctgtacgtac tgctgcgcac gccgcgcatg aagactgtta ccaacgtgtt cattctcaac    240
ctggctatcg cggacgagct cttcaccctc gtgctgccca tcaacatcgc ggacttcctg    300
ctgaggcgct ggcccttcgg ggaagtcatg tgcaagctca tcgtggctgt cgaccagtac    360
aacactttct ctagcctcta cttcctcgcc gtcatgagcg cagaccgcta cctggttgtc    420
ctggccacag ccgagtcgcg ccgggtgtcc gggcgcactt atggtgcagc gcgggctgtc    480
agtctggcgg tgtgggcgct ggtgacattg gtcgtgctgc cttttgcggt attcgcccgg    540
ctggacgaag agcagggtcg gcgtcagtgc gtgctggtct cccgcagcc tgaggccttc    600
```

```
tggtggcgcg ccagccgtct gtacactcta gtgttgggct tcgccatccc ggtgtccacc    660
atctgcgccc tctatatcac cctgttgtgc cgactgcgtg ctatccagct agacagccac    720
gccaaggccc tggaccgtgc caagaagcgc gtgaccttgt tggtggtggc gattctggct    780
gtgtgcctcc tctgctggac accgtaccac ctgagcacca tagtggcgct caccaccgac    840
ctcccgcaaa caccgttggt catcggcatc tcttacttca tcaccagtct gagctatgcc    900
aacagctgcc tcaaccettt cctctatgcc ttcctggacg acagcttccg caggagcctg    960
cggcagctgg tgtcatgccg cacagcc                                        987
```

<210> SEQ ID NO 61
<211> LENGTH: 28
<212> TYPE: DNA
<213> ORGANISM: Artificial Sequence
<220> FEATURE:
<223> OTHER INFORMATION: Primer

<400> SEQUENCE: 61

```
actgatatgc acaacttgtc gctcttcg                                        28
```

<210> SEQ ID NO 62
<211> LENGTH: 28
<212> TYPE: DNA
<213> ORGANISM: Artificial Sequence
<220> FEATURE:
<223> OTHER INFORMATION: Primer

<400> SEQUENCE: 62

```
actagttcag gctgtgcggc atgacacc                                        28
```

<210> SEQ ID NO 63
<211> LENGTH: 22
<212> TYPE: DNA
<213> ORGANISM: Artificial Sequence
<220> FEATURE:
<223> OTHER INFORMATION: Primer

<400> SEQUENCE: 63

```
ctgtcgagtt tccacaggtt cc                                              22
```

<210> SEQ ID NO 64
<211> LENGTH: 20
<212> TYPE: DNA
<213> ORGANISM: Artificial Sequence
<220> FEATURE:
<223> OTHER INFORMATION: Primer

<400> SEQUENCE: 64

```
ttgcgcagag gtacggttcc                                                 20
```

<210> SEQ ID NO 65
<211> LENGTH: 26
<212> TYPE: DNA
<213> ORGANISM: Artificial Sequence
<220> FEATURE:
<223> OTHER INFORMATION: Primer

<400> SEQUENCE: 65

```
cgtgccaaga aacgcgtgac cttgtt                                          26
```

<210> SEQ ID NO 66
<211> LENGTH: 23
<212> TYPE: PRT

```
<213> ORGANISM: Bos sp.
<220> FEATURE:

<400> SEQUENCE: 66

Trp Tyr Lys Pro Thr Ala Gly Gln Gly Tyr Tyr Ser Val Gly Arg Ala
 1               5                  10                  15

Ala Gly Leu Leu Ser Gly Phe
            20

<210> SEQ ID NO 67
<211> LENGTH: 29
<212> TYPE: PRT
<213> ORGANISM: Bos sp.

<400> SEQUENCE: 67

Trp Tyr Lys Pro Thr Ala Gly Gln Gly Tyr Tyr Ser Val Gly Arg Ala
 1               5                  10                  15

Ala Gly Leu Leu Ser Gly Phe His Arg Ser Pro Tyr Ala
            20                  25

<210> SEQ ID NO 68
<211> LENGTH: 13
<212> TYPE: PRT
<213> ORGANISM: Bos sp.

<400> SEQUENCE: 68

Trp Tyr Lys Pro Thr Ala Gly Gln Gly Tyr Tyr Ser Val
 1               5                  10

<210> SEQ ID NO 69
<211> LENGTH: 14
<212> TYPE: PRT
<213> ORGANISM: Bos sp.

<400> SEQUENCE: 69

Trp Tyr Lys Pro Thr Ala Gly Gln Gly Tyr Tyr Ser Val Gly
 1               5                  10

<210> SEQ ID NO 70
<211> LENGTH: 67
<212> TYPE: PRT
<213> ORGANISM: Bos sp.

<400> SEQUENCE: 70

Ser Glu Pro Arg Gly Gly Thr Arg Ser Leu Gly Gly Val Gly Thr Phe
 1               5                  10                  15

Arg Glu Met Arg Pro Asn Leu Arg Ser Leu Ala Val Cys Val Glu Glu
            20                  25                  30

Val Thr Pro Asn Leu Gln Ser Cys Glu Pro Leu Pro Asp Gly Arg Ala
        35                  40                  45

Thr Phe Gln Cys Lys Ala Asp Val Phe Leu Ser Leu Ser Ala Ser Asp
    50                  55                  60

Cys Arg Lys
 65

<210> SEQ ID NO 71
<211> LENGTH: 43
<212> TYPE: PRT
<213> ORGANISM: Bos sp.

<400> SEQUENCE: 71

Ser Leu Ala Val Cys Val Glu Glu Val Thr Pro Asn Leu Gln Ser Cys
```

```
                1               5                  10                 15
        Glu Pro Leu Pro Asp Gly Arg Ala Thr Phe Gln Cys Lys Ala Asp Val
                         20                  25                  30

Phe Leu Ser Leu Ser Ala Ser Asp Cys Arg Lys
                     35                  40

<210> SEQ ID NO 72
<211> LENGTH: 98
<212> TYPE: PRT
<213> ORGANISM: Bos sp.

<400> SEQUENCE: 72

Trp Tyr Lys Pro Thr Ala Gly Gln Gly Tyr Tyr Ser Val Gly Arg Ala
         1               5                  10                 15

Ala Gly Leu Leu Ser Gly Phe His Arg Ser Pro Tyr Ala Arg Arg Ser
                        20                  25                  30

Glu Pro Arg Gly Gly Thr Arg Ser Leu Gly Gly Val Gly Thr Phe Arg
                        35                  40                  45

Glu Met Arg Pro Asn Leu Arg Ser Leu Ala Val Cys Val Glu Glu Val
                50                  55                  60

Thr Pro Asn Leu Gln Ser Cys Glu Pro Leu Pro Asp Gly Arg Ala Thr
        65                  70                  75                  80

Phe Gln Cys Lys Ala Asp Val Phe Leu Ser Leu Ser Ala Ser Asp Cys
                        85                  90                  95

Arg Lys

<210> SEQ ID NO 73
<211> LENGTH: 122
<212> TYPE: PRT
<213> ORGANISM: Bos sp.

<400> SEQUENCE: 73

Met Ala Gly Pro Ala Met Leu Val Ala Ala Leu Ala Leu Cys Leu
                         5                  10                 15

Leu Leu Ala Ser Pro Gly Leu Ala Trp Tyr Lys Pro Thr Ala Gly Gln
                        20                  25                  30

Gly Tyr Tyr Ser Val Gly Arg Ala Ala Gly Leu Leu Ser Gly Phe His
                        35                  40                  45

Arg Ser Pro Tyr Ala Arg Arg Ser Glu Pro Arg Gly Gly Thr Arg Ser
                50                  55                  60

Leu Gly Gly Val Gly Thr Phe Arg Glu Met Arg Pro Asn Leu Arg Ser
        65                  70                  75                  80

Leu Ala Val Cys Val Glu Glu Val Thr Pro Asn Leu Gln Ser Cys Glu
                        85                  90                  95

Pro Leu Pro Asp Gly Arg Ala Thr Phe Gln Cys Lys Ala Asp Val Phe
                       100                 105                 110

Leu Ser Leu Ser Ala Ser Asp Cys Arg Lys
                       115                 120

<210> SEQ ID NO 74
<211> LENGTH: 69
<212> TYPE: DNA
<213> ORGANISM: Bos sp.

<400> SEQUENCE: 74
tggtacaagc cgacggcggg gcaggggtac tactccgtgg ccgcgccgc ggggctgctg     60 tccggcttc                                                            69
```

<210> SEQ ID NO 75
<211> LENGTH: 87
<212> TYPE: DNA
<213> ORGANISM: Bos sp.

<400> SEQUENCE: 75

```
tggtacaagc cgacggcggg gcaggggtac tactccgtgg gccgcgccgc ggggctgctg     60
tccggcttcc acaggtcgcc gtacgca                                        87
```

<210> SEQ ID NO 76
<211> LENGTH: 39
<212> TYPE: DNA
<213> ORGANISM: Bos sp.

<400> SEQUENCE: 76

```
tggtacaagc cgacggcggg gcaggggtac tactccgtg                           39
```

<210> SEQ ID NO 77
<211> LENGTH: 42
<212> TYPE: DNA
<213> ORGANISM: Bos sp.

<400> SEQUENCE: 77

```
tggtacaagc cgacggcggg gcaggggtac tactccgtgg gc                       42
```

<210> SEQ ID NO 78
<211> LENGTH: 201
<212> TYPE: DNA
<213> ORGANISM: Bos sp.

<400> SEQUENCE: 78

```
tccgagcccc gcggggcac gcgatccctg ggaggggtcg gcactttccg ggagatgcgc      60
cccaacctgc ggagtcttgc cgtgtgcgtc gaggaggtca cccccaacct gcagagctgc    120
gagccactcc ccgacggccg cgccactttc cagtgcaagg ccgacgtctt cctgtcgctc    180
agcgcctcgg actgtcgcaa g                                              201
```

<210> SEQ ID NO 79
<211> LENGTH: 129
<212> TYPE: DNA
<213> ORGANISM: Bos sp.

<400> SEQUENCE: 79

```
agtcttgccg tgtgcgtcga ggaggtcacc cccaacctgc agagctgcga gccactcccc     60
gacggccgcg ccactttcca gtgcaaggcc gacgtcttcc tgtcgctcag cgcctcggac    120
tgtcgcaag                                                            129
```

<210> SEQ ID NO 80
<211> LENGTH: 294
<212> TYPE: DNA
<213> ORGANISM: Bos sp.

<400> SEQUENCE: 80

```
tggtacaagc cgacggcggg gcaggggtac tactccgtgg gccgcgccgc ggggctgctg     60
tccggcttcc acaggtcgcc gtacgcacgg cgctccgagc ccgcgggggg cacgcgatcc    120
ctggggaggg tcggcacttt ccgggagatg cgcccaacc tgcggagtct tgccgtgtgc    180
gtcgaggagg tcaccccca actgcagagc tgcgagccac tccccgacgg ccgcgccact    240
```

-continued ttccagtgca aggccgacgt cttcctgtcg ctcagcgcct cggactgtcg caag    294

<210> SEQ ID NO 81
<211> LENGTH: 366
<212> TYPE: DNA
<213> ORGANISM: Bos sp.

<400> SEQUENCE: 81
atggccgggc cgcgatgct ggtggccgcc gctctggcgc tgtgcttact gctggcgtcc    60
cctggcctcg cgtggtacaa gccgacggcg gggcagggt actactccgt gggccgcgcc    120
gcggggctgc tgtccggctt ccacaggtcg ccgtacgcac ggcgctccga gccccgcggg    180
ggcacgcgat ccctgggagg ggtcggcact ttccgggaga tgcgcccaa cctgcggagt    240
cttgccgtgt gcgtcgagga ggtcacccc aacctgcaga gctgcgagcc actccccgac    300
ggccgcgcca ctttccagtg caaggccgac gtcttcctgt cgctcagcgc ctcggactgt    360
cgcaag    366

<210> SEQ ID NO 82
<211> LENGTH: 30
<212> TYPE: DNA
<213> ORGANISM: Artificial Sequence
<220> FEATURE:
<223> OTHER INFORMATION: Primer

<400> SEQUENCE: 82
cccatggccg ggcccgcgat gctggtcgcc    30

<210> SEQ ID NO 83
<211> LENGTH: 30
<212> TYPE: DNA
<213> ORGANISM: Artificial Sequence
<220> FEATURE:
<223> OTHER INFORMATION: Primer

<400> SEQUENCE: 83
tcacttgcga cagtccgagg cgctgagcga    30

<210> SEQ ID NO 84
<211> LENGTH: 333
<212> TYPE: PRT
<213> ORGANISM: Homo sapiens

<400> SEQUENCE: 84

Met Gln Ala Ala Gly His Pro Glu Pro Leu Asp Ser Arg Gly Ser Phe
1               5                   10                  15

Ser Leu Pro Thr Met Gly Ala Asn Val Ser Gln Asp Asn Gly Thr Gly
            20                  25                  30

His Asn Ala Thr Phe Ser Glu Pro Leu Pro Phe Leu Tyr Val Leu Leu
        35                  40                  45

Pro Ala Val Tyr Ser Gly Ile Cys Ala Val Gly Leu Thr Gly Asn Thr
    50                  55                  60

Ala Val Ile Leu Val Ile Leu Arg Ala Pro Lys Met Lys Thr Val Thr
65                  70                  75                  80

Asn Val Phe Ile Leu Asn Leu Ala Val Ala Asp Gly Leu Phe Thr Leu
                85                  90                  95

Val Leu Pro Val Asn Ile Ala Glu His Leu Leu Gln Tyr Trp Pro Phe
            100                 105                 110

Gly Glu Leu Leu Cys Lys Leu Val Leu Ala Val Asp His Tyr Asn Ile
        115                 120                 125

```
Phe Ser Ser Ile Tyr Phe Leu Ala Val Met Ser Val Asp Arg Tyr Leu
                130                 135                 140

Val Val Leu Ala Thr Val Arg Ser Arg His Met Pro Trp Arg Thr Tyr
145                 150                 155                 160

Arg Gly Ala Lys Val Ala Ser Leu Cys Val Trp Leu Gly Val Thr Val
                165                 170                 175

Leu Val Leu Pro Phe Phe Ser Phe Ala Gly Val Tyr Ser Asn Glu Leu
                180                 185                 190

Gln Val Pro Ser Cys Gly Leu Ser Phe Pro Trp Pro Glu Gln Val Trp
                195                 200                 205

Phe Lys Ala Ser Arg Val Tyr Thr Leu Val Leu Gly Phe Val Leu Pro
    210                 215                 220

Val Cys Thr Ile Cys Val Leu Tyr Thr Asp Leu Leu Arg Arg Leu Arg
225                 230                 235                 240

Ala Val Arg Leu Arg Ser Gly Ala Lys Ala Leu Gly Lys Ala Arg Arg
                245                 250                 255

Lys Val Thr Val Leu Val Leu Val Val Leu Ala Val Cys Leu Leu Cys
                260                 265                 270

Trp Thr Pro Phe His Leu Ala Ser Val Val Ala Leu Thr Thr Asp Leu
                275                 280                 285

Pro Gln Thr Pro Leu Val Ile Ser Met Ser Tyr Val Ile Thr Ser Leu
                290                 295                 300

Ser Tyr Ala Asn Ser Cys Leu Asn Pro Phe Leu Tyr Ala Phe Leu Asp
305                 310                 315                 320

Asp Asn Phe Arg Lys Asn Phe Arg Ser Ile Leu Arg Cys
                325                 330

<210> SEQ ID NO 85
<211> LENGTH: 1023
<212> TYPE: DNA
<213> ORGANISM: Homo sapiens

<400> SEQUENCE: 85
atcgattaca atgcaggccg ctgggcaccc agagccccct tgacagcaggg gctccttctc         60 cctccccacg atgggtgcca acgtctctca ggacaatggc actggccaca atgccacctt        120
ctccgagcca ctgccgttcc tctatgtgct cctgcccgcc gtgtactccg ggatctgtgc        180
tgtggggctg actggcaaca cggccgtcat ccttgtaatc ctaagggcgc ccaagatgaa        240
gacggtgacc aacgtgttca tcctgaacct ggccgtcgcc gacgggctct tcacgctggt        300
actgcccgtc aacatcgcgg agcacctgct gcagtactgg cccttcgggg agctgctctg        360
caagctggtg ctggccgtcg accactacaa catcttctcc agcatctact cctagccgt         420 gatgagcgtg gaccgatacc tggtggtgct ggccaccgtg aggtcccgcc acatgccctg        480
gcgcacctac cgggggggcga aggtcgccag cctgtgtgtc tggctgggcg tcacggtcct        540
ggttctgccc ttcttctctt cgctggcgt ctacagcaac gagctgcagg tcccaagctg         600
tgggctgagc ttcccgtggc ccgagcaggt ctggttcaag gccagccgtg tctacacgtt        660
ggtcctgggc ttcgtgctgc ccgtgtgcac catctgtgtg ctctacacag acctcctgcg        720
caggctgcgg gccgtgcggc tccgctctgg agccaaggct ctaggcaagg ccaggcggaa        780
ggtgaccgtc ctggtcctcg tcgtgctggc cgtgtgcctc ctctgctgga cgcccttcca        840
cctggcctct gtcgtggccc tgaccacgga cctgccccag accccactgg tcatcagtat        900
gtcctacgtc atcaccagcc tcagctacgc caactcgtgc ctgaacccct tcctctacgc        960
```

-continued

```
ctttctagat gacaacttcc ggaagaactt ccgcagcata ttgcggtgct gaagggcact    1020
agt                                                                  1023
```

<210> SEQ ID NO 86
<211> LENGTH: 331
<212> TYPE: PRT
<213> ORGANISM: Bos sp.

<400> SEQUENCE: 86

```
Met His Asn Ala Ser Tyr Trp Gly Pro Glu Arg Ala Asn Thr Ser Cys
                 5                  10                  15

Pro Ala Pro Ala Pro Thr Leu Gly Cys Pro Asn Ala Ser Gly Pro Ala
             20                  25                  30

Pro Pro Leu Pro Pro Leu Ala Val Ala Val Pro Val Val Tyr Ala
         35                  40                  45

Val Ile Cys Ala Val Gly Leu Ala Gly Asn Ser Ala Val Leu Phe Val
     50                  55                  60

Leu Leu Arg Ala Pro Arg Arg Lys Thr Val Thr Asn Leu Phe Ile Leu
 65                  70                  75                  80

Asn Leu Ala Val Ala Asp Glu Leu Phe Thr Leu Val Pro Pro Val Asn
                 85                  90                  95

Ile Ala Asp Phe Leu Leu Arg Arg Trp Pro Phe Gly Glu Leu Leu Cys
            100                 105                 110

Lys Leu Val Val Ala Val Asp Gln Tyr Asn Thr Phe Ser Ser Leu Tyr
        115                 120                 125

Phe Leu Thr Val Met Ser Ala Asp Arg Tyr Leu Val Val Leu Ala Thr
    130                 135                 140

Ala Glu Ser Arg Arg Val Ala Gly Arg Thr Tyr Gly Ala Ala Arg Ala
145                 150                 155                 160

Val Ser Leu Ala Val Trp Gly Val Ala Thr Leu Val Val Leu Pro Phe
                165                 170                 175

Ala Val Phe Ala Arg Leu Asp Glu Glu Gln Gly Arg Arg Gln Cys Val
            180                 185                 190

Leu Val Phe Pro Gln Pro Glu Ala Leu Trp Trp Arg Ala Ser Arg Leu
        195                 200                 205

Tyr Thr Leu Val Leu Gly Phe Ala Ile Pro Val Ser Thr Ile Cys Val
    210                 215                 220

Leu Tyr Thr Ser Leu Leu Cys Arg Leu Arg Ala Ile Arg Leu Asp Ser
225                 230                 235                 240

His Ala Lys Ala Leu Asp Arg Ala Lys Lys Arg Val Thr Val Leu Val
                245                 250                 255

Val Ala Ile Leu Ala Val Cys Leu Leu Val Trp Thr Pro Tyr His Leu
            260                 265                 270

Ser Thr Val Val Ala Leu Thr Thr Asp Leu Pro Gln Thr Pro Leu Val
        275                 280                 285

Ile Ala Val Ser Tyr Phe Ile Thr Ser Leu Ser Tyr Ala Asn Ser Cys
    290                 295                 300

Leu Asn Pro Phe Leu Tyr Ala Phe Leu Asp Asp Ser Phe Arg Arg Ser
305                 310                 315                 320

Leu Arg Gln Leu Leu Ala Cys Arg Thr Thr Ser
                325                 330
```

<210> SEQ ID NO 87
<211> LENGTH: 993

-continued

```
<212> TYPE: DNA
<213> ORGANISM: Bos sp.

<400> SEQUENCE: 87
atgcacaacg cgtcgtactg ggggccggag cgcgccaaca cgtcgtgccc cgcgcccgca      60
cccacgctcg gctgtcccaa cgcgtccggg ccggcgccgc cgctgccgcc gccgctggcc     120
gtagccgtgc ccgttgtgta cgcggtgatc tgcgcagtgg gactggcggg caactcggcg     180
gtactgttcg tgctgctgcg ggcgccgcgc aggaagaccg tcaccaacct gttcatcctc     240
aacctggccg tggccgacga gcttttcacg ctcgtgccgc ctgtcaacat cgccgacttt     300
ctgctgaggc gctggcccct cggggagctc ctatgcaagc tcgtcgtggc cgtcgatcag     360
tacaacacct tctccagcct ctatttcctc acggtcatga cgccgaccg ctacctggtg      420 gtgctggcca ccgccgagtc gcgccgggtg gccggccgca cgtacggcgc cgcgcgcgcg     480
gtgagcctgg ccgtctgggg ggtcgcgacc ctggtggtgc tgcccttcgc ggtgttcgcg     540
cggctcgacg aggagcaggg ccggcgccag tgcgtactgg tcttcccgca gcccgaggcc     600
ttgtggtggc gcgcgagccg cctgtacacg ctggtgctcg gcttcgccat cccagtgtcc     660
accatctgcg tcctctacac ctcgctgctg tgccggctgc gcgccatacg cctcgacagc     720
cacgccaagg ccctggaccg cgccaagaag cgggtgaccg tcctggtggt ggccatcctg     780
gccgtgtgcc tcctcgtctg gacgccctac cacctgagca ccgtgtggc gctcaccacc      840 gacctcccgc agacgccgct ggtcatcgcc gtgtcctact tcatcaccag cctgagctac     900
gccaacagct gcctcaaccc tttcctctac gccttcctgg acgacagctt ccgccggagc     960
ctccgccagc tgctggcgtg ccgcaccacc tcc                                  993

<210> SEQ ID NO 88
<211> LENGTH: 336
<212> TYPE: PRT
<213> ORGANISM: Bos sp.

<400> SEQUENCE: 88

Met Met Glu Ala Thr Gly Leu Glu Gly Leu Glu Ser Thr Ser Ser Pro
                 5                  10                  15

Cys Pro Gly Ser Thr Gly Thr Gly Leu Ser Trp Asp Asn Gly Thr Arg
             20                  25                  30

His Asn Ala Thr Phe Pro Glu Pro Leu Pro Ala Leu Tyr Val Leu Leu
         35                  40                  45

Pro Val Val Tyr Ser Val Ile Cys Ala Val Gly Leu Val Gly Asn Ala
     50                  55                  60

Ala Val Ile Cys Val Ile Leu Arg Ala Pro Lys Met Lys Thr Val Thr
 65                  70                  75                  80

His Val Phe Ile Leu Asn Leu Ala Ile Ala Asp Gly Leu Phe Thr Leu
                 85                  90                  95

Val Leu Pro Thr Asn Ile Ala Glu His Leu Leu Gln Arg Trp Pro Phe
            100                 105                 110

Gly Glu Val Leu Cys Lys Leu Val Leu Ala Ile Asp His Cys Asn Ile
        115                 120                 125

Phe Ser Ser Val Tyr Phe Leu Ala Ala Met Ser Ile Asp Arg Tyr Leu
    130                 135                 140

Val Val Leu Ala Thr Ala Arg Ser Arg Arg Met Pro Arg Arg Thr Val
145                 150                 155                 160

His Arg Ala Lys Val Ala Ser Leu Cys Val Trp Leu Gly Val Thr Val
                165                 170                 175
```

```
Ala Val Leu Pro Phe Leu Thr Phe Ala Gly Val Tyr Asn Asn Glu Leu
            180                 185                 190

Gln Val Thr Ser Cys Gly Leu Ser Phe Pro Arg Pro Glu Arg Ala Trp
        195                 200                 205

Phe Gln Ala Ser Arg Ile Tyr Thr Leu Val Leu Gly Phe Val Val Pro
    210                 215                 220

Met Cys Thr Leu Cys Val Leu Tyr Ala Asp Leu Leu Arg Arg Leu Arg
225                 230                 235                 240

Ala Leu Arg Leu His Ser Gly Ala Lys Ala Leu Gly Lys Ala Lys Arg
                245                 250                 255

Lys Val Ser Leu Leu Val Leu Ala Val Leu Ala Val Gly Leu Leu Cys
            260                 265                 270

Trp Thr Pro Phe His Leu Ala Ser Ile Val Ala Leu Thr Thr Asp Leu
        275                 280                 285

Pro Gln Thr Pro Leu Val Ile Ile Val Ser Tyr Val Val Thr Ser Leu
    290                 295                 300

Ser Tyr Thr Ser Ser Cys Leu Asn Pro Phe Leu Tyr Ala Phe Leu Asp
305                 310                 315                 320

His Ser Phe Arg Lys Ser Leu Arg Thr Ala Cys Arg Cys Gln Gly Ala
                325                 330                 335

<210> SEQ ID NO 89
<211> LENGTH: 1008
<212> TYPE: DNA
<213> ORGANISM: Bos sp.

<400> SEQUENCE: 89
atgatggagg ccactgggct ggaaggcctg gaaagcacaa gctcccctg cccaggtagc      60 acaggcaccg gcctctcatg ggacaatggc accagacaca atgccacctt ccccgagccg     120
ctgcctgccc tctacgtgct gctgccggtg gtatactctg tcatctgtgc cgtgggctg     180 gtgggcaacg cagccgtcat ctgtgtgatc ctgagggctc caagatgaa gacagtgacc    240 cacgtgttca tcctgaacct ggccatcgcc gacgggctct tcacgctggt gctgcccacc     300
aatattgctg agcacctgct gcagcgctgg ccctttgggg aggtgctctg caagctggtg     360
ctggccattg accactgcaa catcttctcc agtgtctact cctggccgc catgagtata     420 gaccgctacc tggtggttct ggccacggca cgctcccgcc gcatgccccg cgcaccgtc     480 cacagggcga aggtcgccag cctgtgcgtc tggctgggtg tcacagtcgc agtgctgccc     540
ttccttacct tcgcaggcgt gtacaacaat gagctgcagg tcacaagttg tgggctgagt     600
ttcccgcggc ccgagagggc ctggttccag gcaagccgca tctacacgct ggtgctgggc     660
ttcgtggtgc ccatgtgcac cctctgcgtg ctctacgcag acctgctgcg gaggctaagg     720
gccctgcggc tccactccgg agccaaggct ctgggcaagg ccaagcggaa ggttagcctc     780
ctggtcctgg ccgtgctggc cgtgggcctg ctctgctgga cgcccttcca cctggcctca     840
attgtggccc tgaccacaga cctgccccag acaccgctgg tcatcatcgt ctcctatgtg     900
gtcaccagcc tcagctacac cagctcctgc ctcaaccct tcctctatgc cttcctggat     960
cacagcttcc ggaagagcct ccgcaccgca tgtcggtgcc agggggca             1008

<210> SEQ ID NO 90
<211> LENGTH: 18
<212> TYPE: DNA
<213> ORGANISM: Artificial Sequence
<220> FEATURE:
```

<223> OTHER INFORMATION: Primer

<400> SEQUENCE: 90
cgctcccagc cctacaga                                                 18

<210> SEQ ID NO 91
<211> LENGTH: 20
<212> TYPE: DNA
<213> ORGANISM: Artificial Sequence
<220> FEATURE:
<223> OTHER INFORMATION: Primer

<400> SEQUENCE: 91
tcgccttgca ctggtaggtc                                               20

<210> SEQ ID NO 92
<211> LENGTH: 24
<212> TYPE: DNA
<213> ORGANISM: Artificial Sequence
<220> FEATURE:
<223> OTHER INFORMATION: Primer

<400> SEQUENCE: 92
agcctcgctg tgtgcgtcca ggac                                          24

<210> SEQ ID NO 93
<211> LENGTH: 22
<212> TYPE: DNA
<213> ORGANISM: Artificial Sequence
<220> FEATURE:
<223> OTHER INFORMATION: Primer

<400> SEQUENCE: 93
tgcgtgctat ccagctagac ag                                            22

<210> SEQ ID NO 94
<211> LENGTH: 22
<212> TYPE: DNA
<213> ORGANISM: Artificial Sequence
<220> FEATURE:
<223> OTHER INFORMATION: Primer

<400> SEQUENCE: 94
agaggaggca cacagccaga at                                            22

<210> SEQ ID NO 95
<211> LENGTH: 26
<212> TYPE: DNA
<213> ORGANISM: Artificial Sequence
<220> FEATURE:
<223> OTHER INFORMATION: Primer

<400> SEQUENCE: 95
cgtgccaaga aacgcgtgac cttgtt                                        26

<210> SEQ ID NO 96
<211> LENGTH: 30
<212> TYPE: DNA
<213> ORGANISM: Artificial Sequence
<220> FEATURE:
<223> OTHER INFORMATION: Primer

<400> SEQUENCE: 96
gtcgaccgag tgtctgtcct cgccaggatg                                    30

-continued

<210> SEQ ID NO 97
<211> LENGTH: 33
<212> TYPE: DNA
<213> ORGANISM: Artificial Sequence
<220> FEATURE:
<223> OTHER INFORMATION: Primer

<400> SEQUENCE: 97
gctagctcct tgttatcggg ctcaggaggt ggt                33

<210> SEQ ID NO 98
<211> LENGTH: 33
<212> TYPE: DNA
<213> ORGANISM: Artificial Sequence
<220> FEATURE:
<223> OTHER INFORMATION: Primer

<400> SEQUENCE: 98
gtcgaccatg atggaggcca ctgggctgga agg                33

<210> SEQ ID NO 99
<211> LENGTH: 33
<212> TYPE: DNA
<213> ORGANISM: Artificial Sequence
<220> FEATURE:
<223> OTHER INFORMATION: Primer

<400> SEQUENCE: 99
gctagcttat gccccctggc accgacatgc ggt                33

<210> SEQ ID NO 100
<211> LENGTH: 23
<212> TYPE: PRT
<213> ORGANISM: Homo sapiens

<400> SEQUENCE: 100

Trp Tyr Lys His Val Ala Ser Pro Arg Tyr His Thr Val Gly Arg Ala
1               5                   10                  15

Ala Gly Leu Leu Met Gly Leu
            20

<210> SEQ ID NO 101
<211> LENGTH: 378
<212> TYPE: DNA
<213> ORGANISM: Homo sapiens

<400> SEQUENCE: 101
atggcccggt ccgcgacact ggcggccgcc gccctggcgc tgtgcctgct gctggcgccg      60
cctggcctcg cgtggtacaa gcagcgggcg gggcacagct cctactcggt gggccgcgcc     120
gcggggctgc tgtccggcct ccgcaggtcc ccgtacgcgc ggcgctccca gccctacaga     180
ggggcggaac ccccgggcgg ggccggcgcc tccccggagc tgcaactgca ccccaggctg     240
cggagcctcg ctgtgtgcgt ccaggacgtc gccccaaacc tgcagaggtg cgagcggctc     300
cccgacggcc gcgggaccta ccagtgcaag gcgaacgtct tcctgtccct gcgcgcagcc     360
gactgcctcg ccgcctga                                                   378

<210> SEQ ID NO 102
<211> LENGTH: 360
<212> TYPE: DNA
<213> ORGANISM: Mus sp.

<400> SEQUENCE: 102

```
atggcccggt gtaggacgct ggtggccgct gccctggcgc tgctcctgcc gccagccctc    60
gcgtggtaca agcccgcggc gggaccccac cactactcgg tgggccgcgc ctcggggcta   120
ctgtcgagtt ccacaggtt cccgtccacg cgacgctccg agtctccagc actccgggtg    180
ggaaccggac ctctgcgcaa tttagagatg cgccccagcg taaggagcct tgccctgtgt   240
gtcaaagatg tgaccccgaa cctgcagagc tgccagcggc aactcaacag ccgagggact   300
ttccagtgta aagcggacgt cttcttgtcg ctgcacgaga ctgattgcca gagcacctga   360
```

<210> SEQ ID NO 103
<211> LENGTH: 360
<212> TYPE: DNA
<213> ORGANISM: Rattus sp.

<400> SEQUENCE: 103

```
atggtccggt gtaggacgct ggtggccgcc gccctggcgc tgctcctgac gccagccctc    60
gcgtggtaca agcccgcggc gggatcccac cactactcgg tgggccgcgc tgcggggcta   120
ctgtcgagtt ccacaggtt cccatccacg cgacgttccg agtctccagc actccgggtg    180
ggaaccgtac ctctgcgcaa cttggagatg cgcccaagcg taagaagcct tgccctgtgt   240
gtcaaagatg tgaccccgaa cctgcagagc tgccagcggc aactcaacag ccgagggact   300
ttccagtgta aggcggacgt cttcttgtcg ctgcacaagg ctgaatgcca aagcgcctga   360
```

<210> SEQ ID NO 104
<211> LENGTH: 369
<212> TYPE: DNA
<213> ORGANISM: Bos sp.

<400> SEQUENCE: 104

```
atggccgggc ccgcgatgct ggtggccgcc gctctggcgc tgtgcttact gctggcgtcc    60
cctggcctcg cgtggtacaa gccgacggcg gggcaggggt actactccgt gggccgcgcc   120
gcggggctgc tgtccggctt ccacaggtcg ccgtacgcac ggcgcgctcc gaccccgcggg  180 ggcacgcgat ccctgggagg ggtcggcact ttccgggaga tgcgccccaa cctgcggagt   240
cttgccgtgt gcgtcgagga ggtcaccccc aacctgcaga gctgcgagcc actccccgac   300
ggccgcgcca ctttccagtg caaggccgac gtcttcctgt cgctcagcgc ctcggactgt   360
cgcaagtga                                                            369
```

<210> SEQ ID NO 105
<211> LENGTH: 996
<212> TYPE: DNA
<213> ORGANISM: Bos sp.

<400> SEQUENCE: 105

```
atgcacaacg cgtcgtactg ggggccggag cgcgccaaca cgtcgtgccc cgcgcccgca    60
cccacgctcg gctgtcccaa cgcgtccggg ccggcgccgc cgctgccgcc gccgctggcc   120
gtagccgtgc ccgttgtgta cgcggtgatc tgcgcagtgg gactggcggg caactcggcg   180
gtactgttcg tgctgctgcg ggcgccgcgc aggaagaccg tcaccaacct gttcatcctc   240
aacctggccg tggccgacga gctttcacg ctcgtgccgc tgtcaacat cgccgacttt    300 ctgctgagcg ctggcccctt cggggagctc ctatgcaagc tcgtcgtggc cgtcgatcag   360
tacaacacct tctccagcct ctatttcctc acggtcatga gcgccgaccg ctacctggtg   420
gtgctggcca ccgccgagtc gcgccgggtg gccggccgca cgtacggcgc gcgcgcgcg   480 gtgagcctgg ccgtctgggg ggtcgcgacc ctggtggtgc tgcccttcgc ggtgttcgcg   540
```

```
cggctcgacg aggagcaggg ccggcgccag tgcgtactgg tcttcccgca gcccgaggcc    600
ttgtggtggc gcgcgagccg cctgtacacg ctggtgctcg gcttcgccat cccagtgtcc    660
accatctgcg tcctctacac ctcgctgctg tgccggctgc gcgccatacg cctcgacagc    720
cacgccaagg ccctggaccg cgccaagaag cgggtgaccg tcctggtggt ggccatcctg    780
gccgtgtgcc tcctcgtctg gacgccctac cacctgagca ccgtggtggc gctcaccacc    840
gacctcccgc agacgccgct ggtcatcgcc gtgtcctact tcatcaccag cctgagctac    900
gccaacagct gcctcaaccc tttcctctac gccttcctgg acgacagctt ccgccggagc    960
ctccgccagc tgctggcgtg ccgcaccacc tcctga                              996

<210> SEQ ID NO 106
<211> LENGTH: 1011
<212> TYPE: DNA
<213> ORGANISM: Bos sp.

<400> SEQUENCE: 106
atgatggagg ccactgggct ggaaggcctg gaaagcacaa gctcccctg cccaggtagc      60 acaggcaccg gcctctcatg ggacaatggc accagacaca atgccacctt ccccgagccg    120
ctgcctgccc tctacgtgct gctgccggtg gtatactctg tcatctgtgc cgtggggctg    180
gtgggcaacg cagccgtcat ctgtgtgatc ctgagggctc ccaagatgaa gacagtgacc    240
cacgtgttca tcctgaacct ggccatcgcc gacgggctct tcacgctggt gctgcccacc    300
aatattgctg agcacctgct gcagcgctgg cccttgggg aggtgctctg caagctggtg    360
ctggccattg accactgcaa catcttctcc agtgtctact tcctggccgc catgagtata    420
gaccgctacc tggtggttct ggccacggca cgctcccgcc gcatgccccg cgcaccgtc     480 cacagggcga aggtcgccag cctgtgcgtc tggctgggtg tcacagtcgc agtgctgccc    540
ttccttacct tcgcaggcgt gtacaacaat gagctgcagg tcacaagttg tgggctgagt    600
ttcccgcggc ccgagagggc ctggttccag gcaagccgca tctacacgct ggtgctgggc    660
ttcgtggtgc ccatgtgcac cctctgcgtg ctctacgcag acctgctgcg gaggctaagg    720
gccctgcggc tccactccgg agccaaggct ctgggcaagg ccaagcggaa ggttagcctc    780
ctggtcctgg ccgtgctggc cgtgggcctg tctgctggac gcccttcca cctgcctca    840 attgtggccc tgaccacaga cctgccccag acaccgctgg tcatcatcgt ctcctatgtg    900
gtcaccagcc tcagctacac cagctcctgc ctcaacccct tcctctatgc cttcctggat    960
cacagcttcc ggaagagcct ccgcaccgca tgtcggtgcc aggggggcata a           1011

<210> SEQ ID NO 107
<211> LENGTH: 29
<212> TYPE: PRT
<213> ORGANISM: Homo sapiens
<220> FEATURE:
<221> NAME/KEY: MOD_RES
<222> LOCATION: (1)
<223> OTHER INFORMATION: D-Trp(6Br)

<400> SEQUENCE: 107

Trp Tyr Lys Pro Ala Ala Gly His Ser Tyr Ser Val Gly Arg Ala
              5                  10                  15

Ala Gly Leu Leu Ser Gly Leu Arg Arg Ser Pro Tyr Ala
             20                  25

<210> SEQ ID NO 108
```

-continued

```
<211> LENGTH: 29
<212> TYPE: PRT
<213> ORGANISM: Bos sp.
<220> FEATURE:
<221> NAME/KEY: MOD_RES
<222> LOCATION: (1)
<223> OTHER INFORMATION: D-Trp(6Br)

<400> SEQUENCE: 108

Trp Tyr Lys Pro Thr Ala Gly Gln Gly Tyr Tyr Ser Val Gly Arg Ala
 1               5                  10                  15

Ala Gly Leu Leu Ser Gly Phe His Arg Ser Pro Tyr Ala
                20                  25
```